(12) United States Patent
Darzins et al.

(10) Patent No.: US 8,466,269 B2
(45) Date of Patent: *Jun. 18, 2013

(54) COVALENT TETHERING OF FUNCTIONAL GROUPS TO PROTEINS AND SUBSTRATES THEREFOR

(75) Inventors: Aldis Darzins, Verona, WI (US); Lance Encell, Fitchburg, WI (US); Dieter Klaubert, Arroyo Grande, CA (US); Georgyi V. Los, Madison, WI (US); Mark McDougall, Arroyo Grande, CA (US); Keith V. Wood, Mt. Horeb, WI (US); Monika G. Wood, Mt. Horeb, WI (US); Chad Zimprich, Stoughton, WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/435,970

(22) Filed: Mar. 30, 2012

(65) Prior Publication Data

US 2012/0220013 A1 Aug. 30, 2012

Related U.S. Application Data

(60) Division of application No. 13/046,297, filed on Mar. 11, 2011, now Pat. No. 8,168,405, which is a division of application No. 12/075,160, filed on Mar. 10, 2008, now Pat. No. 7,935,803, which is a division of application No. 11/194,110, filed on Jul. 29, 2005, now Pat. No. 7,425,436, which is a continuation-in-part of application No. 11/006,031, filed on Dec. 6, 2004, now Pat. No. 7,429,472.

(60) Provisional application No. 60/592,499, filed on Jul. 30, 2004.

(51) Int. Cl.
| C07H 21/04 | (2006.01) |
| C12N 9/14 | (2006.01) |
| C12N 1/00 | (2006.01) |
| C12P 21/02 | (2006.01) |

(52) U.S. Cl.
USPC ...... 536/23.2; 435/195; 435/69.1; 435/252.3; 570/101

(58) Field of Classification Search
USPC ....... 536/23.6; 435/195, 69.1, 252.3; 570/101
See application file for complete search history.

(56) References Cited

U.S. PATENT DOCUMENTS

| 3,131,122 A | 4/1964 | Freter |
| 4,574,079 A | 3/1986 | Gavras et al. |

(Continued)

FOREIGN PATENT DOCUMENTS

| BE | 616 245 | 10/1962 |
| BE | 616245 | 10/1962 |

(Continued)

OTHER PUBLICATIONS

Japanese Office Action mailed Apr. 5, 2011, Application No. 2007-523888, 10 pgs.

(Continued)

*Primary Examiner* — Rosanne Kosson
(74) *Attorney, Agent, or Firm* — Casimir Jones, S.C.

(57) ABSTRACT

A mutant hydrolase optionally fused to a protein of interest is provided. The mutant hydrolase is capable of forming a bond with a substrate for the corresponding nonmutant (wild-type) hydrolase which is more stable than the bond formed between the wild-type hydrolase and the substrate and has at least two amino acid substitutions relative to the wild-type hydrolase. Substrates for hydrolases comprising one or more functional groups are also provided, as well as methods of using the mutant hydrolase and the substrates of the invention. Also provided is a fusion protein capable of forming a stable bond with a substrate and cells which express the fusion protein.

12 Claims, 72 Drawing Sheets

U.S. PATENT DOCUMENTS

| | | | |
|---|---|---|---|
| 4,818,807 | A | 4/1989 | Morita et al. |
| 5,071,469 | A | 12/1991 | Artz |
| 5,099,020 | A | 3/1992 | Grote et al. |
| 5,110,833 | A | 5/1992 | Mosbach |
| 5,128,247 | A | 7/1992 | Koller |
| 5,372,944 | A | 12/1994 | Swanson |
| 5,476,770 | A | 12/1995 | Pradelles |
| 5,503,977 | A | 4/1996 | Johnsson et al. |
| 5,523,209 | A | 6/1996 | Ginsberg et al. |
| 5,576,424 | A | 11/1996 | Mao et al. |
| 5,700,908 | A | 12/1997 | Ruoslahti et al. |
| 5,700,935 | A | 12/1997 | Takenishi et al. |
| 5,786,428 | A | 7/1998 | Arnold et al. |
| 5,821,047 | A | 10/1998 | Garrard et al. |
| 5,932,421 | A | 8/1999 | Ginsberg et al. |
| 5,945,526 | A | 8/1999 | Lee et al. |
| 6,255,461 | B1 | 7/2001 | Mosbach et al. |
| 6,333,154 | B1 | 12/2001 | Ladant et al. |
| 6,416,733 | B1 | 7/2002 | Barrett et al. |
| 6,492,560 | B2 | 12/2002 | Wilbur et al. |
| 6,537,776 | B1 | 3/2003 | Short |
| 6,800,453 | B2 | 10/2004 | Labaer et al. |
| 7,078,504 | B2 | 7/2006 | Short et al. |
| 7,238,842 | B2 | 7/2007 | Wood et al. |
| 7,425,436 | B2 * | 9/2008 | Darzins et al. ........... 435/195 |
| 7,429,472 | B2 | 9/2008 | Darzins et al. |
| 7,935,803 | B2 * | 5/2011 | Darzins et al. ........... 536/23.2 |
| 2002/0042055 | A1 | 4/2002 | Affholter |
| 2002/0137171 | A1 | 9/2002 | Short et al. |
| 2003/0166957 | A1 | 9/2003 | Benneteau et al. |
| 2004/0152880 | A1 | 8/2004 | Minden |
| 2004/0214258 | A1 | 10/2004 | Wood et al. |
| 2005/0048580 | A1 | 3/2005 | Labaer et al. |
| 2005/0095651 | A1 | 5/2005 | Camarero et al. |
| 2005/0272114 | A1 | 12/2005 | Darzins et al. |
| 2006/0024808 | A1 | 2/2006 | Darzins et al. |
| 2007/0087400 | A1 | 4/2007 | Darzins et al. |
| 2007/0224620 | A1 | 9/2007 | Hartzell et al. |
| 2008/0026407 | A1 | 1/2008 | Wood et al. |
| 2008/0145882 | A1 | 6/2008 | Darzins et al. |
| 2009/0098627 | A1 | 4/2009 | Darzins et al. |

FOREIGN PATENT DOCUMENTS

| | | |
|---|---|---|
| CZ | 259396 | 10/1988 |
| CZ | PV 3202-87.K | 3/1989 |
| EP | 718300 | 6/1996 |
| WO | WO-98/36080 | 8/1998 |
| WO | WO-01/53303 A1 | 7/2001 |
| WO | WO-0153303 A1 | 7/2001 |
| WO | WO-0160415 A1 | 8/2001 |
| WO | WO-0177668 A2 | 10/2001 |
| WO | WO-02/28841 A2 | 4/2002 |
| WO | WO-02057411 A2 | 7/2002 |
| WO | WO-02068583 A2 | 9/2002 |
| WO | WO-02/083937 | 10/2002 |
| WO | WO-03040096 A2 | 5/2003 |
| WO | WO-2004009788 A2 | 1/2004 |
| WO | WO-2004072232 A2 | 8/2004 |
| WO | WO-2004072232 A3 | 8/2004 |
| WO | WO-2006093529 A2 | 9/2006 |
| WO | WO-2006093529 A3 | 9/2006 |
| WO | WO-2007092579 A2 | 8/2007 |
| WO | WO-2007092579 A3 | 8/2007 |
| WO | WO-2007092579 C1 | 8/2007 |
| WO | 2008/054821 | 5/2008 |

OTHER PUBLICATIONS

Reba et al., "Synthesis of Some Substituted Dibenzodiazopinones and Pyridobenzodiazopinones," J Heterocyclic Chem, 35, pp. 675-686 (1998).

Japanese Patent Publication (Kohyo) 2003-530365, Translation of Abstract.

United States Patent Office Restriction Requirement mailed Sep. 26, 2011, U.S. Appl. No. 13/046,297 (10 pages).

Response to Restriction Requirement Mailed Sep. 26, 2011, U.S. Appl. No. 13/046,297, filed Oct. 26, 2011 (5 pages).

Anonymous: "Lecturer Abstracts"Internet Citation XPOO2301487Retrieved from the InternetURL: http://www.promega-rd.infolbioimage2003labstraetsl1ecturer/default.asp retrieved on Oct. 19, 2004.

United States Patent Office Action for U.S. Appl. No. 12/220,478 dated Jun. 10, 2010 (11 pages).

United States Patent Office Action for U.S. Appl. No. 11/786,792 dated Jun. 7, 2010 (10 pages).

United States Patent Office Action for U.S. Appl. No. 12/284,010 dated Jul. 2, 2010 (9 pages).

"Valence," Hawley's Condensed Chemical Dictionary (14th Edition) Online, John Wiley and Sons, 2002, http://www.knovel.com/knove12/Toc.jsp?BookID=704&VerticlID=0 (Mar. 20, 2007).

Adamczyk et al., "Surface plasmon resonance (SPR) as a tool for antibody conjugate analysis," Bioconjug. Chem., 1999, 10:1032-1037.

Banas et al., "Mechanism of enhanced conversion of 1,2,3-trichloropropane by mutant haloalkane dehalogenase revealed by molecular modeling," J. Computer-Aided Molecular Design, 2006, 20:375-383.

Broom et al., "Two approaches to drug discovery in SOD1-mediated ALS," J. Biomol. Screen, 2006, 11:729-735.

Chan et al., "Microarray-based detection of *Salmonella enterica* serovar typhimurium transposon mutants that cannot survive in macrophages in mice," Infect. Immun., 2005, 73:5438-5449.

Dodson et al., "Catalytic triads and their relatives," Trends Biochem. Sci., 1998, 23:347-352.

Gao et al., "Construction of murine phage antibody library and selection of ricin-specific single-chain antibodies," IUBMB Life, 1999, 48:513-517.

Gibbons et al., "Chipper: discovery transcription-factor targets from chromatin immunoprecipitation microarrays using varlance stabilization," Genome Biol., 2005, 6:R96 (9 pgs).

Gorbalenya et al., "Cysteine proteases of positive strand RNA viruses and chymotrypsin-like serine proteases. A distinct protein superfamily with a common structural fold," FEBS Lett., 1989, 243:103-114.

Grogan, "Emergent mechanistic diversity of enzyme-catalysed beta-diketone cleavage," Biochem. J., 2005, 388:(Pt 3):721-730.

Jeong et al., "Kinase assay based on thiophosphorylation and biothinylation," Biotechniques, 1999, 27:1232-1238.

Keepler et al., "A general method of rht ecovalent labeling of fusion proteins with small molecules in vivo," Nat. Biotech., 2003, 21:86-89.

Krooshof et al., "Repositioning the catalytic triad aspartic acid of haloalkane dehalogenase: effects on stability, kinetics and structure," Biochem., 1997, 36:9571-9580.

Kulakova et al., "The plasmid-located haloalkane dehalogenase gene from *Rhodococcus rhodochrous* NCIMB 13064," Microbiol., 1997, 143:109-115.

Kumar et al., "Large-scale mutagenesis of the yeast genome using a Tn7-derived multipurpose transposon," Genome Res., 2004, 14(10A):1975-1986.

Lewis et al., "Detection and quantification of biotinylated proteins using the storm 840 optical scanner," J. Nutri. Biochem., 2003, 14:196-202.

Miyazaki-Imamura et al., "Improvement of H2O2 stability of manganese peroxidase by combinatorial mutagenesis and high-throughput screening using in vitro expression with protein disulfide isomerase," Protein Eng., 2003, 16:423-438.

Polgar, "The catalytic triad of serine peptidases," Cell Mol. Life Sci., 2005, 62(19-20):2161-2172.

Pompeo et al., "The pharmacogenetics of NAT: structural aspects," Pharmacogenomics, 2002, 3:19-30.

Rouille et al., "Proteolyitc processing mechanisms in the biosynthesis of neuroendocrine peptides: the subtilisin-like proprotein convertases," Front Neuroendocrinol., 1995, 16:322-361.

Zeph et al., "Use of biotinylated DNA probe to detect bacteria transduced by bacteriophage P1 in soil," Appl. Environ. Microbiol., 1989, 55:661-665.

Chinese Patent Office Action for Application No. 200480008194.4 dated Oct. 9, 2009 (21 pages) with English translation.

European Patent Office Action for Application No. 07867352.2 dated Feb. 1, 2010 (4 pages).

Indian Patent Office Action for Application No. 3867/DELNP/2005 dated Sep. 9, 2008 (1 page).
Japanese Patent Office Action for Application No. 2006-503174 mailed Oct. 27, 2009 (18 pages) with English translation.
United States Patent Office Action for U.S. Appl. No. 11/006,031 dated May 7, 2007 (3 pages).
United States Patent Office Action for U.S. Appl. No. 11/509,796 dated Mar. 28, 2008 (12 pages).
United States Patent Office Action for U.S. Appl. No. 11/786,792 dated Nov. 2, 2009 (12 pages).
United States Patent Office Action for U.S. Appl. No. 12/284,010 dated Sep. 29, 2009 (10 pages).
"Instant Notes—Chemistry for Biologists," Second Ed., Garland Science/BIOS Scientific Publishers, 2004, 245-246.
Untied States Patent Office Notice of Allowance for U.S. Appl. No. 11/006,031 mailed Apr. 24, 2008.
Untied States Patent Office Action for U.S. Appl. No. 11/509,796 mailed Nov. 12, 2008 (22 pages).
Untied States Patent Office Notice of Non-Responsive Amendment for U.S. Appl. No. 11/509,796 mailed Jun. 30, 2008 (6 pages).
Response to Notice of Non-Responsive Amendment mailed Jun. 30, 2008 for U.S. Appl. No. 11/509,796, filed Jul. 30, 2008 (10 pages).
Response to Restriction Requirement and Preliminary Amendment filed Apr. 28, 2008 for U.S. Appl. No. 11/509,796.
United States Patent Office Restriction Requirement mailed Mar. 30, 2009 for U.S. Appl. No. 11/704,150 (11 pages).
United States Patent Office Action mailed Sep. 8, 2009 for U.S. Appl. No. 11/704,150 (12 pages).
Response filed to Restriction Requirement mailed Mar. 30, 2009 for U.S. Appl. No. 11/704,150 (12 pages).
United States Patent Office Action for U.S. Appl. No. 11/786,792 mailed Feb. 5, 2009 (10 pages).
Response filed Dec. 23, 2008 to Restriction Requirement mailed Nov. 26, 2008 for U.S. Appl. No. 11/786,792 (15 pages).
United States Patent Office Action for U.S. Appl. No. 11/786,792 mailed Jul. 10, 2009 (14 pages).
Response filed Jun. 2, 2009 to Office Action mailed Feb. 5, 2009 for U.S. Appl. No. 11/786,792 (16 pages).
United States Patent Office Preliminary Amendment filed Dec. 2, 2008 for U.S. Appl. No. 12/220,478 (3 pages).
United States Patent Office Preliminary Amendment filed Aug. 17, 2008 for U.S. Appl. No. 12/284,010 (18 pages).
United States Patent Office Action mailed Mar. 23, 2009 for U.S. Appl. No. 12/284,010 (15 pages).
Response filed Jul. 10, 2009 to Office Action mailed Mar. 23, 2009 for U.S. Appl. No. 12/284,2010 (17 pages).
*The Second Symposium on Biological Imaging: New Dimensions in In Vivo Imaging*, Lecturer Abstracts, obtained from www.promega-rd.info/bioimage2003/abstracts/lecture/default.asp,(2003),5 Pages.
*Database EMBL EBI*, Accession No. BD057138, (2004),1 pg.
*Wayback machine*, http://www.promega-rd.info/bioimage2003/abstracts/lecturer/default.asap,(Mar. 17, 2007).
"U.S. Appl. No. 10/768,976 Final Office Action Mailed Mar. 14, 2006", 9 pgs.
"U.S. Appl. No. 10/768,976 Non Final Office Action mailed Aug. 1, 2006", 7 pgs.
"U.S. Appl. No. 10/768,976 Non Final Office Action mailed Sep. 9, 2005", 12 pgs.
"U.S. Appl. No. 10/768,976 Notice of Allowance mailed Dec. 15, 2006", 11 pgs.
"U.S. Appl. No. 10/768,976 Preliminary Amendment and Response to Restriction Requirement filed Aug. 5, 2005", 22 pgs.
"U.S. Appl. No. 10/768,976 Response filed Jan. 24, 2006 to Non Final Office Action mailed Sep. 9, 2005", 21 pgs.
"U.S. Appl. No. 10/768,976 Response filed Jul. 11, 2006 to Final Office Action mailed Mar. 14, 2006", 13 pgs.
"U.S. Appl. No. 10/768,976 Response filed Nov. 1, 2006 to Non Final Office Action mailed Aug. 1, 2006", 13 pgs.
"U.S. Appl. No. 10/768,976, Restriction Requirement mailed Jun. 2, 2005", 11 pgs.
"U.S. Appl. No. 11/006,031 Advisory Action mailed May 7, 2007", 3 pgs.
"U.S. Appl. No. 11/006,031 Amendment and Response filed Apr. 25, 2007 to Final Office Action mailed Feb. 8, 2007", 34 pgs.
"U.S. Appl. No. 11/006,031 Final Office Action mailed Feb. 8, 2007", 8 pgs.
"U.S. Appl. No. 11/006,031 Non Final Office Action mailed Mar. 15, 2008", 15 pgs.
"U.S. Appl. No. 11/006,031 Non Final Office Action mailed Aug. 9, 2006", 13 pgs.
"U.S. Appl. No. 11/006,031 Notice of Allowance Mailed Oct. 30, 2007", 8 pgs.
"U.S. Appl. No. 11/006,031 Response filed Jul. 6, 2006 to Non Final Office Action mailed Mar. 15, 2006", 35 pgs.
"U.S. Appl. No. 11/006,031 Response filed Jul. 7, 2007 to Advisory Action mailed May 7, 2007", 32 pgs.
"U.S. Appl. No. 11/006,031 Response filed Dec. 22, 2006 to Non Final Office Action mailed Aug. 9, 2006", 37 pgs.
"U.S. Appl. No. 11/006,031, Response filed Feb. 17, 2006 to Restriction Requirement mailed Dec. 21, 2005", 34 pgs.
"U.S. Appl. No. 11/006,031, Response to Restriction Requirement filed Aug. 31, 2007", 37 pgs.
"U.S. Appl. No. 11/006,031, Restriction Requirement mailed Dec. 21, 2005", 20 pgs.
"U.S. Appl. No. 11/006,031, Restriction Requirment mailed Jul. 31, 2007", 8 pgs.
"U.S. Appl. No. 11/194,110, Notice of Allowance Mailed Dec. 3, 2007", 6 pgs.
"U.S. Appl. No. 11/194,110 Non Final Office Action mailed Mar. 29, 2007", 21 pgs.
"U.S. Appl. No. 11/194,110 Preliminary Amendment mailed Oct. 31, 2007", 18 pgs.
"U.S. Appl. No. 11/194,110, Response to Restriction Requirement and Preliminary Amendment mailed Feb. 7, 2007", 21 pgs.
"U.S. Appl. No. 11/194,110, Restriction Requirement mailed Jan. 4, 2007", 14 pgs.
"U.S. Appl. No. 11/194,110, Supplemental Preliminary Amendment mailed Nov. 14, 2007", 6 pgs.
"U.S. Appl. No. 11/194,110 Notice of Allowance mailed Aug. 15, 2007", NOAR,12 pgs.
"U.S. Appl. No. 11/194,110 Response filed Jun. 29, 2007 to Non Final Office Action mailed Mar. 29, 2007", 20 pgs.
"U.S. Appl. No. 11/509,796, Non-Final Office Action Apr. 11, 2007", 29 pgs.
"U.S. Appl. No. 11/509,796, Restriction Requirement mailed Dec. 20, 2007", 9 pgs.
"U.S. Appl. No. 11/509,796 Final Office Action mailed Sep. 24, 2007", 34 pgs.
"U.S. Appl. No. 11/509,796 Non Final Office Action mailed Apr. 11, 2007", 33 pgs.
"U.S. Appl. No. 11/509,796 Preliminary Amendment filed Dec. 22, 2006", 8 pgs.
"U.S. Appl. No. 11/509,796 Response filed Jul. 5, 2007 to Non Final Office Action mailed Apr. 11, 2007", 35 pgs.
"U.S. Appl. No. 11/509,796 Response filed Oct. 31, 2007 to Final Office Action mailed Sep. 24, 2007", 19 pgs.
"U.S. Appl. No. 11/509,796, Response to Restriction Requirement and Preliminary Amendment filed Feb. 20, 2008, to Restriction Requirement mailed Dec. 20, 2007.", 11.
"U.S. Appl. No. 11/509,796, Final Office Action Mailed Sep. 24, 2007", 34 pgs.
"U.S. Appl. No. 11/709,150 Preliminary Amendment filed May 11, 2007", 12 pgs.
"U.S. Appl. No. 11/786,792 Preliminary Amendment filed Apr. 12, 2007", 11 pgs.
"U.S. Appl. No. 11/786,792 Preliminary Amendment filed Aug. 17, 2007", 13 pgs.
"U.S. Appl. No. 11/786,792, Supplemental Preliminary Amendment filed Aug. 17, 2007", 13 pgs.
"Chinese Patent Application No. 20048000819.4, First Office Action mailed Dec. 22, 2006", 8 pgs.
"Chinese Patent Application No. 200480008194, Response filed Jul. 6, 2007 to the First Action mailed mailed Dec. 22, 2206", 27 pgs.

"European Patent Application Ser. No. 0407032.1, Response filed Sep. 18, 2007 to Examining Division's Communication mailed Mar. 12, 2007", 37 pgs.

"European Patent Application Ser. No. 04707032.1, Communication Pursuant to Article 96(2) EPC mailed Mar. 12, 2007", 3 pgs.

"Functional Group" *Encyclopaedia Britannica Article Online*, http://www.search.ed.com/eb/article-9035655,(Mar. 19, 2007).

"Partial Search Report for corresponding PCT Application No. PCT/US2005/027307", (Jun. 11, 2006),5 pgs.

"PCT Application No. PCT/US2004/002607, International Preliminary Report on Patentability mailed Jun. 23, 2005", 16 pgs.

"PCT Application No. PCT/US2004/002607, International Search Report mailed Oct. 26, 2004", 4 pgs.

"PCT Application No. PCT/US2005/027307, International Preliminary Report on Patentability mailed Feb. 20, 2007", 19 pgs.

"PCT Application No. PCT/US2005/027307, International Search Report mailed Jan. 29, 2007", 9 pgs.

"PCT Application No. PCT/US2005/027307, Written Opinion mailed Jan. 29, 2007", 18 pgs.

"PCT Application No. PCT/US2007/003416, International Search Report mailed Sep. 14, 2007", 6 pgs.

"PCT Application No. PCT/US2007/003416, Written Opinion mailed Sep. 14, 2007", 13 pgs.

"Valence", *Hawley's Condensed Chemical Dictionary (14th Edition) Online*, John Wiley and Sons 2002, http://www.knovel.com/knovel2/Toc.jsp?BookID=704&VerticlID=0,(Mar. 20, 2007).

Adachi, H., et al., "Site-directed mutants, at position 166, of RTEM-1 beta-lactamase that form a stable acyl-enzyme intermediate with penicillin", *J Biol Chem.*, 266(5), (Feb. 1991),pp. 3186-3191.

Affholter, J. A., et al., "Recombinant Haloaliphatic Dehalogenases", *EMBL Database*, Genetic Sequence, Entry Name: EMBL:BD057138,(Sep. 4, 2002),1 p.

Akiyama, M., et al., "N-Hydroxy Amides, Part 8. Synthesis and Fe(III) Holding Properties of di- and Trihydroxamic Acids Extending from Benezenedi- and Tricarbonyl Units Through Oligo(ethyleneoxy) Arms", *J. Chem. Soc. Perkin Transactions, 2 Physical Org Chem*, 9, (1989),1213-1218.

Albertson, Noel, et al., "A Synthesis of DL-Proline", *Journal of the American Chemical Society*,71, (1949),2818-2820.

Amat-Guerri, F., et al., "Methacrylate-tethered Analogs of the Laser Dye PM567 Synthesis, Copolymerization with Methyl Methacrylate and Photostabilit of the Copolymers", *Photochemistry and Photobiology*, 77(6), 2003 ,577-584.

Arand, M., et al., "Sequence similarity of mammalian epoxide hydrolases to the bacterial haloalkanedehalogenase and other related proteins" *FEBS Letters*, 338, (1994),251-256.

Aravind, L., "An evolutionary classification of the metallo-beta-lactamase fold proteins", *In Silico Biol.*, 1(2), (1999),pp. 69-91.

Banks, P., et al., "Understanding Fluorescence Polarization and its Data Analysis—Physical Principles of Fluorescence Polarization", http://www.perkinelmer.com/lifesciences, (2001),12 Pages.

Barrett, A., et al., "Synthesis and characterization of a new polymer support for a metallocene catalyst", *Tetrahedron*, 58(19). (2002),3785-3792.

Barrett, A. G., "Synthesis and Characterization of a New Polymer Support for a Metallocene Catalyst", *Tetrahedron*, 58 (19), Elsevier Science Publishers,(May 6, 2002),3785-3792.

Bier, C, "Covalys—one tag does it all", *Market Portrait*, (2003)pp. 46-47.

Bodwell, G. J., et al., "Synthesis, Structure AM1 Conformational Study of [3] Paracyclo[3] (1,3) indolophane, a Novel Chiral and Cyclophane", *Tetrahedron*, 55(45), (Nov. 5, 1999),12939-12956.

Bosma, et al., "Biodegradation of 1,2,3-trichloropropane through directed evolution and heterologous expression of a haloalkane dehalogenase gene", *Appl Environ Microbiol*, (Jul. 2002),3582-7.

Campbell, R. E., et al., "A Monomeric Red Fluorescent Protein" *PNAS*, 99(12), (2002),7877-7882.

Castro, C. E., et al., "Biodehalogenation, Reductive Reactivities of Microbial and Mammalian Cytochromes P-450 Compared with Heme and Whole-cell Models", *Journal of Agricultural & Food Chemistry*, 36, (1988),915-919.

Chaloupova, R, "Modification of activity and specificity of haloalkane dehalogenase from *Sphingomonas paucimobilis* UT26 by engineering of its entrance tunnel", *J Biol Chem.*, (Dec. 26, 2003),52622-8.

Chen, C. H., et al., "Relocation of the Catalytic Carboxylate Group in Class A Beta-lactamase: The Structure and Function of the Mutant Enzyme Glu166-Gln: Asn170", *Protein Engineering*, Oxford University Press, Surrey GB, 12(7), (Jul. 1999),573-579.

Chen, C., et al., "Relocation of the catalytic carboxylate group in class A beta-lactamase: the structure and function of the mutant enzyme Glu166→Gln:Asn170→Asp", *Protein Engineering*, 12(7), (Jul. 1999),573-579.

Chen, I., et al., "Site-specific labeling of proteins with small molecules in live cells", *Current Opinion in Biotechnology*, 16, (2005),35-40.

Cheuk, K. L., "Synthesis of Optically Active Poly(Phenylacetylenes) Containing Amino Acid Pendent Groups", *Polymeric Materials Science and Engineering*, 82, (2000),56-57.

Cohen, V. I., et al., "Synthesis of Some Substituted Dibenzodiazenpinones and Pyridobenzodiazepinones", *Journal of Heterocyclic Chemistry*, 35, (1998),675-686.

Cohen, Victor, et al., "Synthesis of some Substituted Dibenzodiazepinones and Pyridobenzodiazepinones", *Journal of Heterocyclic Chemistry*, 35, (1998),675-686.

Dahl, K. H., et al., "The Reactivity of Affinity Labels: A Kinetic Study of the Reaction of Alkyl Halides with Thiolate Anions—a Model Reaction for Protein Alkylation", *Bioorganic Chemistry*,10, (1981),329-341.

Dorwald, F. A., "Side Reactions in Organic Synthesis", *A Guide of Successful Synthesis Design*, Wiley: VCH, Weinhiem,(2005),4 pgs.

Doubrovin, M., et al., "Reviews—Multimodality in Vivo Molecular-Genetic Imaging", *Bioconiugate Chem.*, 15, (2004),1376-1388.

Farinas, J., "Receptor-mediated Targeting of Fluorescent Probes in Living Cells", *The Journal of Biological Chemistry*, 274(12), (1999),7603-7606.

Franken, S., et al., "Crystal structure of haloalkane dehalogenase: an enzyme to detoxify halogenated alkanes", *EMBO J.*, 10(6), (Jun. 1991),pp. 1297-1302.

Gambhir, S. S., "Molecular Imaging of Cancer With Positron Emission Tomography", *Nature Reviews*, 2, (2002),683-693.

Gibbons, F. D., et al., "Chipper: Discovering Transcription-Factor Targets From Chromatin Immunoprecipitation Microarrays Using Variance Stabilization", *Genome Biology*, 6(11): Article R96, (2005),9 pgs.

Gite, S., et al., "Ultrasensistive Fluorescence-Based Detection of Nascent Proteins in Gels", *Analytical Biochemistry*, 279, (2000),218-225.

Gould, K. L., et al., "Tandem Affinity Purification and Identification of Protein Complex Components", *Methods*, 33, (2004),239-244.

Gray, K, et al., "Rapid evolution of reversible denaturation and elevated melting temperature in a microbial haloalkane dehalogenase", *Adv. Synth. Catal.*, (2001),607-17.

Griffin, B. A., et al., "Specific covalent labeling of recombinant protein molecules inside live cells", *Science*, 281(5374), (Jul. 1998),269-72.

Gurskaya, N. G., et al., "GFP-like Chromoproteins as a Source of Far-red Fluorescent Proteins", *FEBS Letters*, 507 (2001),16-20.

Hall, D. A., et al., "Regulation of Gene Expression by a Metabolic Enzyme", *Science*, 306, (2004),482-484.

Heck, R. F., "Aromatic Haloethylation with Palladium and copper Halides", *Journal of the American Chemical Society*, 90, (1968),5538-5542.

Hodneland, C. D., et al., "Selective Immobilization of Proteins to Self-Assembled Monolayers Presenting Active Site-Directed Capture Ligands", *Proc. Natl. Acad. Sci. USA*, 99(8), (Apr. 16, 2002),5048-5052.

Hodneland, C. D., et al., "Selective immobilization of proteins to self-assembled monolayers presenting active site-directed capture ligands", *Proceedings of the National Academy of Science*,99(8), (Apr. 16, 2002),5048-5052.

Holloway, P., et al., "A Colorimetric Assay for Detecting Haloalkine Dehalogenase Activity", *Journal of Microbiological Materials*, 32, (1998),31-36.

Horton, R. H., et al., "Reactions with Reactive Alkyl Halidies", *Methods in Enzymology*, 11, (1967),556-565.

Huber, W. , et al., "SPR-based Interaction Studies With Small Molecular Weight Ligands Using hAGT Fusion Proteins", *Analytical Biochemistry*, 333, (2004),280-288.

Hynkova, K. , et al., "Identification of the Catalytic Triad in the Haloalkane Dehalogenase from *Sphingomonas paucimobilis* UT26", *FEBS Letters*, 446 (1), (Mar. 5, 1999),177-181.

Ichiyama, S. , et al., "Novel Catalytic Mechanism of Nucleophilic Substitution by Asparagine Residue Involving Cyanoalanine Intermediate Revealed by Mass Spectrometric Monitoring of an Enzyme Reaction", *Journal of Biological Chemistry*, 275 (52), (Dec. 29, 2000),40804-40809.

Jones, T. C., et al., "Solvolysis Mechanisms, SNl-Like Behavior of Methyl Chloromethyl Ether, Sensitivity to Solvent Ionizing Power and alpha-Deuterium Isotope Effect", *Journal of the American Chemical Society*,89, (1967),4863-4867.

Keppler, A. , et al., "A general method for the covalent labeling of fusion proteins with small molecules in vivo", *Nature Biotechnology*, 21(1), (Jan. 20, 2003),86-89.

Keppler, "A general method for the covalent labeling of fusion proteins with small molecules in vivo", *Nat Biotechnol.*, 21(1), (Jan. 2003),pp. 86-89.

Krooshof, G. , et al., "Repositioning the catalytic triad aspartic acid of haloalkane dehalogenase: effects on stability, kinetics, and structure", *Biochemistry*, 36(31), (Aug. 1997),9571-80.

Kulakova, A. , at al., "The Plasmid-Located Haloalkane Dehalogenase Gene from *Rhodococcus rhodochrous* NCIMB 13064", *Microbiology*, 143, (Jan. 1997),109-115.

Kurihara, T. , et al., "Comprehensive Site-directed Mutagenesis of L-2-Halo Acid Dehalogenase to Probe Catalytic Amino Acid Residues", *Journal of Biochemistry*, 117(6), (Mar. 15, 1995),1317-1322.

Kwon, Y. , "Antibody Arrays Prepared by Cutinase-Mediated Immobilization on Self-Assembled Monolayers", *Anal. Chem.*, 76, (2004),5713-5720.

Kwon, Y , et al., "Antibody Arrays Prepared by Cutinase-Mediated Immobilization on Self-Assembled Monolayers", *Analytical Chemistry*,76(19), (Oct. 1, 2004),5713-5720.

Lautens, M. , et al., "An Expedient Route for the Stereoselective Construction of Bridged Polyheterocyclic Ring Systems Using the Tandem "Pincer" Diels-Alder Reaction", *J. Org. Chem.*, 62, (1997),4418-4427.

Lautens, M. , et at, "An Expedient Route to the Stereoselective Construction of Polycyclic Ring Systems Using the Tandem "Pincer" Diels-Alder Reaction", *Journal of Organic Chemistry*, 62, (1997),4418-4427.

Li, Q. , et al., "A Modified Mammalian Tandem Affinity Purification Procedure to Prepare Functional Polycystin-2 Channel", *FEBS Letters*, 576, (2004),231-236.

Lin, Z. , et al., "Methods for Labeling Quantum Dots to Biomolecules", *Journal of Nanoscience and Nanotechnology*, 4(6), (2004),641-645.

Los, G. V., et al., "Chapter 14—The Halo Tagtm—A Novel Technology for Cell Imaging and Protein Analysis", *Methods in Molecular Biology*,356, (2007),195-208.

Luo, X.-L. , et al., "A Glucose Biosensor Based on Chitsosan-Glucose Oxidase-Gold Nanoparticles Biocomposite Formed by One-Step Electrodeposition", *Analytical Biochemistry*, 334, (2004),284-289.

Manoury, P. M., et al., "Synthesis of a Series of Compounds Related to Betaxolol, a New B1-Adrenoceptor Antagonist with a Pharmacological and Pharmacokinetic Profile Optimized for the Treatment of Chronic Cardiovascular Diseases", *J. Med. Chem.*, 30(6), (1987),1003-1011.

Manoury, P. , et al., "Synthesis of a series of compounds related to betaxolol, a new beta 1-adrenoceptor antagonist with a pharmacological and pharmacokinetic profile optimized for the treatment of chronic cardiovascular diseases.", *J Med Chem.*, 30(6), (1987),1003-1011.

Mathieu, S. , et al., "Monitoring E-Selection-Mediated Adhesion Using Green and Red Fluorescent Proteins", *Journal of Immunological Methods*, 272, (2003),81-92.

Michl, J., et al., *Electronic Aspects of Organic Photochemistry*, (John Wiley & Sons, 1990),61-78.

Miller, L. W., et al., "Selective Chemical Labeling of proteins in Living Cells", *Current opinion in chemical Biology*, 9, (2005),56-61.

Momose, Y. , et al., "Novel 5-Substituted-1H-Tetrazole Derivatives as Potent Glucose and Lipid Lowering Agents", *Chemical and Pharmaceutical Bulletin*, 50(1), (Jan. 2002),100-111.

Morzycki, J. W., et al., "Synthesis of Dimeric Steroids as Components of Lipid Membranes", *Tetrahedron*, 53(30), (1997),10579-10590.

Newman, J. , et al., "Haloalkane Dehalogenases: Structure of a *Rhodococcus* Enzyme", *Biochemistry, American Chemical Society*, 38, (1999),16105-16114.

Newman, J. , et al., "Haloalkane Dehalogenases: Structure of a *Rhodococcus* Enzyme", *Biochemistry*, 38(49), (1999),16105-16114.

Pieters, R. , et al., "Design and synthesis of reagents for phage display screening of dehalogenases", *Bioorganic & Medicinal Chemistry Letters*, 9(2), (Jan. 1999),pp. 161-166.

Pries, F. , et al., "Activation of an Asp-124-> Asn Mutant of Haloalkane Dehalogenase by Hydrolytic Deamidation of Asparagine", *FEBS Letters*, 358 (2), (1995),171-174.

Pries, F. , et al., "Histidine 289 is essential for hydrolysis of the alkyl-enzyme intermediate of haloalkane dehalogenase" *Journal of Biological Chemistry*, 270(18), (May 1995),10405-10411.

Pries, F. , et al., "Histidine 289 is Essential for Hydrolysis of the Alkyl-enzyme Intermediate of Haloalkane Dehalogenase", *Journal of Biological Chemistry, American Society of BioChem. Biologists, BHM, US*; 270(18), (Feb. 21, 1995),pp. 10405-10411.

Pulig, O. , et al., "The Tandem Affinity Purification (TAP) Method: A General Procedure of Protein Complex Purification", *Methods*, 24, (2001),218-229.

Rohila, J. S., et al., "Improved Tandem Affinity Purification Tag and Methods for Isolation of Protein Heterocomplexes from Plants" *The Plant Journal*, 38, (2004),172-181.

Santra, S. , et al., "Luminescent Nanoparticle Probes for Bioimaging", *Journal of Nanoscience and Nanotechnology*, 4(6), (2004),590-599.

Scholten, J. D., et al., "Novel Enzymatic hydrolytic degalogenation of a chlorinated aromatic", *Science*,253, (1991),182-185.

Stroffekova, K. , et al., "The protein-labeling reagent FLASH-EDT2 binds not only to CCXXCC motifs but also non-specifically to endogenous cysteine-rich proteins", *Pflugers Arch.*, 442(6), (Sep. 2001),859-66.

Stryer, Lubert , "Biochemistry", *Third Edition*, (1988),757-758.

Tou, J. C., et al., "Kinetic Study of the Stabilities of Chloromethyl Methyl Ether and Bis(Chloromethyl) Ether in Humid Air", *Analytical Chemistry*, 46, (1974),1866-1869.

Vincze, L. , et al., "Three-Dimensional Trace Element Analysis by Confocal X-Ray Microfluorescence Imaging", *Analytical Chemistry*, 76, 2004 ,6786-6791.

Wada, K. , et al., "Codon usage tabulated from the GenBank genetic sequence data", *Nucleic Acids Res.*, (May 1992),pp. 2111-2118.

Wang, H.-Z. , et al., "Detection of Tumor Marker CA125 in Ovarian Carcinoma Using Quantum Dots", *Acta Biochimica et Biophysica Sinica 2004*, 36(10), (2004),681-686.

Weissleder, R. , et al., "Shedding Light Onto Live Molecular Targets", *Nature Medicine*, 9(1), (2003),123-128.

Wheeler, J. B., et al., "Conjugation of Haloalkanes by Bacterial and Mammalian Glutathione Transferases: Mono- and Vicinal Dihaloethanes", *Chemical Research in Toxicology*, 14, (2001),1107-1117.

Winberg, J. , "The catalytic triad in short-chain dehydrogenases", *Dept. of Biochemistry, Institute of Medical Biology*, University of Tromso, Abstract,(Nov. 2002),2 pgs.

Wolfgang, M. J., et al., "Nonhuman primate transgenesis: progress and prospects", *Trends in Biotechnology*, 20 (11), (Nov. 2002),479-484.

Yang, G. , et al., "Identification of Active Site Residues Essential to 4-Chlorobenzoyl-Coenzyme A Dehalogenase Catalysis by Chemical Modification and Site Directed Mutagenesis", *Biochemistry*, 35, (1996),10879-10885.

Yang, M., et al., "Whole-Body Optical Imaging of Green Fluorescent Protein-Expressing Tumors and Metastases", *PNAS*, 97(3), (2000),1206-1211.

Yokota, T., et al., "Purification and Properties of Haloalkane Dehalogenase from *Corynebacterium* sp. strain m15-3", *Journal of Bacteriology*, 169(9), (Sep. 1987),4049-4054.

Yokota, T., et al., "Purification and properties of haloalkane dehalogenase from *Corynebacterium* sp. strain m15-3", *J Bacteriol.*, 169(9), 1987 ,4049-54.

Zawadzke, L., "Elimination of the hydrolytic water molecule in a class A beta-lactamase mutant: crystal structure and kinetics", *Biochemistry*, (Dec. 1996),pp. 16475-16482.

Australian Patent Office First Examiner Report mailed Jan. 6, 2009 for Appl. 2004211584 (3 pages).

Response filed Sep. 9, 2009 to First Examiner Report mailed Jan. 6, 2009 for Appl. 2004211584 (28 pages).

Chinese Patent Office Second Office Action mailed May 22, 2009 for Appl 200480008194.4 (15 pages).

Response filed to Second Office Action mailed May 22, 2009 for Appl 200480008194.4 (14 pages) (2009).

European Patent Office Communication mailed Jun. 22, 2009 for Appl. 04707032.1 (6 pages).

European Patent Office Communication mailed May 7, 2009 for Appl. 05857556.4 (3 pages).

European Patent Office Action mailed Dec. 17, 2008 for Appl. 07763411.1 (2 pages).

European Patent Office Action mailed Mar. 17, 2009 for Appl. 07763411.1 (5 pages).

Indian Patent Office First Examination Report dated Sep. 28, 2007 for Appl. 3867/DELNP/2005 (19 pages).

Response filed Mar. 19, 2008 to First Examination Report dated Sep. 28, 2007 for Appl. 3867/DELNP/2005 (21 pages).

Response filed Sep. 23, 2008 to Examination Report dated Sep. 9, 2008 for Appl. 3867/DELNP/2005 (5 pages).

Cheuk et al., "Synthesis of optically active poly (phenylacetylenes) containing amino acid pendant groups," Polymeric materials science and engineering, 2000, 82:56-57.

Henze et al., "The number of structurally isomeric alcohols of the methanol series," Journal of the American Chemical Society, 1931, 53:3042-3046.

Result 1, alignment of Applicants' dehalogenase sequence (instant SEQ ID No. 82 having C and G substituted at positions 106 and 176, respectively) with SEQ ID No. 40 of Short et al., US 7,078,504, search of issued patents database, May 19, 2010 (2 pages).

International Search Report and Written Opinion for Application No. PCT/US2007/023205 dated Nov. 3, 2008 (12 pages).

* cited by examiner

```
                                                                      60
             .         .         .         .         .         .
DhaA         MSEIGTGFPFDPHYVEVLGERMHYVDVGPRDGTPVLFLHGNPTSSYLWRNIIPHVAPSHR
DhaA.H272F   ------------------------------------------------------------
DhaA.D106C   ------------------------------------------------------------

120
             .         .         .         .         .         .
DhaA         CIAPDLIGMGKSDKPDLDYFFDDHVRYLDAFIEALGLEEVVLVIHDWGSALGFHWAKRNP
DhaA.H272F   ------------------------------------------------------------
DhaA.D106C   ---------------------------------------------C--------------

180
             .         .         .         .         .         .
DhaA         ERVKGIACMEFIRPIPTWDEWPEFARETFQAFRTADVGRELIIDQNAFIEGALPKCVVRP
DhaA.H272F   ------------------------------------------------------------
DhaA.D106C   ------------------------------------------------------------

240
             .         .         .         .         .         .
DhaA         LTEVEMDHYREPFLKPVDREPLWRFPNELPIAGEPANIVALVEAYMNWLHQSPVPKLLFW
DhaA.H272F   ------------------------------------------------------------
DhaA.D106C   ------------------------------------------------------------

290
             .         .         .         .         .
DhaA         GTPGVLIPPAEAARLAESLPNCKTVDIGPGLHYLQEDNPDLIGSEIARWLPAL
DhaA.H272F   -------------------------------F---------------------
DhaA.D106C   -----------------------------------------------------
```

*FIG. 2B*

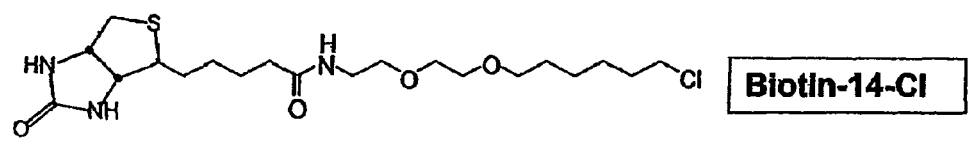
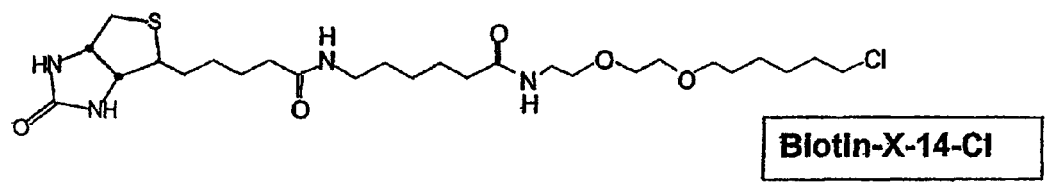
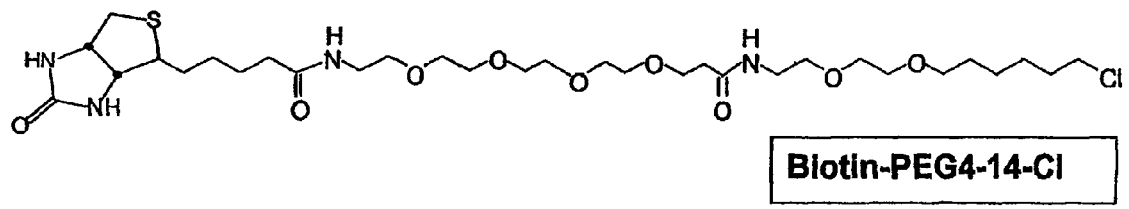
FIG. 7B

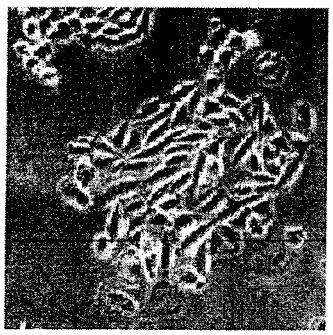  
FIG. 16A　　FIG. 16B　　FIG. 16C
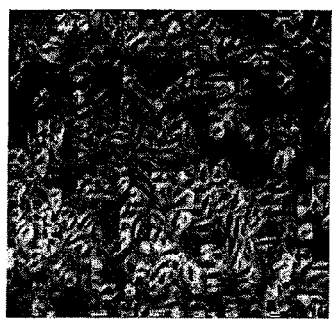 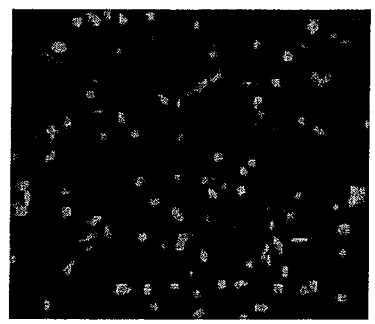 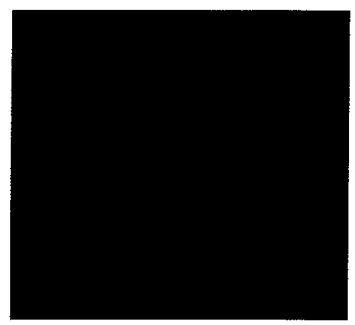
FIG. 17A　　FIG. 17B　　FIG. 17C
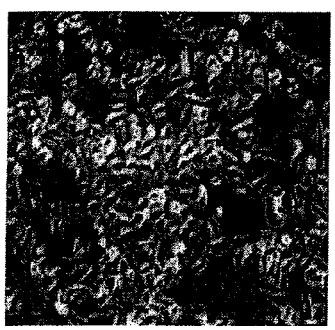  
FIG. 17D　　FIG. 17E　　FIG. 17F 1 2 3 4 5 6 7 8

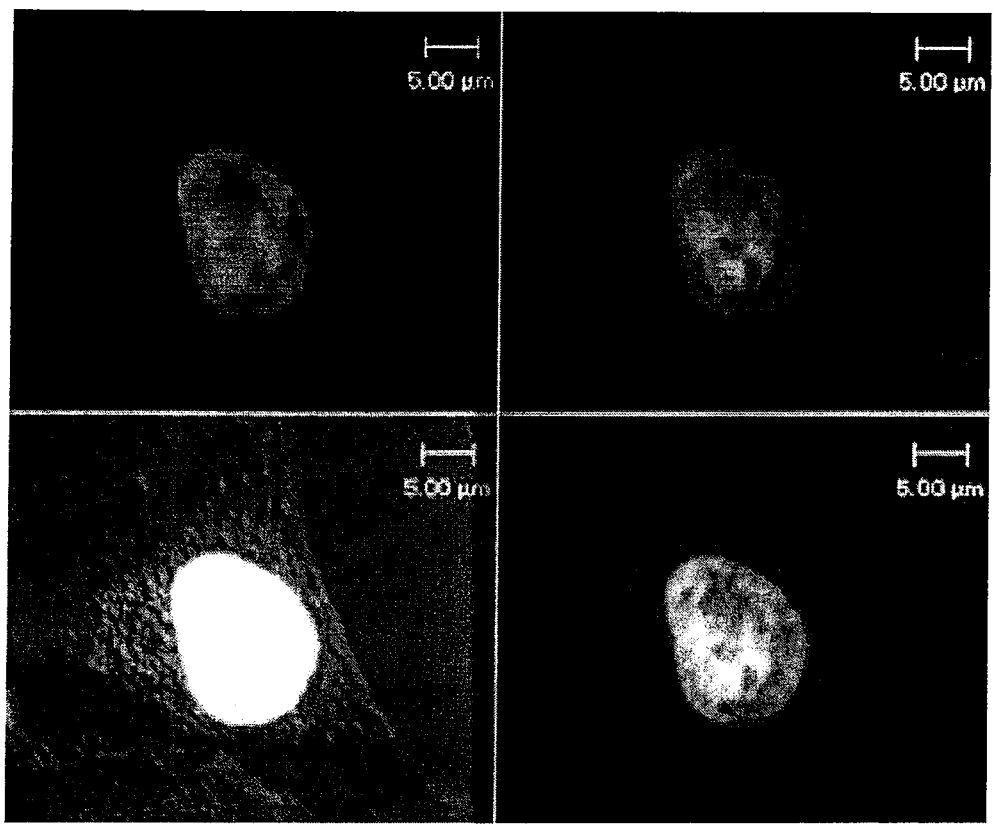
*FIG. 24*
 
*FIG. 25A*  *FIG. 25B*

| Clone | Codon 175 | Codon 176 | Codon 273 |
|---|---|---|---|
| H272F | AAA (Lys) | TGC (Cys) | TAC (Tyr) |
| D11 | --- --- | TCG (Ser) | --- --- |
| H5b | --- --- | AGT (Ser) | --- --- |
| F11B | --- --- | TCT (Ser) | --- --- |
| G4B | --- --- | AAT (Asn) | --- --- |
| A7 | --- --- | GGT (Gly) | --- --- |
| G9C | --- --- | GAT (Asp) | --- --- |
| E7C | --- --- | ACG (Thr) | --- --- |
| 3A7 | --- --- | GCT (Ala) | --- --- |
| C176R | --- --- | AGG (Arg) | --- --- |
| 2A4 | ATG (Met) | AAT (Asn) | --- --- |
| VN | GTG (Val) | AAT (Asn) | --- --- |
| ES | GAG (Glu) | TCG (Ser) | --- --- |
| 1C6 | GCG (Ala) | AGT (Ser) | --- --- |
| 2G7 | GCT (Ala) | AGT (Ser) | --- --- |
| H11 | ATG (Met) | GGG (Gly) | --- --- |
| 1G6 | TGT (Cys) | GGT (Gly) | --- --- |
| 1G5 | CTT (Leu) | GGT (Gly) | --- --- |
| 1H4 | TCT (Ser) | GGG (Gly) | --- --- |
| K175M | ATG (Met) | --- --- | --- --- |
| YL | --- --- | --- --- | TTG (Leu) |
| YM | --- --- | --- --- | ATG (Met) |
| YC | --- --- | --- --- | TGT (Cys) |

*FIG. 35A*

| Clone | Codon 175 | Codon 176 |
|---|---|---|
| D106C | AAA (Lys) | TGC (Cys) |
| E2 | --- --- | GGC (Gly) |
| D9 | AGT (Ser) | GGT (Gly) |
| 15-F3 | TGT (Cys) | GGT (Gly) |
| 2-B9 | TGT (Cys) | GGG (Gly) |
| 11-E8 | TTG (Leu) | GGT (Gly) |
| 9-C11 | AGT (Ser) | GGG (Gly) |
| D5 | GAG (Glu) | GGT (Gly) |
| 30H4 | ATG (Met) | GGG (Gly) |
| 7A6 | CCG (Pro) | GGT (Gly) |
| 35- | CCT (Pro) | GGG (Gly) |
| 21-F3 | GCG (Ala) | GGT (Gly) |
| 9-H8 | AAT (Asn) | GGG (Gly) |
| 9-F5 | CAG (Gln) | GGT (Gly) |
| 15-B5 | GTT (Val) | GGG (Gly) |
| 27D10 | ATT (Ile) | GCG (Ala) |
| 4-F2 | AGT (Ser) | GCG (Ala) |
| 33- | TCG (Ser) | GCT (Ala) |
| 2-D7 | GCG (Ala) | GCT (Ala) |
| 14-F1 | GTT (Val) | GCT (Ala) |
| 17-G9 | ATG (Met) | CAG (Gln) |

*FIG. 35B*

| Clone | Rate constant ($M^{-1} sec^{-1}$) | |
| --- | --- | --- |
| | carboxytetramethylrhodamine-$C_{10}H_{21}NO_2$-Cl | carboxyfluorescein-$C_{10}H_{21}NO_2$-Cl |
| Parental | | |
| H272F | $6.7 \times 10^1$ | 2.7 |
| 1st generation | | |
| H272F.3A7 | $1.1 \times 10^3$ | $6.7 \times 10^2$ |
| H272F.H11 | $1.6 \times 10^3$ | $3.4 \times 10^2$ |
| H272F.1G5 | $1.8 \times 10^3$ | $5.4 \times 10^2$ |
| H272F.A7 | $2.0 \times 10^3$ | $5.4 \times 10^2$ |
| H272F.1G6 | $2.2 \times 10^3$ | $6.1 \times 10^2$ |
| H272F.2G7 | $2.6 \times 10^3$ | $2.7 \times 10^2$ |
| H272F.Y273C | $6.9 \times 10^4$ | $1.5 \times 10^3$ |
| H272F.Y273L | $7.2 \times 10^4$ | $9.6 \times 10^3$ |
| H272F.Y273M | $9.0 \times 10^4$ | $5.9 \times 10^3$ |
| 2nd generation | | |
| H272F.H11YL | $2.2 \times 10^6$ | $2.2 \times 10^4$ |
| H272F.H11YM | $7.9 \times 10^5$ | $6.7 \times 10^3$ |
| H272F.A7YM | $4.0 \times 10^5$ | $2.0 \times 10^4$ |
| H272F.A7YL | $3.3 \times 10^4$ | $5.2 \times 10^3$ |
| Parental | | |
| D106C | $2.7 \times 10^1$ | 0.7 |
| 1st generation | | |
| D106C.E2 | $2.0 \times 10^2$ | ND* |
| D106C.11-E8 | $2.0 \times 10^2$ | ND* |
| D106C.4-F2 | $2.7 \times 10^2$ | ND* |
| D106C.D9 | $4.7 \times 10^2$ | ND* |

ND*, not determined

FIG. 40

DhaA.H272F

DhaA.H272F.H11YL

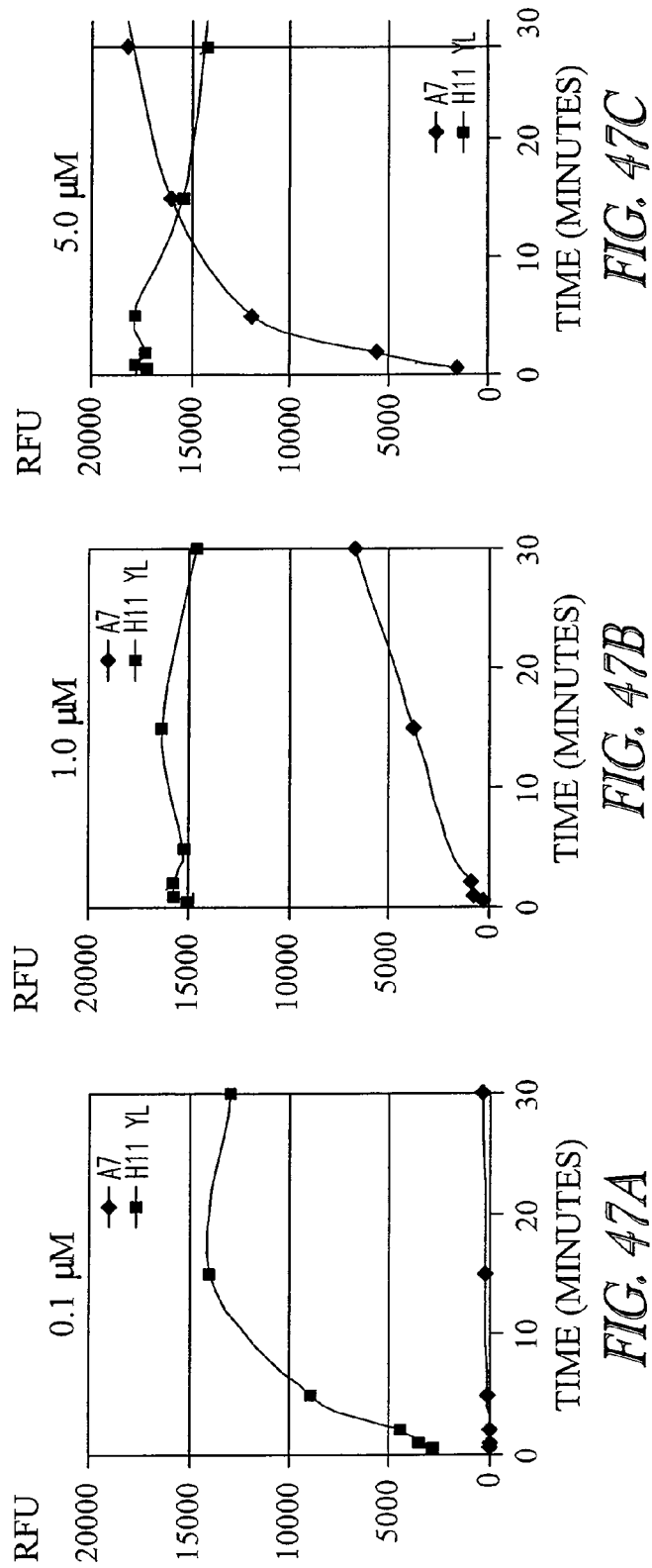

```
                    PvuII              NcoI
                   ~~~~~~~            ~~~~~~~
         NheI             EcoRV            BamHI
        ~~~~~~           ~~~~~~           ~~~~~~
                                       MetGlySerGlu IleGlyThr·
                                      ~~~~~~~~~~~~~~~~~~~~~~~~
1051 GCTAGCCAG CTGGCGCGGA TATCGCCACC ATGGGATCCG AAATCGGTAC
     CGATCGGTC GACCGCGCCT ATAGCGGTGG TACCCTAGGC TTTAGCCATG

·GlyPhePro PheAspProHis TyrValGlu ValLeuGly GluArgMetHis·
     ~~~~~~~~~~~~~~~~~~~~~~~~~~~~~~~~~~~~~~~~~~~~~~~~~~~~~~~~~
1101 AGGCTTCCCC TTCGACCCCC ATTATGTGGA AGTCCTGGGC GAGCGTATGC
     TCCGAAGGGG AAGCTGGGGG TAATACACCT TCAGGACCCG CTCGCATACG

·HTyrValAsp ValGlyPro ArgAspGlyThr ProValLeu PheLeuHis
     ~~~~~~~~~~~~~~~~~~~~~~~~~~~~~~~~~~~~~~~~~~~~~~~~~~~~~
1151 ACTACGTCGA TGTTGGACCG CGGGATGGCA CGCCTGTGCT GTTCCTGCAC
     TGATGCAGCT ACAACCTGGC GCCCTACCGT GCGGACACGA CAAGGACGTG

GlyAsnProThr SerSerTyr LeuTrpArg AsnIleIlePro HisValAla·
     ~~~~~~~~~~~~~~~~~~~~~~~~~~~~~~~~~~~~~~~~~~~~~~~~~~~~~~~
1201 GGTAACCCGA CCTCGTCCTA CCTGTGGCGC AACATCATCC CGCATGTAGC
     CCATTGGGCT GGAGCAGGAT GGACACCGCG TTGTAGTAGG GCGTACATCG

·ProSerHis ArgCysIleAla ProAspLeu IleGlyMet GlyLysSerAsp·
     ~~~~~~~~~~~~~~~~~~~~~~~~~~~~~~~~~~~~~~~~~~~~~~~~~~~~~~~~~
1251 ACCGAGTCAT CGGTGCATTG CTCCAGACCT GATCGGGATG GGAAAATCGG
     TGGCTCAGTA GCCACGTAAC GAGGTCTGGA CTAGCCCTAC CCTTTTAGCC

·ALysProAsp LeuAspTyr PhePheAspAsp HisValArg TyrLeuAsp
     ~~~~~~~~~~~~~~~~~~~~~~~~~~~~~~~~~~~~~~~~~~~~~~~~~~~~~~
1301 ACAAACCAGA CCTCGATTAT TTCTTCGACG ACCACGTCCG CTACCTCGAT
     TGTTTGGTCT GGAGCTAATA AAGAAGCTGC TGGTGCAGGC GATGGAGCTA

AlaPheIleGlu AlaLeuGly LeuGluGlu ValValLeuVal IleHisAsp·
     ~~~~~~~~~~~~~~~~~~~~~~~~~~~~~~~~~~~~~~~~~~~~~~~~~~~~~~~
1351 GCCTTCATCG AAGCCTTGGG TTTGGAAGAG GTCGTCCTGG TCATCCACGA
     CGGAAGTAGC TTCGGAACCC AAACCTTCTC CAGCAGGACC AGTAGGTGCT

·TrpGlySer AlaLeuGlyPhe HisTrpAla LysArgAsn ProGluArgVal·
     ~~~~~~~~~~~~~~~~~~~~~~~~~~~~~~~~~~~~~~~~~~~~~~~~~~~~~~~~~
1401 CTGGGGCTCA GCTCTCGGAT TCCACTGGGC CAAGCGCAAT CCGGAACGGG
     GACCCCGAGT CGAGAGCCTA AGGTGACCCG GTTCGCGTTA GGCCTTGCCC
```

*FIG. 49A*

```
            ·VLysGlyIle AlaCysMet GluPheIleArg ProIlePro ThrTrpAsp
            ~~~~~~~~~~~~~~~~~~~~~~~~~~~~~~~~~~~~~~~~~~~~~~~~~~~~~~
  1451 TCAAAGGTAT TGCATGTATG GAATTCATCC GGCCTATCCC GACGTGGGAC
       AGTTTCCATA ACGTACATAC CTTAAGTAGG CCGGATAGGG CTGCACCCTG

GluTrpProGlu PheAlaArg GluThrPhe GlnAlaPheArg ThrAlaAsp·
       ~~~~~~~~~~~~~~~~~~~~~~~~~~~~~~~~~~~~~~~~~~~~~~~~~~~~~~
  1501 GAATGGCCAG AATTCGCCCG TGAGACCTTC CAGGCCTTCC GGACCGCCGA
       CTTACCGGTC TTAAGCGGGC ACTCTGGAAG GTCCGGAAGG CCTGGCGGCT

·ValGlyArg GluLeuIleIle AspGlnAsn AlaPheIle GluGlyAlaLeu·
            ~~~~~~~~~~~~~~~~~~~~~~~~~~~~~~~~~~~~~~~~~~~~~~~~~~~~~~
  1551 CGTCGGCCGA GAGTTGATCA TCGATCAGAA CGCTTTCATC GAGGGTGCGC
       GCAGCCGGCT CTCAACTAGT AGCTAGTCTT GCGAAAGTAG CTCCCACGCG

·LProMetGly ValValArg ProLeuThrGlu ValGluMet AspHisTyr
            ~~~~~~~~~~~~~~~~~~~~~~~~~~~~~~~~~~~~~~~~~~~~~~~~~~~~~~
  1601 TCCCGATGGG GGTCGTCCGT CCGCTTACGG AGGTCGAGAT GGACCACTAT
       AGGGCTACCC CCAGCAGGCA GGCGAATGCC TCCAGCTCTA CCTGGTGATA

ArgGluProPhe LeuLysPro ValAspArg GluProLeuTrp ArgPhePro·
       ~~~~~~~~~~~~~~~~~~~~~~~~~~~~~~~~~~~~~~~~~~~~~~~~~~~~~~
  1651 CGCGAGCCCT TCCTCAAGCC TGTTGACCGA GAGCCACTGT GGCGATTCCC
       GCGCTCGGGA AGGAGTTCGG ACAACTGGCT CTCGGTGACA CCGCTAAGGG

·AsnGluLeu ProIleAlaGly GluProAla AsnIleVal AlaLeuValGlu·
            ~~~~~~~~~~~~~~~~~~~~~~~~~~~~~~~~~~~~~~~~~~~~~~~~~~~~~~
  1701 CAACGAGCTG CCCATCGCCG GTGAGCCCGC GAACATCGTC GCGCTCGTCG
       GTTGCTCGAC GGGTAGCGGC CACTCGGGCG CTTGTAGCAG CGCGAGCAGC

·GAlaTyrMet AsnTrpLeu HisGlnSerPro ValProLys LeuLeuPhe
            ~~~~~~~~~~~~~~~~~~~~~~~~~~~~~~~~~~~~~~~~~~~~~~~~~~~~~~
  1751 AGGCATACAT GAACTGGCTG CACCAGTCAC CTGTCCCGAA GTTGTTGTTC
       TCCGTATGTA CTTGACCGAC GTGGTCAGTG GACAGGGCTT CAACAACAAG

TrpGlyThrPro GlyValLeu IleProPro AlaGluAlaAla ArgLeuAla·
       ~~~~~~~~~~~~~~~~~~~~~~~~~~~~~~~~~~~~~~~~~~~~~~~~~~~~~~
  1801 TGGGGCACAC CCGGCGTACT GATCCCCCCG GCCGAAGCCG CGAGACTTGC
       ACCCCGTGTG GGCCGCATGA CTAGGGGGGC CGGCTTCGGC GCTCTGAACG

·GluSerLeu ProAsnCysLys ThrValAsp IleGlyPro GlyLeuPheLeu·
            ~~~~~~~~~~~~~~~~~~~~~~~~~~~~~~~~~~~~~~~~~~~~~~~~~~~~~~
  1851 CGAAAGCCTC CCCAACTGCA AGACAGTGGA CATCGGCCCG GGATTGTTCT
       GCTTTCGGAG GGGTTGACGT TCTGTCACCT GTAGCCGGGC CCTAACAAGA
```

*FIG. 49B*

```
                ·LLeuGlnGlu AspAsnPro AspLeuIleGly SerGluIle AlaArgTrp
                ~~~~~~~~~~~~~~~~~~~~~~~~~~~~~~~~~~~~~~~~~~~~~~~~~~~~~
       1901 TGCTCCAGGA AGACAACCCG GACCTTATCG GCAGTGAGAT CGCGCGCTGG
            ACGAGGTCCT TCTGTTGGGC CTGGAATAGC CGTCACTCTA GCGCGCGACC

NgoMIV
                       ~~~~~~
                       NaeI         PacI         NotI
                       ~~~~~~    ~~~~~~~~~    ~~~~~~~~~
            LeuProGlyLeu AlaGly** *
            ~~~~~~~~~~~~~~~~~~~~~~
       1951 CTCCCCGGGC TGGCCGGCTA ATAGTTAATT AAGTAGGCGG CCGC
            GAGGGGCCCG ACCGGCCGAT TATCAATTAA TTCATCCGCC GGCG
```

*FIG. 49C*

NO CASPASE OR PROTEASE EXPRESSION IN CELLS
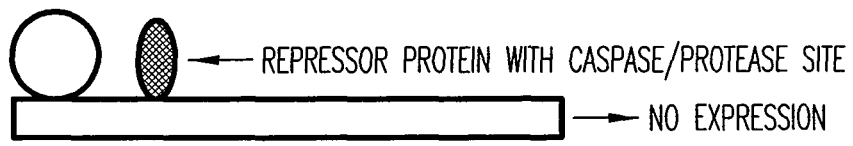
IN PRESENCE OF CASPASE OR PROTEASE EXPRESSION IN CELLS
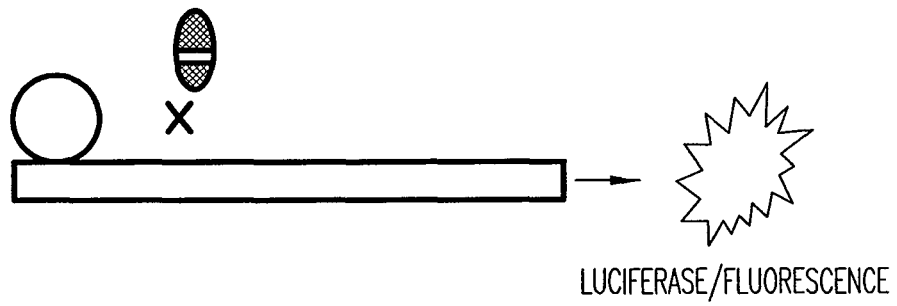
*FIG. 60A*

SEQUENCE LISTING

<160> NUMBER OF SEQ ID NOS: 85

<210> SEQ ID NO 1
<211> LENGTH: 31
<212> TYPE: DNA
<213> ORGANISM: Artificial Sequence
<220> FEATURE:
<223> OTHER INFORMATION: Synthetic

<400> SEQUENCE: 1
gcttcacttg tcgtcatcgt ccttgtagtc a                                       31

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
gcttcacttg tcgtcatcgt ccttgtagtc a                                       31

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
ccgggattgt tctacctcca ggaagac                                            27

<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
ccgggattgg cctacctcca ggaagac                                            27

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
ccgggattgc agtacctcca ggaagac                                            27

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
ccgggattgg gctacctcca ggaagac                                            27

<210> SEQ ID NO 7
<211> LENGTH: 37
<212> TYPE: DNA

```
<213> ORGANISM: Artificial Sequence
<220> FEATURE:
<223> OTHER INFORMATION: Synthetic

<400> SEQUENCE: 7
acgcgtcgac gccgccatgt cagaaatcgg tacaggc                        37

<210> SEQ ID NO 8
<211> LENGTH: 55
<212> TYPE: DNA
<213> ORGANISM: Artificial Sequence
<220> FEATURE:
<223> OTHER INFORMATION: Synthetic

<400> SEQUENCE: 8
ataagaatgc ggccgctcaa gcgcttcaac cggtgagtgc ggggagccag cgcgc    55

<210> SEQ ID NO 9
<211> LENGTH: 35
<212> TYPE: DNA
<213> ORGANISM: Artificial Sequence
<220> FEATURE:
<223> OTHER INFORMATION: Synthetic

<400> SEQUENCE: 9
ccggtgacta caaggacgat gacgacaagt gaagc                          35

<210> SEQ ID NO 10
<211> LENGTH: 31
<212> TYPE: DNA
<213> ORGANISM: Artificial Sequence
<220> FEATURE:
<223> OTHER INFORMATION: Synthetic

<400> SEQUENCE: 10
gcttcacttg tcgtcatcgt ccttgtagtc a                              31

<210> SEQ ID NO 11
<211> LENGTH: 31
<212> TYPE: DNA
<213> ORGANISM: Artificial Sequence
<220> FEATURE:
<223> OTHER INFORMATION: Synthetic

<400> SEQUENCE: 11
gcttcacttg tcgtcatcgt ccttgtagtc a                              31

<210> SEQ ID NO 12
<211> LENGTH: 31
<212> TYPE: DNA
<213> ORGANISM: Artificial Sequence
<220> FEATURE:
<223> OTHER INFORMATION: Synthetic

<400> SEQUENCE: 12
gcttcacttg tcgtcatcgt ccttgtagtc a                              31

<210> SEQ ID NO 13
<211> LENGTH: 43
<212> TYPE: DNA
<213> ORGANISM: Artificial Sequence
<220> FEATURE:
<223> OTHER INFORMATION: Synthetic

<400> SEQUENCE: 13
cttgggtttg gaagaggtcg tcctggtcat ccactgctgg ggc                 43
```

<210> SEQ ID NO 14
<211> LENGTH: 42
<212> TYPE: DNA
<213> ORGANISM: Artificial Sequence
<220> FEATURE:
<223> OTHER INFORMATION: Synthetic

<400> SEQUENCE: 14
tgagccccag cagtggatga ccaggacgac ctcttccaaa cc       42

<210> SEQ ID NO 15
<211> LENGTH: 29
<212> TYPE: DNA
<213> ORGANISM: Artificial Sequence
<220> FEATURE:
<223> OTHER INFORMATION: Synthetic

<400> SEQUENCE: 15
ggaatgggcc ctctagagcg acgatgtca                      29

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
cagtcagtca cgatggatcc gctc                           24

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Asp Glu Val Asp
1

<210> SEQ ID NO 18
<211> LENGTH: 37
<212> TYPE: PRT
<213> ORGANISM: Artificial Sequence
<220> FEATURE:
<223> OTHER INFORMATION: Synthetic

<400> SEQUENCE: 18

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

His His His His His
1               5

```
<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

His His His His His His
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic

<400> SEQUENCE: 21

Glu Gln Lys Leu Ile Ser Glu Glu Asp Leu
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Asp Tyr Lys Asp Asp Asp Asp Lys
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Trp Ser His Pro Gln Phe Glu Lys
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Tyr Pro Tyr Asp Val Pro Asp Tyr Ala
1               5

<210> SEQ ID NO 25
<211> LENGTH: 26
<212> TYPE: PRT
<213> ORGANISM: Artificial Sequence
<220> FEATURE:
<223> OTHER INFORMATION: Synthetic

<400> SEQUENCE: 25

Met Gly Ile Gln Gly Gly Ser Val Leu Phe Gly Leu Leu Leu Val Leu
1               5                   10                  15

Ala Val Phe Cys His Ser Gly His Ser Leu
```

<210> SEQ ID NO 26
<211> LENGTH: 45
<212> TYPE: DNA
<213> ORGANISM: Artificial Sequence
<220> FEATURE:
<223> OTHER INFORMATION: Synthetic

<400> SEQUENCE: 26
atcgaaggtc gtgggatccc caggaattcc cgggtcgacg ccgcc    45

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Ile Glu Gly Arg Gly Ile Pro Arg Asn Ser Arg Val Asp Ala Ala
1               5                   10                  15

<210> SEQ ID NO 28
<211> LENGTH: 51
<212> TYPE: DNA
<213> ORGANISM: Artificial Sequence
<220> FEATURE:
<223> OTHER INFORMATION: Synthetic

<400> SEQUENCE: 28
tccggatcaa gcttgggcga cgaggtggac ggcgggccct ctagagccac c    51

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Ser Gly Ser Ser Leu Gly Asp Glu Val Asp Gly Gly Pro Ser Arg Ala
1               5                   10                  15

Thr

<210> SEQ ID NO 30
<211> LENGTH: 45
<212> TYPE: DNA
<213> ORGANISM: Artificial Sequence
<220> FEATURE:
<223> OTHER INFORMATION: Synthetic

<400> SEQUENCE: 30
accggttccg gatcaagctt gcggtaccgc gggccctcta gagcc    45

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Thr Gly Ser Gly Ser Ser Leu Arg Tyr Arg Gly Pro Ser Arg Ala
1               5                   10                  15

<210> SEQ ID NO 32
<211> LENGTH: 51
<212> TYPE: DNA
<213> ORGANISM: Artificial Sequence
<220> FEATURE:
<223> OTHER INFORMATION: Synthetic

<400> SEQUENCE: 32
tccggatcaa gcttgcggta ccgcgggccc tctagagccg tcgacgccgc c        51

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Ser Gly Ser Ser Leu Arg Tyr Arg Gly Pro Ser Arg Ala Val Asp Ala
1               5                   10                  15

Ala

<210> SEQ ID NO 34
<211> LENGTH: 43
<212> TYPE: DNA
<213> ORGANISM: Artificial Sequence
<220> FEATURE:
<223> OTHER INFORMATION: Synthetic

<400> SEQUENCE: 34
cttgggtttg aagaggtcg tcctggtcat ccaccagtgg ggc                43

<210> SEQ ID NO 35
<211> LENGTH: 42
<212> TYPE: DNA
<213> ORGANISM: Artificial Sequence
<220> FEATURE:
<223> OTHER INFORMATION: Synthetic

<400> SEQUENCE: 35
tgagccccac tggtggatga ccaggacgac ctcttccaaa cc                 42

<210> SEQ ID NO 36
<211> LENGTH: 1053
<212> TYPE: DNA
<213> ORGANISM: Staphylococcus aureus

<400> SEQUENCE: 36
agcttactat gccattatta ataacttagc catttcaaca ccttctttca aatatttata      60
ataaactatt gacaccgata ttacaattgt aatattattg atttataaaa attacaactg     120
taatatcgga gggtttattt tgaaaaagtt aatattttta attgtaattg ctttagtttt     180
aagtgcatgt aattcaaaca gttcacatgc caaagagtta aatgatttag aaaaaaata     240
taatgctcat attggtgttt atgctttaga tactaaaagt ggtaaggaag taaaatttaa     300
ttcagataag agatttgcct atgcttcaac ttcaaaagcg ataaatagtg ctattttgtt     360
agaacaagta ccttataata agttaaataa aaaagtacat attaacaaag atgatatagt     420
tgcttattct cctatttag aaaaatatgt aggaaaagat atcactttaa aagcacttat     480
tgaggcttca atgacatata gtgataatac agcaaacaat aaaattataa agaaatcgg     540
tggaatcaaa aaagtaaac aacgtctaaa agaactagga gataaagtaa caaatccagt     600
tagatatgag atagaattaa attactattc accaagagc aaaaaagata cttcaacacc     660

```
tgctgccttc ggtaagaccc ttaataaact tatcgccaat ggaaaattaa gcaaagaaaa    720
caaaaaattc ttacttgatt taatgttaaa taataaaagc ggagatactt taattaaaga    780
cggtgttcca aaagactata aggttgctga taaaagtggt caagcaataa catatgcttc    840
tagaaatgat gttgcttttg tttatcctaa gggccaatct gaacctattg ttttagtcat    900
ttttacgaat aaagacaata aaagtgataa gccaaatgat aagttgataa gtgaaaccgc    960
caagagtgta atgaaggaat tttaatattc taaatgcata ataaatactg ataacatctt   1020
atattttgta ttatattttg tattatcgtt gac                                1053

<210> SEQ ID NO 37
<211> LENGTH: 81
<212> TYPE: DNA
<213> ORGANISM: Artificial Sequence
<220> FEATURE:
<223> OTHER INFORMATION: Synthetic

<400> SEQUENCE: 37
ccggtgatcc aaaaaagaag agaaaggtag atccaaaaaa gaagagaaag gtagatccaa    60
aaaagaagag aaaggtatga g                                              81

<210> SEQ ID NO 38
<211> LENGTH: 81
<212> TYPE: DNA
<213> ORGANISM: Artificial Sequence
<220> FEATURE:
<223> OTHER INFORMATION: Synthetic

<400> SEQUENCE: 38
gatcctcata cctttctctt cttttttgga tctacctttc tcttcttttt tggatctacc    60
tttctcttct tttttggatc a                                              81

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
attatgctga gtgatatccc                                                20

<210> SEQ ID NO 40
<211> LENGTH: 25
<212> TYPE: DNA
<213> ORGANISM: Artificial Sequence
<220> FEATURE:
<223> OTHER INFORMATION: Synthetic

<400> SEQUENCE: 40
ctcggtacca agctccttgt agtca                                          25

<210> SEQ ID NO 41
<211> LENGTH: 40
<212> TYPE: DNA
<213> ORGANISM: Artificial Sequence
<220> FEATURE:
<223> OTHER INFORMATION: Synthetic

<400> SEQUENCE: 41
caaaggtatt gcatgtatgc agttcatccg gcctatcccg                          40

<210> SEQ ID NO 42
```

```
<210> SEQ ID NO 42
<211> LENGTH: 44
<212> TYPE: DNA
<213> ORGANISM: Artificial Sequence
<220> FEATURE:
<223> OTHER INFORMATION: Synthetic

<400> SEQUENCE: 42
gtcaaaggta ttgcatgtat gctgttcatc cggcctatcc cgac        44

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
aggtattgca tgtatggcgt tcatccggcc tatccc              36

<210> SEQ ID NO 44
<211> LENGTH: 36
<212> TYPE: PRT
<213> ORGANISM: Artificial Sequence
<220> FEATURE:
<223> OTHER INFORMATION: Synthetic

<400> SEQUENCE: 44

Phe Glu His Cys Asn Phe Asn Asp Val Thr Thr Arg Leu Arg Glu Asn
1               5                   10                  15

Glu Leu Thr Tyr Tyr Cys Cys Lys Lys Asp Leu Cys Asn Phe Asn Glu
            20                  25                  30

Gln Leu Glu Asn
        35

<210> SEQ ID NO 45
<211> LENGTH: 10
<212> TYPE: DNA
<213> ORGANISM: Artificial Sequence
<220> FEATURE:
<223> OTHER INFORMATION: Synthetic

<400> SEQUENCE: 45
gccaccatgg                                            10

<210> SEQ ID NO 46
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 46
nnnngctagc cagctggcga tatcgccacc atggga              36

<210> SEQ ID NO 47
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(30)
<223> OTHER INFORMATION: n is a, c, g, or t
```

<400> SEQUENCE: 47
taatagttaa ttaagtaagc ggccgcnnnn                                    30

<210> SEQ ID NO 48
<211> LENGTH: 296
<212> TYPE: PRT
<213> ORGANISM: Artificial Sequence
<220> FEATURE:
<223> OTHER INFORMATION: Synthetic

<400> SEQUENCE: 48

Met Gly Ser Glu Ile Gly Thr Gly Phe Pro Phe Asp Pro His Tyr Val
1               5                   10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala
    50                  55                  60

Pro Asp Leu Ile Gly Met Gly Lys Ser Asp Lys Pro Asp Leu Asp Tyr
65                  70                  75                  80

Phe Phe Asp Asp His Val Arg Tyr Leu Asp Ala Phe Ile Glu Ala Leu
                85                  90                  95

Gly Leu Glu Glu Val Val Leu Val Ile His Asp Trp Gly Ser Ala Leu
            100                 105                 110

Gly Phe His Trp Ala Lys Arg Asn Pro Glu Arg Val Lys Gly Ile Ala
        115                 120                 125

Cys Met Glu Phe Ile Arg Pro Ile Pro Thr Trp Asp Glu Trp Pro Glu
    130                 135                 140

Phe Ala Arg Glu Thr Phe Gln Ala Phe Arg Thr Ala Asp Val Gly Arg
145                 150                 155                 160

Glu Leu Ile Ile Asp Gln Asn Ala Phe Ile Glu Gly Ala Leu Pro Lys
                165                 170                 175

Cys Val Val Arg Pro Leu Thr Glu Val Glu Met Asp His Tyr Arg Glu
            180                 185                 190

Pro Phe Leu Lys Pro Val Asp Arg Glu Pro Leu Trp Arg Phe Pro Asn
        195                 200                 205

Glu Leu Pro Ile Ala Gly Glu Pro Ala Asn Ile Val Ala Leu Val Glu
    210                 215                 220

Ala Tyr Met Asn Trp Leu His Gln Ser Pro Val Pro Lys Leu Leu Phe
225                 230                 235                 240

Trp Gly Thr Pro Gly Val Leu Ile Pro Pro Ala Glu Ala Ala Arg Leu
                245                 250                 255

Ala Glu Ser Leu Pro Asn Cys Lys Thr Val Asp Ile Gly Pro Gly Leu
            260                 265                 270

Phe Tyr Leu Gln Glu Asp Asn Pro Asp Leu Ile Gly Ser Glu Ile Ala
        275                 280                 285

Arg Trp Leu Pro Gly Leu Ala Gly
    290                 295

<210> SEQ ID NO 49
<211> LENGTH: 948
<212> TYPE: DNA
<213> ORGANISM: Artificial Sequence
<220> FEATURE:
<223> OTHER INFORMATION: Synthetic
<220> FEATURE:

<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (945)..(948)
<223> OTHER INFORMATION: n is a, c, g, or t

<400> SEQUENCE: 49

```
nnnngctagc cagctggcga tatcgccacc atgggatccg agattgggac agggtttcct      60
tttgatcctc attatgtgga ggtgctgggg gagagaatgc attatgtgga tgtggggcct     120
agagatggga cacctgtgct gtttctgcat gggaatccta catcttctta tctgtggaga     180
aatattattc ctcatgtggc tccttctcat agatgtattg ctcctgatct gattgggatg     240
gggaagtctg ataagcctga tctggattat ttttttgatg atcatgtgag atatctggat     300
gcttttattg aggctctggg gctggaggag gtggtgctgg tgattcatga ttgggggtct     360
gctctggggt ttcattgggc taagagaaat cctgagagag tgaaggggat tgcttgtatg     420
gagtttatta gacctattcc tacatgggat gagtggcctg agtttgctag agagacattt     480
caggctttta gaacagctga tgtggggaga gagctgatta ttgatcagaa tgcttttatt     540
gagggggctc tgcctaagtg tgtggtgaga cctctgacag aggtggagat ggatcattat     600
agagagcctt ttctgaagcc tgtggataga gagcctctgt ggagatttcc taatgagctg     660
cctattgctg gggagcctgc taatattgtg gctctggtgg aggcttatat gaattggctg     720
catcagtctc ctgtgcctaa gctgctgttt tgggggacac tgggggtgct gattcctcct     780
gctgaggctg ctagactggc tgagtctctg cctaattgta agacagtgga tattgggcct     840
gggctgtttt atctgcagga ggataatcct gatctgattg gtctgagatt gctagatgg     900
ctgcccgggc tggccggcta atagttaatt aagtaagcgg ccgcnnnn                  948
```

<210> SEQ ID NO 50
<211> LENGTH: 951
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (948)..(951)
<223> OTHER INFORMATION: n is a, c, g, or t

<400> SEQUENCE: 50

```
nnnngctagc cagctggcgc ggatatcgcc accatgggat ccgagattgg gacagggttc      60
ccttttgatc ctcactatgt tgaagtgctg ggggaaagaa tgcactacgt ggatgtgggg     120
cctagagatg ggaccccagt gctgttcctc acgggaacc ctacatctag ctacctgtgg      180
agaaatatta tacctcatgt tgctcctagt cataggtgca ttgctcctga tctgatcggg     240
atggggaagt ctgataagcc tgacttagac tacttttttg atgatcatgt tcgatacttg     300
gatgctttca ttgaggctct ggggctggag gaggtggtgc tggtgataca cgactggggg     360
tctgctctgg ggtttcactg gctaaaaagg aatccggaga gagtgaaggg gattgcttgc     420
atggagttta ttcgacctat tcctacttgg gatgaatggc cagagtttgc cagagagaca     480
tttcaagcct ttagaactgc cgatgtgggc agggagctga ttatagacca gaatgctttc     540
atcgagggg ctctgcctaa atgtgtagtc agacctctca ctgaagtaga gatggaccat      600
```

-continued

```
tatagagagc cctttctgaa gcctgtggat cgcgagcctc tgtggaggtt tccaaatgag      660
ctgcctattg ctggggagcc tgctaatatt gtggctctgg tggaagccta tatgaactgg      720
ctgcatcaga gtccagtgcc caagctactc ttttggggga ctccgggagt tctgattcct      780
cctgccgagg ctgctagact ggctgaatcc ctgcccaatt gtaagaccgt ggacatcggc      840
cctgggctgt tttacctcca agaggacaac cctgatctca tcgggtctga gatcgcacgg      900
tggctgcccg ggctggccgg ctaatagtta attaagtagg cggccgcnnn n              951
```

<210> SEQ ID NO 51
<211> LENGTH: 882
<212> TYPE: DNA
<213> ORGANISM: Rhodococcus rhodochrous

<400> SEQUENCE: 51

```
atgtcagaaa tcggtacagg cttcccctcc gaccccatt atgtggaagt cctgggcgag       60
cgtatgcact acgtcgatgt tggaccgcgg gatggcacgc tgtgctgtt cctgcacggt      120 aacccgacct cgtcctacct gtggcgcaac atcatcccgc atgtagcacc gagtcatcgg     180
tgcattgctc cagacctgat cgggatggga aaatcggaca aaccagacct cgattatttc     240
ttcgacgacc acgtccgcta cctcgatgcc ttcatcgaag ccttgggttt ggaagaggtc     300
gtcctggtca tccacgactg gggctcagct ctcggattcc actgggccaa gcgcaatccg     360
gaacgggtca aggtattgc atgtatggaa ttcatccggc ctatcccgac gtgggacgaa      420
tggccggaat cgcccgtga gaccttccag gccttccgga ccgccgacgt cggccgagag     480
ttgatcatcg atcagaacgc tttcatcgag ggtgcgctcc cgaaatgcgt cgtccgtccg     540
cttacgaggg tcgagatgga ccactatcgc gagcccttcc tcaagcctgt tgaccgagag     600
ccactgtggc gattccccaa cgagctgccc atcgccggtg agcccgcgaa catcgtcgcg     660
ctcgtcgagg catacatgaa ctggctgcac cagtcacctg tcccgaagtt gttgttctgg     720
ggcacacccg gcgtactgat cccccggcc gaagccgcga gcttgccga aagcctcccc      780 aactgcaaga cagtggacat cggcccggga ttgcactacc tccaggaaga caacccggac     840
cttatcggca gtgagatcgc gcgctggctc cccgcactct ag                        882
```

<210> SEQ ID NO 52
<211> LENGTH: 43
<212> TYPE: DNA
<213> ORGANISM: Artificial Sequence
<220> FEATURE:
<223> OTHER INFORMATION: Synthetic

<400> SEQUENCE: 52

```
cttgggtttg gaagaggtcg tcctggtcat ccacgaatgg ggc                        43
```

<210> SEQ ID NO 53
<211> LENGTH: 42
<212> TYPE: DNA
<213> ORGANISM: Artificial Sequence
<220> FEATURE:
<223> OTHER INFORMATION: Synthetic

<400> SEQUENCE: 53

```
tgagccccat tcgtggatga ccaggacgac ctcttccaaa cc                         42
```

<210> SEQ ID NO 54
<211> LENGTH: 43
<212> TYPE: DNA
<213> ORGANISM: Artificial Sequence
<220> FEATURE:

```
<223> OTHER INFORMATION: Synthetic

<400> SEQUENCE: 54
cttgggtttg aagaggtcg tcctggtcat ccactactgg ggc         43

<210> SEQ ID NO 55
<211> LENGTH: 42
<212> TYPE: DNA
<213> ORGANISM: Artificial Sequence
<220> FEATURE:
<223> OTHER INFORMATION: Synthetic

<400> SEQUENCE: 55
tgagccccag tagtggatga ccaggacgac ctcttccaaa cc          42

<210> SEQ ID NO 56
<211> LENGTH: 38
<212> TYPE: DNA
<213> ORGANISM: Artificial Sequence
<220> FEATURE:
<223> OTHER INFORMATION: Synthetic

<400> SEQUENCE: 56
ccagttagat atgacataga attaaattac tattcacc               38

<210> SEQ ID NO 57
<211> LENGTH: 38
<212> TYPE: DNA
<213> ORGANISM: Artificial Sequence
<220> FEATURE:
<223> OTHER INFORMATION: Synthetic

<400> SEQUENCE: 57
ggtgaatagt aatttaattc tatgtcatat ctaactgg               38

<210> SEQ ID NO 58
<211> LENGTH: 38
<212> TYPE: DNA
<213> ORGANISM: Artificial Sequence
<220> FEATURE:
<223> OTHER INFORMATION: Synthetic

<400> SEQUENCE: 58
ccagttagat atgagataga attacagtac tattcacc               38

<210> SEQ ID NO 59
<211> LENGTH: 38
<212> TYPE: DNA
<213> ORGANISM: Artificial Sequence
<220> FEATURE:
<223> OTHER INFORMATION: Synthetic

<400> SEQUENCE: 59
ggtgaatagt actgtaattc tatctcatat ctaactgg               38

<210> SEQ ID NO 60
<211> LENGTH: 38
<212> TYPE: DNA
<213> ORGANISM: Artificial Sequence
<220> FEATURE:
<223> OTHER INFORMATION: Synthetic

<400> SEQUENCE: 60
ccagttagat atgacataga attacagtac tattcacc               38

<210> SEQ ID NO 61
```

```
<211> LENGTH: 38
<212> TYPE: DNA
<213> ORGANISM: Artificial Sequence
<220> FEATURE:
<223> OTHER INFORMATION: Synthetic

<400> SEQUENCE: 61
ggtgaatagt actgtaattc tatgtcatat ctaactgg                                  38

<210> SEQ ID NO 62
<211> LENGTH: 40
<212> TYPE: DNA
<213> ORGANISM: Artificial Sequence
<220> FEATURE:
<223> OTHER INFORMATION: Synthetic

<400> SEQUENCE: 62
caacaggtcg acgccgccat gaaagagtta aatgatttag                                40

<210> SEQ ID NO 63
<211> LENGTH: 36
<212> TYPE: DNA
<213> ORGANISM: Artificial Sequence
<220> FEATURE:
<223> OTHER INFORMATION: Synthetic

<400> SEQUENCE: 63
gtagtcaccg gtaaattcct tcattacact cttggc                                    36

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
gggctggcaa gccacgtttg gtg                                                  23

<210> SEQ ID NO 65
<211> LENGTH: 23
<212> TYPE: DNA
<213> ORGANISM: Artificial Sequence
<220> FEATURE:
<223> OTHER INFORMATION: Synthetic

<400> SEQUENCE: 65
ccgggagctg catgtgtcag agg                                                  23

<210> SEQ ID NO 66
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 66
atcgagggtg cgctcccgnn ktgcgtcgtc cgtccgctta cgg                            43

<210> SEQ ID NO 67
<211> LENGTH: 43
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (22)..(23)
<223> OTHER INFORMATION: n is a, c, g, or t

<400> SEQUENCE: 67
atcgagggtg cgctcccgaa annkgtcgtc cgtccgctta cgg              43

<210> SEQ ID NO 68
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 68
atcgagggtg cgctcccgnn knnkgtcgtc cgtccgctta cgg              43

<210> SEQ ID NO 69
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t

<400> SEQUENCE: 69
atcggcccgg gattgttcnn kctccaggaa gacaacccgg                  40

<210> SEQ ID NO 70
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(18)
<223> OTHER INFORMATION: n is a, c, g, or t

<400> SEQUENCE: 70
cggcccggga ttgcacnnkc tccaggaaga caacccgga                   39

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
gcctatcccg acgtgggacg                                        20

<210> SEQ ID NO 72
<211> LENGTH: 24
<212> TYPE: DNA
<213> ORGANISM: Artificial Sequence
<220> FEATURE:
```

```
<223> OTHER INFORMATION: Synthetic

<400> SEQUENCE: 72
aggtctcgcg gcttcggccg gggg                                          24

<210> SEQ ID NO 73
<211> LENGTH: 23
<212> TYPE: DNA
<213> ORGANISM: Artificial Sequence
<220> FEATURE:
<223> OTHER INFORMATION: Synthetic

<400> SEQUENCE: 73
aaaatcggac aaaccagacc tcg                                           23

<210> SEQ ID NO 74
<211> LENGTH: 24
<212> TYPE: DNA
<213> ORGANISM: Artificial Sequence
<220> FEATURE:
<223> OTHER INFORMATION: Synthetic

<400> SEQUENCE: 74
atcgcgagcc cttcctcaag cctg                                          24

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
gttccggatt gcgcttggcc cagt                                          24

<210> SEQ ID NO 76
<211> LENGTH: 60
<212> TYPE: DNA
<213> ORGANISM: Artificial Sequence
<220> FEATURE:
<223> OTHER INFORMATION: Synthetic

<400> SEQUENCE: 76
ctataggcta gccagctggc gcggatatcg ccaccatggg ggagaaaccc gggaccaggg    60

<210> SEQ ID NO 77
<211> LENGTH: 79
<212> TYPE: DNA
<213> ORGANISM: Artificial Sequence
<220> FEATURE:
<223> OTHER INFORMATION: Synthetic

<400> SEQUENCE: 77
gatttcggat cccattctag agggcccgcg gtaccgcaag cttgatccgg agcagagttg    60
atcatcatag tcgtcatcc                                                79

<210> SEQ ID NO 78
<211> LENGTH: 41
<212> TYPE: DNA
<213> ORGANISM: Artificial Sequence
<220> FEATURE:
<223> OTHER INFORMATION: Synthetic

<400> SEQUENCE: 78
gccctctaga gccgtcgacg ctgccatggg atccgaaatc g                       41
```

<210> SEQ ID NO 79
<211> LENGTH: 40
<212> TYPE: DNA
<213> ORGANISM: Artificial Sequence
<220> FEATURE:
<223> OTHER INFORMATION: Synthetic

<400> SEQUENCE: 79
gtagtcaccg gtgccggcca gcccggggag ccagcgcgcg                    40

<210> SEQ ID NO 80
<211> LENGTH: 943
<212> TYPE: DNA
<213> ORGANISM: Artificial Sequence
<220> FEATURE:
<223> OTHER INFORMATION: Synthetic

<400> SEQUENCE: 80
gctagccagc tggcgcggat atcgccacca tgggatccga aatcggtaca ggcttcccct    60 tcgacccca ttatgtggaa gtcctgggcg agcgtatgca ctacgtcgat gttggaccgc    120
gggatggcac gcctgtgctg ttcctgcacg gtaacccgac ctcgtcctac ctgtggcgca    180
acatcatccc gcatgtagca ccgagtcatc ggtgcattgc tccagacctg atcgggatgg    240
gaaaatcgga caaccagac ctcgattatt cttcgacga ccacgtccgc tacctcgatg     300
ccttcatcga agccttgggt ttggaagagg tcgtcctggt catccacgac tggggctcag    360
ctctcggatt ccactgggcc aagcgcaatc cggaacgggt caaaggtatt gcatgtatgg    420
aattcatccg gcctatcccg acgtgggacg aatggccaga attcgcccgt gagaccttcc    480
aggccttccg gaccgccgac gtcggccgag agttgatcat cgatcagaac gctttcatcg    540
agggtgcgct cccgatgggg gtcgtccgtc cgcttacgga ggtcgagatg gaccactatc    600
gcgagccctt cctcaagcct gttgaccgag agccactgtg gcgattcccc aacgagctgc    660
ccatcgccgg tgagcccgcg aacatcgtcg cgctcgtcga ggcatacatg aactggctgc    720
accagtcacc tgtcccgaag ttgttgttct ggggcacacc cggcgtactg atcccccgg    780 ccgaagccgc gagacttgcc gaaagcctcc ccaactgcaa gacagtggac atcggcccgg    840
gattgttctt gctccaggaa gacaacccgg accttatcgg cagtgagatc gcgcgctggc    900
tccccgggct ggccggctaa tagttaatta agtaggcggc cgc                    943

<210> SEQ ID NO 81
<211> LENGTH: 298
<212> TYPE: PRT
<213> ORGANISM: Artificial Sequence
<220> FEATURE:
<223> OTHER INFORMATION: Synthetic

<400> SEQUENCE: 81

Met Gly Ser Glu Ile Gly Thr Gly Phe Pro Phe Asp Pro His Tyr Val
1               5                   10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala
    50                  55                  60

Pro Asp Leu Ile Gly Met Gly Lys Ser Asp Ala Lys Pro Asp Leu Asp
65                  70                  75                  80

Tyr Phe Phe Asp Asp His Val Arg Tyr Leu Asp Ala Phe Ile Glu Ala

```
            85                  90                  95
Leu Gly Leu Glu Glu Val Val Leu Val Ile His Asp Trp Gly Ser Ala
        100                 105                 110
Leu Gly Phe His Trp Ala Lys Arg Asn Pro Glu Arg Val Val Lys Gly
        115                 120                 125
Ile Ala Cys Met Glu Phe Ile Arg Pro Ile Pro Thr Trp Asp Glu Trp
        130                 135                 140
Pro Glu Phe Ala Arg Glu Thr Phe Gln Ala Phe Arg Thr Ala Asp Val
145                 150                 155                 160
Gly Arg Glu Leu Ile Ile Asp Gln Asn Ala Phe Ile Glu Gly Ala Leu
                165                 170                 175
Pro Met Gly Val Val Arg Pro Leu Thr Glu Val Glu Met Asp His Tyr
            180                 185                 190
Arg Glu Pro Phe Leu Lys Pro Val Asp Arg Glu Pro Leu Trp Arg Phe
            195                 200                 205
Pro Asn Glu Leu Pro Ile Ala Gly Glu Pro Ala Asn Ile Val Ala Leu
        210                 215                 220
Val Glu Ala Tyr Met Asn Trp Leu His Gln Ser Pro Val Pro Lys Leu
225                 230                 235                 240
Leu Phe Trp Gly Thr Pro Gly Val Leu Ile Pro Pro Ala Glu Ala Ala
                245                 250                 255
Arg Leu Ala Glu Ser Leu Pro Asn Cys Lys Thr Val Asp Ile Gly Pro
            260                 265                 270
Gly Leu Phe Leu Leu Gln Glu Asp Asn Pro Asp Leu Ile Gly Ser Glu
            275                 280                 285
Ile Ala Arg Trp Leu Pro Gly Leu Ala Gly
        290                 295

<210> SEQ ID NO 82
<211> LENGTH: 293
<212> TYPE: PRT
<213> ORGANISM: Rhodococcus rhodochrous

<400> SEQUENCE: 82

Met Ser Glu Ile Gly Thr Gly Phe Pro Phe Asp Pro His Tyr Val Glu
1               5                   10                  15
Val Leu Gly Glu Arg Met His Tyr Val Asp Val Gly Pro Arg Asp Gly
            20                  25                  30
Thr Pro Val Leu Phe Leu His Gly Asn Pro Thr Ser Ser Tyr Leu Trp
        35                  40                  45
Arg Asn Ile Ile Pro His Val Ala Pro Ser His Arg Cys Ile Ala Pro
50                  55                  60
Asp Leu Ile Gly Met Gly Lys Ser Asp Lys Pro Asp Leu Asp Tyr Phe
65                  70                  75                  80
Phe Asp Asp His Val Arg Tyr Leu Asp Ala Phe Ile Glu Ala Leu Gly
                85                  90                  95
Leu Glu Glu Val Val Leu Val Ile His Asp Trp Gly Ser Ala Leu Gly
            100                 105                 110
Phe His Trp Ala Lys Arg Asn Pro Glu Arg Val Lys Gly Ile Ala Cys
        115                 120                 125
Met Glu Phe Ile Arg Pro Ile Pro Thr Trp Asp Glu Trp Pro Glu Phe
        130                 135                 140
Ala Arg Glu Thr Phe Gln Ala Phe Arg Thr Ala Asp Val Gly Arg Glu
145                 150                 155                 160
Leu Ile Ile Asp Gln Asn Ala Phe Ile Glu Gly Ala Leu Pro Lys Cys
```

```
                        165                 170                 175
Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Ala
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
            245                 250                 255

Glu Ser Leu Pro Asn Cys Lys Thr Val Asp Ile Gly Pro Gly Leu His
            260                 265                 270

Tyr Leu Gln Glu Asp Asn Pro Asp Leu Ile Gly Ser Glu Ile Ala Arg
            275                 280                 285

Trp Leu Pro Ala Leu
        290
```

<210> SEQ ID NO 83
<211> LENGTH: 29
<212> TYPE: DNA
<213> ORGANISM: Artificial Sequence
<220> FEATURE:
<223> OTHER INFORMATION: Synthetic

<400> SEQUENCE: 83
gggcacaccc ggcaccctga tcccccgg                                   29

<210> SEQ ID NO 84
<211> LENGTH: 69
<212> TYPE: DNA
<213> ORGANISM: Artificial Sequence
<220> FEATURE:
<223> OTHER INFORMATION: Synthetic

<400> SEQUENCE: 84
ctataggcta gccagctggc gcggatatcg ccaccatggg atccgaaatc ggtacaggct    60
tccccttcg                                                           69

<210> SEQ ID NO 85
<211> LENGTH: 70
<212> TYPE: DNA
<213> ORGANISM: Artificial Sequence
<220> FEATURE:
<223> OTHER INFORMATION: Synthetic

<400> SEQUENCE: 85
agggaagcgg ccgcctactt aattaactat tagccggcca gcccggggag ccagcgcgcg    60
atctcactgc                                                          70

COVALENT TETHERING OF FUNCTIONAL GROUPS TO PROTEINS AND SUBSTRATES THEREFOR

CROSS-REFERENCE TO RELATED APPLICATIONS

This application is a divisional of U.S. patent application Ser. No. 13/046,297, filed Mar. 11, 2011, which is a divisional of U.S. Pat. No. 7,935,803, issued May 3, 2012, which is a divisional of U.S. Pat. No. 7,425,436, issued Sep. 16, 2008, which claims the benefit of expired U.S. Provisional Application Ser. No. 60/592,499, filed Jul. 30, 2004 and is a continuation-in-part of U.S. Pat. No. 7,429,472, issued Sep. 30, 2008, which claims the benefit of expired U.S. Provisional Application Ser. No. 60/592,499, filed Jul. 30, 2004, each of which is incorporated by reference in its entirety.

FIELD OF THE INVENTION

This invention relates to the field of biochemical assays and reagents. More specifically, this invention relates to mutant proteins covalently linked (tethered) to one or more functional groups and to methods for their use.

BACKGROUND OF THE INVENTION

The specific detection of molecules is a keystone in understanding the role of that molecule in the cell. Labels, e.g., those that are covalently linked to a molecule of interest, permit the ready detection of that molecule in a complex mixture. The label may be one that is added by chemical synthesis in vitro or attached in vivo, e.g., via recombinant techniques. For instance, the attachment of fluorescent or other labels onto proteins has traditionally been accomplished by in vitro chemical modification after protein purification (Hermanson, 1996). For in vivo attachment of a label, green fluorescent protein (GFP) from the jellyfish *Aequorea victoria* can be genetically fused with many host proteins to produce fluorescent chimeras in situ (Tsien, 1998; Chalfie et al., 1998). However, while GFP-based indicators are currently employed in a variety of assays, e.g., measuring pH (Kneen et al., 1998; Llopis et al., 1998; Miesenböck et al., 1998), $Ca^{2+}$ (Miyawaki et al., 1997; Rosomer et al., 1997), and membrane potential (Siegel et al., 1997), the fluorescence of intrinsically labeled proteins such as GFP is limited by the properties of protein structure, e.g., a limited range of fluorescent colors and relatively low intrinsic brightness (Cubitt et al., 1995; Ormö et al., 1996).

To address the deficiencies of GFP labeling in situ, Griffen et al. (1998) synthesized a tight-binding pair of molecular components: a small receptor domain composed of as few as six natural amino acids and a small (<700 dalton), synthetic ligand that could be linked to various spectroscopic probes or crosslinks. The receptor domain included four cysteines at the i, i+1, i+4, and i+5 positions of an a helix and the ligand was 4',5'-bis(1,3,2-dithioarsolan-2-yl)fluorescein (FLASH). Griffen et al. disclose that the ligand had relatively few binding sites in nontransfected mammalian cells, was membrane-permeant and was nonfluorescent until it bound with high affinity and specificity to a tetracysteine domain in a recombinant protein, resulting in cells being fluorescently labeled ("FLASH" labeled) with a nanomolar or lower dissociation constant. However, with respect to background binding in cells, Stroffekova et al. (2001) disclose that FLASH-$EDT_2$ binds non-specifically to endogenous cysteine-rich proteins. Furthermore, labeling proteins by FLASH is limited by the range of fluorophores that may be used.

Receptor-mediated targeting methods use genetically encoded targeting sequences to localize fluorophores to virtually any cellular site, provided that the targeted protein is able to fold properly. For example, Farinas et al. (1999) disclose that cDNA transfection was used to target a single-chain antibody (sFv) to a specified site in a cell. Farinas et al. disclose that conjugates of a hapten (4-ethoxymethylene-2-phenyl-2-oxazolin-5-one, phOx) and a fluorescent probe (e.g., BODIPY Fl, tetramethylrhodamine, and fluorescein) were bound with high affinity (about 5 nM) to the subcellular site for the sFv in living Chinese hamster ovary cells, indicating that the targeted antibody functioned as a high affinity receptor for the cell-permeable hapten-fluorophore conjugates. Nevertheless, functional sFv expression may be relatively poor in reducing environments.

Thus, what is needed is an improved method to label a desired molecule.

SUMMARY OF THE INVENTION

The invention provides methods, compositions and kits for tethering (linking), e.g., via a covalent or otherwise stable bond, one or more functional groups to a protein of the invention or to a fusion protein (chimera) which includes a protein of the invention. A protein of the invention is structurally related to a wild-type (native) hydrolase but includes at least one amino acid substitution, and in some embodiments at least two amino acid substitutions, relative to the corresponding wild-type hydrolase, and binds a substrate of the corresponding wild-type hydrolase but lacks or has reduced catalytic activity relative to the corresponding wild-type hydrolase (which mutant protein is referred to herein as a mutant hydrolase). The aforementioned tethering occurs, for instance, in solution or suspension, in a cell, on a solid support or at solution/surface interfaces, by employing a substrate for a hydrolase which includes a reactive group and which has been modified to include one or more functional groups. As used herein, a "substrate" includes a substrate having a reactive group and optionally one or more functional groups. A substrate which includes one or more functional groups is generally referred to herein as a substrate of the invention. As used herein, a "functional group" is a molecule which is detectable or is capable of detection, for instance, a molecule which is measurable by direct or indirect means (e.g., a photoactivatable molecule, digoxigenin, nickel NTA (nitrilotriacetic acid), a chromophore, fluorophore or luminophore), can be bound or attached to a second molecule (e.g., biotin, hapten, or a cross-linking group), or may be a solid support.

A functional group may have more than one property such as being capable of detection and of being bound to another molecule. As used herein a "reactive group" is the minimum number of atoms in a substrate which are specifically recognized by a particular wild-type or mutant hydrolase of the invention. The interaction of a reactive group in a substrate and a wild-type hydrolase results in a product and the regeneration of the wild-type hydrolase. A substrate, e.g., a substrate of the invention, may also optionally include a linker, e.g., a cleavable linker, which physically separates one or more functional groups from the reactive group in the substrate, and in one embodiment, the linker is preferably 12 to 30 atoms in length. The linker may not always be present in a substrate of the invention, however, in some embodiments, the physical separation of the reactive group and the functional group may be needed so that the reactive group can interact with the reactive residue in the mutant hydrolase to form a covalent bond. Preferably, when present, the linker does not substantially alter, e.g., impair, the specificity or reactivity of a substrate having the linker with the wild-type or mutant hydrolase relative to the specificity or reactivity of a corresponding substrate which lacks the linker with the wild-type or mutant hydrolase. Further, the presence of the linker preferably does not substantially alter, e.g., impair, one or more properties, e.g., the function, of the functional group. For instance, for some mutant hydrolases, i.e., those with deep catalytic pockets, a substrate of the invention can include a linker of sufficient length and structure so that the one or more functional groups of the substrate of the invention do not disturb the 3-D structure of the hydrolase (wild-type or mutant). For example, one example of a substrate of the invention for a dehalogenase includes a reactive group such as $(CH_2)_{2\text{-}3}X$ where X is a halide and a functional group such as carboxytetramethylrhodamine, e.g., carboxytetramethylrhodamine-$C_{10}H_{21}NO_2$—Cl.

In one embodiment, the invention provides a compound of formula (I): R-linker-A-X, wherein R is one or more functional groups, wherein the linker is a multiatom straight or branched chain including C, N, S, or O, or a group that comprises one or more rings, e.g., saturated or unsaturated rings, such as one or more aryl rings, heteroaryl rings, or any combination thereof, wherein A-X is a substrate for a dehalogenase, e.g., a haloalkane dehalogenase or a dehalogenase that cleaves carbon-halogen bonds in an aliphatic or aromatic halogenated substrate, such as a substrate for *Rhodococcus, Sphingomonas, Staphylococcus, Pseudomonas, Burkholderia, Agrobacterium* or *Xanthobacter* dehalogenase, and wherein X is a halogen. In one embodiment, an alkylhalide is covalently attached to a linker, L, which is a group or groups that covalently attach one or more functional groups to form a substrate for a dehalogenase. As described herein, a mutant of a *Rhodococcus* dehalogenase (DhaA) (see FIG. 2 for an exemplary wild-type *Rhodococcus* dehalogenase "DhaA.WT" sequence), DhaA.H272F, was bound to substrates for DhaA which included 5-(and 6-) carboxyfluorescein, e.g., carboxyfluorescein-$C_{10}H_{21}NO_2$—Cl, carboxytetramethylrhodamine, e.g., carboxytetramethylrhodamine-$C_{10}H_{21}NO_2$—Cl, and biotin, e.g., biotin-$C_{10}H_{21}NO_2$—Cl, and there was no significant quenching effect of this binding on carboxyfluorescein or carboxytetramethylrhodamine fluorescence or on biotin binding to streptavidin. As also described herein, a mutant dehalogenase, e.g., DhaA.D106C and DhaA.D106E as well as DhaA.D106C:H272F and DhaA.D106E:H272F, bound carboxyfluorescein-$C_{10}H_{21}NO_2$—Cl and/or carboxytetramethylrhodamine-$C_{10}H_{21}NO_2$—Cl. In one embodiment, the substrate is R—$(CH_2)_2O(CH_2)_2O(CH_2)_2O(CH_2)_6Cl$, wherein R is a functional group. To prepare such a substrate, a functional group may be reacted with a molecule such as $NH(CH_2)_2O(CH_2)_2O(CH_2)_2O(CH_2)_6Cl$.

In one embodiment, substrates of the invention are permeable to the plasma membranes of cells. For instance, as described herein the plasma membranes of prokaryotic (*E. coli*) and eukaryotic (CHO-K1) cells were permeable to carboxytetramethylrhodamine-$C_{10}H_{21}NO_2$—Cl and biotin-$C_{10}H_{21}NO_2$—Cl and, these substrates were rapidly and efficiently loaded into and washed out of cells in the absence of a mutant hydrolase. In the presence of a mutant hydrolase, at least a portion of the substrate was prevented from being washed out of the cells. Thus, the bound portion of the substrate can serve as a marker or as a means to capture the mutant hydrolase or a fusion thereof.

In one embodiment, the substrate of the invention includes two or more functional groups. In one embodiment, one of the functional groups is an enzyme. In another embodiment, one of the functional groups is a substrate for an enzyme. For example, one functional group may be luciferin and the other a protease recognition site, i.e., one which contains sequences sufficient for recognition by the protease including the site to be cleaved, one functional group may be biotin and the other a fluorophore, or one functional group may be a protease recognition site and the other a fluorophore.

The invention further provides methods for preparing a substrate for a hydrolase which substrate is modified to include one or more functional groups.

A mutant hydrolase of the invention, as described in more detail herein, comprises at least one amino acid substitution relative to a corresponding wild-type hydrolase, wherein the at least one amino acid substitution results in the mutant hydrolase forming a bond with the substrate which is more stable than the bond formed between the corresponding wild-type hydrolase and the substrate. The at least one amino acid substitution in the mutant hydrolase is a substitution at an amino acid residue in the corresponding wild-type hydrolase that is associated with activating a water molecule which cleaves the bond formed between the corresponding wild-type hydrolase and the substrate or at an amino acid residue in the corresponding wild-type hydrolase that forms an ester intermediate with the substrate. In one embodiment, the mutant hydrolase comprises at least two amino acid substitutions relative to a corresponding wild-type hydrolase, wherein one substitution is in a residue which, in the wild-type hydrolase, is associated with activating a water molecule or in a residue which, in the wild-type hydrolase, forms an ester intermediate by nucleophilic attack of a substrate for the hydrolase, and another substitution in a residue which, in the wild-type hydrolase, is at or near a binding site(s) for a hydrolase substrate, e.g., the residue within 3 to 5 Å of a hydrolase substrate bound to a wild-type hydrolase but is not in a residue that in the corresponding wild-type hydrolase is associated with activating a water molecule or which forms ester intermediate with a substrate. In one embodiment, the second substitution is in a residue which, in the wild-type hydrolase lines the site(s) for substrate entry into the catalytic pocket of the hydrolase, e.g., a residue that is within the active site cavity and within 3 to 5 Å of a hydrolase substrate bound to the wild-type hydrolase such as a residue in a tunnel for the substrate that is not a residue in the corresponding wild-type hydrolase which is associated with activating a water molecule or which forms an ester intermediate with a substrate. The additional substitution(s) preferably increase the rate of stable covalent bond formation of those mutants binding to a substrate of a corresponding wild-type hydrolase.

The mutant hydrolase may be a fusion protein, e.g., a fusion protein expressed from a recombinant DNA which encodes the mutant hydrolase and at least one protein of interest or a fusion protein formed by chemical synthesis. For instance, the fusion protein may comprise a mutant hydrolase and an enzyme of interest, e.g., luciferase, RNasin or RNase, and/or a channel protein, a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, a transporter protein and/or a targeting sequence, e.g., a myristilation sequence, a mitochondrial localization sequence, or a nuclear localization sequence, that directs the mutant hydrolase, for example, a fusion protein, to a particular location. The protein of interest may be fused to the N-terminus or the C-terminus of the mutant hydrolase. In one embodiment, the fusion protein comprises a protein of interest at the N-terminus, and another protein, e.g., a different protein, at the C-terminus, of the mutant hydrolase. For example, the protein of interest may be a fluorescent protein or an antibody. Optionally, the proteins in the fusion are separated by a connector sequence, e.g., preferably one having at least 2 amino acid residues, such as one having 13 to 17 amino acid residues. The presence of a connector sequence in a fusion protein of the invention does not substantially alter the function of either protein in the fusion relative to the function of each individual protein.

Also provided is an isolated nucleic acid molecule (polynucleotide) comprising a nucleic acid sequence encoding a hydrolase, e.g., a mutant hydrolase of the invention. In one embodiment, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. In one embodiment, the polynucleotide includes a nucleic acid sequence encoding a dehalogenase, which nucleic acid sequence is optimized for expression is a selected host cell. In one embodiment, the optimized polynucleotide no longer hybridizes to the corresponding non-optimized sequence, e.g., does not hybridize to the non-optimized sequence under medium or high stringency conditions. In another embodiment, the polynucleotide has less than 90%, e.g., less than 80%, nucleic acid sequence identity to the corresponding non-optimized sequence and optionally encodes a polypeptide having at least 80%, e.g., at least 85%, 90% or more, amino acid sequence identity with the polypeptide encoded by the non-optimized sequence. Constructs, e.g., expression cassettes, and vectors comprising the isolated nucleic acid molecule, as well as kits comprising the isolated nucleic acid molecule, construct or vector are also provided.

The invention also includes compositions and kits comprising a substrate for a hydrolase which includes a linker, a substrate for a hydrolase which includes one or more functional groups and optionally a linker, a linker which includes one or more functional groups, a substrate for a hydrolase which lacks one or more functional groups and optionally includes a linker, a linker, or a mutant hydrolase, or any combination thereof. For example, the invention includes a solid support comprising a substrate of the invention, a solid support comprising a mutant hydrolase of the invention or a fusion thereof, a kit comprising a substrate of the invention, a kit comprising a vector encoding a dehalogenase of the invention or a fusion thereof, or a kit comprising a vector encoding a serine beta-lactamase of the invention or a fusion thereof.

The substrates and mutant hydrolases of the invention are useful to isolate, detect, identify, image, display, or localize molecules of interest, label cells, including live cell imaging, or label proteins in vitro and/or in vivo. For instance, a substrate of the invention bound to a solid support or a mutant hydrolase bound to a solid support may be used to generate protein arrays, cell arrays, vesicle/organelle arrays, gene arrays, and/or cell membrane arrays. Thus, in one embodiment, the invention provides a method to isolate a molecule of interest. The method includes providing a sample comprising one or more fusion proteins at least one of which comprises a mutant hydrolase of the invention and a protein which is bound to the molecule of interest, and a solid support comprising one or more hydrolase substrates. The sample and the solid support are then contacted so as to isolate the molecule of interest. For instance, the method may be employed to isolate DNA bound to a protein fused to a mutant hydrolase.

In one embodiment, the invention provides a method to detect or determine the presence or amount of a mutant hydrolase. The method includes contacting a mutant hydrolase of the invention with a hydrolase substrate which comprises one or more functional groups. The presence or amount of the functional group is detected or determined, thereby detecting or determining the presence or amount of the mutant hydrolase. In one embodiment, the mutant hydrolase is in or on the surface of a cell. In another embodiment, the mutant hydrolase is in a cell lysate.

Also provided are methods of using a mutant hydrolase of the invention and a substrate for a corresponding hydrolase which includes one or more functional groups, e.g., to isolate a molecule or to detect or determine the presence or amount of, location, e.g., intracellular, subcellular or extracellular location, or movement of certain molecules in cells.

In another embodiment, the invention includes a method to identify an agent that alters the interaction of a protein of interest with a molecule suspected of interacting with the protein of interest. The method includes contacting at least one agent with the molecule suspected of interacting with the protein of interest, a fusion protein comprising mutant hydrolase of the invention and the protein of interest, and a hydrolase substrate which comprises one or more functional groups. Then it is determined whether the agent alters the interaction between the protein of interest and the molecule suspected of interacting with the protein of interest.

The invention thus provides methods to monitor the expression, location and/or movement (trafficking) of proteins in a cell as well as to monitor changes in microenvironments within a cell. In one embodiment, the use of a mutant hydrolase of the invention and a substrate of the invention permits functional analysis of proteins, e.g., ion channels. In another embodiment, the use of two pairs of a mutant hydrolase/substrate permits multiplexing, simultaneous detection, and FRET- or BRET-based assays.

To isolate, sort or purify cells, a mutant hydrolase of the invention may be expressed on the outside surface of cells (e.g., via a fusion with a plasma membrane protein or a membrane anchoring signal). For instance, cells which express a fusion of a cytoplasmic and transmembrane domains of an integrin with a mutant hydrolase, or a fusion of a glycosylphosphatidyl inositol signal sequence and a mutant hydrolase, may be isolated ("captured") by contacting those cells with a substrate of the invention, for instance, one bound to a solid support. To isolate, purify or separate organelles, the mutant hydrolase is expressed on the cytosolic surface of the organelle of interest. In another embodiment, to create an optimal platform for growing different cells, the mutant hydrolase is fused with an extracellular matrix component or an outer membrane protein and tethered to a three-dimensional cell culture or a platform for tissue engineering. As an example, primary neurons or embryonic stem cells may be grown on the platform to form a feeder layer.

Other applications include detecting or labeling cells. Thus, the use of a mutant hydrolase of the invention and a corresponding substrate of the invention permits the detection of cells, for instance, to detect cell migration in vitro or in vivo after implantation or injection into animals (e.g., angiogenesis/chemotaxis assays, migration of implanted neurons, normal, malignant, or recombinantly modified cells implanted/injected into animals, and the like), and live cell imaging followed by immunocytochemistry. In another embodiment, the invention provides a method to label newly synthesized proteins. For example, cells comprising a vector which expresses a mutant hydrolase of the invention or a fusion thereof, are contacted with a substrate for the hydrolase which lacks a functional group. Cells are then contacted with an agent, e.g., an inducer of gene expression, and a substrate for the hydrolase which contains one or more functional groups. The presence, amount or location of the mutant hydrolase or fusion thereof is then detected or determined. The presence, amount or location of the mutant hydrolase or fusion thereof is due to newly synthesized mutant hydrolase or a fusion thereof. Alternatively, cells comprising a vector which expresses a mutant hydrolase of the invention or a fusion thereof, are contacted with a substrate for the hydrolase having a functional group, e.g., a green fluorophore, then contacted with an agent and a substrate having a different functional group, e.g., a red fluorophore. In one embodiment, the mutant hydrolase is fused to a membrane localization signal and so can be employed to monitor events in or near the membrane.

The invention also provides a method to label a cell, e.g., in a transgenic or non-transgenic non-human animal. For instance, to label cells, the mutant hydrolase may be expressed on the outside surface of cells (e.g., via a fusion with a plasma membrane protein or a membrane anchoring signal). For instance, cells which express a fusion of a cytoplasmic and transmembrane domains of an integrin with a mutant hydrolase of the invention, or a fusion of a glycosylphosphatidyl inositol signal sequence and a mutant hydrolase of the invention, may be identified or labeled by contacting those cells with a substrate of the invention. In one embodiment, the invention includes a method to label cells in a transgenic animal. The method includes providing a transgenic non-human animal, the genome of cells of which is augmented with an expression cassette comprising a transcriptional regulatory element which is optionally tissue- or cell-specific operably linked to nucleic acid fragment encoding a mutant hydrolase of the invention and optionally a targeting peptide. The transgenic non-human animal is then contacted with a hydrolase substrate that comprises one or more functional groups, thereby labeling cells that express the mutant hydrolase.

Cells expressing selectable marker proteins, such as ones encoding resistance to neomycin, hygromycin, or puromycin, are used to stably transform cells with foreign DNA. It may be desirable to observe which cells contain selectable marker proteins as well as fluorescently labeled molecules. For instance, it may be preferable to label the selectable marker protein with a fluorescent molecule that is added exogenously to living cells. By this method, the selectable marker protein becomes visible when only when needed by addition of the fluorophore, and the fluorescence will subsequently be lost when selectable marker proteins are naturally regenerated through cellular metabolism. Thus, in one embodiment, the invention provides a method for labeling a cell which expresses a selectable marker protein. The method includes providing a cell comprising an expression cassette comprising a nucleic acid sequence encoding a fusion protein. The fusion protein comprises a selectable marker protein, e.g., one which confers resistance to at least one antibiotic, and a second protein that is capable of stably and optionally irreversibly binding a substrate or a portion thereof which includes an optically detectable molecule. For instance, the protein may be an alkyl transferase which irreversibly transfers an alkyl group and an optically detectable molecule from a substrate to itself, thereby labeling the alkyl transferase, e.g., an alkyl transferase such as $O^6$-alkylguanine DNA alkyltransferase. Exemplary proteins useful in this embodiment of the invention include, but are not limited to, alkyl transferases, peptidyl glycine-alpha-amidating monoxygenases, type I topoisomerases, hydrolases, e.g., serine and epoxide hydrolases as well as the mutant hydrolases described herein, aminotransferases, cytochrome P450 monooxygenases, acetyl transferases, decarboxylases, oxidases, e.g., monoamine oxidases, reductases, e.g., ribonucleotide reductase, synthetases, e.g., cyclic ADP ribose synthetase or thymidylate synthetase, dehydrogenases, e.g., aldehyde dehydrogenase, synthases, e.g., nitric oxide synthase (NOS), lactamases, cystathionine gamma-lyases, peptidases, e.g., carboxypeptidase A, aromatase, proteases, e.g., serine protease, xylanases, glucosidases, mannosidases, and demethylases and other proteins, including wild-type proteins, which form an irreversible or otherwise stable bond with one or more substrates, e.g., enzymes which are capable of mechanism-based inactivation. Thus, in this embodiment, a stable bond, i.e., one which is formed between a substrate and a wild-type or mutant enzyme, has a $t_{1/2}$ of at least 30 minutes and preferably at least 4 hours, and up to at least 10 hours, and is resistant to disruption by washing, protein denaturants, and/or high temperatures, e.g., the bond is stable to boiling in SDS.

The cell which expresses the fusion protein is contacted with the substrate so as to label the cell. In one embodiment, the cell is fixed prior to contact with the substrate. In another embodiment, the substrate and fixative are contacted with the cell at the same time. In yet another embodiment, the fixative is added to the cell after the cell is contacted with the substrate. In one embodiment, the fusion protein forms an ester bond with the substrate. In another embodiment, the fusion protein forms a thioester bond with the substrate.

The invention also provides processes and intermediates disclosed herein that are useful for preparing compounds, compositions, nucleic acids, proteins, or other materials of the invention.

BRIEF DESCRIPTION OF THE FIGURES

FIG. 2B shows the sequence of a *Rhodococcus rhodochrous* dehalogenase (DhaA) protein (Kulakova et al., 1997) (SEQ ID NO:82). The catalytic triad residues Asp(D), Glu(E) and His(H) are underlined. The residues that make up the cap domain are shown in italics. The DhaA.H272F and DhaA.D106C protein mutants, capable of generating covalent linkages with alkylhalide substrates, contain replacements of the catalytic triad His (H) and Asp (D) residues with Phe (F) and Cys (C), respectively.

FIGS. 7A-B show substrates for DhaA which include a functional group (e.g., 5-(and 6-)-carboxyfluorescein, Anth (anthracene) or biotin) and a linker. "Biotin-14-Cl" refers to biotin-$C_{10}H_{21}NO_2$—Cl; "biotin-X-14-Cl" refers to biotin-$C_{16}H_{32}N_2O_3$—Cl; and "biotin-PEG4-14-Cl" refers to biotin-$C_{21}H_{42}N_2O_7$—Cl.

FIGS. 16A-C illustrate the permeability of carboxytetramethylrhodamine-$C_{10}H_{21}NO_2$—Cl to CHO-K1 cells. CHO-K1 cells (panel A, bright field image) were treated with carboxytetramethylrhodamine-$C_{10}H_{21}NO_2$—Cl (25 µM, for 5 minutes at 37° C.) and quickly washed with PBS (panel B). Panel C shows the cells after the washing procedure.

FIG. 17 shows images of cells transfected with GFP-connector-DhaA.WT-Flag or GFP-connector-DhaA.H272F-Flag. CHO-K1 cells were transfected with DNA coding GFP-connector-DhaA.WT-Flag (panels A-C) or GFP-connector-DhaA.H272F-Flag (panels D-F) and treated with carboxytetramethylrhodamine-$C_{10}H_{21}NO_2$—Cl. Panels A, D-bright field; panels B, E-GFP filter set; and panels C, F-carboxytetramethylrhodamine filter set.

μM) for 0, 5, 15 or 60 minutes, washed with PBS (4×1.0 ml), and collected in SDS-sample buffer. The samples were resolved on SDS-PAGE, and analyzed on a fluoroimager. Lanes 1-4, GFP-connector-DhaA.WT-Flag treated for 0, 5, 15, or 60 minutes, respectively. Lanes 5-8, GFP-connector-DhaA.H272F-Flag treated for 0, 5, 15, 60 minutes, respectively. Arrows mark proteins with $M_r$ corresponding to $M_r$ of GFP-connector-DhaA.H272F-Flag.

Figure 19A:
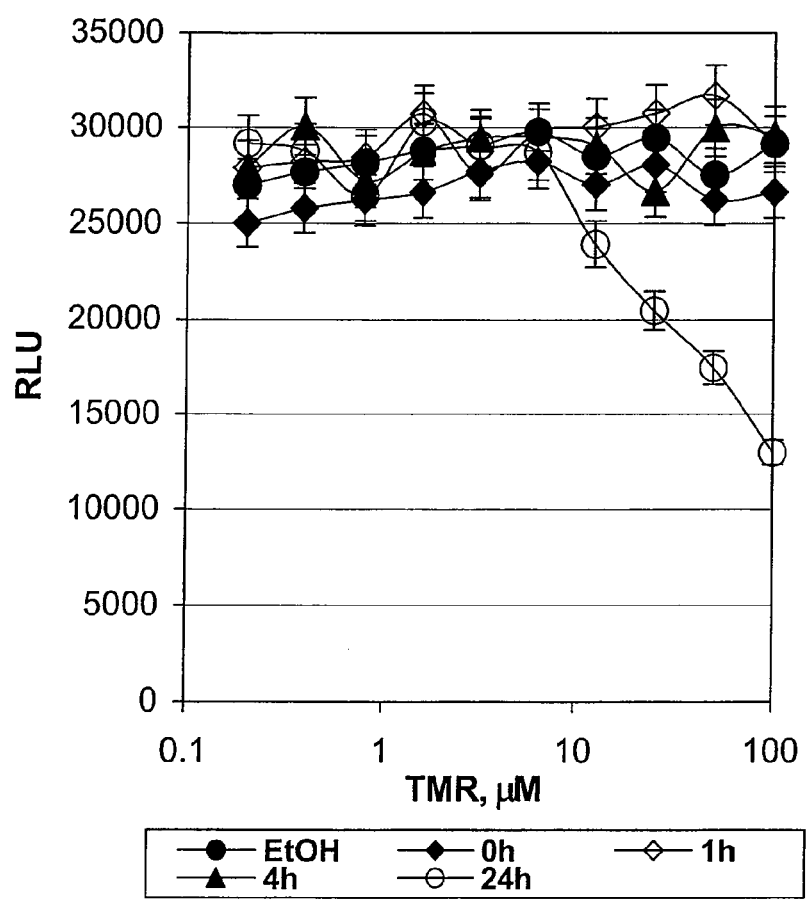
Figure 19B:
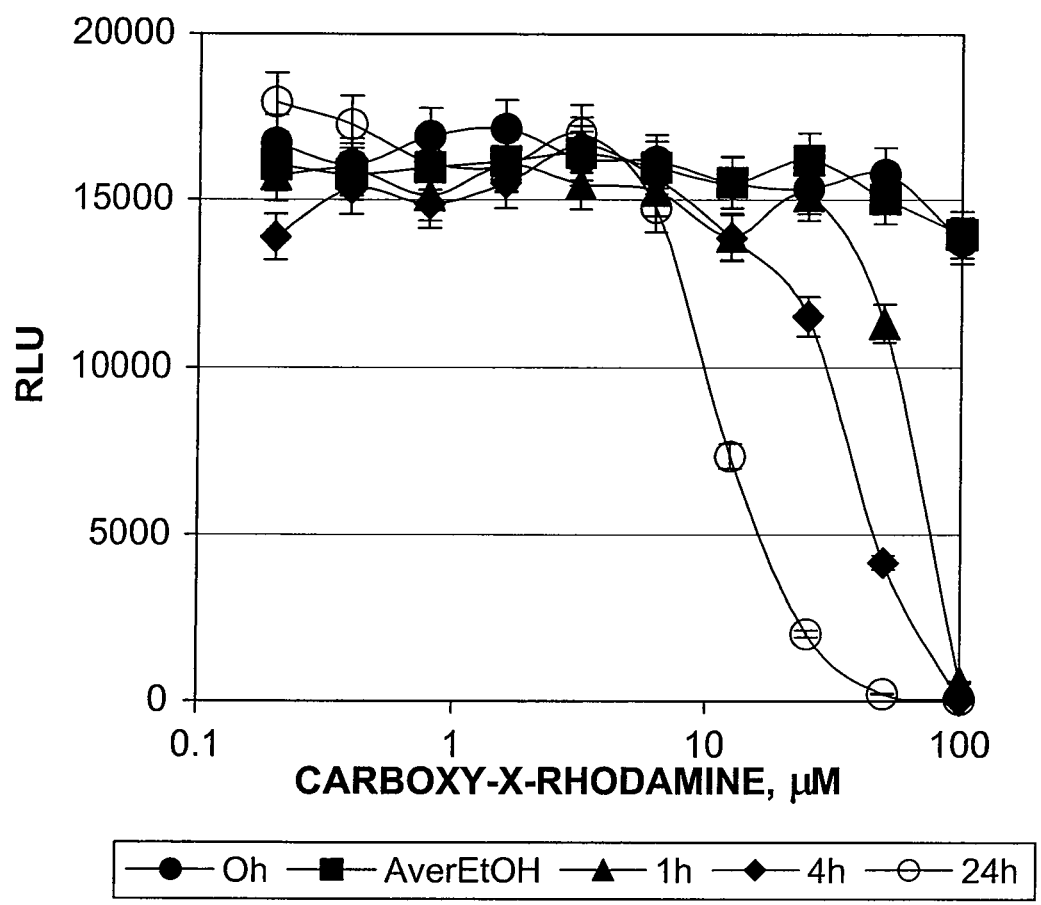

FIGS. 19A-B illustrate the toxicity of selected substrates (panel A, carboxytetramethylrhodamine and panel B, carboxy-X-rhodamine) for CHO-K1 cells.

Figure 20:
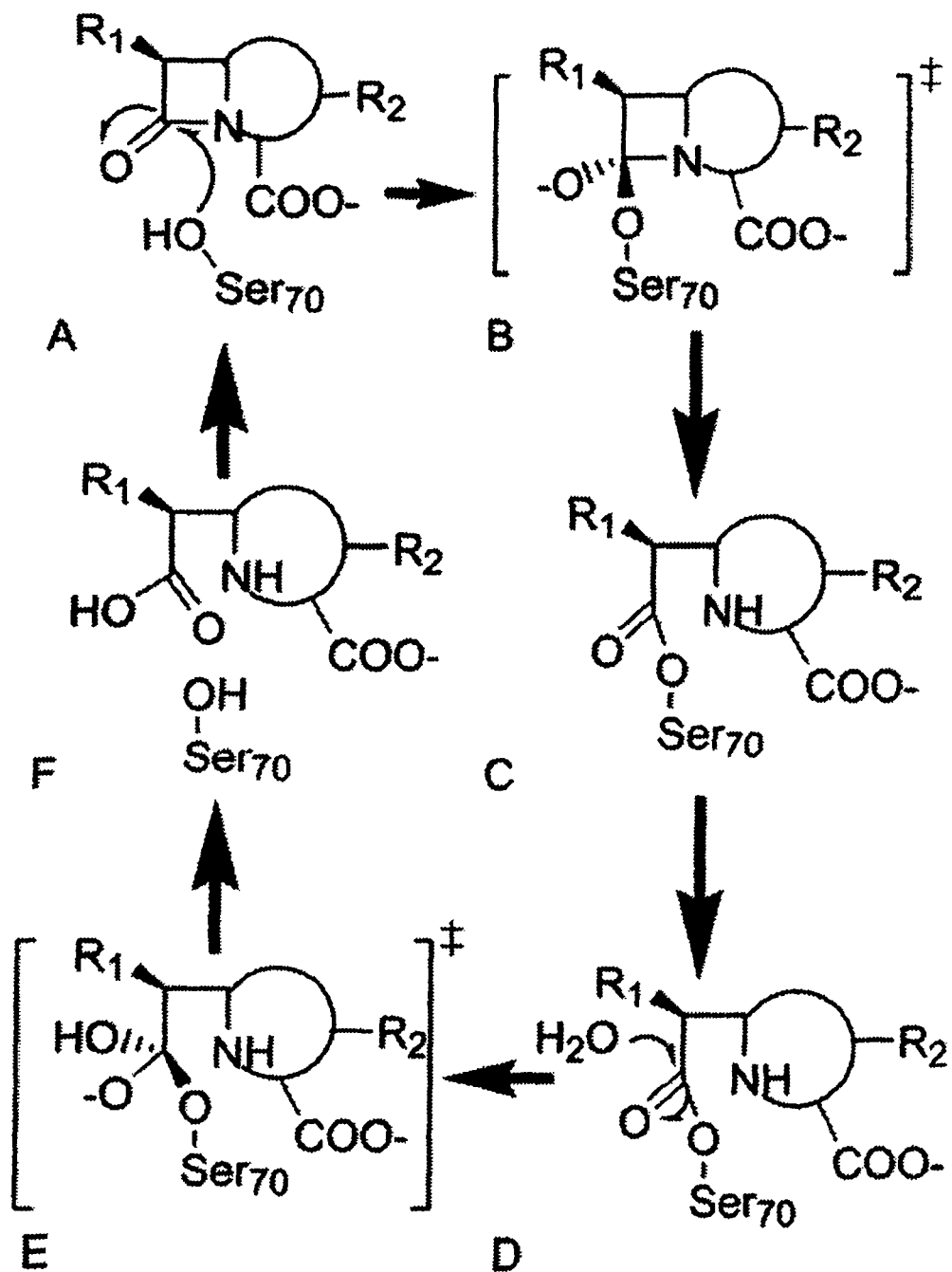

FIG. 20 illustrates a reaction scheme for a serine beta-lactamase. The reaction begins with the formation of a pre-covalent encounter complex (FIG. 20A), and moves through a high-energy acylation tetrahedral intermediate (FIG. 20B) to form a transiently stable acyl-enzyme intermediate, forming an ester through the catalytic residue Ser70 (FIG. 20C). Subsequently, the acyl-enzyme is attacked by hydrolytic water (FIG. 20D) to form a high-energy deacylation intermediate (FIG. 20E) (Minasov et al., 2002), which collapses to form the hydrolyzed product (FIG. 20F). The product is then expelled, regenerating free enzyme.

Figure 21:
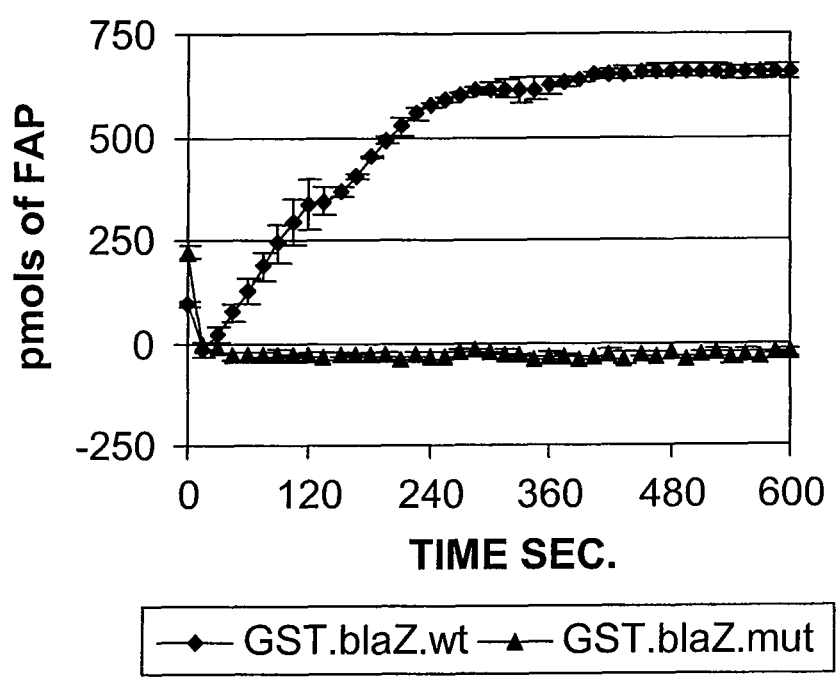

FIG. 21 shows hydrolysis of FAP by GST-BlaZ over time.

Figure 22:
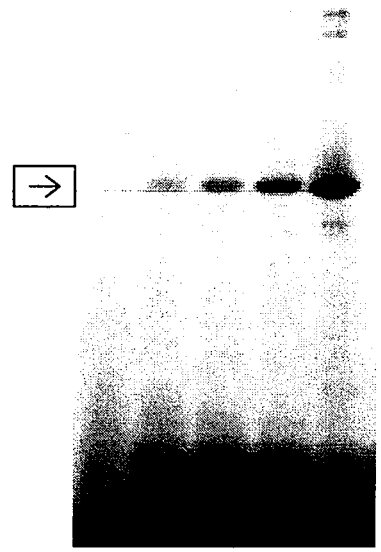

FIG. 22 shows the binding of bocellin to fusions of GST and BlaZ.E166D, BlaZ.N170Q or BlaZ.E166D:N170Q. Lane 1-dye/no BlaZ; lane 2-BlaZ.WT; lane 3-BlaZ.E166D; lane 4-BlaZ.N170Q; and lane 5-BlaZ.E166D:N170Q.

Figure 23:
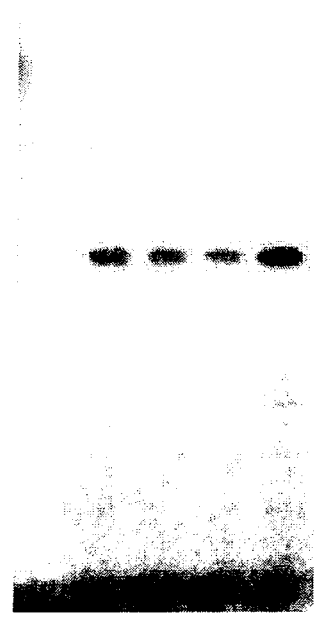

FIG. 23 shows the binding of CCF2 to fusions of GST and BlaZ.E166D, BlaZ.N170Q or BlaZ.E166D:N170Q. Lane 1-dye/no BlaZ; lane 2-GST-BlaZ.WT; lane 3-GST-BlaZ.E166D; lane 4-GST-BlaZ.N170Q; and lane 5-GST-BlaZ.E166D:N170Q.

FIG. 24 provides fluorescence and DIC images of living CHO-K1 cells transfected with a construct encoding GFP-connector-DhaA.H272F-NLS3 and stained with carboxytetramethylrhodamine-$C_{10}H_{21}NO_2$—Cl. Carboxytetramethylrhodamine filter-top left; GFP filter-top right; "A" and "B" overlaid-bottom left; overlaid image "C" and DIC image of the cell-bottom right. NLS3=tandem repeat of a nuclear localization sequence from SV40 T antigen.

FIG. 25 shows fluorescence images of living CHO-K1 cells transfected with a construct encoding GFP-β-arrestin2 (panel A) and a construct encoding DhaA.H272F-β-arrestin2 and stained with carboxytetramethylrhodamine-$C_{10}H_{21}NO_2$—Cl (panel B).

Figure 26:
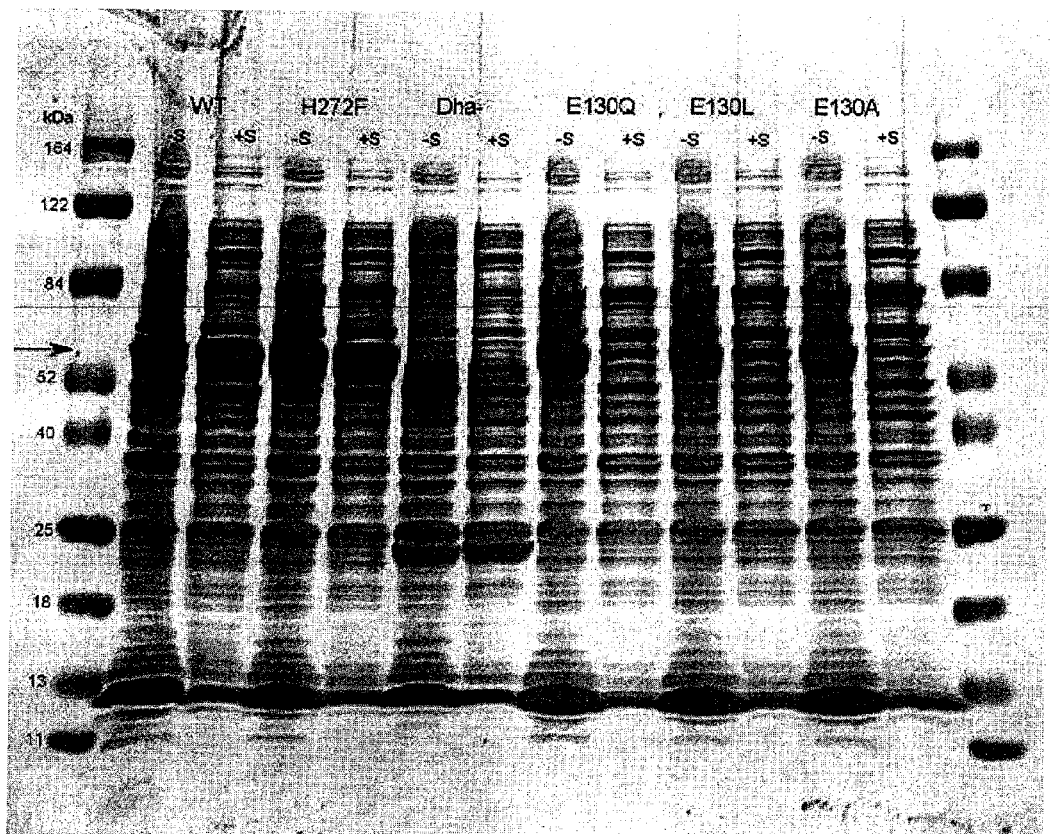

FIG. 26 shows an SDS-PAGE analysis of DhaA expression in E. coli. Lanes: 1, Molecular weight standards; 2, DhaA.WT crude lysate; 3, DhaA.WT cell-free lysate; 4, DhaA.H272F crude lysate; 5, DhaA.H272F cell-free lysate; 6, vector control crude lysate; 7, vector control cell-free lysate; 8, DhaA.E130Q Cl crude lysate; 9, DhaA.E130Q C1 cell-free lysate; 10, DhaA.E130L AS crude lysate; 11, DhaA.E130L AS cell-free lysate; 12, DhaA.E130A A12 crude lysate; 13, DhaA.E130A A12 cell-free lysate; 14, Molecular weight standards. The arrow indicates the location of the DhaA protein. -s, lysate before centrifugation; +s, lysate after centrifugation.

Figure 27:
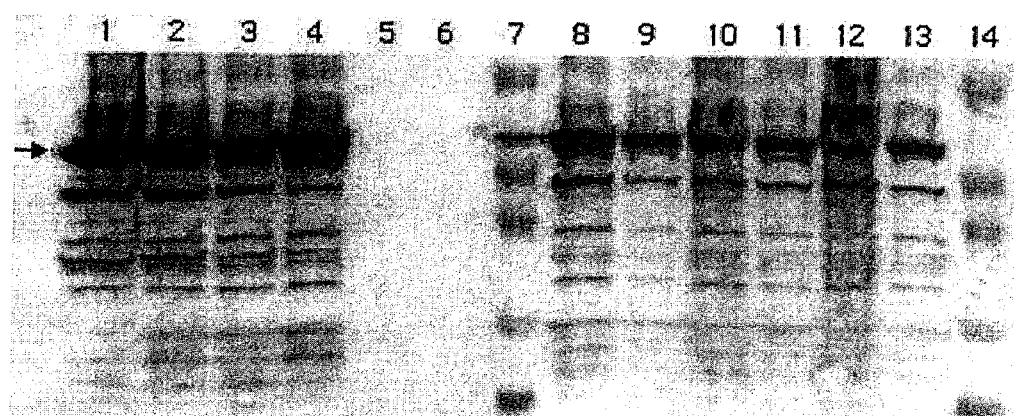

FIG. 27 shows an immunoblot analysis of DhaA containing lysates. Lanes: 1, DhaA.WT crude lysate; 2, DhaA.WT cell-free lysate; 3, DhaA.H272F crude lysate; 4, DhaA.H272F cell-free lysate; 5, vector control crude lysate; 6, vector control cell-free lysate; 7, Molecular weight standards; 8, DhaA.E130Q C1 crude lysate; 9, DhaA.E130Q C1 cell-free lysate; 10, DhaA.E130L AS crude lysate; 11, DhaA.E130L AS cell-free lysate; 12, DhaA.E130A A12 crude lysate; 13, DhaA.E130A A12 cell-free lysate; 14, Molecular weight standards. The arrow indicates the location of the DhaA protein.

Figure 28:
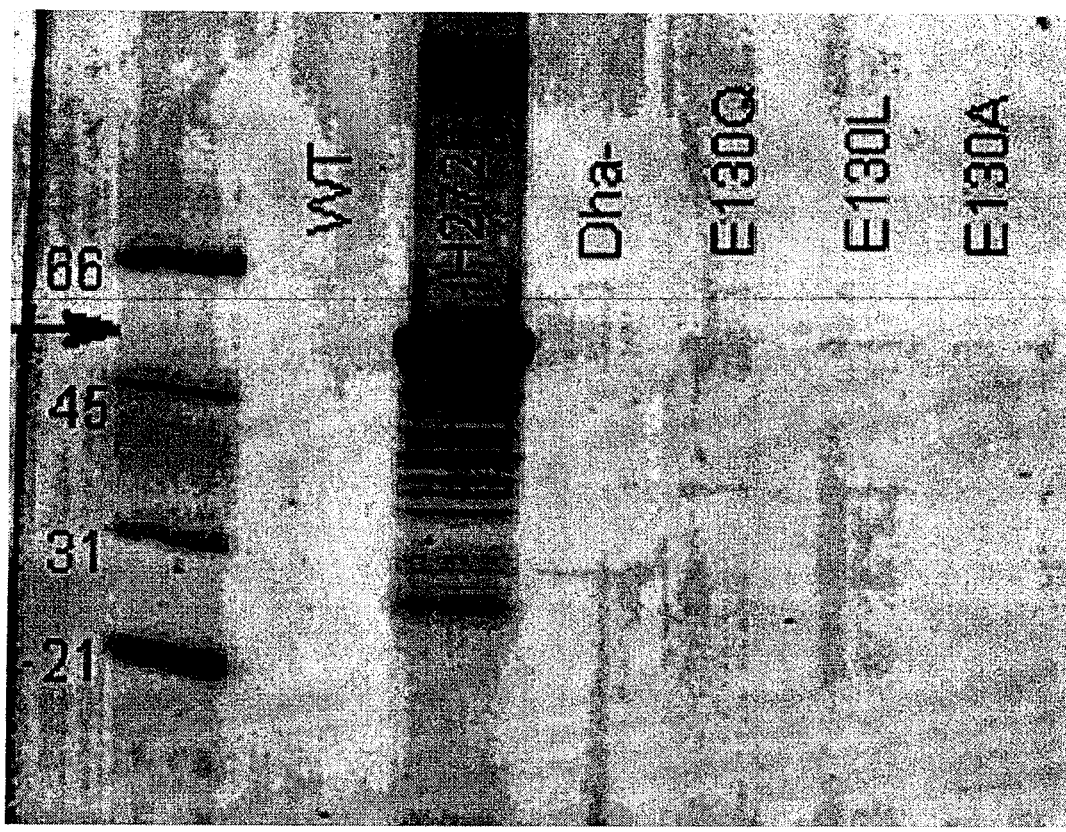

FIG. 28 provides fluoroimage analysis of in vitro covalent alkyl-enzyme formation. Lanes: 1, Fluorescent molecular weight standards; 2, DhaA.WT; 3, DhaA.H272F mutant; 4, DhaA-(vector only control); 5, DhaA.E130Q mutant; 6, DhaA.E130L mutant; 7, DhaA.E130A mutant. The arrow indicates the location of the fluorescent enzyme-alkyl covalent intermediate.

Figure 29:

FIG. 29 provides fluoroimage analysis of covalent alkyl-enzyme formation in whole cells. Lanes: 1, Fluorescent molecular weight standards; 2, DhaA.WT; 3, DhaA.H272F; 4, DhaA-(vector only control); 5, DhaA.E130Q; 6, DhaA.E130L; 7, DhaA.E130A; 8, Fluorescent molecular weight standards. The arrow indicates the location of the fluorescent enzyme-alkyl covalent intermediate.

Figure 30A:
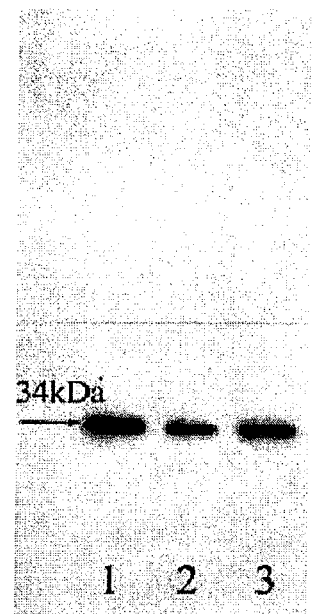
Figure 30B:
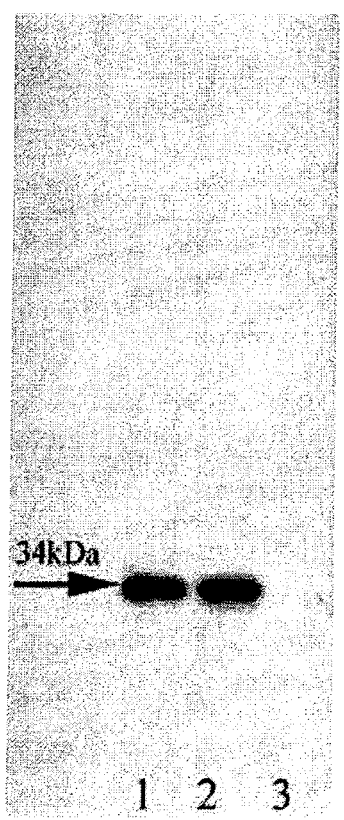

FIGS. 30A-B show Western blot analyses of DhaA-Flag captured on streptavidin (SA) coated beads. CHO-K1 cells transiently expressing DhaA.H272F-Flag were treated with (A) or without (B) biotin-$C_{10}H_{21}NO_2$—Cl (25 μM, 0.1% DMSO, 60 minutes, 37° C.). Excess biotin-$C_{10}H_{21}N_1O_2$—Cl was washed out, cells were lysed, and 10 μl of cell lysate was incubated with 5 μl of SA-coated beads (Pierce) for 60 minutes at room temperature (RT). Cell lysates (lane 1), proteins which were not bound to beads (lane 2), and proteins which were bound to beads (lane 3) were resolved on SDS-PAGE, transferred to nitrocellulose membrane, and probed with anti-Flag antibody (Sigma).

Figure 30C:
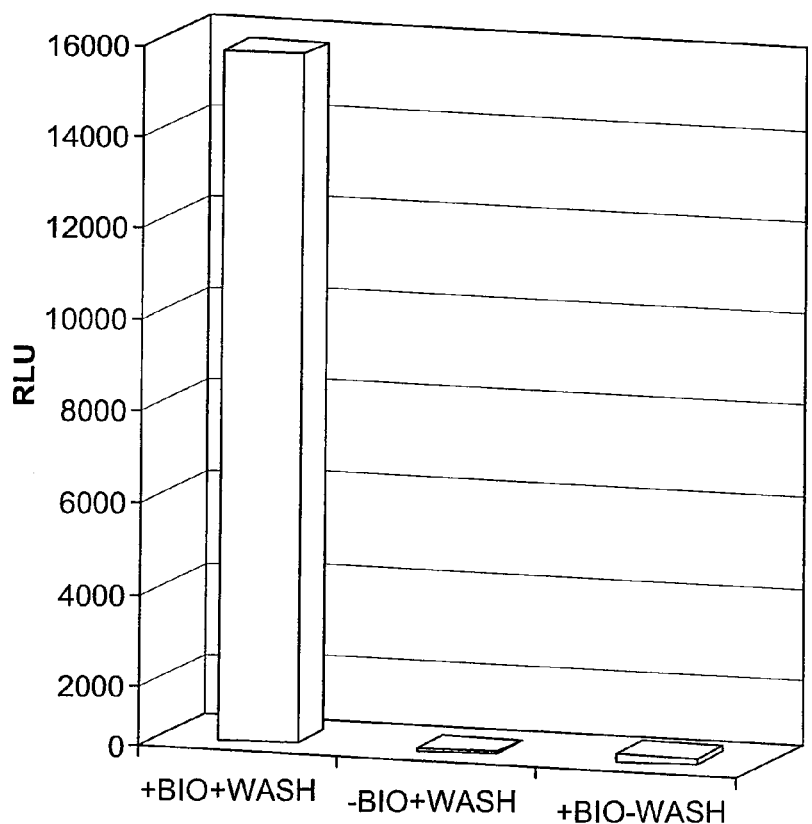
Figure 30D:

FIGS. 30C-D illustrate analyses of hR.Luc-DhaA captured on SA coated beads. CHO-K1 cells transiently expressing hR.Luc-connector-DhaA.H272F-Flag were treated with or without biotin-$C_{10}H_{21}N_1O_2$—Cl (25 μM, 0.1% DMSO, 60 minutes, 37° C.). Cells were lysed, and 10 μl of cell lysate was incubated with 5 μl of SA-coated beads (Pierce) for 60 minutes at room temperature. Unbound material was washed out, and hR.Luc activity determined using Promega's "*Renilla* Luciferase Assay System" (C) or captured hR.Luc analyzed by Western blot (D). C) Column 1, cells treated with biotin-$C_{10}H_{21}NO_2$—Cl, and excess biotin-$C_{10}H_{21}NO_2$—Cl washed out; column 2, untreated cells; and column 3, cells treated with biotin-$C_{10}H_{21}NO_2$—Cl without washing out excess biotin-$C_{10}H_{21}N_1O_2$—Cl. D) Cell lysate (lane 1), proteins which were not bound to beads (lane 2), and proteins which were bound to beads (lane 3) were resolved on SDS-PAGE, transferred to nitrocellulose membrane, and probed with anti-R.Luc antibody (Chemicon).

Figure 31A:
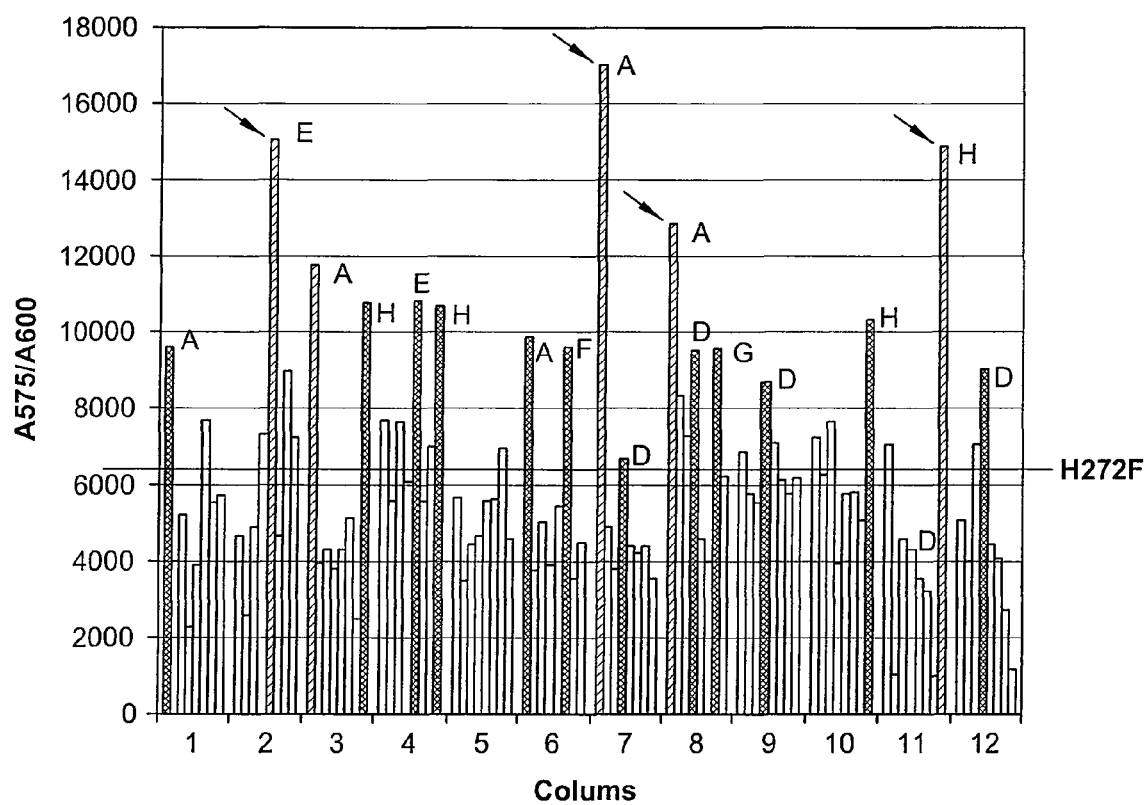
Figure 31B:
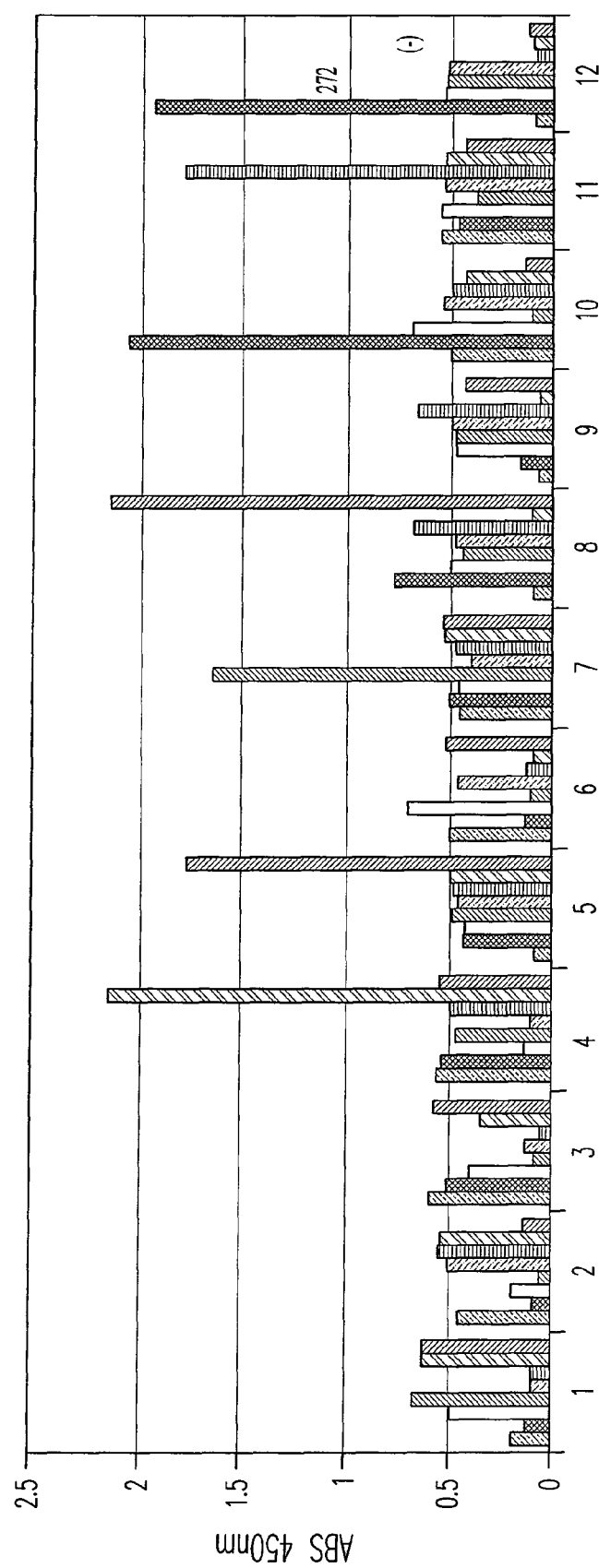

FIGS. 31A-B show the identification of potential improvements from a DhaA.H272F K175/C176 library using an in vivo carboxytetramethylrhodamine-$C_{10}H_{21}NO_2$—Cl labeling screening assay (panel A) and the identification of potential improvements from a DhaA.H272F K175/C176 library using an anti-FLAG immobilized protein assay (panel B). DhaA mutants with 2-fold higher activity than the H272F parent (horizontal line) are identified by arrows in panel A. DhaA mutants with signals 3- to 4-fold higher than DhaA.H272F are identified in panel B. DhaA.H272F parental and DhaA-controls (in triplicate) are located in wells 12C-E and 12F-H, respectively.

Figure 32:
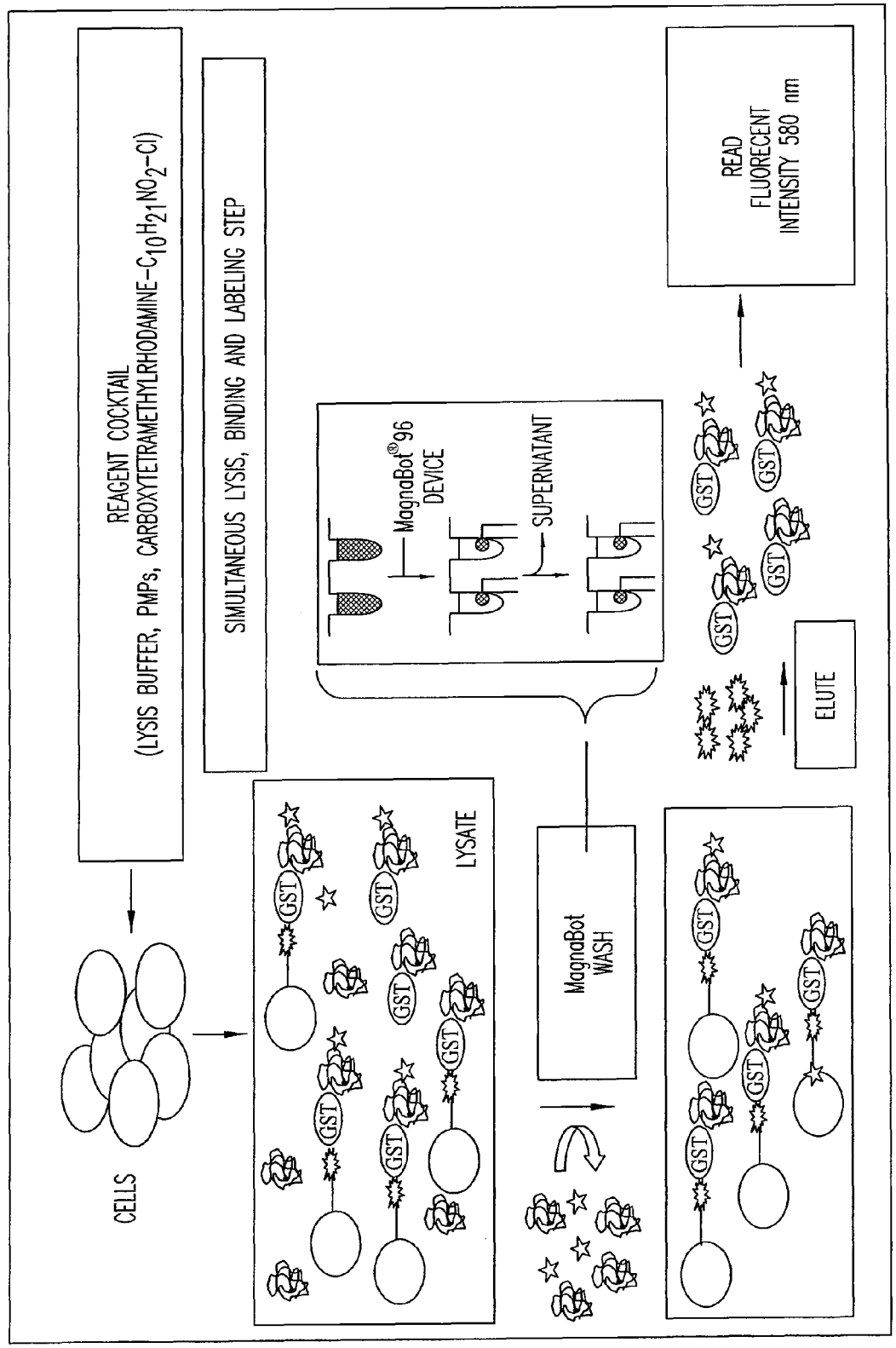

FIG. 32 depicts an overview of the MagneGST™ assay developed for high-throughput screening of DhaA libraries using carboxytetramethylrhodamine-$C_{10}H_{21}NO_2$—Cl.

Figure 33A:
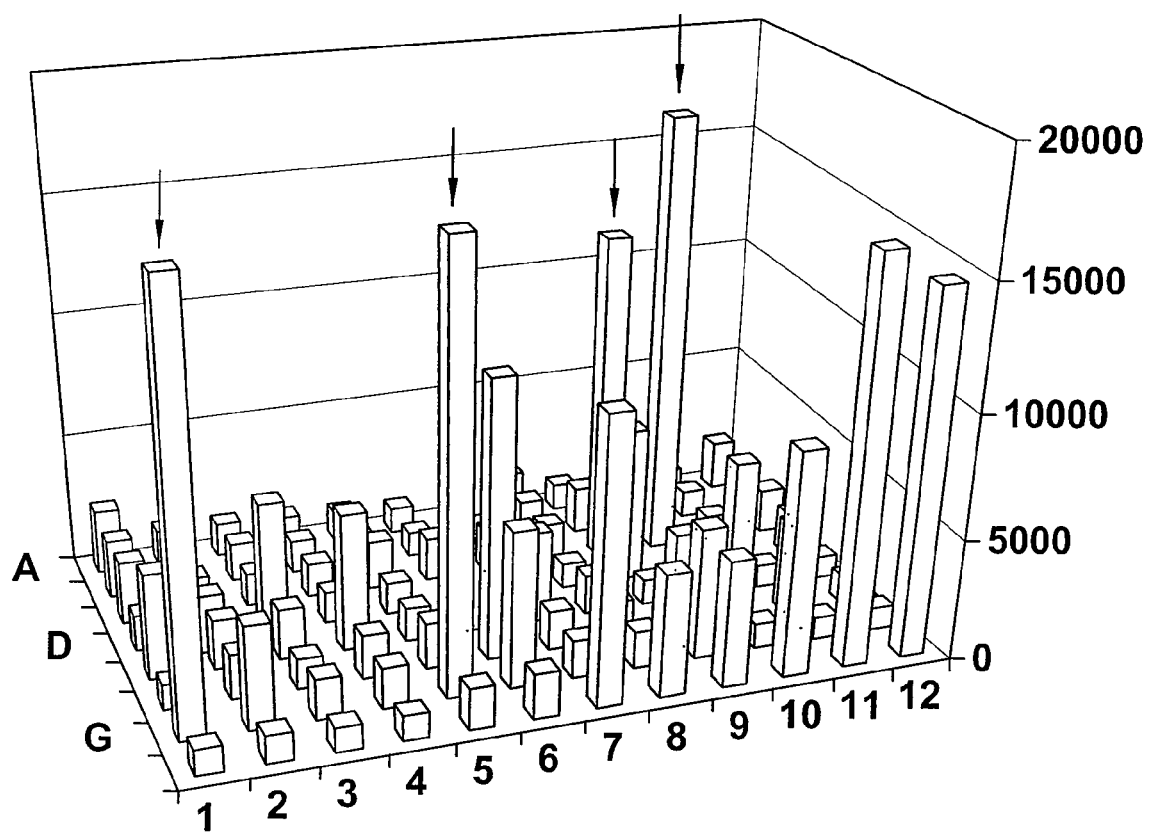
Figure 33B:
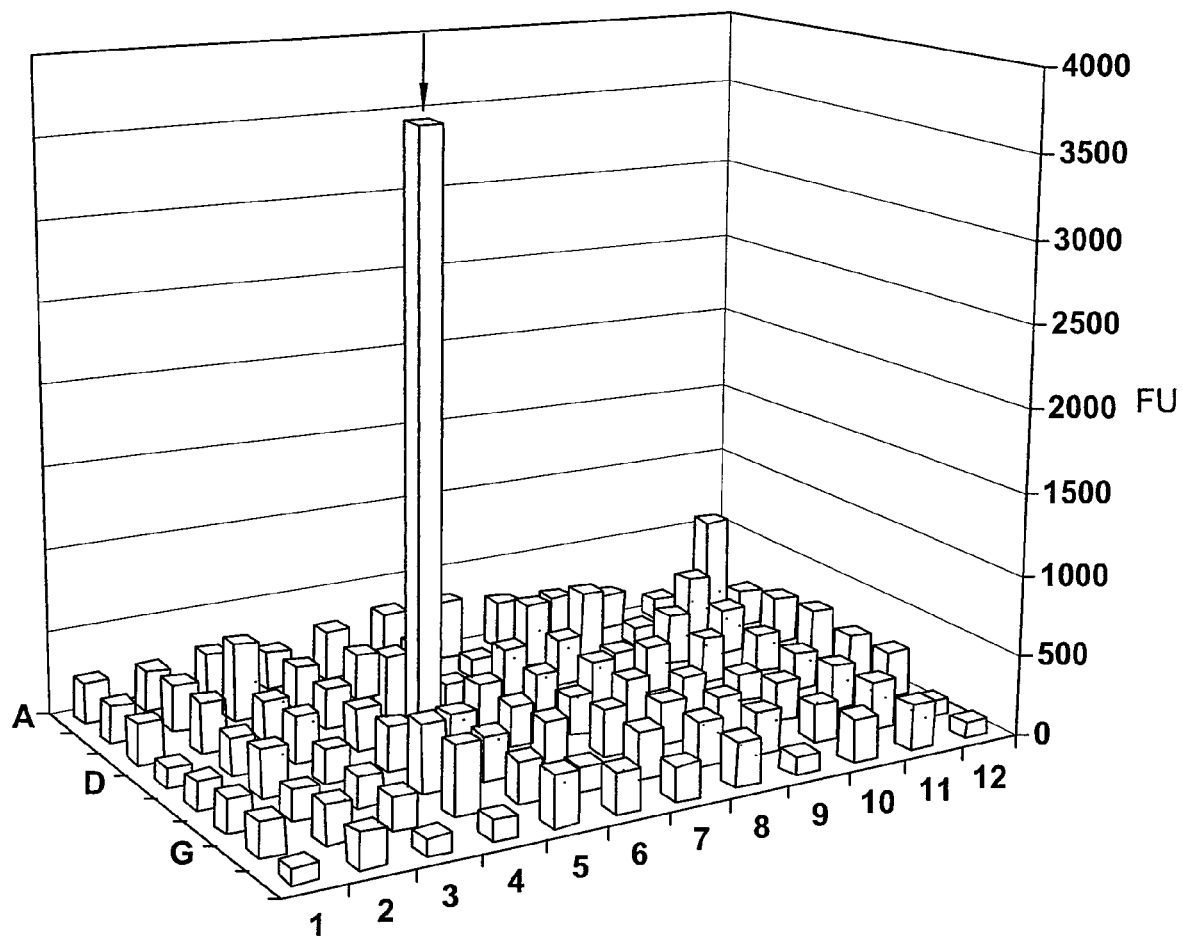

FIGS. 33A-B shows the identification of potential improvements (i.e., hits) from mutant DhaA protein libraries. Representative screening plates from the DhaA.H272F C176

(panel A) and DhaA.D106C K175/C176 NNK (panel B) libraries are shown. Arrows indicate potentially improved clones.

Figure 34A:
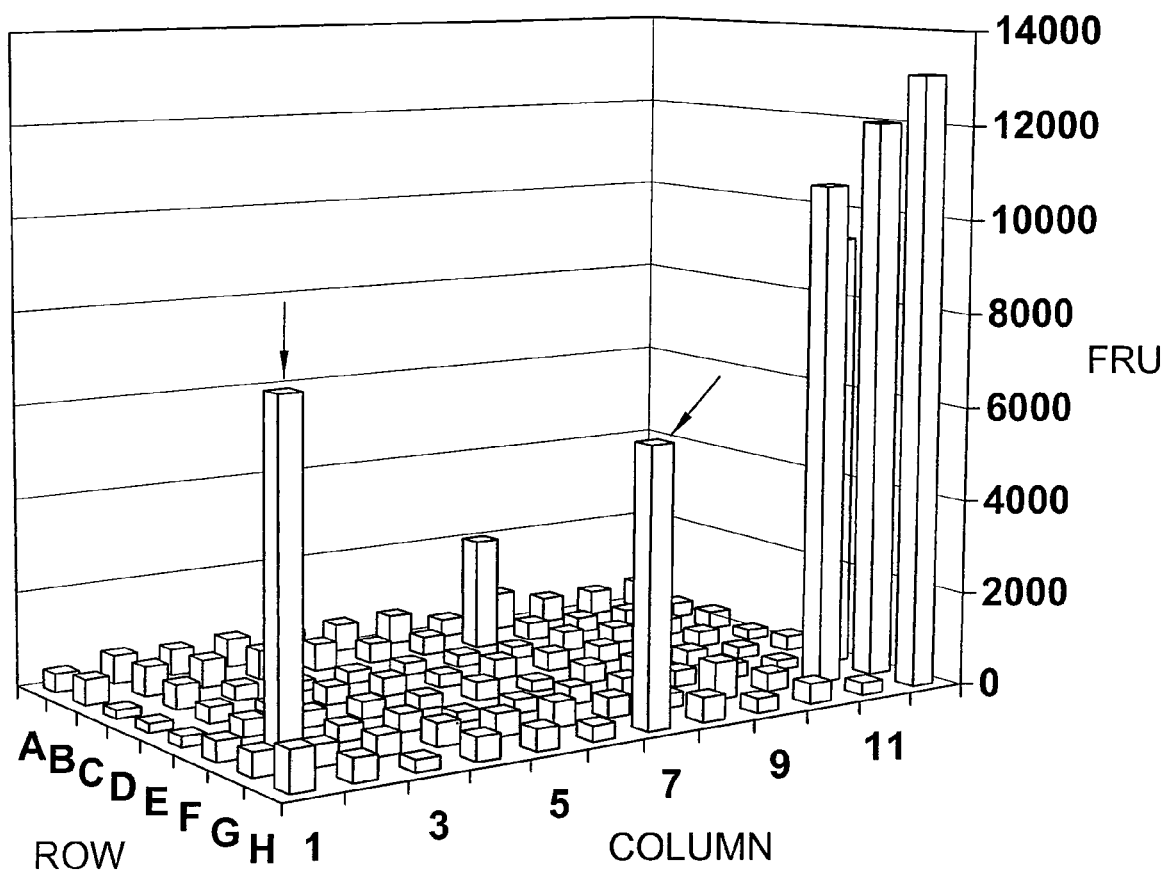
Figure 34B:
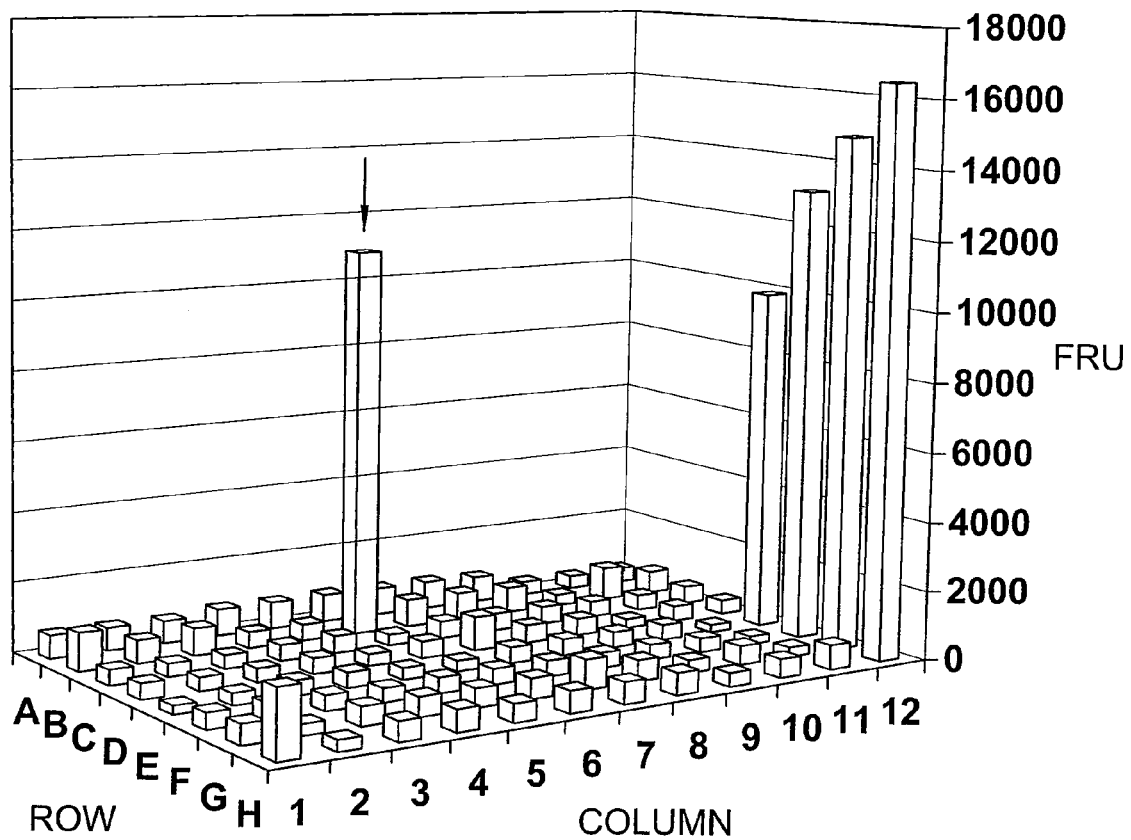

FIGS. 34A-B show the identification of potential improvements (i.e., hits) from mutant DhaA protein libraries. Shown are two representative plates from the DhaA.H272F Y273 (NNK) library screening using the MagneGST™-based screening assay. Arrows indicate potentially improved clones.

FIGS. 35A-B show the sequence of hits at positions 175, 176 and 273 for DhaA.H272F (panel A) and the sequence hits at positions 175 and 176 for DhaA.D106C (panel B).

Figure 36A:
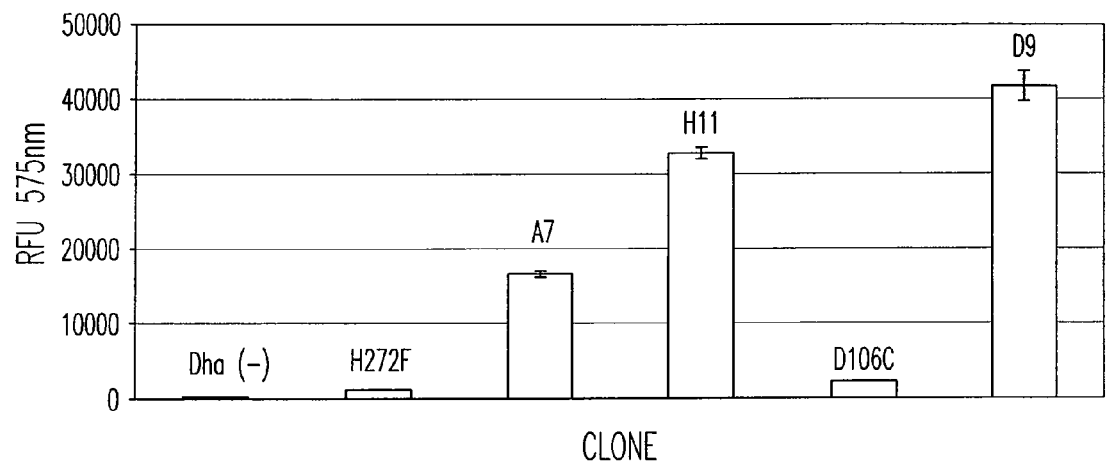
Figure 36B:
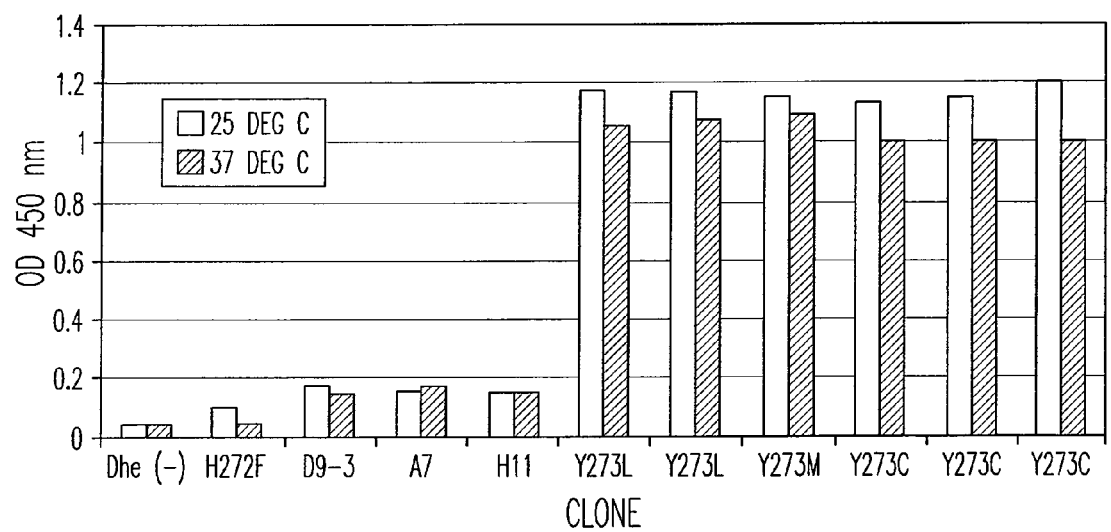

FIGS. 36A-B illustrate the relative activity of identified DhaA hits compared to parental proteins in secondary assays. A). The indicated DhaA mutants were re-assayed using the MagneGST™ assay and carboxytetramethylrhodamine-$C_{10}H_{21}NO_2$—Cl (n=3). B). The indicated DhaA mutants were analyzed using the protein immobilization assay and biotin-PEG4-14-Cl.

Figure 37A:
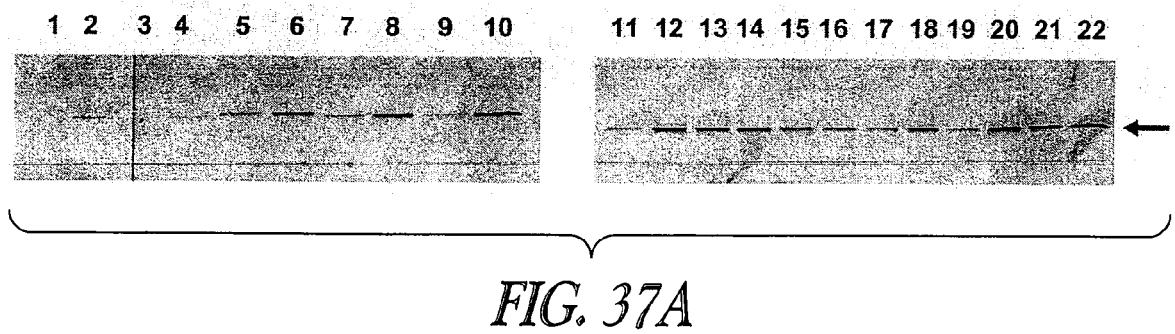
Figure 37B:
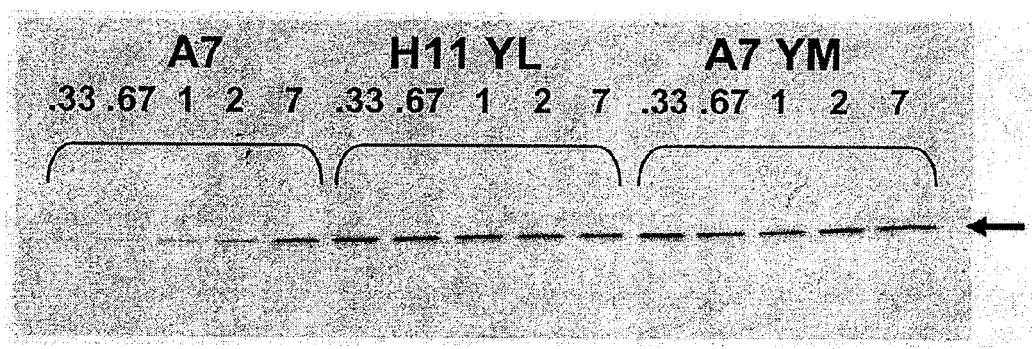
Figure 37C:
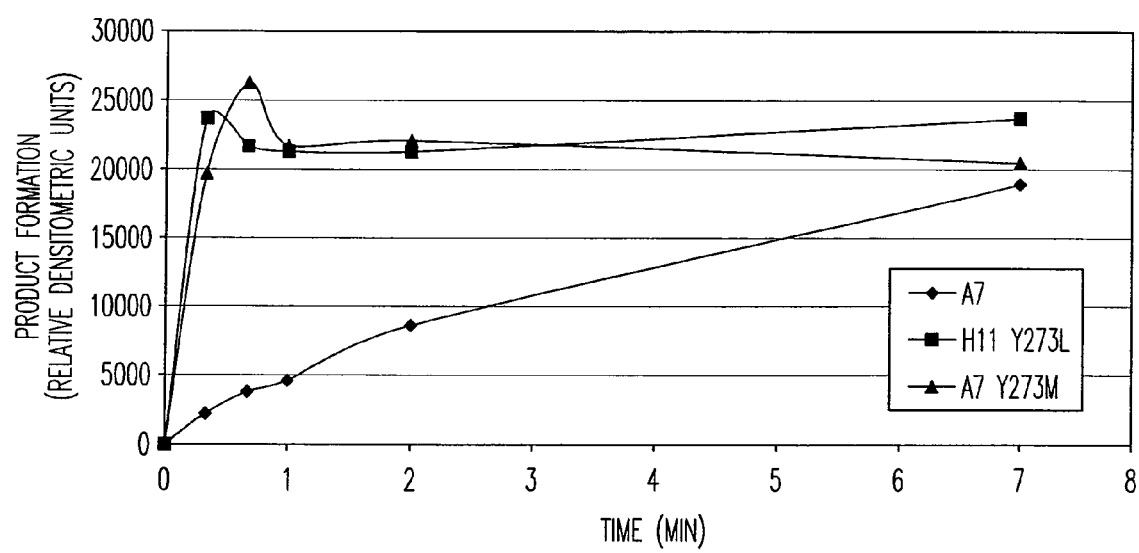

FIGS. 37A-C demonstrate the relative labeling rates of purified DhaA mutants with carboxytetramethylrhodamine-$C_{10}H_{21}NO_2$—Cl. A). SDS-PAGE and fluorimage gel analysis of labeling time-course. Lanes 1 and 2, DhaA.D106 30H4; lanes: 3 and 4, H272F; lanes 5 and 6, DhaA.H272F ES; lanes 7 and 8, DhaA.H272F H11; lanes 9 and 10, DhaA.H272F A7; lanes 11 and 12, DhaA.H272F A7; lanes 13 and 14, DhaA.H272F A7YM; lanes 15 and 16, DhaA.H272F YL; lanes 17 and 18, DhaA.H272F 2G7; lanes 19 and 20, DhaA.H272F 3A7; lanes 21 and 22, DhaA.H272F H11YL. Reactions in odd and even numbered lanes were incubated for 2 and 30 minutes, respectively, at room temperature. B). SDS-PAGE and fluorimage gel analysis of labeling time-course of first generation, DhaA.H272F A7, and second-generation, DhaA.H272F H11YL and DhaA.H272F A7YM mutants. Lane: 1, 20 seconds; lane 2, 40 seconds; lane 3, 1 minute; lane 4, 2 minutes; and lane 5, 7 minutes. Arrows indicate the presence of fluorescently labeled DhaA fusion proteins. C). Rates of DhaA labeling with carboxytetramethylrhodamine-$C_{10}H_{21}NO_2$—Cl. The fluorescent products shown in panel B were quantitated and plotted versus time.

Figure 38A:
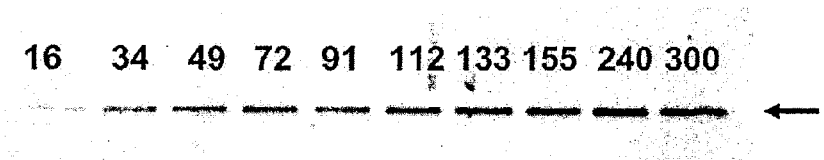
Figure 38B:
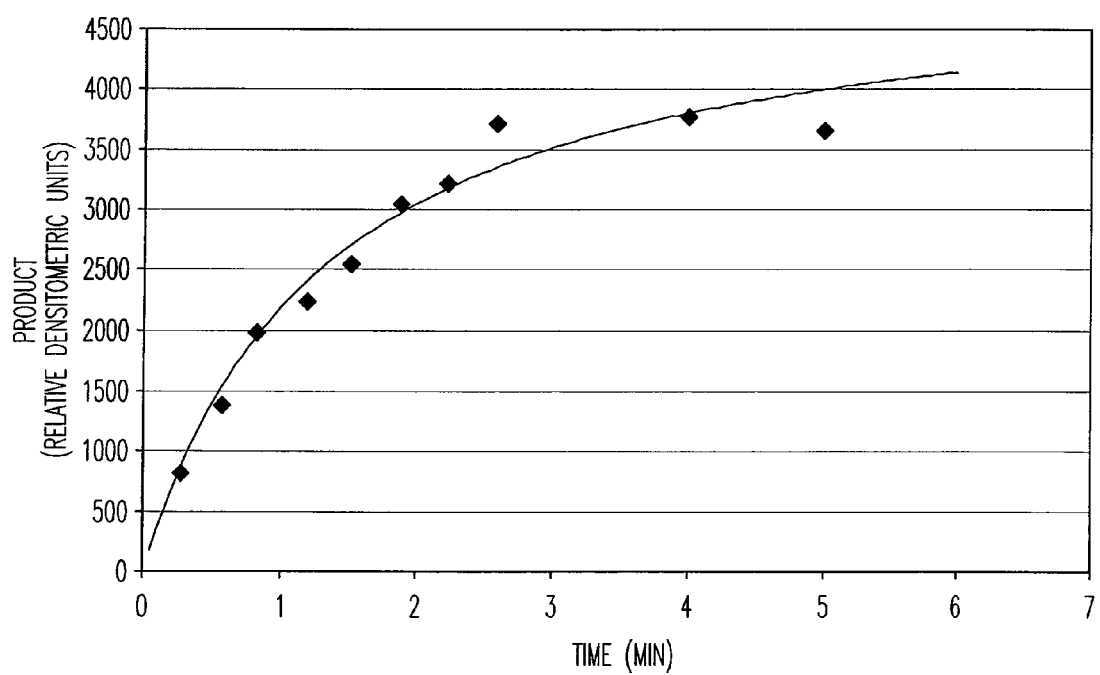

FIGS. 38A-B depict the labeling time-course of DhaA.H272F H11YL. A). SDS-PAGE and fluorimage gel analysis of purified DhaA.H272F H11YL with carboxytetramethylrhodamine-$C_{10}H_{21}NO_2$—Cl. The indicated times are in seconds. An arrow indicates the location of labeled DhaA.H272F H11YL. B). Rate of DhaA.H272F H11YL labeling. The fluorescent products shown in panel A were quantitated and plotted versus time.

Figure 39A:
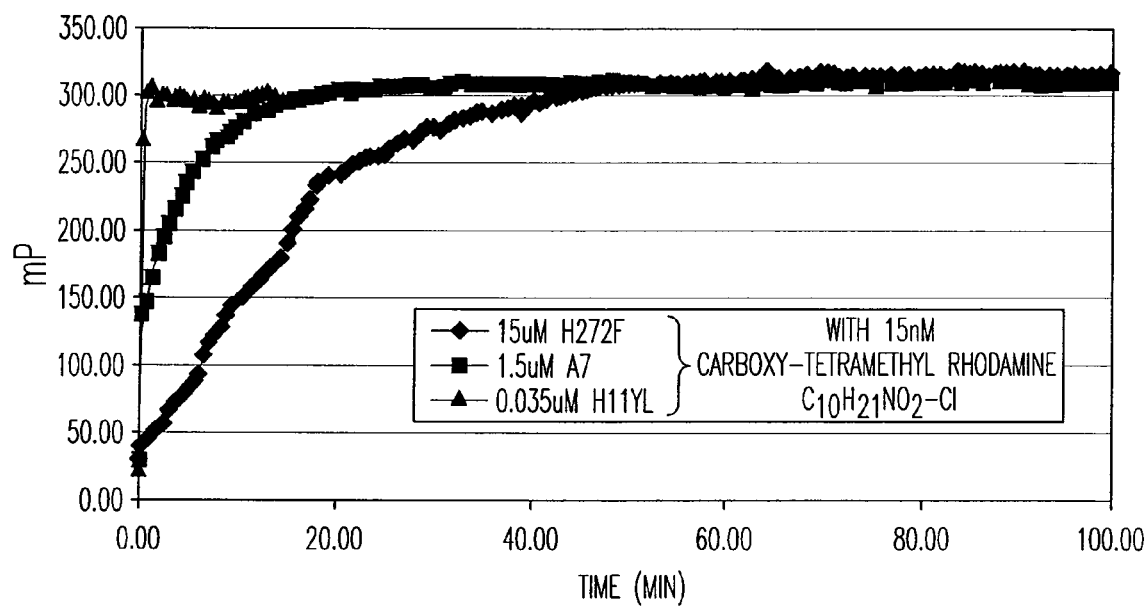
Figure 39B:
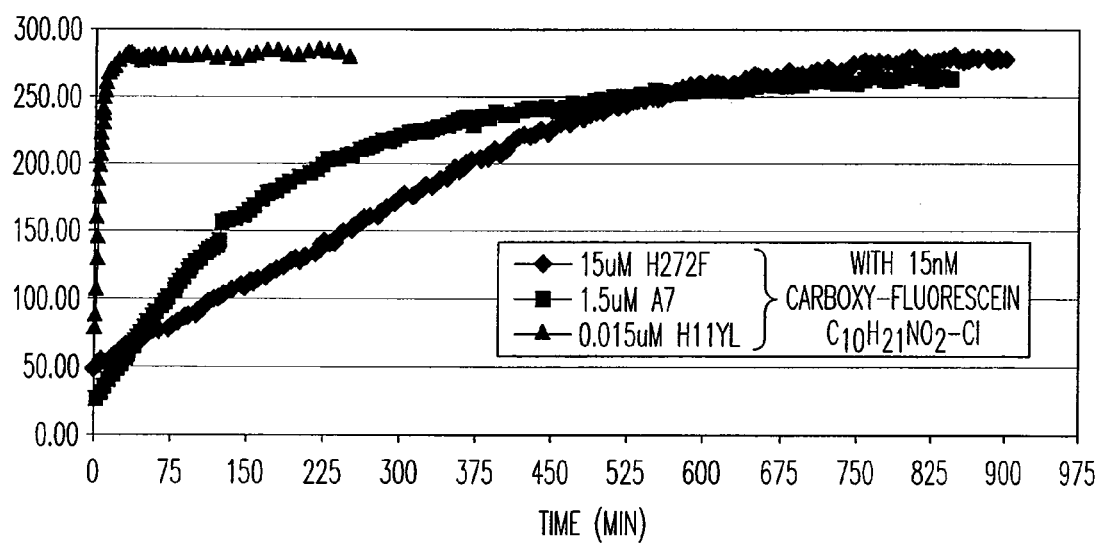

FIGS. 39A-B show fluorescence polarization analysis of DhaA mutants using (A) carboxytetramethylrhodamine-$C_{10}H_{21}NO_2$—Cl and (B) carboxyfluorescein-$C_{10}H_{21}NO_2$—Cl.

FIG. 40 shows the second order rate constants ($M^{-1}$ $sec^{-1}$) of parental (DhaA.H272F and DhaA.D106C), and first and second generation DhaA mutants determined by fluorescence polarization (FP).

Figure 41:
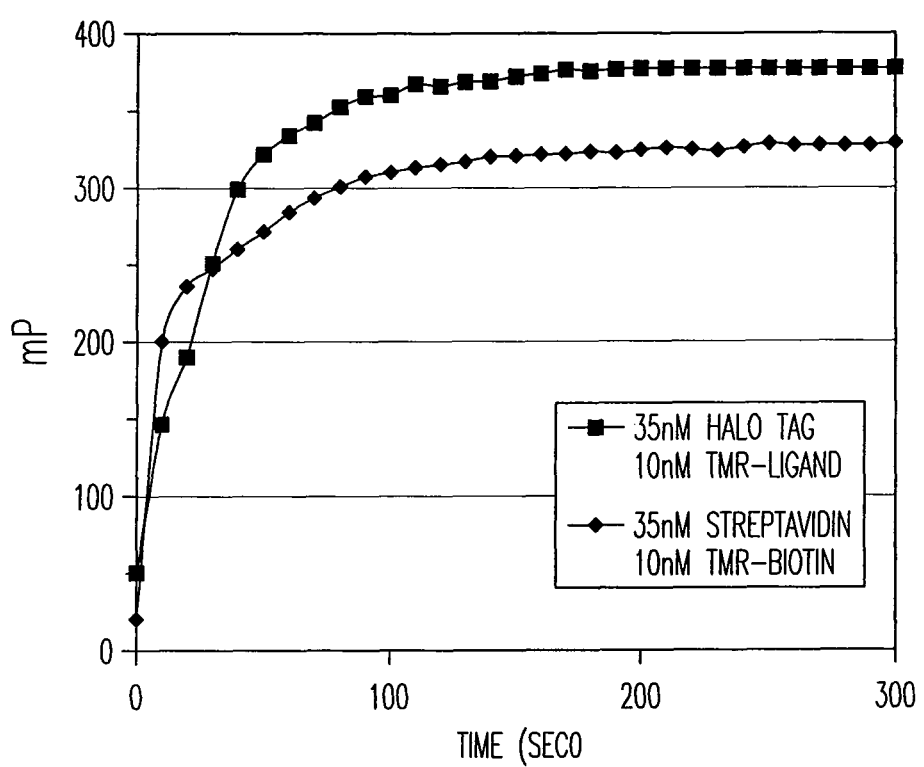

FIG. 41 illustrates a comparison of the labeling rates of DhaA.H272F H11YL("HaloTag") to carboxytetramethylrhodamine-$C_{10}H_{21}NO_2$—Cl and carboxytetramethylrhodamine-coupled biotin to streptavidin using fluorescence polarization.

FIG. 42 depicts the structural models of the DhaA.H272F and DhaA.H272F H11YL substrate tunnels without (panels A and C) and with (panels B and D) carboxytetramethylrhodamine-coupled substrate.

FIG. 43 shows the results of thermostability studies of purified DhaA proteins. A). Analysis of DhaA.H272F parental and select first generation DhaA mutants. B). Analysis of DhaA.H272F-based second generation DhaA mutants.

Figure 44:
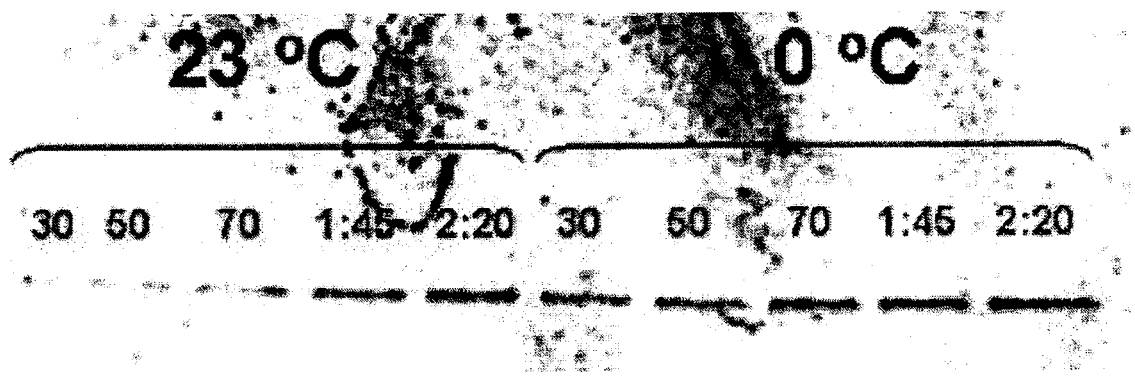

FIG. 44 demonstrates the effect of low temperature on DhaA.H272F H11YL reaction rates. Following incubation at either 4° C. or 23° C., 10 μL aliquots of the reaction mixture were quickly added to an equivalent amount of SDS-loading dye preincubated at 95° C. The resulting SDS-PAGE gel was examined by fluorimage analysis.

FIG. 45 illustrates the immobilization of DhaA to solid supports. A). General reaction scheme between DhaA.H272F mutants and immobilized biotin-chloroalkanes. B). Titration of select DhaA mutants against immobilized biotin-PEG-14-Cl.

Figure 46A:
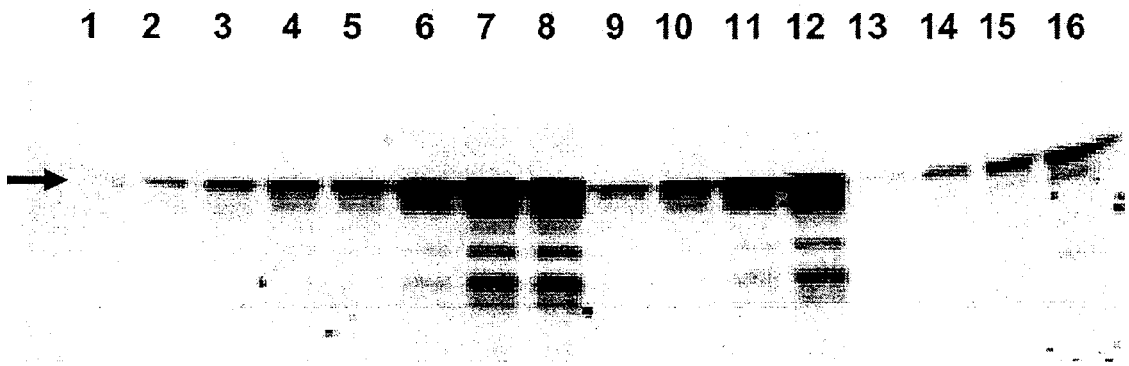
Figure 46B:
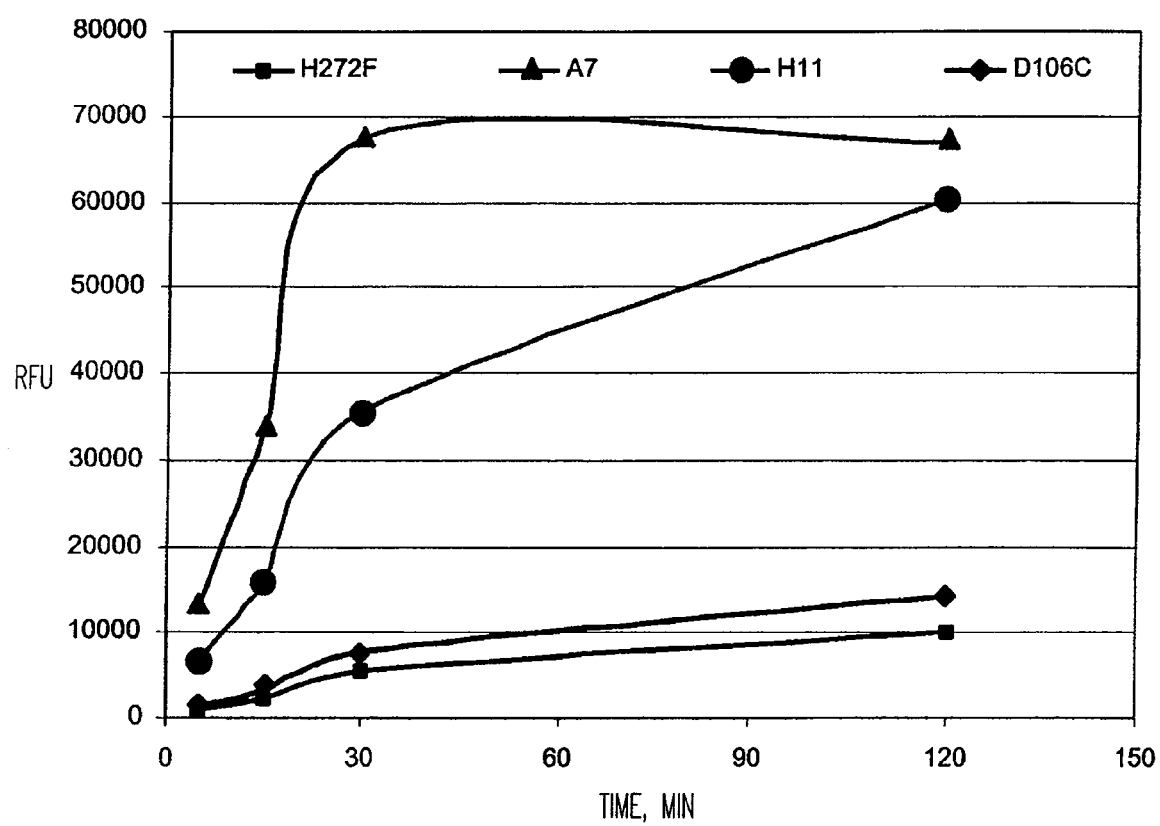

FIGS. 46A-B show the in vivo labeling of parental and first generation DhaA mutants expressed in CHO-K1 cells. A). SDS-PAGE fluorimage gel analysis of DhaA mutants following in vivo labeling with carboxytetramethylrhodamine-$C_{10}H_{21}NO_2$—Cl (5 μM). Lanes: 1-4, DhaA.H272F; lanes 5-8, DhaA.H272F A7; lanes 9-12, DhaA.H272F H11; and lanes 13-16, DhaA.D106C. Each lane in the series represents 5, 15, 30 and 120 minute time points. An arrow denotes the location of labeled DhaA. B). Quantitation of carboxytetramethylrhodamine-$C_{10}H_{21}NO_2$—Cl binding to DhaA mutants.

Figure 46C:
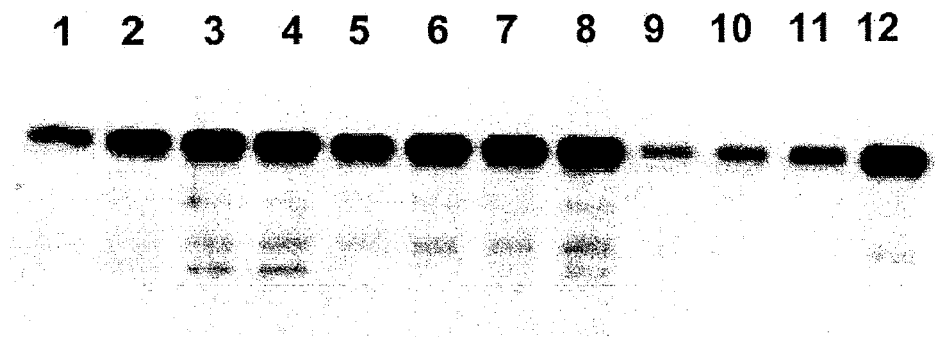
Figure 46D:
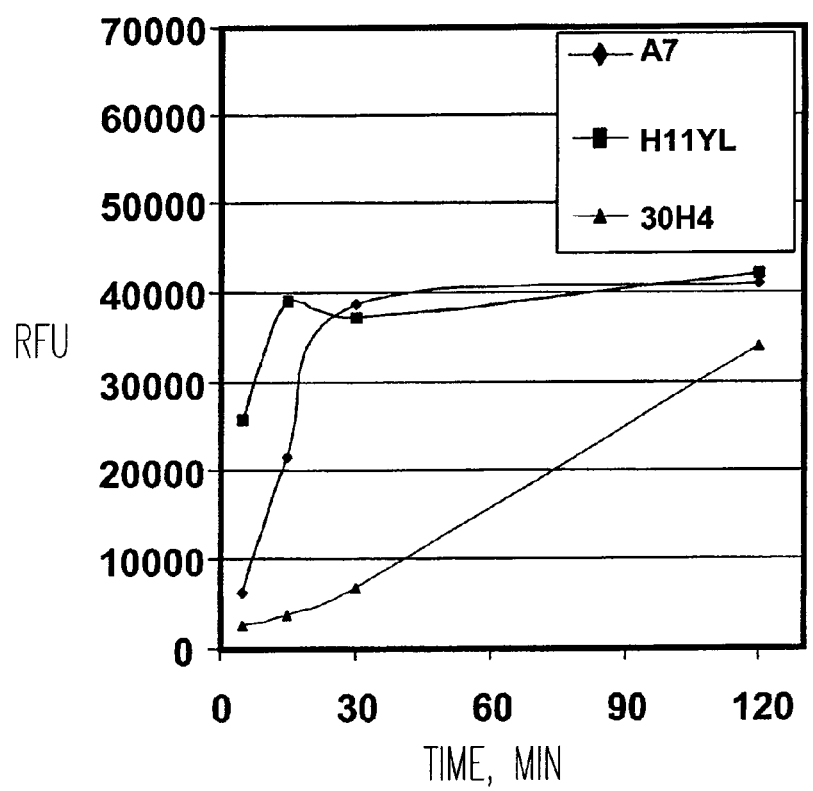

FIGS. 46C-D demonstrate the in vivo labeling of first and second generation DhaA mutants expressed in CHO-K1 cells. C). SDS-PAGE fluorimage gel analysis of DhaA mutants following in vivo labeling with carboxytetramethylrhodamine-$C_{10}H_{21}NO_2$—Cl (5 μM). Lanes: 1-4, DhaA.H272F A7; lanes 5-8, DhaA.H272F H11YL; and lanes 9-12, DhaA.D106C 30H4. Each lane in the series represents 5, 15, 30 and 120 minute time points. D). Quantitation of carboxytetramethylrhodamine-$C_{10}H_{21}NO_2$—Cl binding to DhaA mutants.

FIG. 47A-C show the labeling of DhaA.H272F A7 and DhaA.H272F H11YL with different concentrations of carboxytetramethylrhodamine-$C_{10}H_{21}NO_2$—Cl in mammalian cell lysates.

Figure 48A:
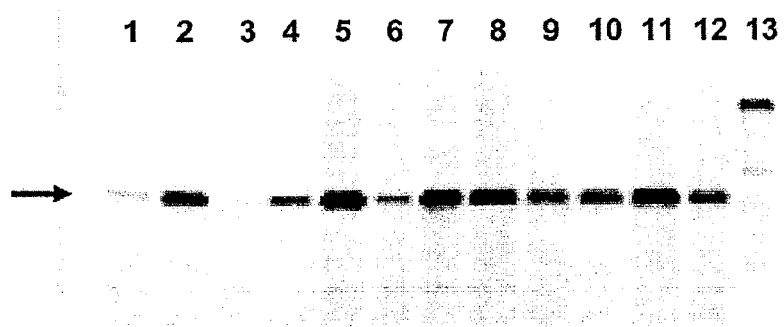
Figure 48B:
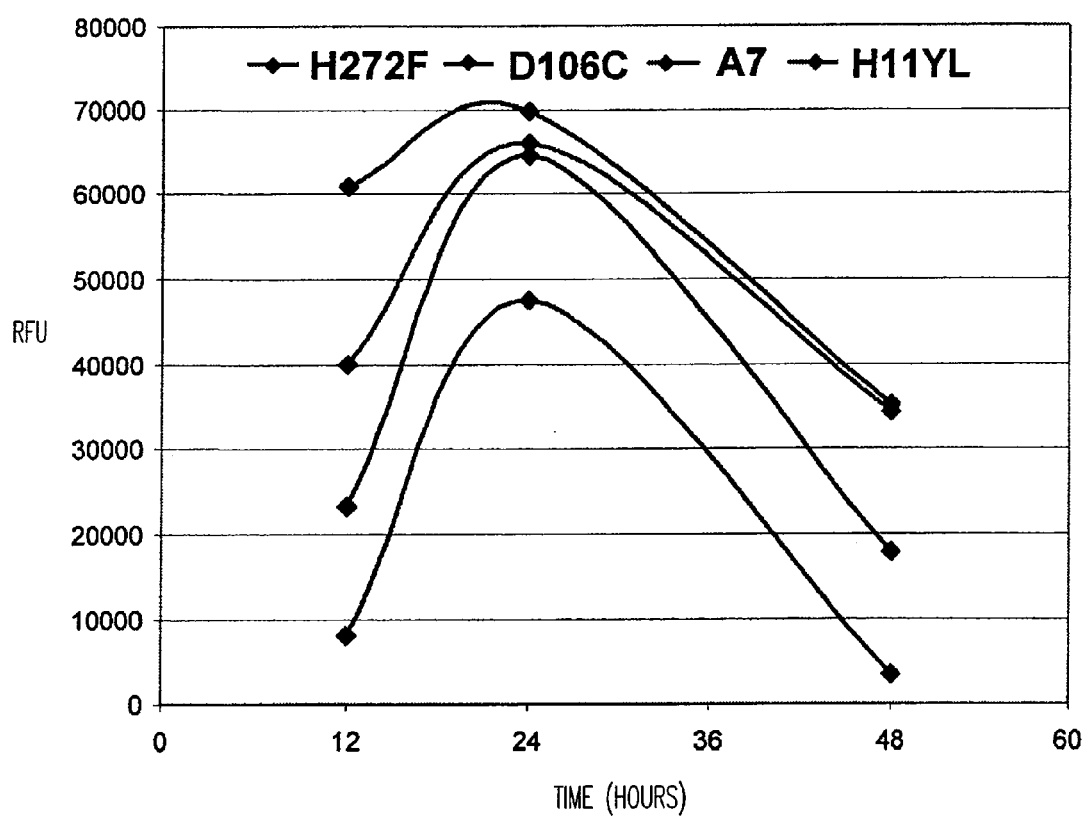

FIGS. 48A-B show the stability of parental and first generation DhaA mutants in vivo. A). Fluorimage gel analysis of carboxytetramethylrhodamine-$C_{10}H_{21}NO_2$—Cl labeled DhaA mutants. Lanes: 1-3, DhaA.H272F; lanes 4-6, DhaA.D106C; lanes 7-9, DhaA.H272F A7; lanes 10-12, DhaA.H272F H11; and lane 13 standards. Lanes 1, 4, 7 and 10 represent samples taken 12 hours post-transfection. Lanes 2, 5, 8, and 11 represent samples taken 24 hours post-transfection. Lanes 3, 5, 8 and 12 represent samples taken 48 hours post-transfection. Arrow indicates the location of labeled DhaA mutants. B). Quantitation of fluorimaged gel.

Figure 48C:
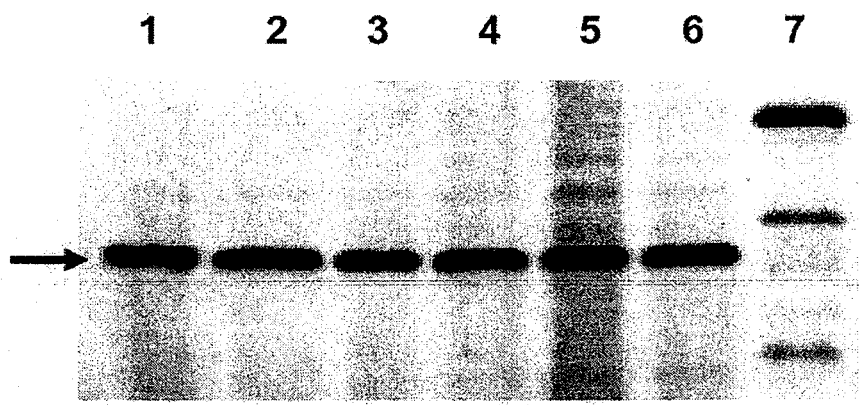
Figure 48D:
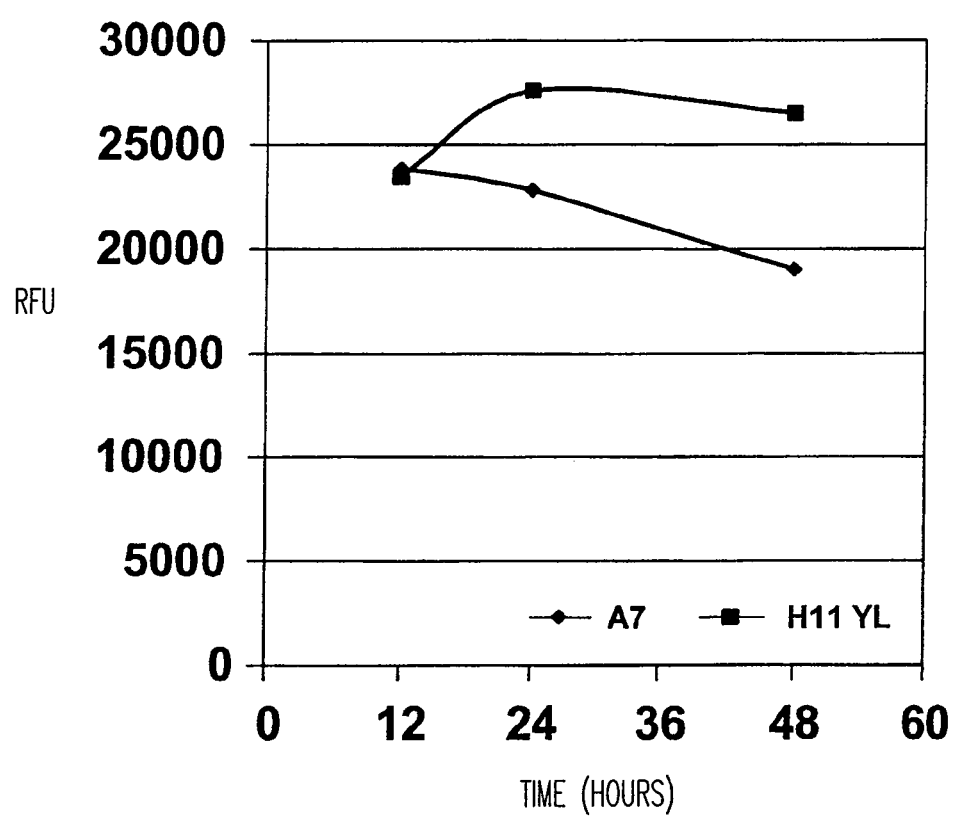

FIGS. 48C-D shows a comparison of the stability of DhaA.H272 mutants in vivo. A). Fluorimage gel analysis of carboxytetramethylrhodamine-$C_{10}H_{21}NO_2$—Cl labeled DhaA mutants. Lanes: 1-3, DhaA.H272F A7; lanes 4-6, DhaA.H272F H11YL; and lane 7 standards. Lanes 1 and 4 represent samples taken 12 hours post-transfection. Lanes 2 and 5 represent samples taken 24 hours post-transfection. Lanes 3 and 6 represent samples taken 48 hours post-transfection. Arrow indicates location of DhaA variants. B). Quantitation of the fluorimaged gel.

FIG. 49 shows the nucleotide (SEQ ID NO:80) and amino acid (SEQ ID NO:81) sequence of DhaA.H272 H11YL which is in pHT2. The restriction sites listed were incorporated to facilitate generation of functional N- and C-terminal fusions.

Figure 50A:
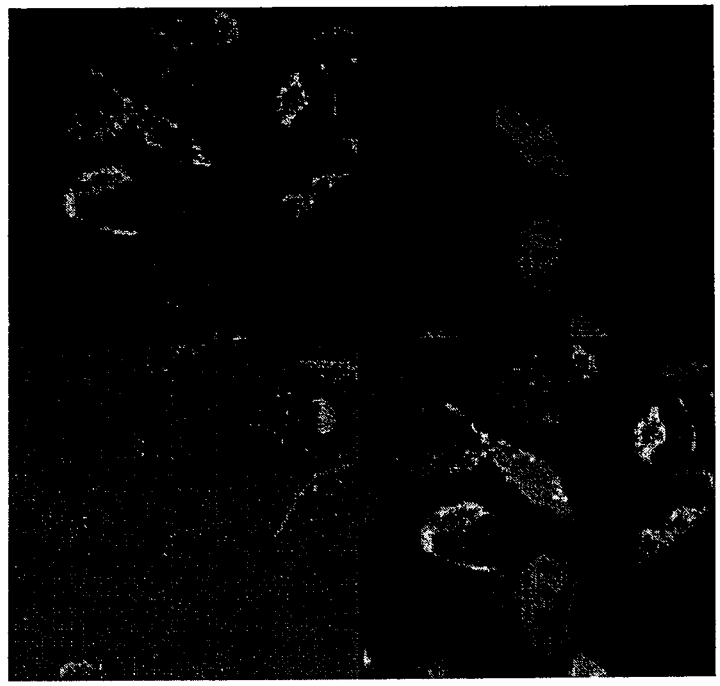
Figure 50B:

FIGS. 50A-B provide fluorescence and DIC images of living HeLa cells transfected with a vector coding for DhaA.H272F H11YL stained with carboxytetramethylrhodamine-$C_{10}H_{21}NO_2$—Cl, and counterstained with MitoTracker$^R$ Green FM (left panel); or stained with DiAc-carboxyfluorescein-$C_{10}H_{21}NO_2$—Cl and counterstained with MitoTracker$^R$ Orange CMTMRos (right panel). Carboxyfluorescein filter-top left; carboxytetramethylrhodamine filter-top right; carboxyfluorescein and carboxytetramethylrhodamine overlaid image-bottom right; DIC image of the cell-bottom left.

Figures 50C, 50D:
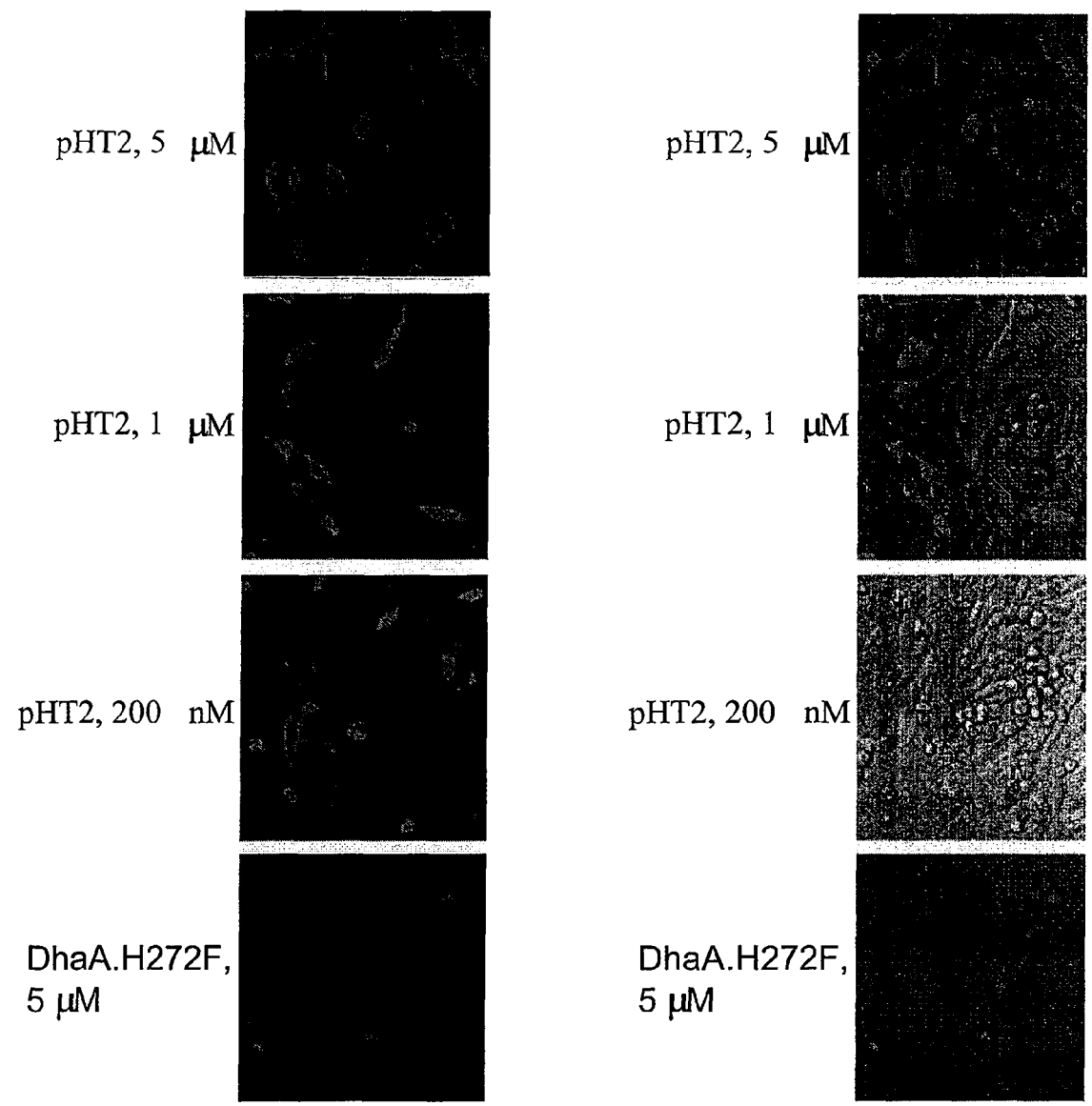

FIGS. 50C-D provide fluorescence and DIC images of living CHO-K1 cells transfected with a vector plasmid pHT2 coding for DhaA.H272F H11YL HT2 (see FIG. 49) or pCI-neo harboring DhaA.H272F, stained with 0.2, 1.0 or 5.0 μM carboxytetramethylrhodamine-$C_{10}H_{21}NO_2$—Cl, and fixed with 3.7% of paraformaldehyde. Carboxytetramethylrhodamine filter-left image of each panel; carboxytetramethylrhodamine and DIC overlaid image-right image in each panel.

Figure 50E:
Figure 50F:
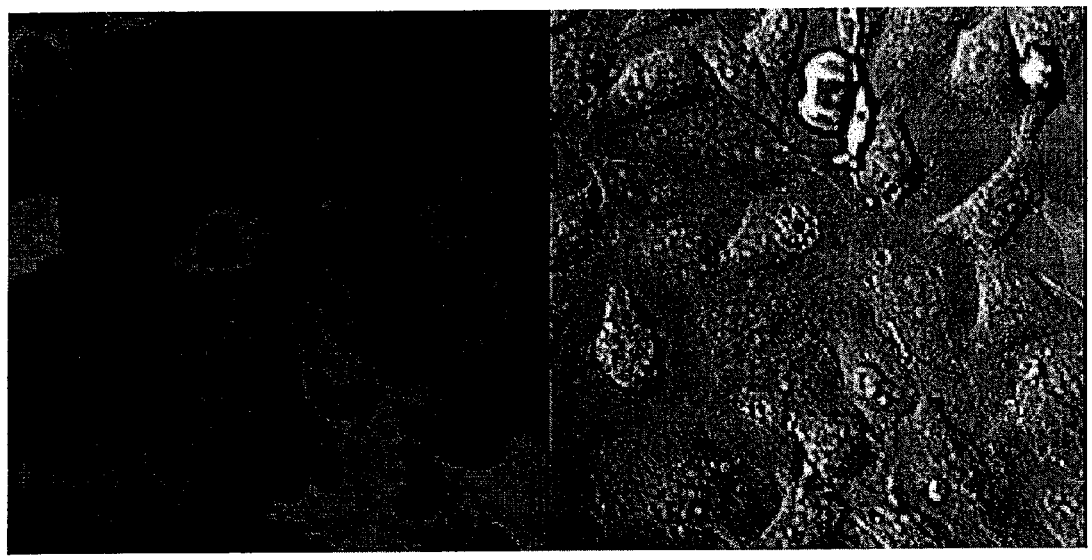

FIGS. 50E-F depict the localization of β-arrestin2-DhaA.H272F H11YLHT2 protein fusions in HeLa cells. Photomicrographs of DiAc-carboxyfluorescein-$C_{10}H_{21}NO_2$—Cl (E) and carboxytetramethylrhodamine-$C_{10}H_{21}NO_2$—Cl (F) labeled cells.

Figure 51A:
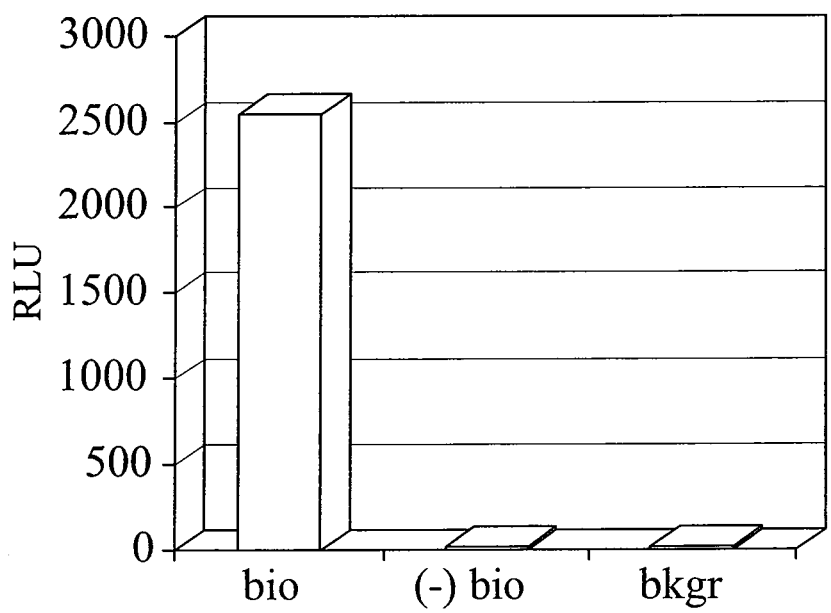
Figure 51B:
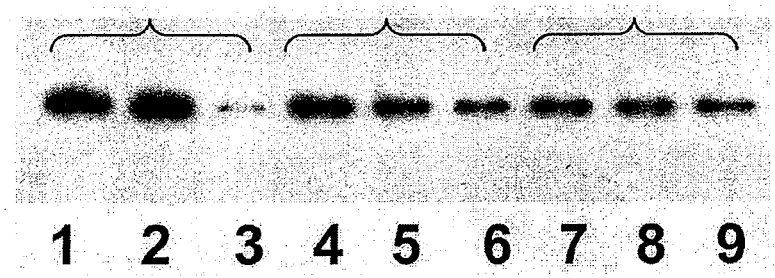

FIG. 51A-B show the capture of a hRLuc-DhaA.H272F H11YLHT2 fusion protein expressed in transiently transfected CHO-K1 cells. Capturing hRLuc activity on streptavidin coated 96-well plates (A) and streptavidin-MagneSphere paramagnetic particles (B).

Figure 52A:
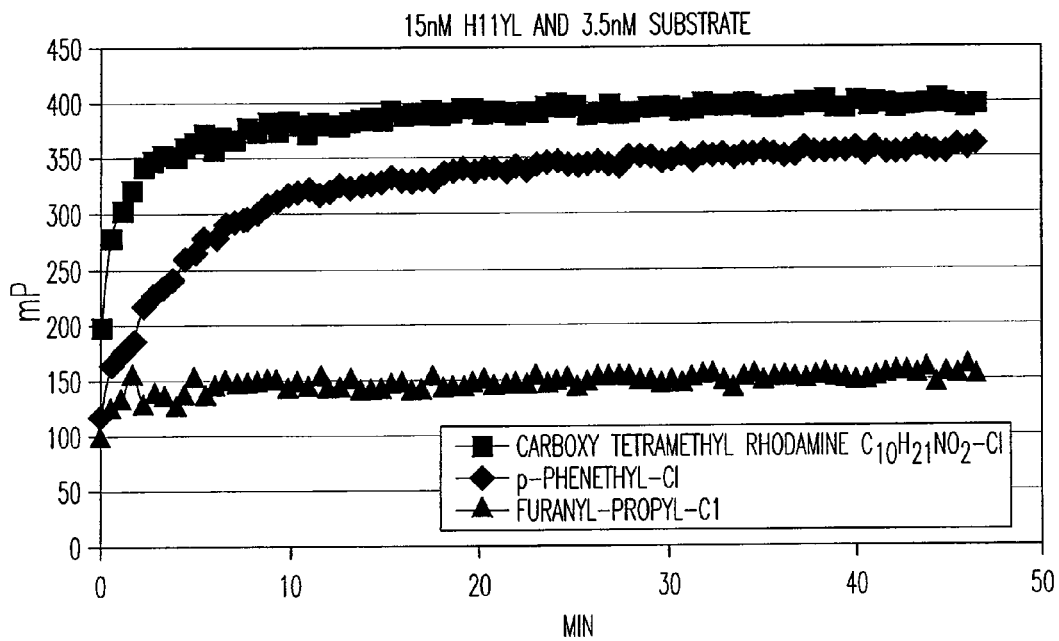
Figure 52B:
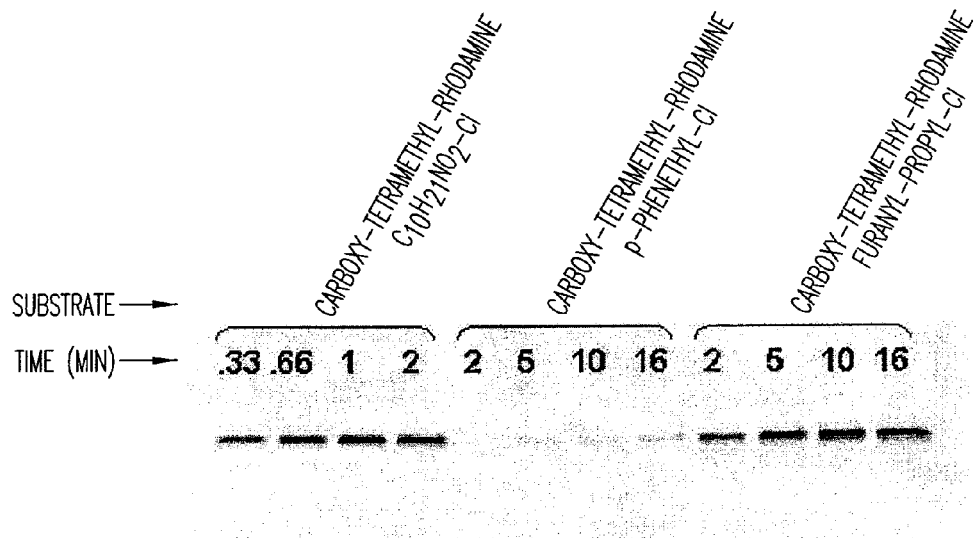
Figure 52C:
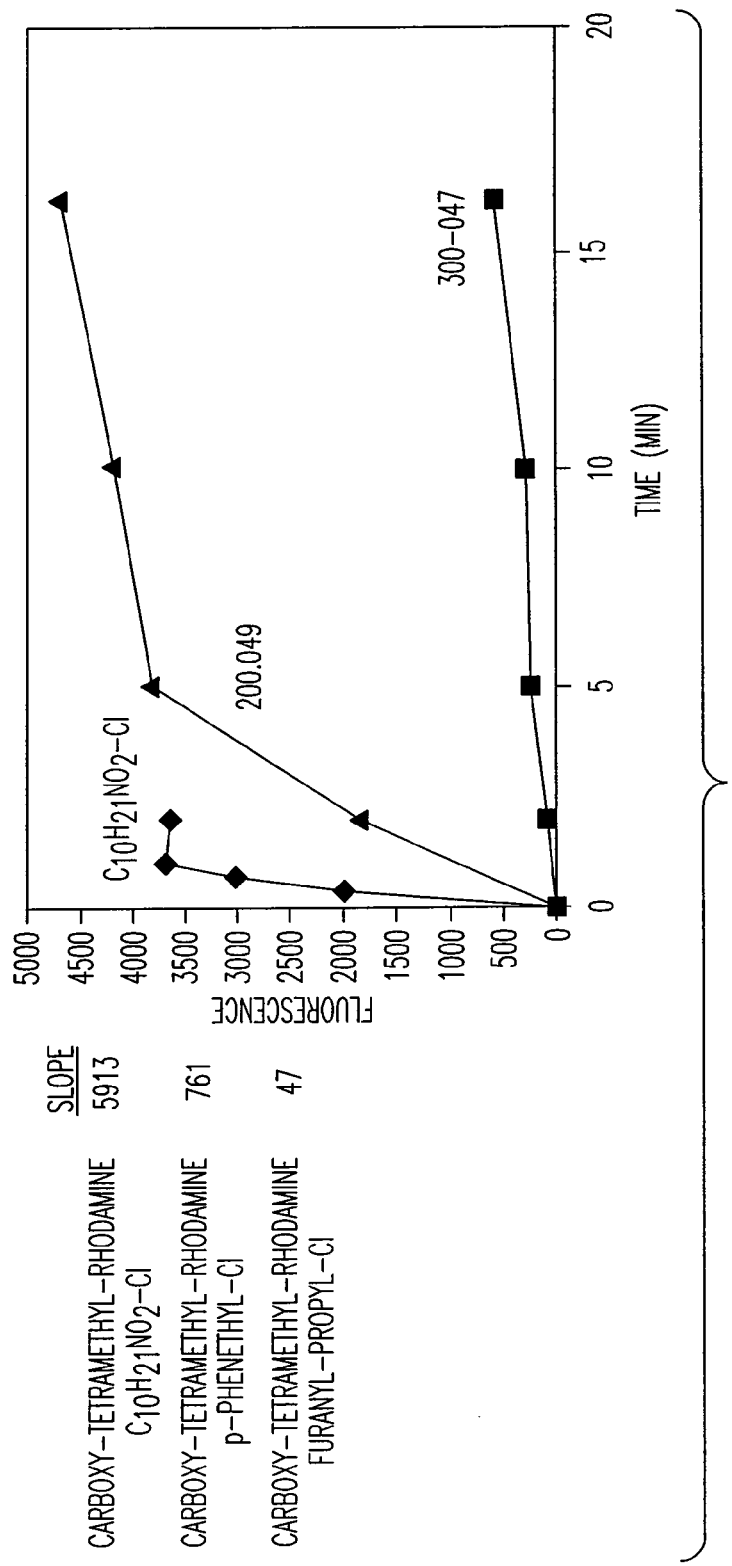

FIGS. 52A-C show the relative labeling rates of and product accumulation for purified DhaA.H272F H11YL with carboxytetramethylrhodamine-$C_{10}H_{21}NO_2$—Cl, carboxytetramethylrhodamine-p-phenethyl-Cl and carboxytetramethylrhodamine-furanyl-propyl-Cl. A). Fluorescence polarization (FP) analysis. B). SDS-PAGE and fluorimage gel analysis. C). Quantitation of fluorescent product accumulation.

Figure 53A:
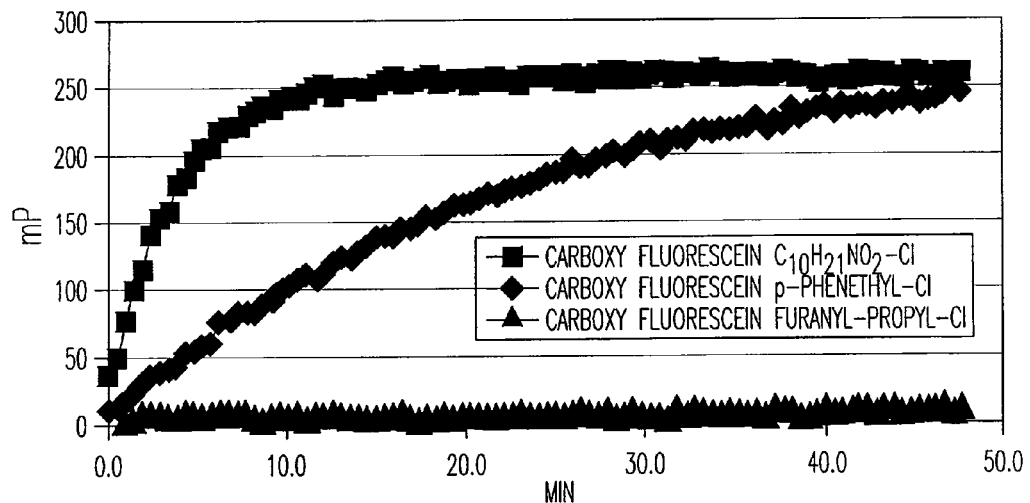
Figure 53B:
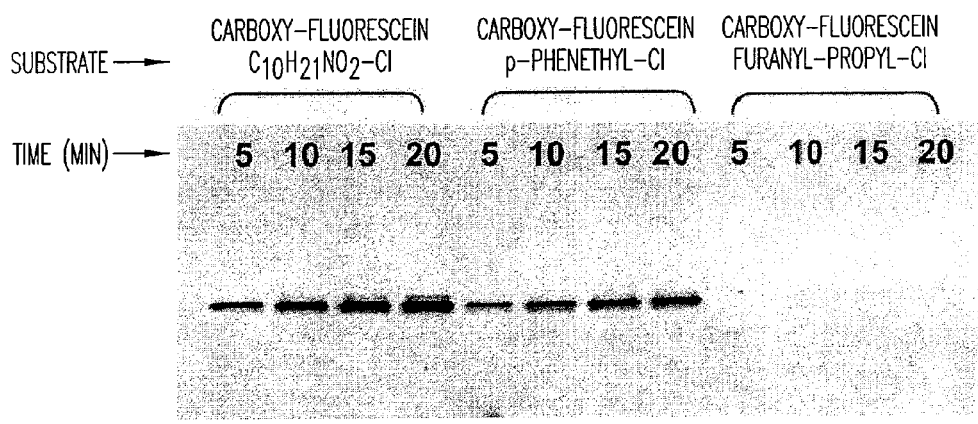
Figure 53C:
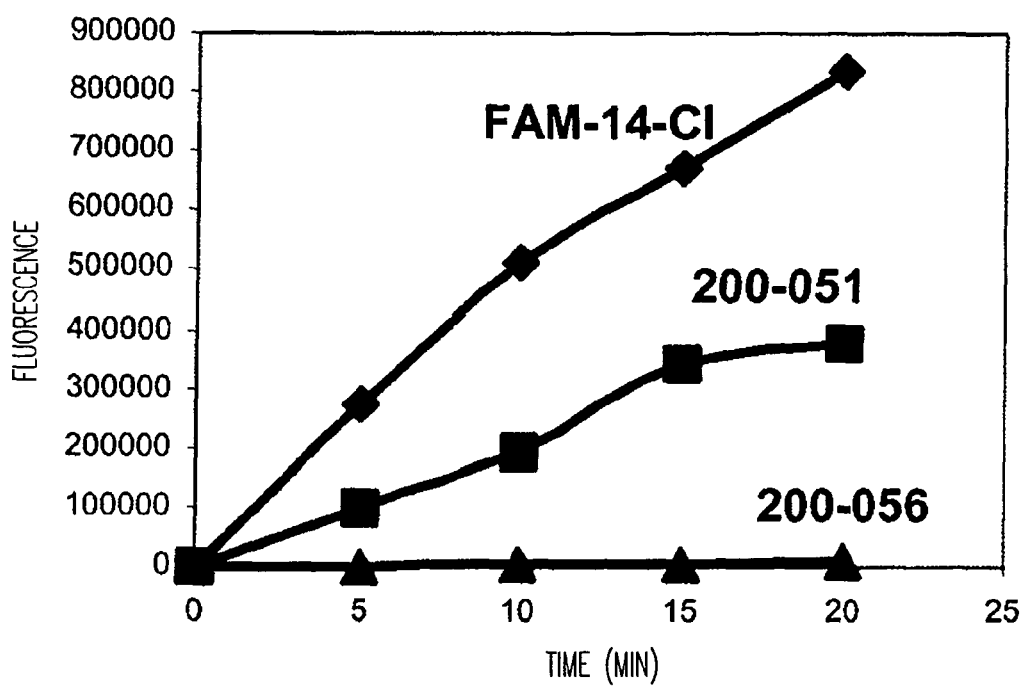

FIGS. 53A-C show the relative labeling rates of and product accumulation for purified DhaA.H272F H11YL with carboxyfluorescein-$C_{10}H_{21}NO_2$—Cl, carboxyfluorescein-p-phenethyl-Cl and carboxyfluorescein-furanyl-propyl-Cl. A). Fluorescence polarization (FP) analysis. B). SDS-PAGE and fluorimage gel analysis. C). Quantitation of fluorescent product accumulation.

Figure 54A:
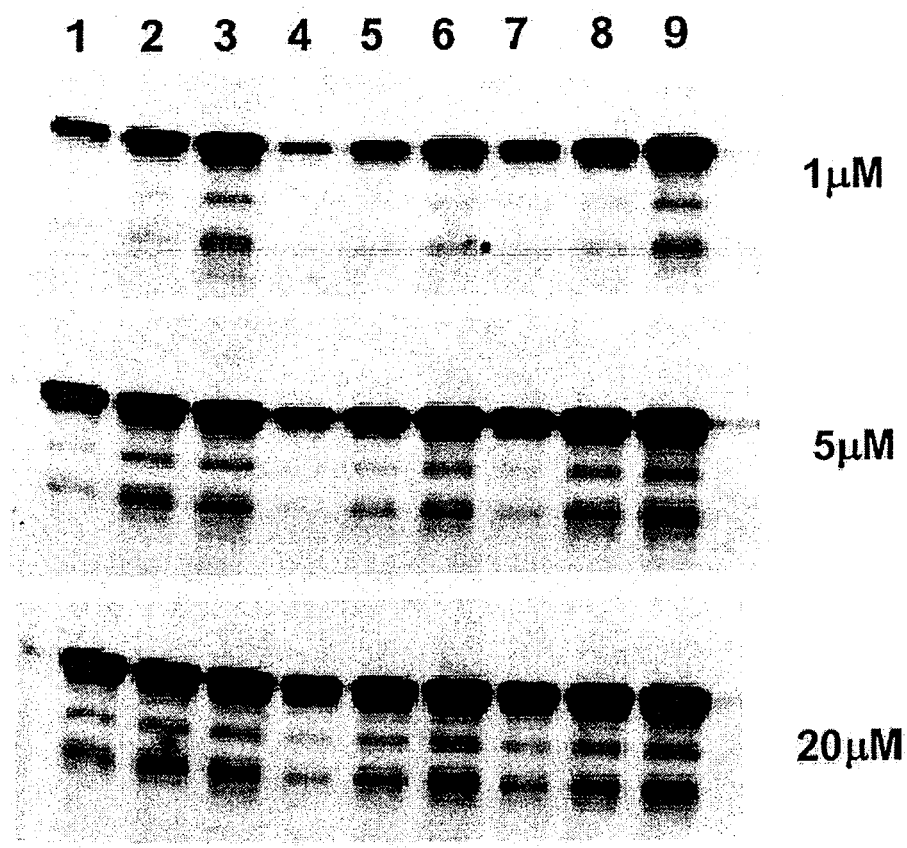
Figure 54B:
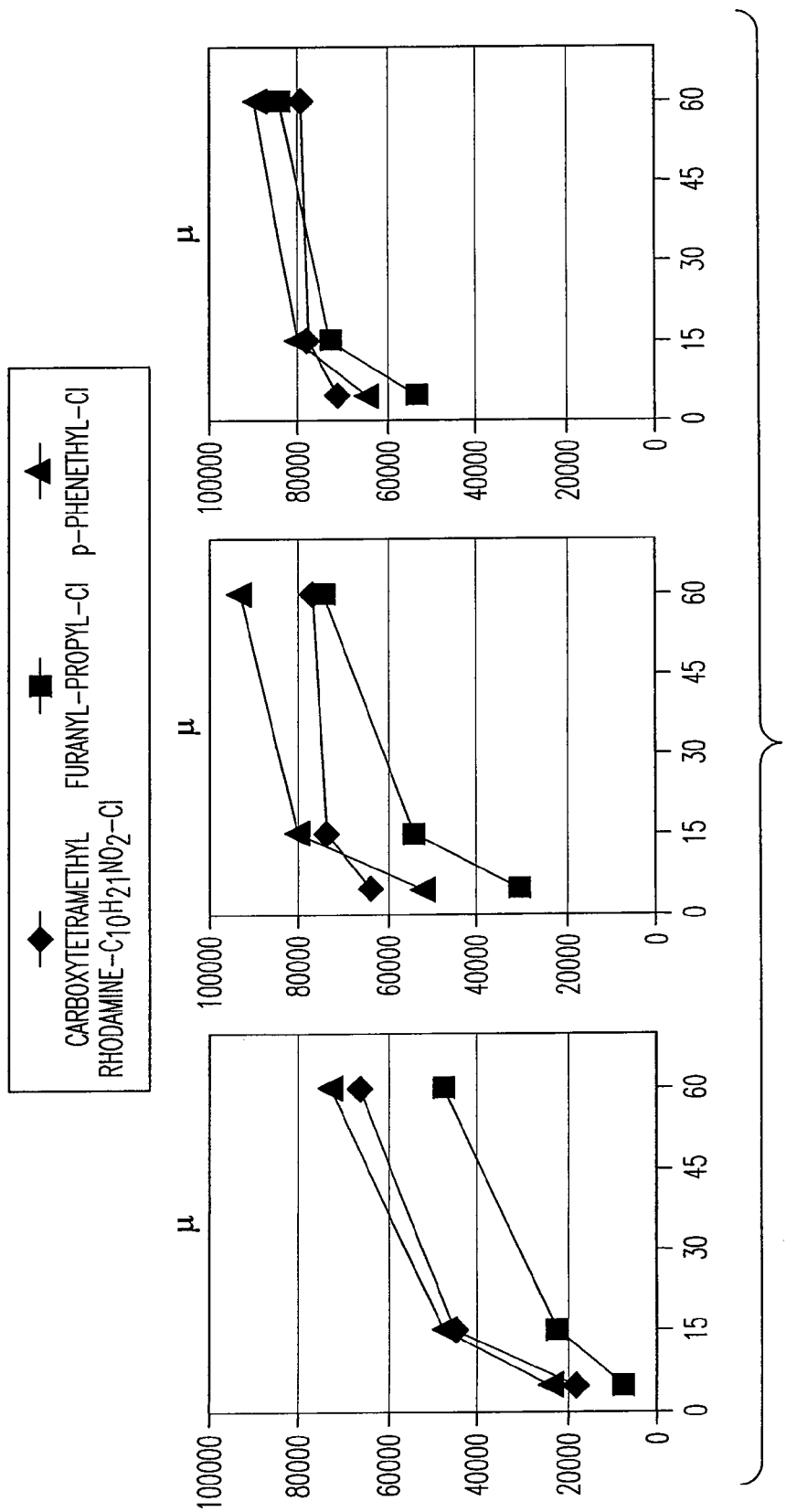

FIGS. 54A-B demonstrate the in vivo labeling of DhaA.H272F H11YL with different carboxytetramethylrhodamine chloroalkanes. A). Fluorimage gel analysis. Lanes: 1-3, carboxytetramethylrhodamine-14-Cl, 5, 15 and 60 minutes, respectively; lanes 4-6, carboxytetramethylrhodamine-furanyl-propyl-Cl, 5, 15 and 60 minutes, respectively; and lanes 7-9, carboxytetramethylrhodamine-p-phenethyl-Cl, 5, 15 and 60 minutes, respectively. B). Quantitation of the DhaA.H11Y273L in vivo labeling rates using 1, 5 and 20 μM substrate.

Figure 55A:
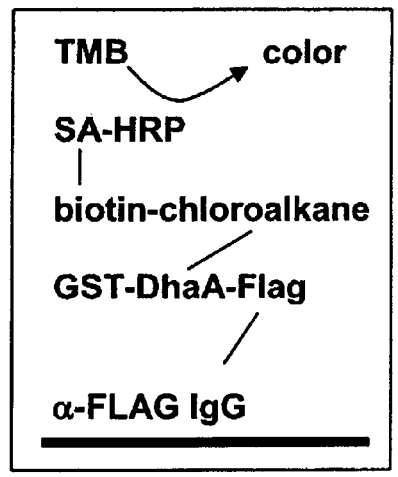
Figure 55B:
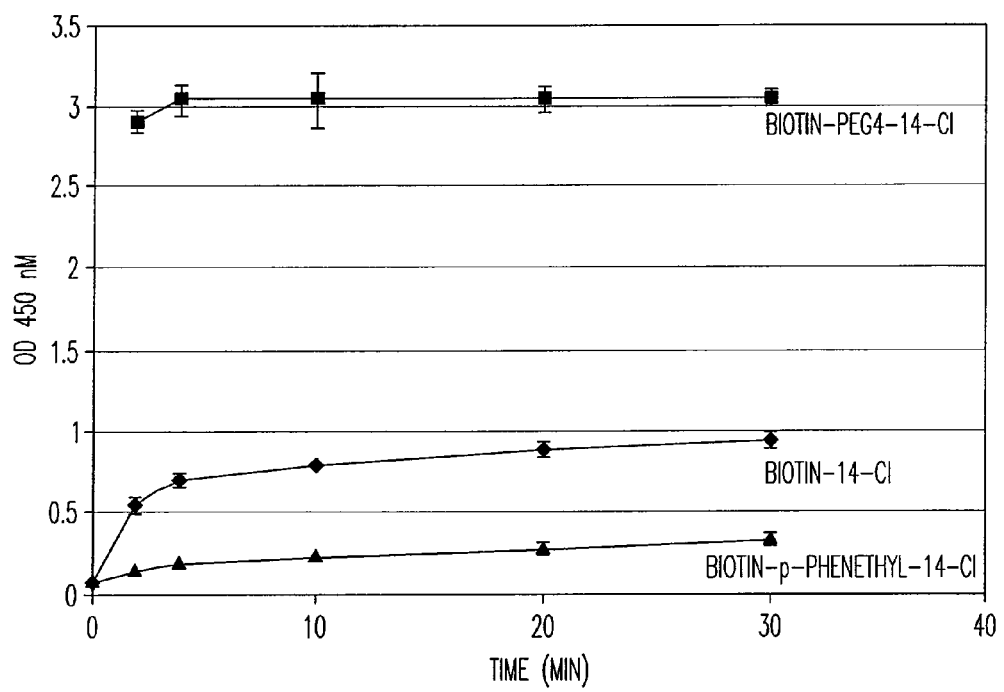

FIGS. 55A-B demonstrate the reactivity of immobilized DhaA.H272F H11YL to biotin-coupled chloroalkane substrates. A). General reaction and detection scheme. B). Reactivity of biotin-PEG4-14-Cl, biotin-14-Cl and biotin-p-phenethyl-14-Cl with immobilized DhaA.H272F H11Y273L protein.

Figure 56:
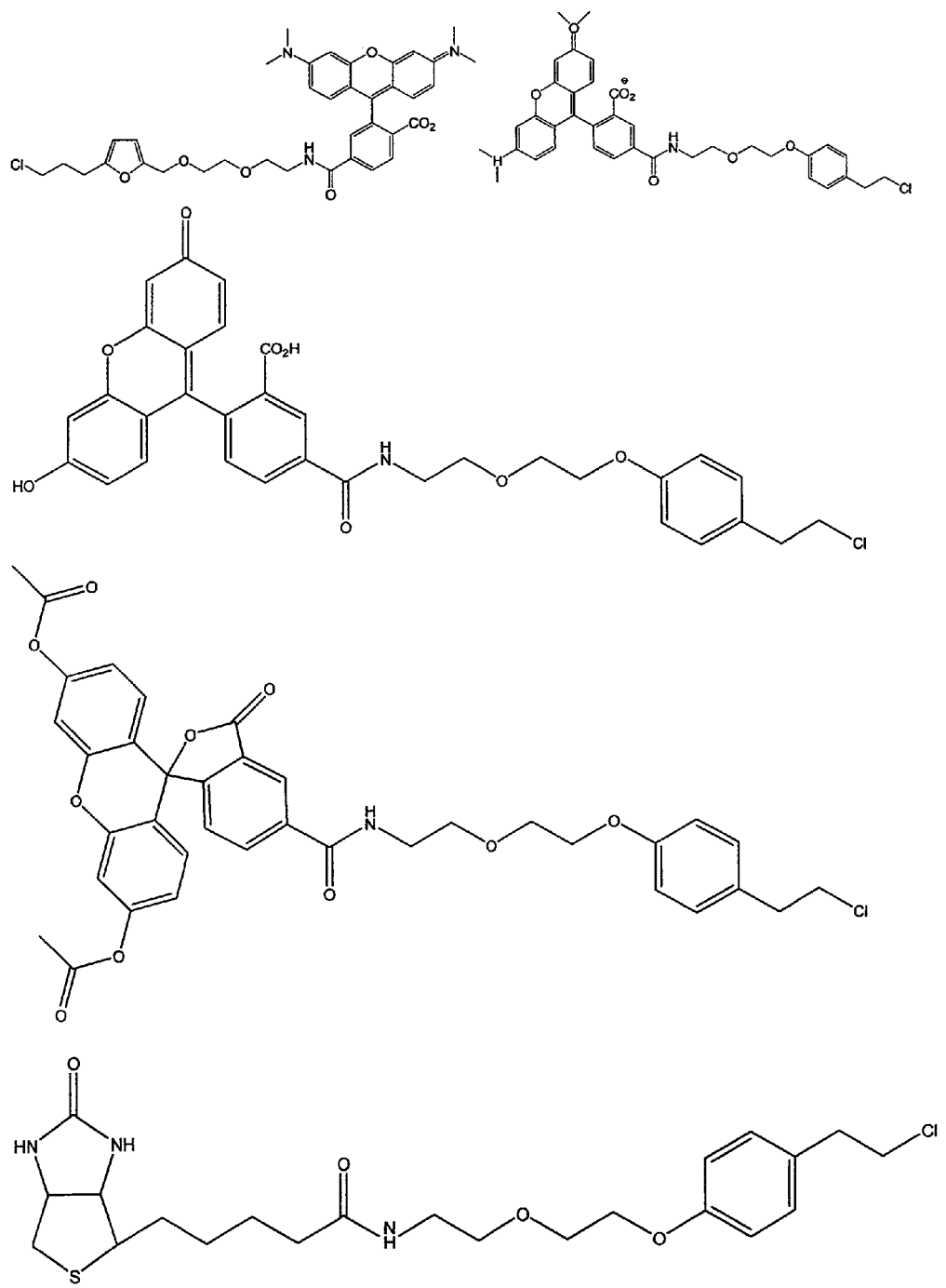

FIG. 56 shows exemplary substrates with ring structures.

Figure 57:
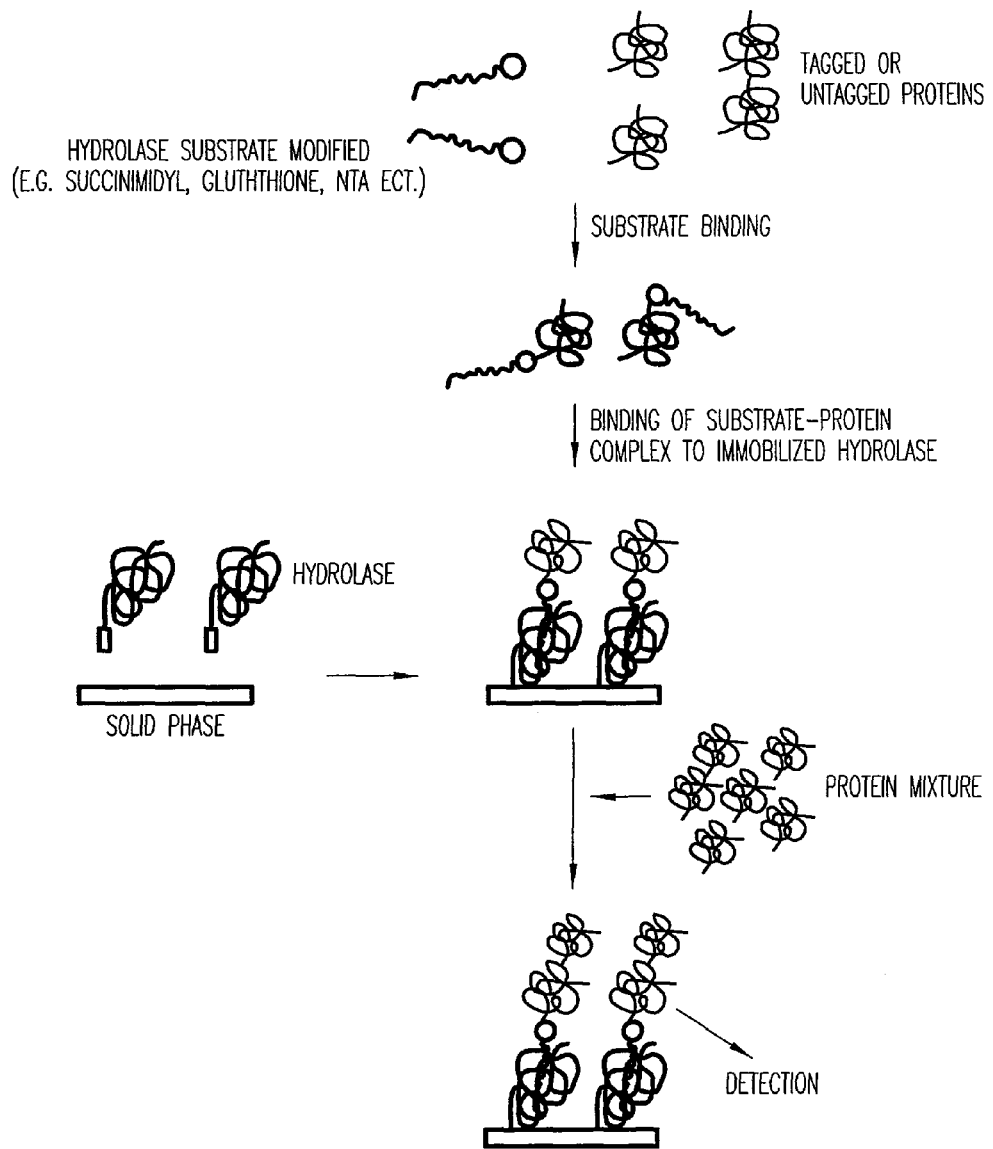

FIG. 57 illustrates the use of a hydrolase substrate of the invention and a mutant hydrolase of the invention for the immobilization and capture of proteins of interest.

Figure 58:
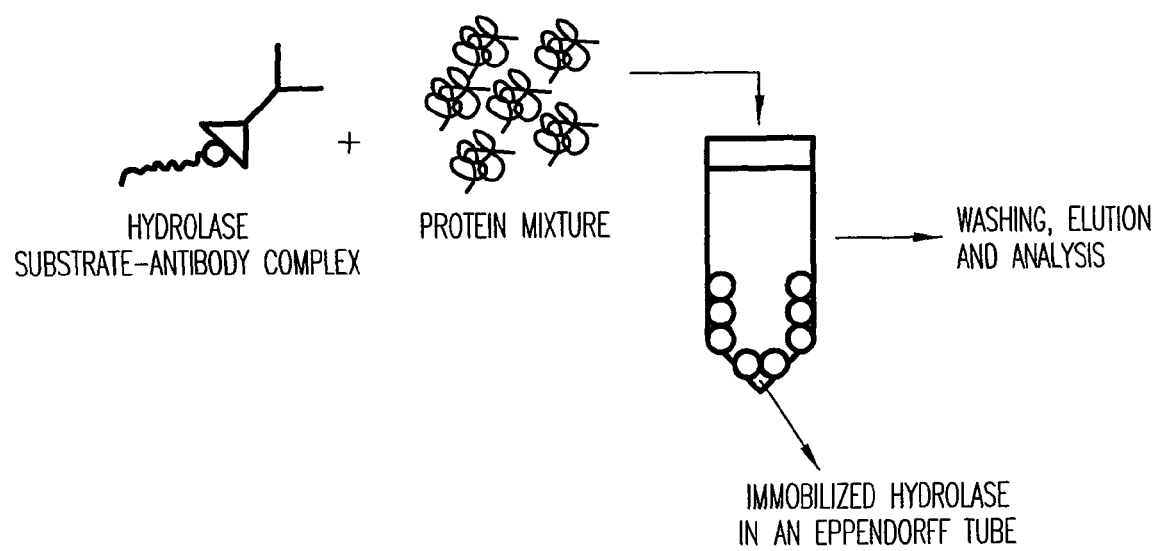

FIG. 58 is a schematic of a hydrolase substrate of the invention and a mutant hydrolase of the invention for immunoprecipitation.

Figure 59A:
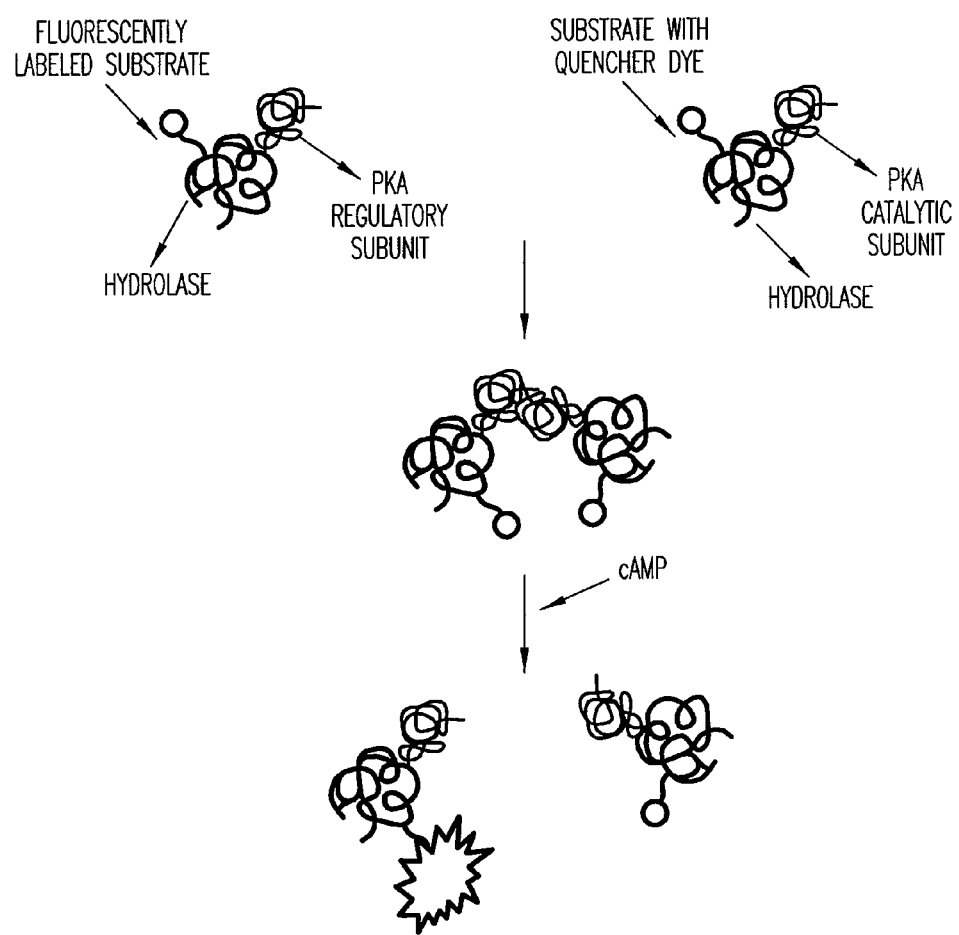
Figure 59B:
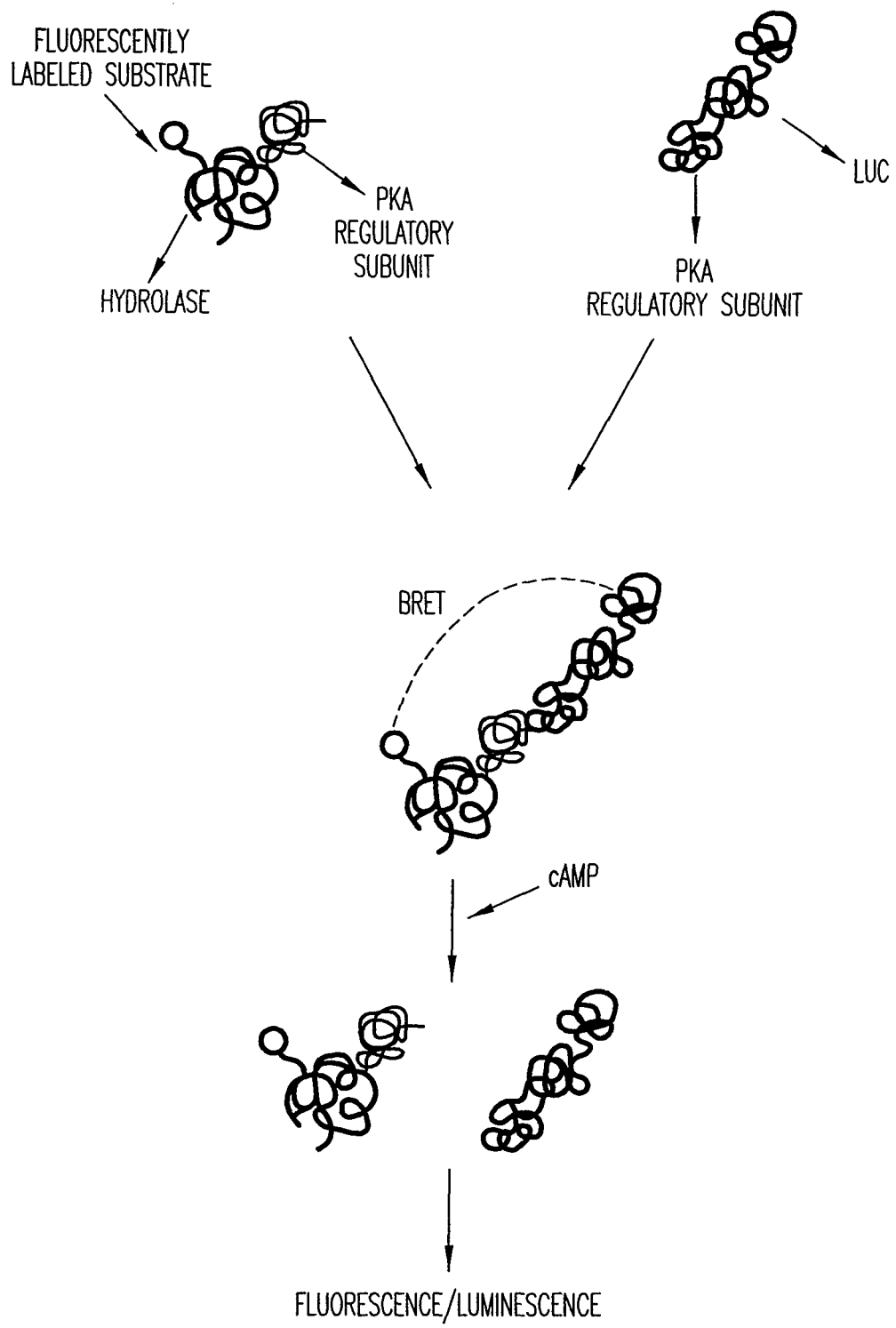

FIGS. 59A-B illustrate the use of a hydrolase substrate of the invention and a mutant hydrolase of the invention to detect cAMP.

FIG. 60A is a schematic of a cell-based protease detection system.

Figure 60B:
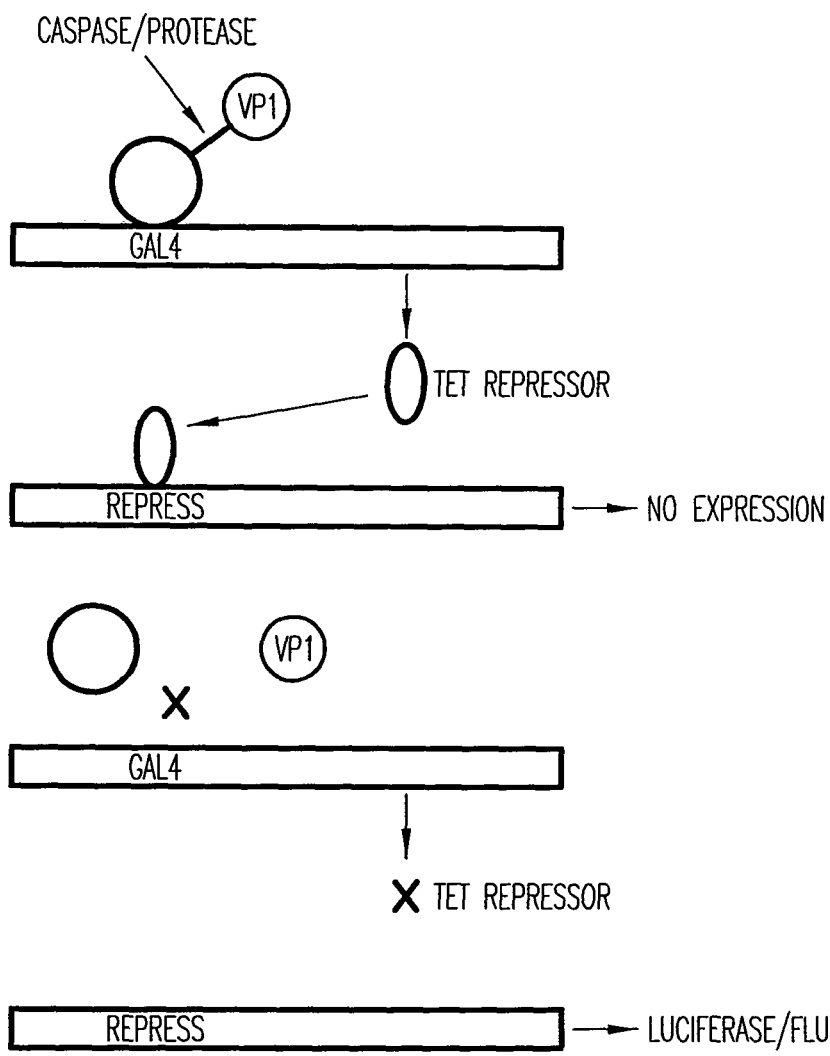

FIG. 60B is a schematic of a cell-based protease detection system.

Figure 60C:
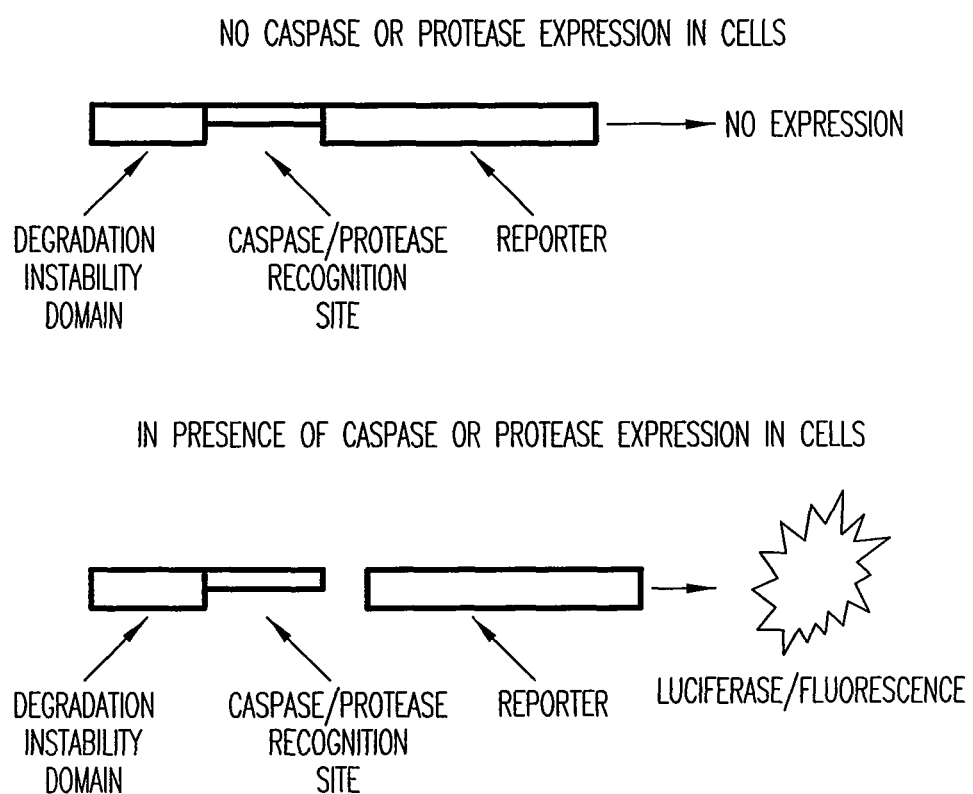

FIG. 60C is a schematic of the use of short lived reporters to detect a protease of interest.

DETAILED DESCRIPTION OF THE INVENTION

Definitions

A "nucleophile" is a molecule which donates electrons.

A "selectable marker protein" encodes an enzymatic activity that confers to a cell the ability to grow in medium lacking what would otherwise be an essential nutrient (e.g., the TRP1 gene in yeast cells) or in a medium with an antibiotic or other drug, i.e., the expression of the gene encoding the selectable marker protein in a cell confers resistance to an antibiotic or drug to that cell relative to a corresponding cell without the gene. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers. Common selectable marker gene sequences include those for resistance to antibiotics such as ampicillin, tetracycline, kanamycin, puromycin, bleomycin, streptomycin, hygromycin, neomycin, Zeocin™, and the like. Selectable auxotrophic gene sequences include, for example, hisD, which allows growth in histidine free media in the presence of histidinol. Suitable selectable marker genes include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides, and includes analogs thereof, such as those having one or more modified bases, sugars and/or phosphate backbones. A "polynucleotide", as used herein, is a nucleic acid containing a sequence that is greater than about 100 nucleotides in length. An "oligonucleotide" or "primer", as used herein, is a short polynucleotide or a portion of a polynucleotide. The term "oligonucleotide" or "oligo" as used herein is defined as a molecule comprised of 2 or more deoxyribonucleotides or ribonucleotides, preferably more than 3, and usually more than 10, but less than 250, preferably less than 200, deoxyribonucleotides or ribonucleotides. The oligonucleotide may be generated in any manner, including chemical synthesis, DNA replication, amplification, e.g., polymerase chain reaction (PCR), reverse transcription (RT), or a combination thereof. A "primer" is an oligonucleotide which is capable of acting as a point of initiation for nucleic acid synthesis when placed under conditions in which primer extension is initiated. A primer is selected to have on its 3' end a region that is substantially complementary to a specific sequence of the target (template). A primer must be sufficiently complementary to hybridize with a target for primer elongation to occur. A primer sequence need not reflect the exact sequence of the target. For example, a non-complementary nucleotide fragment may be attached to the 5' end of the primer, with the remainder of the primer sequence being substantially complementary to the target. Non-complementary bases or longer sequences can be interspersed into the primer provided that the primer sequence has sufficient complementarity with the sequence of the target to hybridize and thereby form a complex for synthesis of the extension product of the primer. Primers matching or complementary to a gene sequence may be used in amplification reactions, RT-PCR and the like.

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporation into a polypeptide chain, or a start or stop signal. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the terms "isolated and/or purified" refer to in vitro preparation, isolation and/or purification of a nucleic acid molecule, a polypeptide, peptide or protein, so that it is not associated with in vivo substances. Thus, the term "isolated" when used in relation to a nucleic acid, as in "isolated oligonucleotide" or "isolated polynucleotide" refers to a nucleic acid sequence that is identified and separated from at least one contaminant with which it is ordinarily associated in its source. An isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. Hence, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. The isolated nucleic acid molecule may be present in single-stranded or double-stranded form. When a nucleic acid molecule is to be utilized to express a protein, the nucleic acid contains at a minimum, the sense or coding strand (i.e., the nucleic acid may be single-stranded), but may contain both the sense and anti-sense strands (i.e., the nucleic acid may be double-stranded).

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA molecule" means a hybrid DNA sequence comprising at least two nucleotide sequences not normally found together in nature. The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector", "expression vector" or "construct" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence "encoding a peptide, protein or polypeptide" means a nucleic acid sequence comprising the coding region of a gene, or a fragment thereof which encodes a gene product having substantially the same activity as the corresponding full-length peptide, protein or polypeptide. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements, and include elements which increase or decrease transcription of linked sequences, e.g., in the presence of trans-acting elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene and the long terminal repeats of the Rous sarcoma virus; and the human cytomegalovirus.

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook et al., 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook et al., 1989).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in situ" refers to cell culture. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of sources (e.g., the American Type Culture Collection, Rockland, Md.). The method of transformation or transfection and the choice of expression vehicle will depend on the host system selected. Transformation and transfection methods are described, e.g., in Sambrook et al., 1989. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

The term "gene" refers to a DNA sequence that comprises coding sequences and optionally control sequences necessary for the production of a polypeptide from the DNA sequence. The polypeptide can be encoded by a full-length coding sequence or by any portion of the coding sequence so long as the portion encodes a gene product with substantially the same activity as the full-length polypeptide.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989; Nucleic Acid Hybridization, A Practical Approach, IRL Press, Washington D.C., 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42EC in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42EC when a probe of about 500 nucleotides in length is employed.

"Medium stringency conditions" when used in reference to nucleic acid hybridization include conditions equivalent to binding or hybridization at 42EC in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42EC when a probe of about 500 nucleotides in length is employed.

"Low stringency conditions" include conditions equivalent to binding or hybridization at 42EC in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42EC when a probe of about 500 nucleotides in length is employed.

By "peptide", "protein" and "polypeptide" is meant any chain of amino acids, regardless of length or post-translational modification (e.g., glycosylation or phosphorylation). Unless otherwise specified, the terms are interchangeable. The nucleic acid molecules of the invention encode a variant (mutant) of a naturally-occurring (wild-type) protein or fragment thereof which has substantially the same activity as the full length mutant protein. Preferably, such a mutant protein has an amino acid sequence that is at least 85%, preferably 90%, and most preferably 95% or 99%, identical to the amino acid sequence of a corresponding wild-type protein.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide (1) is not associated with proteins found in nature, (2) is free of other proteins from the same source, e.g., free of human proteins, (3) is expressed by a cell from a different species, or (4) does not occur in nature. In contrast, non-isolated polypeptides (e.g., proteins and enzymes) are found in the state they exist in nature. The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The term "fusion polypeptide" as used herein refers to a chimeric protein containing a protein of interest (e.g., luciferase, an affinity tag or a targeting sequence) joined to a different protein, e.g., a mutant hydrolase.

As used herein, the term "antibody" refers to a protein having one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins, or as modifications in a variety of forms including, for example, $FabFc_2$, Fab, Fv, Fd, $(FabN)_2$, an Fv fragment containing only the light and heavy chain variable regions, a Fab or $(Fab)N_2$ fragment containing the variable regions and parts of the constant regions, a single-chain antibody, e.g., scFv, CDR-grafted antibodies and the like. The heavy and light chain of a Fv may be derived from the same antibody or different antibodies thereby producing a chimeric Fv region. The antibody may be of animal (especially mouse or rat) or human origin or may be chimeric or humanized. As used herein the term "antibody" includes these various forms.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably transfected cell line capable of producing the protein or polypeptide encoded by the nucleic acid molecule. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide, or a precursor thereof, e.g., the pre- or preproform of the protein or polypeptide, is produced.

All amino acid residues identified herein are in the natural L-configuration. In keeping with standard polypeptide nomenclature, abbreviations for amino acid residues are as shown in the following Table of Correspondence.

TABLE OF CORRESPONDENCE

| 1-Letter | 3-Letter | AMINO ACID |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

As used herein, the term "poly-histidine tract" or (His tag) refers to a molecule comprising two to ten histidine residues, e.g., a poly-histidine tract of five to ten residues. A poly-histidine tract allows the affinity purification of a covalently linked molecule on an immobilized metal, e.g., nickel, zinc, cobalt or copper, chelate column or through an interaction with another molecule (e.g., an antibody reactive with the His tag).

As used herein, "pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a "substantially pure" composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

A "quantum dot" is an ultrasmall, bright, highly photostable semiconductor crystallite with a broad excitation band that a narrow emission band, i.e., it is a fluorescent crystalline nanoparticle.

As used herein, an "upconverting nanoparticle" means a nanoparticle which is a combination of an absorber which is excited by infrared (IR) light and an emitter ion in a crystal lattice, which converts IR light into visible radiation.

As used herein, a "triplet sensitizer" is a molecule or a group that is substantially chemically inert and that can absorb light at wavelengths that are not or are only weakly absorbed by a substrate. The "sensitizer" can then release energy which will cause an oxygen atom in the substrate or compound to be excited to a singlet oxygen state. The substrate with an oxygen atom in a singlet oxygen state can destroy molecules, such as proteins in close proximity thereto. Examples of triplet sensitizers include, for example, eosin or malachite green.

A radionuclide useful in a diagnostic application includes, e.g., metallic radionuclides (i.e., metallic radioisotopes or metallic paramagnetic ions), including Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Titanium-44, Tungsten-185, Vanadium-48, Vanadium-49, Ytterbium-169, Yttrium-86, Yttrium-88, Yttrium-90, Yttrium-91, Zinc-65, and Zirconium-95. Radionuclides useful for imaging include radioisotopes of copper (Cu), gallium (Ga), indium (In), rhenium (Rh), and technetium (Tc), including isotopes $^{64}Cu$, $^{67}Cu$, $^{111}In$, $^{99}mTc$, $^{67}Ga$ or $^{68}Ga$. Metals useful for X-ray contrast agents include radioisotopes of Re, Sm, Ho, Lu, Yt, Pm, Bi, Pd, Gd, La, Au, Yb, Dy, Cu, Rh, Ag and Ir.

A "protein destabilization sequence" or "protein destabilization domain" includes one or more amino acid residues, which, when present at the N-terminus or C-terminus of a protein, reduces or decreases the half-life of the linked protein of by at least 80%, preferably at least 90%, more preferably at least 95% or more, e.g., 99%, relative to a corresponding protein which lacks the protein destabilization sequence or domain. A protein destabilization sequence includes, but is not limited to, a PEST sequence, for example, a PEST sequence from cyclin, e.g., mitotic cyclins, uracil permease or ODC, a sequence from the C-terminal region of a short-lived protein such as ODC, early response proteins such as cytokines, lymphokines, protooncogenes, e.g., c-myc or c-fos, MyoD, HMG CoA reductase, S-adenosyl methionine decarboxylase, CL sequences, a cyclin destruction box, N-degron, or a protein or a fragment thereof which is ubiquitinated in vivo.

I. Mutant Hydrolases and Fusions Thereof

Mutant hydrolases within the scope of the invention include but are not limited to those prepared via recombinant techniques, e.g., site-directed mutagenesis or recursive mutagenesis, and comprise one or more amino acid substitutions which render the mutant hydrolase capable of forming a stable, e.g., covalent, bond with a substrate, such as a substrate modified to contain one or more functional groups, for a corresponding nonmutant (wild-type) hydrolase which bond is more stable than the bond formed between a corresponding wild-type hydrolase and the substrate. Hydrolases within the scope of the invention include, but are not limited to, peptidases, esterases (e.g., cholesterol esterase), glycosidases (e.g., glucosamylase), phosphatases (e.g., alkaline phosphatase) and the like. For instance, hydrolases include, but are not limited to, enzymes acting on ester bonds such as carboxylic ester hydrolases, thiolester hydrolases, phosphoric monoester hydrolases, phosphoric diester hydrolases, triphosphoric monoester hydrolases, sulfuric ester hydrolases, diphosphoric monoester hydrolases, phosphoric triester hydrolases, exodeoxyribonucleases producing 5'-phosphomonoesters, exoribonucleases producing 5'-phosphomonoesters, exoribonucleases producing 3'-phosphomonoesters, exonucleases active with either ribo- or deoxyribonucleic acid, exonucleases active with either ribo- or deoxyribonucleic acid, endodeoxyribonucleases producing 5'-phosphomonoesters, endodeoxyribonucleases producing other than 5'-phosphomonoesters, site-specific endodeoxyribonucleases specific for altered bases, endoribonucleases producing 5'-phosphomonoesters, endoribonucleases producing other than 5'-phosphomonoesters, endoribonucleases active with either ribo- or deoxyribonucleic, endoribonucleases active with either ribo- or deoxyribonucleic glycosylases; glycosidases, e.g., enzymes hydrolyzing O- and S-glycosyl, and hydrolyzing N-glycosyl compounds; acting on ether bonds such as trialkylsulfonium hydrolases or ether hydrolases; enzymes acting on peptide bonds (peptide hydrolases) such as aminopeptidases, dipeptidases, dipeptidyl-peptidases and tripeptidyl-peptidases, peptidyl-dipeptidases, serine-type carboxypeptidases, metallocarboxypeptidases, cysteine-type carboxypeptidases, omega peptidases, serine endopeptidases, cysteine endopeptidases, aspartic endopeptidases, metalloendopeptidases, threonine endopeptidases, and endopeptidases of unknown catalytic mechanism; enzymes acting on carbon-nitrogen bonds, other than peptide bonds, such as those in linear amides, in cyclic amides, in linear amidines, in cyclic amidines, in nitriles, or other compounds; enzymes acting on acid anhydrides such as those in phosphorous-containing anhydrides and in sulfonyl-containing anhydrides; enzymes acting on acid anhydrides (catalyzing transmembrane movement); enzymes acting on acid anhydrides or involved in cellular and subcellular movement; enzymes acting on carbon-carbon bonds (e.g., in ketonic substances); enzymes acting on halide bonds (e.g., in C-halide compounds), enzymes acting on phosphorus-nitrogen bonds; enzymes acting on sulfur-nitrogen bonds; enzymes acting on carbon-phosphorus bonds; and enzymes acting on sulfur-sulfur bonds. Exemplary hydrolases acting on halide bonds include, but are not limited to, alkylhalidase, 2-haloacid dehalogenase, haloacetate dehalogenase, thyroxine deiodinase, haloalkane dehalogenase, 4-chlorobenzoate dehalogenase, 4-chlorobenzoyl-CoA dehalogenase, and atrazine chlorohydrolase. Exemplary hydrolases that act on carbon-nitrogen bonds in cyclic amides include, but are not limited to, barbiturase, dihydropyrimidinase, dihydroorotase, carboxymethylhydantoinase, allantoinase, β-lactamase, imidazolonepropionase, 5-oxoprolinase (ATP-hydrolysing), creatininase, L-lysine-lactamase, 6-aminohexanoate-cyclic-dimer hydrolase, 2,5-dioxopiperazine hydrolase, N-methylhydantoinase (ATP-hydrolysing), cyanuric acid amidohydrolase, maleimide hydrolase. "Beta-lactamase" as used herein includes Class A, Class C and Class D beta-lactamases as well as D-ala carboxypeptidase/transpeptidase, esterase EstB, penicillin binding protein 2×, penicillin binding protein 5, and D-amino peptidase. Preferably, the beta-lactamase is a serine beta-lactamase, e.g., one having a catalytic serine residue at a position corresponding to residue 70 in the serine beta-lactamase of *S. aureus* PC1, and a glutamic acid residue at a position corresponding to residue 166 in the serine beta-lactamase of *S. aureus* PC1, optionally having a lysine residue at a position corresponding to residue 73, and also optionally having a lysine residue at a position corresponding to residue 234, in the beta-lactamase of *S. aureus* PC1.

In one embodiment, the mutant hydrolase of the invention comprises at least one amino acid substitution in a residue which, in the wild-type hydrolase, is associated with activating a water molecule, e.g., a residue in a catalytic triad or an auxiliary residue, wherein the activated water molecule cleaves the bond formed between a catalytic residue in the wild-type hydrolase and a substrate of the hydrolase. As used herein, an "auxiliary residue" is a residue which alters the activity of another residue, e.g., it enhances the activity of a residue that activates a water molecule. Residues which activate water within the scope of the invention include but are not limited to those involved in acid-base catalysis, for instance, histidine, aspartic acid and glutamic acid. In another embodiment, the mutant hydrolase of the invention comprises at least one amino acid substitution in a residue which, in the wild-type hydrolase, forms an ester intermediate by nucleophilic attack of a substrate for the hydrolase. A substrate useful with a mutant hydrolase of the invention is one which is specifically bound by a mutant hydrolase, and preferably results in a bond formed with an amino acid, e.g., the reactive residue, of the mutant hydrolase which bond is more stable than the bond formed between the substrate and the corresponding amino acid of the wild-type hydrolase. While the mutant hydrolase specifically binds substrates which may be specifically bound by the corresponding wild-type hydrolase, no product or substantially less product, e.g., 2-, 10-, 100-, or 1000-fold less, is formed from the interaction between the mutant hydrolase and the substrate under conditions which result in product formation by a reaction between the corresponding wild-type hydrolase and substrate. The lack of, or reduced amounts of, product formation by the mutant hydrolase is due to at least one substitution in the mutant hydrolase, which substitution results in the mutant hydrolase forming a bond with the substrate which is more stable than the bond formed between the corresponding wild-type hydrolase and the substrate. Preferably, the bond formed between a mutant hydrolase and a substrate of the invention has a half-life (i.e., $t_{1/2}$) that is greater than, e.g., at least 2-fold, and more preferably at least 4- or even 10-fold, and up to 100-, 1000- or 10.000-fold greater or more, than the $t_{1/2}$ of the bond formed between a corresponding wild-type hydrolase and the substrate under conditions which result in product formation by the corresponding wild-type hydrolase. Preferably, the bond formed between the mutant hydrolase and the substrate has a $t_{1/2}$ of at least 30 minutes and preferably at least 4 hours, and up to at least 10 hours, and is resistant to disruption by washing, protein denaturants, and/or high temperatures, e.g., the bond is stable to boiling in SDS.

In yet another embodiment, the mutant hydrolase of the invention comprises at least two amino acid substitutions, one substitution in a residue which, in the wild-type hydrolase, is associated with activating a water molecule or in a residue which, in the wild-type hydrolase, forms an ester intermediate by nucleophilic attack of a substrate for the hydrolase, and another substitution in a residue which, in the wild-type hydrolase, is at or near a binding site(s) for a hydrolase substrate, e.g., the residue is within 3 to 5 Å of a hydrolase substrate bound to a wild-type hydrolase but is not in a residue that, in the corresponding wild-type hydrolase, is associated with activating a water molecule or which forms ester intermediate with a substrate. In one embodiment, the second substitution is in a residue which, in the wild-type hydrolase lines the site(s) for substrate entry into the catalytic pocket of the hydrolase, e.g., a residue that is within the active site cavity and within 3 to 5 Å of a hydrolase substrate bound to the wild-type hydrolase such as a residue in a tunnel for the substrate that is not a residue in the corresponding wild-type hydrolase which is associated with activating a water molecule or which forms an ester intermediate with a substrate. The additional substitution(s) preferably increase the rate of stable covalent bond formation of those mutants to a substrate of a corresponding wild-type hydrolase. In one embodiment, one substitution is at a residue in the wild-type hydrolase that activates the water molecule, e.g., a histidine residue, and is at a position corresponding to amino acid residue 272 of a *Rhodococcus rhodochrous* dehalogenase, e.g., the substituted amino acid at the position corresponding to amino acid residue 272 is phenylalanine or glycine. In another embodiment, one substitution is at a residue in the wild-type hydrolase which forms an ester intermediate with the substrate, e.g., an aspartate residue, and at a position corresponding to amino acid residue 106 of a *Rhodococcus rhodochrous* dehalogenase. In one embodiment, the second substitution is at an amino acid residue corresponding to a position 175, 176 or 273 of *Rhodococcus rhodochrous* dehalogenase, e.g., the substituted amino acid at the position corresponding to amino acid residue 175 is methionine, valine, glutamate, aspartate, alanine, leucine, serine or cysteine, the substituted amino acid at the position corresponding to amino acid residue 176 is serine, glycine, asparagine, aspartate, threonine, alanine or arginine, and/or the substituted amino acid at the position corresponding to amino acid residue 273 is leucine, methionine or cysteine. In yet another embodiment, the mutant hydrolase further comprises a third and optionally a fourth substitution at an amino acid residue in the wild-type hydrolase that is within the active site cavity and within 3 to 5 Å of a hydrolase substrate bound to the wild-type hydrolase, e.g., the third substitution is at a position corresponding to amino acid residue 175, 176 or 273 of a *Rhodococcus rhodochrous* dehalogenase, and the fourth substitution is at a position corresponding to amino acid residue 175, 176 or 273 of a *Rhodococcus rhodochrous* dehalogenase. A mutant hydrolase may include other substitution(s), e.g., those which are introduced to facilitate cloning of the corresponding gene or a portion thereof, and/or additional residue(s) at or near the N- and/or C-terminus, e.g., those which are introduced to facilitate cloning of the corresponding gene or a portion thereof but which do not necessarily have an activity, e.g., are not separately detectable.

For example, wild-type dehalogenase DhaA cleaves carbon-halogen bonds in halogenated hydrocarbons (HaloC$_3$-HaloC$_{10}$). The catalytic center of DhaA is a classic catalytic triad including a nucleophile, an acid and a histidine residue. The amino acids in the triad are located deep inside the catalytic pocket of DhaA (about 10 Å long and about 20 Å$^2$ in cross section). The halogen atom in a halogenated substrate for DhaA, for instance, the chlorine atom of a Cl-alkane substrate, is positioned in close proximity to the catalytic center of DhaA. DhaA binds the substrate, likely forms an ES complex, and an ester intermediate is formed by nucleophilic attack of the substrate by Asp106 (the numbering is based on the protein sequence of DhaA) of DhaA. His272 of DhaA then activates water and the activated water hydrolyzes the intermediate, releasing product from the catalytic center. As described herein, mutant DhaAs, e.g., a DhaA.H272F mutant, which likely retains the 3-D structure based on a computer modeling study and basic physico-chemical characteristics of wild-type DhaA (DhaA.WT), were not capable of hydrolyzing one or more substrates of the wild-type enzyme, e.g., for Cl-alkanes, releasing the corresponding alcohol released by the wild-type enzyme. As further described herein, mutant serine beta-lactamases, e.g., a BlaZ.E166D mutant, a BlaZ.N170Q mutant and a BlaZ.E166D:N170Q mutant, were not capable of hydrolyzing one or more substrates of a wild-type serine beta-lactamase.

Thus, in one embodiment of the invention, a mutant hydrolase is a mutant dehalogenase comprising at least one amino acid substitution in a residue which, in the wild-type dehalogenase, is associated with activating a water molecule, e.g., a residue in a catalytic triad or an auxiliary residue, wherein the activated water molecule cleaves the bond formed between a catalytic residue in the wild-type dehalogenase and a substrate of the dehalogenase. In one embodiment, at least one substitution is in a residue corresponding to residue 272 in DhaA from *Rhodococcus rhodochrous*. A "corresponding residue" is a residue which has the same activity (function) in one wild-type protein relative to a reference wild-type protein and optionally is in the same relative position when the primary sequences of the two proteins are aligned. For example, a residue which forms part of a catalytic triad and activates a water molecule in one enzyme may be residue 272 in that enzyme, which residue 272 corresponds to residue 73 in another enzyme, wherein residue 73 forms part of a catalytic triad and activates a water molecule. Thus, in one embodiment, a mutant dehalogenase of the invention has a residue other than histidine, e.g., a phenylalanine residue, at a position corresponding to residue 272 in DhaA from *Rhodococcus rhodochrous*. In another embodiment of the invention, a mutant hydrolase is a mutant dehalogenase comprising at least one amino acid substitution in a residue corresponding to residue 106 in DhaA from *Rhodococcus rhodochrous*, e.g., a substitution to a residue other than aspartate. For example, a mutant dehalogenase of the invention has a cysteine or a glutamate residue at a position corresponding to residue 106 in DhaA from *Rhodococcus rhodochrous*. In a further embodiment, the mutant hydrolase is a mutant dehalogenase comprising at least two amino acid substitutions, one in a residue corresponding to residue 106 and one in a residue corresponding to residue 272 in DhaA from *Rhodococcus rhodochrous*. In one embodiment, the mutant hydrolase is a mutant dehalogenase comprising at least two amino acid substitutions, one in a residue corresponding to residue 272 in DhaA from *Rhodococcus rhodochrous* and another in a residue corresponding to residue 175, 176, 245 and/or 273 in DhaA from *Rhodococcus rhodochrous*. In yet a further embodiment, the mutant hydrolase is a mutant serine beta-lactamase comprising at least one amino acid substitution in a residue corresponding to residue 166 or residue 170 in a serine beta-lactamase of *Staphylococcus aureus* PC1.

In one embodiment, the mutant hydrolase is a haloalkane dehalogenase, e.g., such as those found in Gram-negative (Keuning et al., 1985) and Gram-positive haloalkane-utilizing bacteria (Keuning et al., 1985; Yokota et al., 1987; Scholtz et al., 1987; Sallis et al., 1990). Haloalkane dehalogenases, including DhlA from *Xanthobacter autotrophicus* GJ10 (Janssen et al., 1988, 1989), DhaA from *Rhodococcus rhodochrous*, and LinB from Spingomonas paucimobilis UT26 (Nagata et al., 1997) are enzymes which catalyze hydrolytic dehalogenation of corresponding hydrocarbons. Halogenated aliphatic hydrocarbons subject to conversion include $C_2$-$C_{10}$ saturated aliphatic hydrocarbons which have one or more halogen groups attached, wherein at least two of the halogens are on adjacent carbon atoms. Such aliphatic hydrocarbons include volatile chlorinated aliphatic (VCA) hydrocarbons. VCA's include, for example, aliphatic hydrocarbons such as dichloroethane, 1,2-dichloro-propane, 1,2-dichlorobutane and 1,2,3-trichloropropane. The term "halogenated hydrocarbon" as used herein means a halogenated aliphatic hydrocarbon. As used herein the term "halogen" includes chlorine, bromine, iodine, fluorine, astatine and the like. A preferred halogen is chlorine.

In one embodiment, the mutant hydrolase is a thermostable hydrolase such as a thermostable dehalogenase comprising at least one substitution at a position corresponding to amino acid residue 117 and/or 175 of a *Rhodococcus rhodochrous* dehalogenase, which substitution is correlated with enhanced thermostability. In one embodiment, the thermostable hydrolase is capable of binding a hydrolase substrate at low temperatures, e.g., from 0° C. to about 25° C. In one embodiment, a thermostable hydrolase is a thermostable mutant hydrolase, i.e., one having one or more substitutions in addition to the substitution at a position corresponding to amino acid residue 117 and/or 175 of a *Rhodococcus rhodochrous* dehalogenase. In one embodiment, a thermostable mutant dehalogenase has a substitution which results in removal of a charged residue, e.g., lysine. In one embodiment, a thermostable mutant dehalogenase has a serine or methionine at a position corresponding to residue 117 and/or 175 in DhaA from *Rhodococcus rhodochrous*.

The invention also provides a fusion protein comprising a mutant hydrolase and amino acid sequences for a protein or peptide of interest, e.g., sequences for a marker protein, e.g., a selectable marker protein, affinity tag, e.g., a polyhistidine sequence, an enzyme of interest, e.g., luciferase, RNasin, RNase, and/or GFP, a nucleic acid binding protein, an extracellular matrix protein, a secreted protein, an antibody or a portion thereof such as Fc, a bioluminescence protein, a receptor ligand, a regulatory protein, a serum protein, an immunogenic protein, a fluorescent protein, a protein with reactive cysteines, a receptor protein, e.g., NMDA receptor, a channel protein, e.g., an ion channel protein such as a sodium-, potassium- or a calcium-sensitive channel protein including a HERG channel protein, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, e.g., a protease substrate, a transcription factor, a protein destabilization sequence, or a transporter protein, e.g., EAAT1-4 glutamate transporter, as well as targeting signals, e.g., a plastid targeting signal, such as a mitochondrial localization sequence, a nuclear localization signal or a myristilation sequence, that directs the mutant hydrolase to a particular location.

The fusion protein may be expressed from a recombinant DNA which encodes the mutant hydrolase and at least one protein of interest, or formed by chemical synthesis. The protein of interest may be fused to the N-terminus or the C-terminus of the mutant hydrolase. In one embodiment, the fusion protein comprises a protein of interest at the N-terminus, and another protein, e.g., a different protein, at the C-terminus, of the mutant hydrolase. For example, the protein of interest may be a fluorescent protein or an antibody. Optionally, the proteins in the fusion are separated by a connector sequence, e.g., preferably one having at least 2 amino acid residues, such as one having 13 to 17 amino acid residues. The presence of a connector sequence in a fusion protein of the invention does not substantially alter the function of either protein in the fusion relative to the function of each individual protein. Thus, for a fusion of a mutant dehalogenase and *Renilla* luciferase, the presence of a connector sequence does not substantially alter the stability of the bond formed between the mutant dehalogenase and a substrate therefor or the activity of the luciferase. For any particular combination of proteins in a fusion, a wide variety of connector sequences may be employed. In one embodiment, the connector sequence is a sequence recognized by an enzyme, e.g., a cleavable sequence. For instance, the connector sequence may be one recognized by a caspase, e.g., DEVD (SEQ ID NO:17), or is a photocleavable sequence.

In one embodiment, the fusion protein may comprise a protein of interest at the N-terminus and, optionally, a different protein of interest at the C-terminus of the mutant hydrolase. As described herein, fusions of a mutant DhaA with GST (at the N-terminus), a Flag sequence (at the C-terminus) and *Renilla* luciferase (at the N-terminus or C-terminus) had no detectable effect on bond formation between the mutant DhaA and a substrate for wild-type DhaA which includes a functional group. Moreover, a fusion of a Flag sequence and DhaA.H272F could be attached to a solid support via a streptavidin-biotin-$C_{10}H_{21}N_1O_2$—Cl-DhaA.H272F bridge (an SFlag-ELISA experiment).

In one embodiment, a fusion protein includes a mutant hydrolase and a protein that is associated with a membrane or a portion thereof, e.g., targeting proteins such as those for endoplasmic reticulum targeting, cell membrane bound proteins, e.g., an integrin protein or a domain thereof such as the cytoplasmic, transmembrane and/or extracellular stalk domain of an integrin protein, and/or a protein that links the mutant hydrolase to the cell surface, e.g., a glycosylphosphoinositol signal sequence.

II. Optimized Hydrolase Sequences, and Vectors and Host Cells Encoding the Hydrolase Also provided is an isolated nucleic acid molecule (polynucleotide) comprising a nucleic acid sequence encoding a hydrolase or a fusion thereof. In one embodiment, the isolated nucleic acid molecule comprises a nucleic acid sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. In one embodiment, the polynucleotide includes a nucleic acid sequence encoding a dehalogenase, which nucleic acid sequence is optimized for expression is a selected host cell. In one embodiment, the optimized polynucleotide no longer hybridizes to the corresponding non-optimized sequence, e.g., does not hybridize to the non-optimized sequence under medium or high stringency conditions. In another embodiment, the polynucleotide has less than 90%, e.g., less than 80%, nucleic acid sequence identity to the corresponding non-optimized sequence and optionally encodes a polypeptide having at least 80%, e.g., at least 85%, 90% or more, amino acid sequence identity with the polypeptide encoded by the non-optimized sequence. Constructs, e.g., expression cassettes, and vectors comprising the isolated nucleic acid molecule, as well as kits comprising the isolated nucleic acid molecule, construct or vector are also provided.

A nucleic acid molecule comprising a nucleic acid sequence encoding a fusion with hydrolase is optionally optimized for expression in a particular host cell and also optionally operably linked to transcription regulatory sequences, e.g., one or more enhancers, a promoter, a transcription termination sequence or a combination thereof, to form an expression cassette.

In one embodiment, a nucleic acid sequence encoding a hydrolase or a fusion thereof is optimized by replacing codons in a wild-type or mutant hydrolase sequence with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. Thus, the optimized nucleic acid product has an improved level of expression due to improved codon usage frequency, and a reduced risk of inappropriate transcriptional behavior due to a reduced number of undesirable transcription regulatory sequences.

An isolated and optimized nucleic acid molecule of the invention may have a codon composition that differs from that of the corresponding wild-type nucleic acid sequence at more than 30%, 35%, 40% or more than 45%, e.g., 50%, 55%, 60% or more of the codons. Preferred codons for use in the invention are those which are employed more frequently than at least one other codon for the same amino acid in a particular organism and, more preferably, are also not low-usage codons in that organism and are not low-usage codons in the organism used to clone or screen for the expression of the nucleic acid molecule. Moreover, preferred codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In one embodiment of the invention, the codons that are different are those employed more frequently in a mammal, while in another embodiment the codons that are different are those employed more frequently in a plant. Preferred codons for different organisms are known to the art, e.g., see www.kazusa.or.jp./codon/. A particular type of mammal, e.g., a human, may have a different set of preferred codons than another type of mammal. Likewise, a particular type of plant may have a different set of preferred codons than another type of plant. In one embodiment of the invention, the majority of the codons that differ are ones that are preferred codons in a desired host cell. Preferred codons for organisms including mammals (e.g., humans) and plants are known to the art (e.g., Wada et al., 1990; Ausubel et al., 1997). For example, preferred human codons include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, in one embodiment, synthetic nucleic acid molecules of the invention have a codon composition which differs from a wild type nucleic acid sequence by having an increased number of the preferred human codons, e.g., CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the nucleic acid molecule of the invention may have an increased number of CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof, relative to the wild-type nucleic acid sequence. In another embodiment, preferred *C. elegans* codons include, but are not limited to, UUC (Phe), UUU (Phe), CUU (Leu), UUG (Leu), AUU (Ile), GUU (Val), GUG (Val), UCA (Ser), UCU (Ser), CCA (Pro), ACA (Thr), ACU (Thr), GCU (Ala), GCA (Ala), UAU (Tyr), CAU (His), CAA (Gln), AAU (Asn), AAA (Lys), GAU (Asp), GAA (Glu), UGU (Cys), AGA (Arg), CGA (Arg), CGU (Arg), GGA (Gly), or any combination thereof. In yet another embodiment, preferred *Drosophilia* codons include, but are not limited to, UUC (Phe), CUG (Leu), CUC (Leu), AUC (Ile), AUU (Ile), GUG (Val), GUC (Val), AGC (Ser), UCC (Ser), CCC (Pro), CCG (Pro), ACC (Thr), ACG (Thr), GCC (Ala), GCU (Ala), UAC (Tyr), CAC (His), CAG (Gln), AAC (Asn), AAG (Lys), GAU (Asp), GAG (Glu), UGC (Cys), CGC (Arg), GGC (Gly), GGA (gly), or any combination thereof. Preferred yeast codons include but are not limited to UUU (Phe), UUG (Leu), UUA (Leu), CCU (Leu), AUU (Ile), GUU (Val), UCU (Ser), UCA (Ser), CCA (Pro), CCU (Pro), ACU (Thr), ACA (Thr), GCU (Ala), GCA (Ala), UAU (Tyr), UAC (Tyr), CAU (His), CAA (Gln), AAU (Asn), AAC (Asn), AAA (Lys), AAG (Lys), GAU (Asp), GAA (Glu), GAG (Glu), UGU (Cys), CGU (Trp), AGA (Arg), CGU (Arg), GGU (Gly), GGA (Gly), or any combination thereof. Similarly, nucleic acid molecules having an increased number of codons that are employed more frequently in plants, have a codon composition which differs from a wild-type or parent nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

In one embodiment, an optimized nucleic acid sequence encoding a hydrolase or fusion thereof has less than 100%, e.g., less than 90% or less than 80%, nucleic acid sequence identity relative to a non-optimized nucleic acid sequence encoding a corresponding hydrolase or fusion thereof. For instance, an optimized nucleic acid sequence encoding DhaA has less than about 80% nucleic acid sequence identity relative to non-optimized (wild-type) nucleic acid sequence encoding a corresponding DhaA, and the DhaA encoded by the optimized nucleic acid sequence optionally has at least 85% amino acid sequence identity to a corresponding wild-type DhaA. In one embodiment, the activity of a DhaA encoded by the optimized nucleic acid sequence is at least 10%, e.g., 50% or more, of the activity of a DhaA encoded by the non-optimized sequence, e.g., a mutant DhaA encoded by the optimized nucleic acid sequence binds a substrate with substantially the same efficiency, i.e., at least 50%, 80%, 100% or more, as the mutant DhaA encoded by the non-optimized nucleic acid sequence binds the same substrate.

An exemplary optimized DhaA gene has the following sequence:

```
hDhaA.v2.1-6F (FINAL, with flanking sequences)
                                                  (SEQ ID NO: 50)
NNNNGCTAGCCAGCTGGCgcgGATATCGCCACCATGGGATCCGAGATTGGGACAGGG TTcCCTTTTGATCCTCAcTATGTtGAaGTGCTGGGgGAaAGAATGCAcTAcGTGGATGTG GGGCCTAGAGATGGGACcCCaGTGCTGTTcCTcCAcGGGAAcCCTACATCTagcTAcCTG TGGAGaAAtATTATaCCTCATGTtGCTCCTagtCATAGgTGcATTGCTCCTGATCTGATcGG GATGGGGAAGTCTGATAAGCCTGActtaGAcTAcTTTTTTGATGAtCATGTtcGATActTGG ATGCTTTcATTGAGGCTCTGGGGCTGGAGGAGGTGGTGCTGGTGATaCAcGAcTGGGG GTCTGCTCTGGGGTTTCAcTGGGCTAAaAGgAATCCgGAGAGAGTGAAGGGGATTGCT TGcATGGAgTTTATTcGACCTATTCCTACtTGGGAtGAaTGGCCaGAGTTTGCcAGAGAG ACATTTCAaGCcTTTAGAACtGCcGATGTGGGcAGgGAGCTGATTATaGAcCAGAATGCT TTcATcGAGGGGGCTCTGCCTAAaTGTGTaGTcAGACCTCTcACtGAaGTaGAGATGGAc CATTATAGAGAGCCcTTTCTGAAGCCTGTGGATcGcGAGCCTCTGTGGAGgTTtCCaAA TGAGCTGCCTATTGCTGGGGAGCCTGCTAATATTGTGGCTCTGGTGGAaGCcTATATG AAcTGGCTGCATCAGagTCCaGTGCCcAAGCTaCTcTTTTGGGGGACtCCgGGaGTtCTGA TTCCTCCTGCcGAGGCTGCTAGACTGGCTGAaTCcCTGCCcAAtTGTAAGACcGTGGAcA TcGGcCCtGGgCTGTTTTAcCTcCAaGAGGAcAAcCCTGATCTcATcGGGTCTGAGATcGCa cGgTGGCTGCCCGGGCTGGCCGGCTAATAGTTAATTAAGTAggCGGCCGCNNNN.
```

The nucleic acid molecule or expression cassette may be introduced to a vector, e.g., a plasmid or viral vector, which optionally includes a selectable marker gene, and the vector introduced to a cell of interest, for example, a prokaryotic cell such as *E. coli, Streptomyces* spp., *Bacillus* spp., *Staphylo-*

*coccus* spp. and the like, as well as eukaryotic cells including a plant (dicot or monocot), fungus, yeast, e.g., *Pichia, Saccharomyces* or *Schizosaccharomyces*, or mammalian cell. Preferred mammalian cells include bovine, caprine, ovine, canine, feline, non-human primate, e.g., simian, and human cells. Preferred mammalian cell lines include, but are not limited to, CHO, COS, 293, Hela, CV-1, SH-SY5Y (human neuroblastoma cells), HEK293, and NIH3T3 cells.

The expression of the encoded mutant hydrolase may be controlled by any promoter capable of expression in prokaryotic cells or eukaryotic cells. Preferred prokaryotic promoters include, but are not limited to, SP6, T7, T5, tac, bla, trp, gal, lac or maltose promoters. Preferred eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Preferred vectors for bacterial expression include pGEX-5X-3, and for eukaryotic expression include pCIneo-CMV.

The nucleic acid molecule, expression cassette and/or vector of the invention may be introduced to a cell by any method including, but not limited to, calcium-mediated transformation, electroporation, microinjection, lipofection, particle bombardment and the like.

III. Functional Groups

Functional groups useful in the substrates and methods of the invention are molecules that are detectable or capable of detection. A functional group within the scope of the invention is capable of being covalently linked to one reactive substituent of a bifunctional linker or a substrate for a hydrolase, and, as part of a substrate of the invention, has substantially the same activity as a functional group which is not linked to a substrate found in nature and is capable of forming a stable complex with a mutant hydrolase. Functional groups thus have one or more properties that facilitate detection, and optionally the isolation, of stable complexes between a substrate having that functional group and a mutant hydrolase. For instance, functional groups include those with a characteristic electromagnetic spectral property such as emission or absorbance, magnetism, electron spin resonance, electrical capacitance, dielectric constant or electrical conductivity as well as functional groups which are ferromagnetic, paramagnetic, diamagnetic, luminescent, electrochemiluminescent, fluorescent, phosphorescent, chromatic, antigenic, or have a distinctive mass. A functional group includes, but is not limited to, a nucleic acid molecule, i.e., DNA or RNA, e.g., an oligonucleotide or nucleotide, such as one having nucleotide analogs, DNA which is capable of binding a protein, single stranded DNA corresponding to a gene of interest, RNA corresponding to a gene of interest, mRNA which lacks a stop codon, an aminoacylated initiator tRNA, an aminoacylated amber suppressor tRNA, or double stranded RNA for RNAi, a protein, e.g., a luminescent protein, a peptide, a peptide nucleic acid, an epitope recognized by a ligand, e.g., biotin or streptavidin, a hapten, an amino acid, a lipid, a lipid bilayer, a solid support, a fluorophore, a chromophore, a reporter molecule, a radionuclide, such as a radioisotope for use in, for instance, radioactive measurements or a stable isotope for use in methods such as isotope coded affinity tag (ICAT), an electron opaque molecule, an X-ray contrast reagent, a MRI contrast agent, e.g., manganese, gadolinium (III) or iron-oxide particles, and the like. In one embodiment, the functional group is an amino acid, protein, glycoprotein, polysaccharide, triplet sensitizer, e.g., CALI, nucleic acid molecule, drug, toxin, lipid, biotin, or solid support, such as self-assembled monolayers (see, e.g., Kwon et al., 2004), binds $Ca^{2+}$, binds $K^+$, binds $Na^+$, is pH sensitive, is electron opaque, is a chromophore, is a MRI contrast agent, fluoresces in the presence of NO or is sensitive to a reactive oxygen, a nanoparticle, an enzyme, a substrate for an enzyme, an inhibitor of an enzyme, for instance, a suicide substrate (see, e.g., Kwon et al., 2004), a cofactor, e.g., NADP, a coenzyme, a succinimidyl ester or aldehyde, luciferin, glutathione, NTA, biotin, cAMP, phosphatidylinositol, a ligand for cAMP, a metal, a nitroxide or nitrone for use as a spin trap (detected by electron spin resonance (ESR), a metal chelator, e.g., for use as a contrast agent, in time resolved fluorescence or to capture metals, a photocaged compound, e.g., where irradiation liberates the caged compound such as a fluorophore, an intercalator, e.g., such as psoralen or another intercalator useful to bind DNA or as a photoactivatable molecule, a triphosphate or a phosphoramidite, e.g., to allow for incorporation of the substrate into DNA or RNA, an antibody, or a heterobifunctional cross-linker such as one useful to conjugate proteins or other molecules, cross-linkers including but not limited to hydrazide, aryl azide, maleimide, iodoacetamide/bromoacetamide, N-hydroxysuccinimidyl ester, mixed disulfide such as pyridyl disulfide, glyoxal/phenylglyoxal, vinyl sulfone/vinyl sulfonamide, acrylamide, boronic ester, hydroxamic acid, imidate ester, isocyanate/isothiocyanate, or chlorotriazine/dichlorotriazine.

For instance, a functional group includes but is not limited to one or more amino acids, e.g., a naturally occurring amino acid or a non-natural amino acid, a peptide or polypeptide (protein) including an antibody or a fragment thereof, a His-tag, a FLAG tag, a Strep-tag, an enzyme, a cofactor, a coenzyme, a peptide or protein substrate for an enzyme, for instance, a branched peptide substrate (e.g., Z-aminobenzoyl (Abz)-Gly-Pro-Ala-Leu-Ala-4-nitrobenzyl amide (NBA), a suicide substrate, or a receptor, one or more nucleotides (e.g., ATP, ADP, AMP, GTP or GDP) including analogs thereof, e.g., an oligonucleotide, double stranded or single stranded DNA corresponding to a gene or a portion thereof, e.g., DNA capable of binding a protein such as a transcription factor, RNA corresponding to a gene, for instance, mRNA which lacks a stop codon, or a portion thereof, double stranded RNA for RNAi or vectors therefor, a glycoprotein, a polysaccharide, a peptide-nucleic acid (PNA), lipids including lipid bilayers; or is a solid support, e.g., a sedimental particle such as a magnetic particle, a sepharose or cellulose bead, a membrane, glass, e.g., glass slides, cellulose, alginate, plastic or other synthetically prepared polymer, e.g., an eppendorf tube or a well of a multi-well plate, self assembled monolayers, a surface plasmon resonance chip, or a solid support with an electron conducting surface, and includes a drug, for instance, a chemotherapeutic such as doxorubicin, 5-fluorouracil, or camptosar (CPT-11; Irinotecan), an aminoacylated tRNA such as an aminoacylated initiator tRNA or an aminoacylated amber suppressor tRNA, a molecule which binds $Ca^{2+}$, a molecule which binds $K^+$, a molecule which binds $Na^+$, a molecule which is pH sensitive, a radionuclide, a molecule which is electron opaque, a contrast agent, e.g., barium, iodine or other MRI or X-ray contrast agent, a molecule which fluoresces in the presence of NO or is sensitive to a reactive oxygen, a nanoparticle, e.g., an immunogold particle, paramagnetic nanoparticle, upconverting nanoparticle, or a quantum dot, a nonprotein substrate for an enzyme, an inhibitor of an enzyme, either a reversible or irreversible inhibitor, a chelating agent, a cross-linking group, for example, a succinimidyl ester or aldehyde, glutathione, biotin or other avidin binding molecule, avidin, streptavidin, cAMP, phosphatidylinositol, heme, a ligand for cAMP, a metal, NTA, and, in one embodiment, includes one or more dyes, e.g., a xanthene dye, a calcium sensitive dye, e.g., 1-[2-amino-5-(2,7-dichloro-6-hydroxy-3-oxy-9-xanthenyl)-phenoxy]-2-(2'-amino-5'-methylphenoxy)ethane-N,N,N',N'-tetraacetic acid (Fluo-3), a sodium sensitive dye, e.g., 1,3-benzenedicarboxylic acid, 4,4'-[1,4,10,13-tetraoxa-7,16-diazacyclooctadecane-7,16-diylbis(5-methoxy-6,2-benzofurandiyl)]bis (PBFI), a NO sensitive dye, e.g., 4-amino-5-methylamino-2',7'-difluorescein, or other fluorophore. In one embodiment, the functional group is a hapten or an immunogenic molecule, i.e., one which is bound by antibodies specific for that molecule. In one embodiment, the functional group is not a radionuclide. In another embodiment, the functional group is a radionuclide, e.g., $^3$H, $^{14}$C, $^{35}$S, $^{125}$I, $^{131}$I, including molecule useful in diagnostic methods.

Methods to detect a particular functional group are known to the art. For example, a nucleic acid molecule can be detected by hybridization, amplification, binding to a nucleic acid binding protein specific for the nucleic acid molecule, enzymatic assays (e.g., if the nucleic acid molecule is a ribozyme), or, if the nucleic acid molecule itself comprises a molecule which is detectable or capable of detection, for instance, a radiolabel or biotin, it can be detected by an assay suitable for that molecule.

Exemplary functional groups include haptens, e.g., molecules useful to enhance immunogenicity such as keyhole limpet hemacyanin (KLH), cleavable labels, for instance, photocleavable biotin, and fluorescent labels, e.g., N-hydroxysuccinimide (NHS) modified coumarin and succinimide or sulfonosuccinimide modified BODIPY (which can be detected by UV and/or visible excited fluorescence detection), rhodamine, e.g., R110, rhodols, CRG6, Texas Methyl Red (carboxytetramethylrhodamine), 5-carboxy-X-rhodamine, or fluoroscein, coumarin derivatives, e.g., 7 aminocoumarin, and 7-hydroxycoumarin, 2-amino-4-methoxynapthalene, 1-hydroxypyrene, resorufin, phenalenones or benzphenalenones (U.S. Pat. No. 4,812,409), acridinones (U.S. Pat. No. 4,810,636), anthracenes, and derivatives of α- and β-napthol, fluorinated xanthene derivatives including fluorinated fluoresceins and rhodols (e.g., U.S. Pat. No. 6,162,931), bioluminescent molecules, e.g., luciferin, coelenterazine, luciferase, chemiluminescent molecules, e.g., stabilized dioxetanes, and electrochemiluminescent molecules. A fluorescent (or luminescent) functional group linked to a mutant hydrolase by virtue of being linked to a substrate for a corresponding wild-type hydrolase, may be used to sense changes in a system, like phosphorylation, in real time. Moreover, a fluorescent molecule, such as a chemosensor of metal ions, e.g., a 9-carbonylanthracene modified glycyl-histidyl-lysine (GHK) for $Cu^{2+}$, in a substrate of the invention may be employed to label proteins which bind the substrate. A luminescent or fluorescent functional group such as BODIPY, rhodamine green, GFP, or infrared dyes, also finds use as a functional group and may, for instance, be employed in interaction studies, e.g., using BRET, FRET, LRET or electrophoresis.

Another class of functional group is a molecule that selectively interacts with molecules containing acceptor groups (an "affinity" molecule). Thus, a substrate for a hydrolase which includes an affinity molecule can facilitate the separation of complexes having such a substrate and a mutant hydrolase, because of the selective interaction of the affinity molecule with another molecule, e.g., an acceptor molecule, that may be biological or non-biological in origin. For example, the specific molecule with which the affinity molecule interacts (referred to as the acceptor molecule) could be a small organic molecule, a chemical group such as a sulfhydryl group (—SH) or a large biomolecule such as an antibody or other naturally occurring ligand for the affinity molecule. The binding is normally chemical in nature and may involve the formation of covalent or non-covalent bonds or interactions such as ionic or hydrogen bonding. The acceptor molecule might be free in solution or itself bound to a solid or semi-solid surface, a polymer matrix, or reside on the surface of a solid or semi-solid substrate. The interaction may also be triggered by an external agent such as light, temperature, pressure or the addition of a chemical or biological molecule that acts as a catalyst. The detection and/or separation of the complex from the reaction mixture occurs because of the interaction, normally a type of binding, between the affinity molecule and the acceptor molecule.

Examples of affinity molecules include molecules such as immunogenic molecules, e.g., epitopes of proteins, peptides, carbohydrates or lipids, i.e., any molecule which is useful to prepare antibodies specific for that molecule; biotin, avidin, streptavidin, and derivatives thereof; metal binding molecules; and fragments and combinations of these molecules. Exemplary affinity molecules include His5 (HHHHH) (SEQ ID NO:19), HisX6 (HHHHHH) (SEQ ID NO:20), C-myc (EQKLISEEDL) (SEQ ID NO:21), Flag (DYKDDDDK) (SEQ ID NO:22), SteptTag (WSHPQFEK) (SEQ ID NO:23), HA Tag (YPYDVPDYA) (SEQ ID NO:24), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein. For example, a substrate for a hydrolase which includes biotin is contacted with a mutant hydrolase. The presence of the biotin in a complex between the mutant hydrolase and the substrate permits selective binding of the complex to avidin molecules, e.g., streptavidin molecules coated onto a surface, e.g., beads, microwells, nitrocellulose and the like. Suitable surfaces include resins for chromatographic separation, plastics such as tissue culture surfaces or binding plates, microtiter dishes and beads, ceramics and glasses, particles including magnetic particles, polymers and other matrices. The treated surface is washed with, for example, phosphate buffered saline (PBS), to remove molecules that lack biotin and the biotin-containing complexes isolated. In some case these materials may be part of biomolecular sensing devices such as optical fibers, chemfets, and plasmon detectors.

Another example of an affinity molecule is dansyllysine. Antibodies which interact with the dansyl ring are commercially available (Sigma Chemical; St. Louis, Mo.) or can be prepared using known protocols such as described in Antibodies: A Laboratory Manual (Harlow and Lane, 1988). For example, the anti-dansyl antibody is immobilized onto the packing material of a chromatographic column. This method, affinity column chromatography, accomplishes separation by causing the complex between a mutant hydrolase and a substrate of the invention to be retained on the column due to its interaction with the immobilized antibody, while other molecules pass through the column. The complex may then be released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.). Dansyllysine may conveniently be detected because of its fluorescent properties.

When employing an antibody as an acceptor molecule, separation can also be performed through other biochemical separation methods such as immunoprecipitation and immobilization of antibodies on filters or other surfaces such as beads, plates or resins. For example, complexes of a mutant hydrolase and a substrate of the invention may be isolated by coating magnetic beads with an affinity molecule-specific or a hydrolase-specific antibody. Beads are oftentimes separated from the mixture using magnetic fields.

Another class of functional molecules includes molecules detectable using electromagnetic radiation and includes but is not limited to xanthene fluorophores, dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In one embodiment, an optionally detectable functional group includes one of:

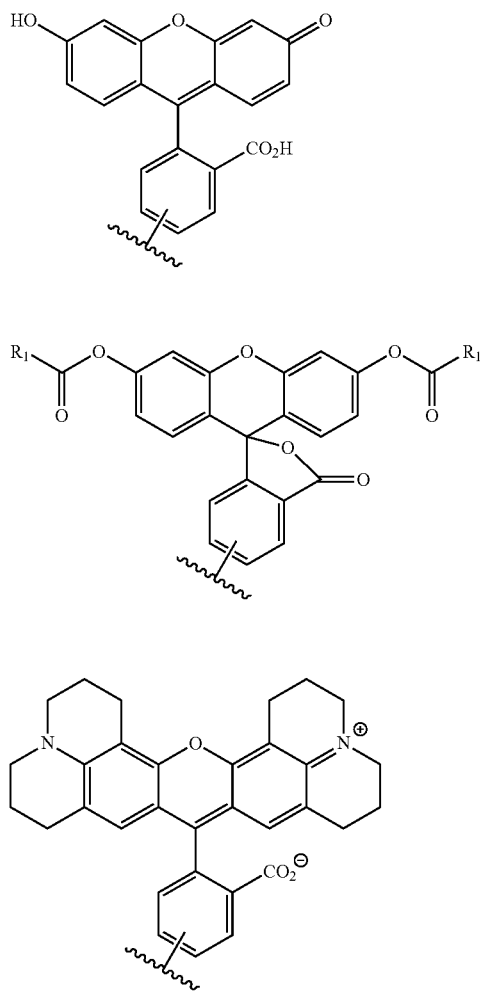

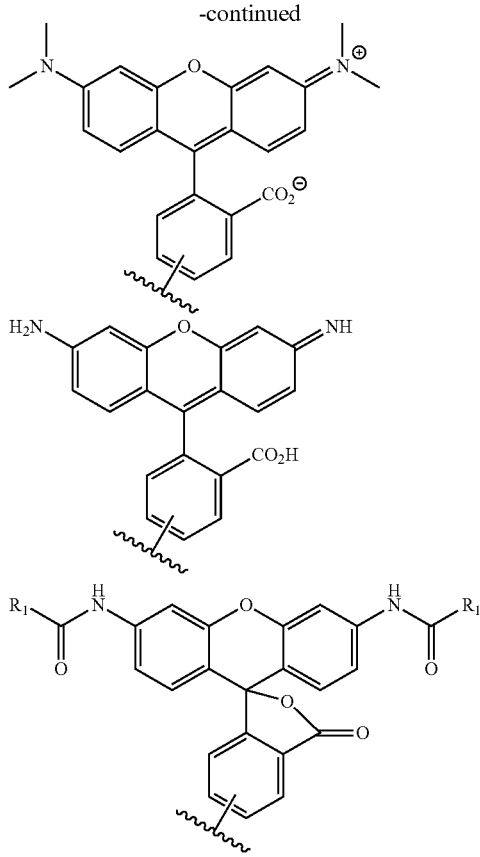

wherein $R_1$ is $C_1$-$C_8$.

In addition to fluorescent molecules, a variety of molecules with physical properties based on the interaction and response of the molecule to electromagnetic fields and radiation can be used to detect complexes between a mutant hydrolase and a substrate of the invention. These properties include absorption in the UV, visible and infrared regions of the electromagnetic spectrum, presence of chromophores which are Raman active, and can be further enhanced by resonance Raman spectroscopy, electron spin resonance activity and nuclear magnetic resonances and molecular mass, e.g., via a mass spectrometer.

Methods to detect and/or isolate complexes having affinity molecules include chromatographic techniques including gel filtration, fast-pressure or high-pressure liquid chromatography, reverse-phase chromatography, affinity chromatography and ion exchange chromatography. Other methods of protein separation are also useful for detection and subsequent isolation of complexes between a mutant hydrolase and a substrate of the invention, for example, electrophoresis, isoelectric focusing and mass spectrometry.

IV. Linkers

The term "linker", which is also identified by the symbol >L=, refers to a group or groups that covalently attach one or more functional groups to a substrate which includes a reactive group or to a reactive group. A linker, as used herein, is not a single covalent bond. The structure of the linker is not crucial, provided it yields a substrate that can be bound by its target enzyme. In one embodiment, the linker can be a divalent group that separates a functional group (R) and the reactive group by about 5 angstroms to about 1000 angstroms, inclusive, in length. Other suitable linkers include linkers that separate R and the reactive group by about 5 angstroms to about 100 angstroms, as well as linkers that separate R and the substrate by about 5 angstroms to about 50 angstroms, by about 5 angstroms to about 25 angstroms, by about 5 angstroms to about 500 angstroms, or by about 30 angstroms to about 100 angstroms.

In one embodiment the linker is an amino acid.

In another embodiment, the linker is a peptide.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (═O) groups, wherein one or more (e.g., 1, 2, 3, or 4) of the carbon atoms in the chain is optionally replaced with a non-peroxide —O—, —S— or —NH— and wherein one or more (e.g., 1, 2, 3, or 4) of the carbon atoms in the chain is replaced with an aryl or heteroaryl ring.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (═O) groups, wherein one or more (e.g., 1, 2, 3, or 4) of the carbon atoms in the chain is replaced with a non-peroxide —O—, —S— or —NH— and wherein one or more (e.g., 1, 2, 3, or 4) of the carbon atoms in the chain is replaced with one or more (e.g., 1, 2, 3, or 4) aryl or heteroaryl rings.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (═O) groups, wherein one or more (e.g., 1, 2, 3, or 4) of the carbon atoms in the chain is replaced with a non-peroxide —O—, —S— or —NH— and wherein one or more (e.g., 1, 2, 3, or 4) of the carbon atoms in the chain is replaced with one or more (e.g., 1, 2, 3, or 4) heteroaryl rings.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (═O) groups, wherein one or more (e.g., 1, 2, 3, or 4) of the carbon atoms in the chain is optionally replaced with a non-peroxide —O—, —S— or —NH—.

In another embodiment, the linker is a divalent group of the formula —W-F-W— wherein F is ($C_1$-$C_{30}$)alkyl, ($C_2$-$C_{30}$)alkenyl, ($C_2$-$C_{30}$)alkynyl, ($C_3$-$C_8$)cycloalkyl, or ($C_6$-$C_{10}$), wherein W is —N(Q)C(═O)—, —C(═O)N(Q)—, —OC(═O)—, —C(═O)O—, —O—, —S—, —S(O)—, —S(O)$_2$—, —N(Q)-, —C(═O)—, or a direct bond; wherein each Q is independently H or ($C_1$-$C_6$)alkyl In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (═O) groups.

In another embodiment, the linker is a divalent branched or unbranched carbon chain comprising from about 2 to about 30 carbon atoms, which chain optionally includes one or more (e.g., 1, 2, 3, or 4) double or triple bonds.

In another embodiment, the linker is a divalent branched or unbranched carbon chain comprising from about 2 to about 30 carbon atoms.

In another embodiment, the linker is a divalent branched or unbranched carbon chain comprising from about 2 to about 20 carbon atoms, which chain optionally includes one or more (e.g., 1, 2, 3, or 4) double or triple bonds, and which chain is optionally substituted with one or more (e.g., 2, 3, or 4) hydroxy or oxo (═O) groups.

In another embodiment, the linker is a divalent branched or unbranched carbon chain comprising from about 2 to about 20 carbon atoms, which chain optionally includes one or more (e.g., 1, 2, 3, or 4) double or triple bonds.

In another embodiment, the linker is a divalent branched or unbranched carbon chain comprising from about 2 to about 20 carbon atoms.

In another embodiment, the linker is —($CH_2CH_2O$)—$_{1-10}$.

In another embodiment, the linker is —C(═O)NH($CH_2$)$_3$—; —C(═O)NH($CH_2$)$_5$C(═O)NH($CH_2$)—; —$CH_2$OC(═O)NH($CH_2$)$_2$O($CH_2$)$_2$O ($CH_2$)—; —C(═O)NH($CH_2$)$_2$O($CH_2$)$_2$O($CH_2$)$_3$—; —$CH_2$C(═O)NH($CH_2$)$_2$O($CH_2$)$_2$O($CH_2$)$_3$—; —($CH_2$)$_4$C(═O)NH($CH_2$)$_2$O($CH_2$)$_2$O ($CH_2$)$_3$—; —C(═O)NH($CH_2$)$_5$C(═O)NH($CH_2$)$_2$O ($CH_2$)$_2$O($CH_2$)$_3$—.

In another embodiment, the linker comprises one or more divalent heteroaryl groups.

Specifically, ($C_1$-$C_{30}$)alkyl can be methyl, ethyl, propyl, isopropyl, butyl, iso-butyl, sec-butyl, pentyl, 3-pentyl, hexyl, heptyl, octyl, nonyl, or decyl; ($C_3$-$C_8$)cycloalkyl can be cyclopropyl, cyclobutyl, cyclopentyl, or cyclohexyl;($C_2$-$C_{30}$) alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, heptenyl, octenyl, nonenyl, or decenyl; ($C_2$-$C_{30}$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, heptynyl, octynyl, nonynyl, or decynyl; ($C_6$-$C_{10}$) aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term aromatic includes aryl and heteroaryl groups.

Aryl denotes a phenyl radical or an ortho-fused bicyclic carbocyclic radical having about nine to ten ring atoms in which at least one ring is aromatic.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "amino acid," when used with reference to a linker, comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes natural and unnatural amino acids bearing a conventional amino protecting group (e.g., acetyl or benzyloxycarbonyl), as well as natural and unnatural amino acids protected at the carboxy terminus (e.g. as a $(C_1-C_6)$alkyl, phenyl or benzyl ester or amide). Other suitable amino and carboxy protecting groups are known to those skilled in the art (see for example, Greene, *Protecting Groups In Organic Synthesis*; Wiley: New York, 1981, and references cited therein). An amino acid can be linked to another molecule through the carboxy terminus, the amino terminus, or through any other convenient point of attachment, such as, for example, through the sulfur of cysteine.

The term "peptide" when used with reference to a linker, describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to another molecule through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

In one embodiment, a substrate of the invention for a dehalogenase which has a linker has the formula (I):

R-linker-A-X     (I)

wherein R is one or more functional groups (such as a fluorophore, biotin, luminophore, or a fluorogenic or luminogenic molecule, or is a solid support, including microspheres, membranes, polymeric plates, glass beads, glass slides, and the like), wherein the linker is a multiatom straight or branched chain including C, N, S, or O, wherein A-X is a substrate for a dehalogenase, and wherein X is a halogen. In one embodiment, A-X is a haloaliphatic or haloaromatic substrate for a dehalogenase. In one embodiment, the linker is a divalent branched or unbranched carbon chain comprising from about 12 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH—. In one embodiment, the linker comprises 3 to 30 atoms, e.g., 11 to 30 atoms. In one embodiment, the linker comprises $(CH_2CH_2O)_y$, and y=2 to 8. In one embodiment, A is $(CH_2)_n$ and n=2 to 10, e.g., 4 to 10. In one embodiment, A is $CH_2CH_2$ or $CH_2CH_2CH_2$. In another embodiment, A comprises an aryl or heteroaryl group. In one embodiment, a linker in a substrate for a dehalogenase such as a *Rhodococcus* dehalogenase, is a multiatom straight or branched chain including C, N, S, or O, and preferably 11-30 atoms when the functional group R includes an aromatic ring system or is a solid support.

In another embodiment, a substrate of the invention for a dehalogenase which has a linker has formula (II):

R-linker-$CH_2$—$CH_2$—$CH_2$—X     (II)

where X is a halogen, preferably chloride. In one embodiment, R is one or more functional groups, such as a fluorophore, biotin, luminophore, or a fluorogenic or luminogenic molecule, or is a solid support, including microspheres, membranes, glass beads, and the like. When R is a radiolabel, or a small detectable atom such as a spectroscopically active isotope, the linker can be 0-30 atoms.

V. Syntheses for Exemplary Substrates

[2-(2-Hydroxy-ethoxy)-ethyl]-carbamic acid anthracen-9-ylmethyl ester. To a stirring slurry of 9-anthracenemethanol (10 g, 48 mmol) and 4-nitrophenyl chloroformate (13.6 g, 67.5 mmol) in 200 ml $CH_2Cl_2$ was added triethylamine (6.7 ml, 0.19 mol). The resulting gold colored solution was allowed to stir 16 hrs at room temperature. At this point, 2-(2-aminoethoxy)ethanol (14.4 ml, 0.144 mol) was added and stirring continued for another 24 hours. The $CH_2Cl_2$ reaction mixture was then washed with a 2% sodium hydroxide (w/w) solution until no p-nitrophenol was observed in the organic layer. The dichloromethane was dried with sodium sulfate, filtered, and evaporated under reduced pressure.

The crude product was further purified by column chromatography on silica gel 60, progressively eluting with 1% to 3% methanol in dichloromethane. 7.6 g (58% yield) of a yellow solid was isolated: $^1$H NMR (CDCl$_3$) δ 8.38 (s, H-10), 8.28 (d, H-1, 8), 7.94 (d, H-4, 5), 7.44 (m, H-2, 3, 6, 7), 6.06 (s, C$\overline{H_2}$-anth), 5.47 (t, exchangeable, N$\overline{H}$), 3.53 (bs, CH$_2$—O$\overline{H}$) 3.33 (m, three —CH$_2$—). Mass spectrum, m/e Calcd for $C_{20}H_{22}NO_4^+$: 340.15. Found: 340.23. Calcd for $C_{20}H_{21}NNaO_4^+$: 340.15. Found: 340.23.

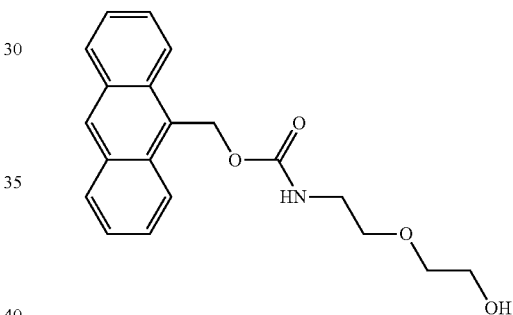

a compound of formula III

{2-[2-(6-Chloro-hexyloxy)-ethoxy]-ethyl}-carbamic acid anthracen-9-ylmethyl ester. A 100 ml round bottom flask was charged with [2-(2-Hydroxy-ethoxy)-ethyl]-carbamic acid anthracen-9-ylmethyl ester (1.12 g, 3 mmol) and fresh sodium hydride, 60% dispersion in mineral oil (360 mg, 9 mmol) under inert atmosphere. 20 ml anhydrous THF was added and the reaction allowed to stir for 30 minutes. The flask is then cooled to between −10 and −20° C. by means of an ice/NaCl bath. When the temperature is reached 1-chloro-6-Iodohexane (1 ml, 6 mmol) is added via syringe. The reaction is maintained at ice/NaCl temperature for 2 hours, then slowly allowed to warm to room temperature overnight. At this point silica gel 60 is co-absorbed onto the reaction mixture with loss of solvent under reduced pressure. Silica gel chromatography takes place initially with heptane as eluent, followed by 10%, 20%, and 25% ethyl acetate. A total of 0.57 g (41% yield) of product is isolated from appropriate fractions: $^1$H NMR (CDCl$_3$) δ 8.48 (s, H-10), 8.38 (d, H-1, 8), 8.01 (d, H-4, 5), 7.52 (dt, H-2, 3, 6, 7), 6.13 (s, CH$_2$-anth), 5.29 (bs, exchangeable, N$\overline{H}$), 3.74 (m, 4H), 3.55-$\overline{3}$.15 (m, 8H), 1.84 (m, 4H), 1.61 (m, $\overline{1}$H), 1.43 (m, 1H), 1.25 (m, 2H). Mass spectrum, m/e Calcd for $C_{26}H_{32}ClNO_4\cdot H_2O$: 475.21 (100%), 476.22 (29.6%). Found: 475.21, 476.52.

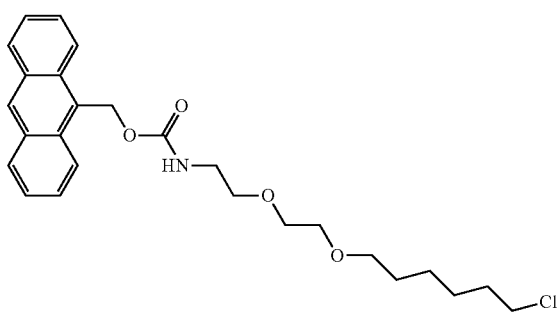

a compound of formula IV

2-[2-(6-chlorohexyloxy)-ethoxy]-ethyl-ammonium trifluoro-acetate. To {2-[2-(6-Chloro-hexyloxy)-ethoxy]-ethyl}-carbamic acid anthracen-9-ylmethyl ester (0.56 g, 1.2 mmol) dissolved in 4 ml dichloromethane was added 2 drops of anisole. The reaction mixture is cooled by means of an ice/NaCl bath. After 10 minutes trifluoroacetic acid (2 ml) is added. The reaction mixture turns dark brown upon addition and is allowed to stir for 30 minutes. All volatiles are removed under reduced atmosphere. The residue is re-dissolved in $CH_2Cl_2$ and washed twice with water. The aqueous fractions are frozen and lyophilized overnight. An oily residue remains and is dissolved in anhydrous DMF to be used as a stock solution in further reactions. Mass spectrum, m/e Calcd for $C_{10}H_{23}ClNO_2^+$: 224.14 (100%), 226.14 (32%). Found: 224.2, 226.2.

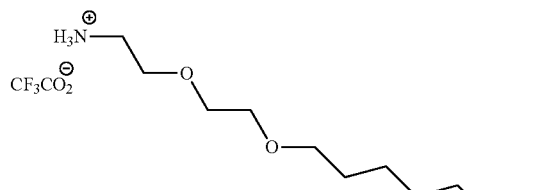

a compound of formula V

General Methodology for Reporter Group Conjugation to 2-[2-(6-chloro-hexyloxy)-ethoxy]-ethylamine. To one equivalent of the succinimidyl ester of the reporter group in DMF is added 3 equivalence of 2-[2-(6-chlorohexyloxy)-ethoxy]-ethyl-ammonium trifluoro-acetate stock solution, followed by diisopropylethylamine. The reaction is stirred from 8 to 16 hours at room temperature. Purification is accomplished by preparative scale HPLC or silica gel chromatography.

N-{2-[2-(6-Chlorohexyloxy)-ethoxy]-ethyl}-fluorescein-5-amide. The title compound was prepared using the above methodology. Purification was accomplished using preparative scale HPLC. Mass spectrum, m/e Calcd for $C_{31}H_{31}ClNO_8^-$: 580.17 (100%), 581.18 (32%). Found: 580.18, 581.31.

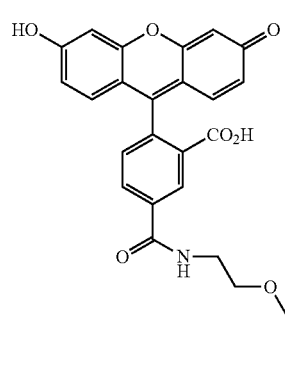

a compound of formula VI

N-{2-[2-(6-Chlorohexyloxy)-ethoxy]ethyl}-biotin-amide. The title compound was prepared using the above methodology. Purification was accomplished using silica gel chromatography (2% to 5% methanol in dichloromethane). Mass spectrum, m/e Calcd for $C_{20}H_{37}ClN_3O_4S^+$: 450.22 (100%), 452.22 (32%). Found: 449.95, 451.89.

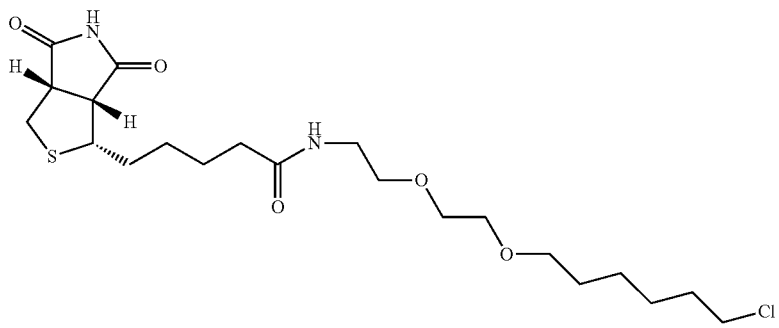

a compound of formula VII

N-{2-[2-(6-Chlorohexyloxy)-ethoxy]-ethyl}-tetramethyl-rhodamine-5-(and -6)-amide. The title compound was prepared using the above methodology. Purification was accomplished using preparative scale HPLC. Separation of structural isomers was realized. Mass spectrum, m/e Calcd for $C_{35}H_{43}ClN_3O_6^+$: 636.28 (100%), 637.29 (39.8%), 638.28 (32.4%). Found: 636.14, 637.15, 638.14.

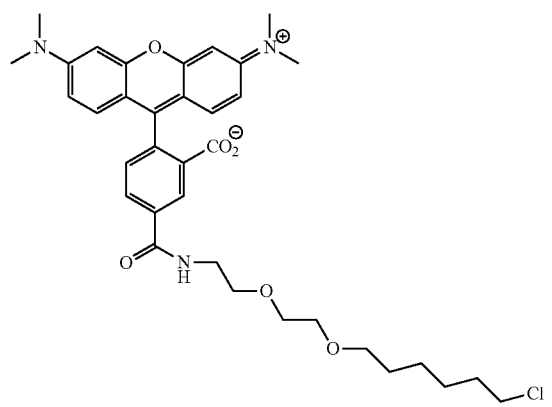

a compound of formula VIII

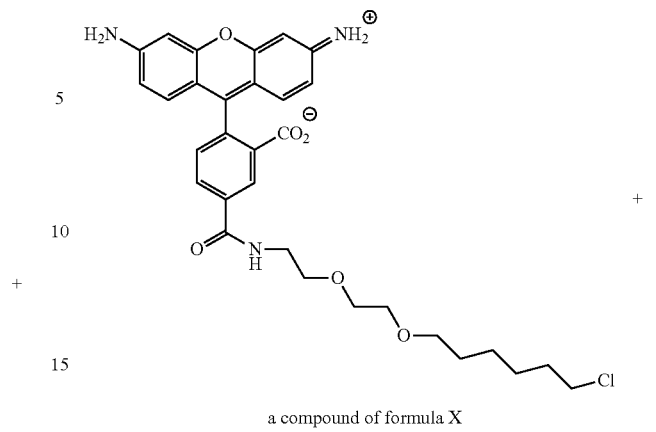

a compound of formula X

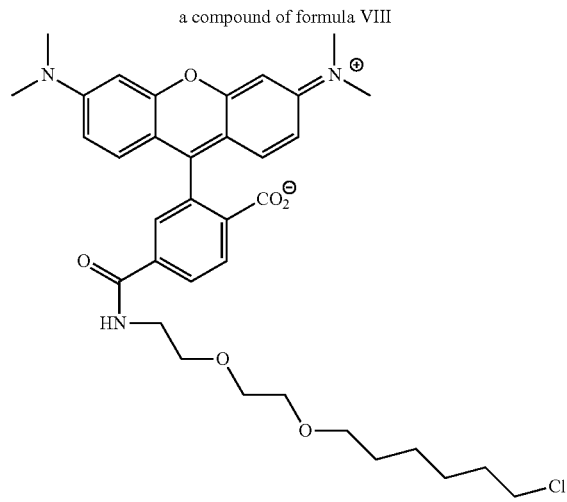

a compound of formula IX

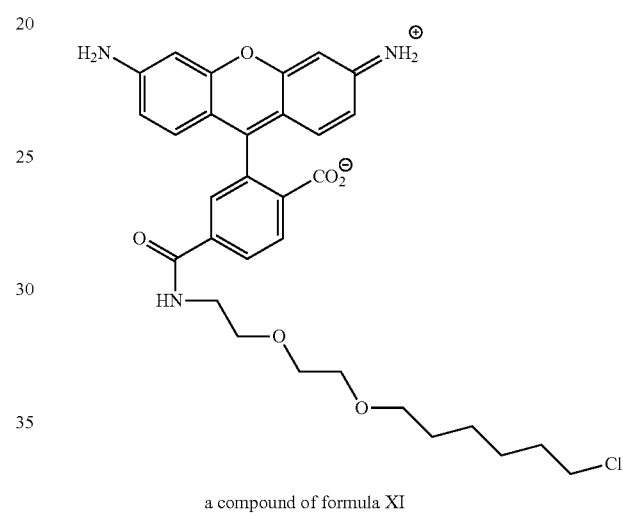

a compound of formula XI

N-{2-[2-(6-Chlorohexyloxy)-ethoxy]ethyl}-rhodamine R110-5-(and -6)-amide. The title compound was prepared using the above methodology. Purification was accomplished using preparative scale HPLC. Separation of structural isomers was realized. Mass spectrum, m/e Calcd for $C_{31}H_{35}ClN_3O_6^+$: 580.2 (100%), 581.2 (35.6%), 582.2 (32.4%). Found: 580.4, 581.4, 582.2.

6-({4-[4,4-difluoro-5-(thiophen-2-yl)-4-bora-3a-4-a-diaza-s-indacene-3-yl]phenoxy}-acetylamino)-hexanoic acid {2-[2-(6-chlorohexyloxy)-ethoxy]-ethyl}-amide. The title compound was prepared using the above methodology. Purification was accomplished using silica gel chromatography (3% to 5% methanol in dichloromethane). Mass spectrum, m/e Calcd for $C_{37}H_{47}BClF_2N_4O_5S^+$: 743.3 (100%). Found: 743.4.

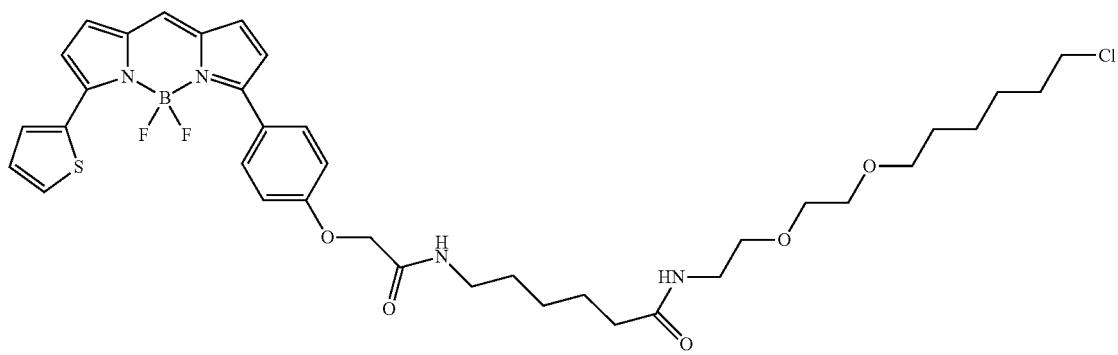

a compound of formula XII 6-({4-[4,4difluoro-5-(thiophen-2-yl)-4-bora-3a-4-a-diaza-s-indacene-3-yl]styryloxy}-acetylamino)-hexanoic acid {2-[2-(6-chlorohexyloxy)-ethoxy]-ethyl}-amide. The title compound was prepared using the above methodology. Purification was accomplished using silica gel chromatography (3% methanol in dichloromethane). Mass spectrum, m/e Calcd for $C_{39}H_{48}BClF_2N_4NaO_5S^+$: 791.3 (100%). Found: 7.91.3.

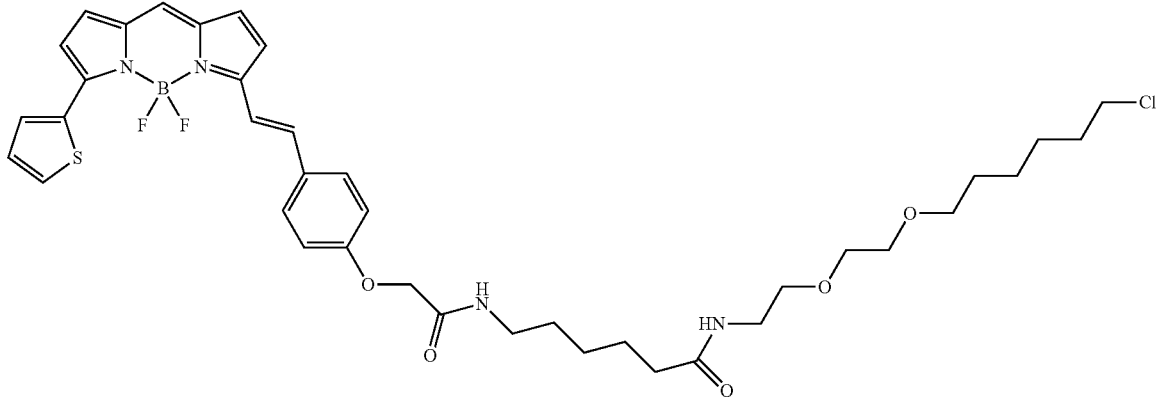

a compound of formula XIII

Triethylammonium 3-[5-[2-(4-tert-Butyl-7-diethylamino-chromen-2-ylidene)-ethylidene]-3-(5-{2-[2-(6-chlorohexyloxy)-ethoxy]-ethylcarbamoyl}-pentyl)-2,4,6-trioxo-tetrahydro-pyrimidin-1-yl]-propane-1-sulfonic acid anion. The title compound was prepared using the above methodology. Purification was accomplished using preparative scale HPLC. Mass spectrum, m/e Calcd for $C_{42}H_{62}ClN_4O_{10}S^-$: 849.4 (100%), 850.4 (48.8%), 851.4 (36.4%). Found: 849.6, 850.5, 851.5.

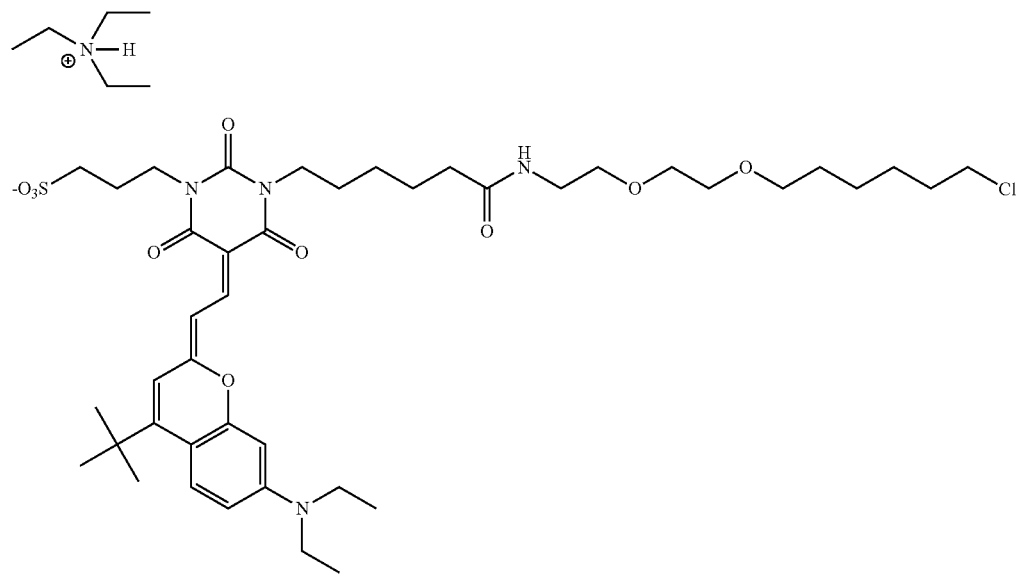

a compound of formula XIV 2-tert-Butyl-4-{3-[1-(5-{2-[2-(6-chlorohexyloxy)-ethoxy]-ethylcarbamoyl}-pentyl)-3,3-dimethyl-5-sulfo-1,3-dihydro-indol-2-ylidene]-propenyl}-7-diethylamino-chromenylium chloride. The title compound was prepared using the above methodology. Purification was accomplished using preparative scale HPLC. Mass spectrum, m/e Calcd for $C_{46}H_{67}ClN_3O_7S^-$: 840.4 (100%), 841.4 (54.4%). Found: 840.5, 841.5.

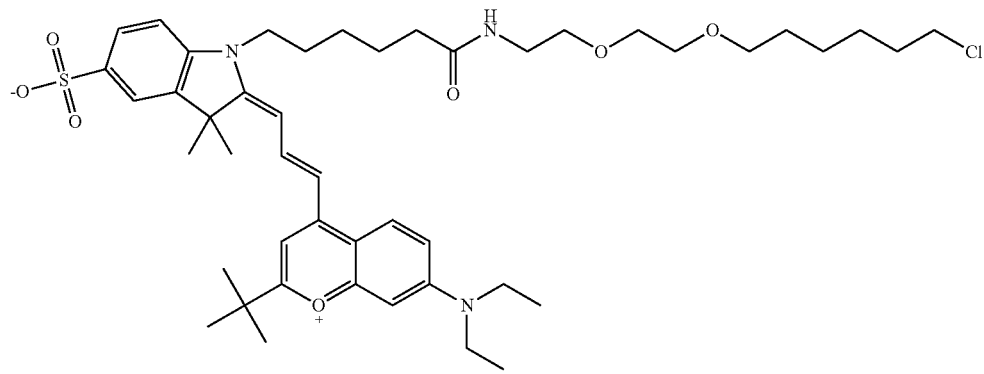

a compound of formula XV

N-{2-[2-(6-Chlorohexyloxy)-ethoxy]-ethyl}-3-{4-[5-(4-dimethylamino-phenyl)-oxazol-2-yl]-benzenesulfonylamino}-propionamide. The title compound was prepared using the above methodology. Purification was accomplished using preparative scale HPLC. Mass spectrum, m/e Calcd for $C_{30}H_{40}ClN_4O_6S^-$: 619.2 (100%), 620.2 (35%). Found: 619.5, 620.7.

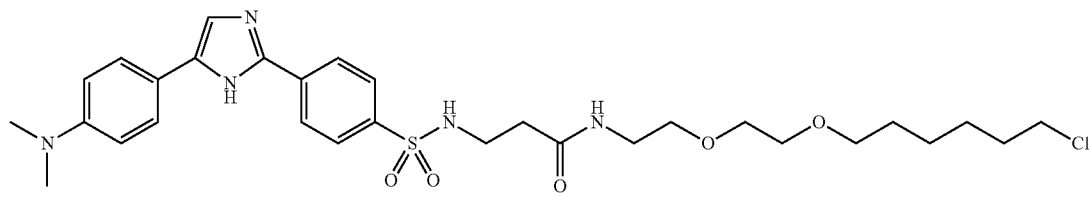

a compound of formula XVI

N-{2-[2-(6-Chlorohexyloxy)-ethoxy]-ethyl}-9'-chloroseminaphthofluorescein-5-(and -6)-amide. The title compound was prepared using the above methodology. Purification was accomplished using preparative scale HPLC. Separation of structural isomers was realized. Mass spectrum, m/e Calcd for $C_{35}H_{34}Cl_2NO_8^+$: 666.17 (100%), 668.16 (64%), 667.17 (39.8%). Found: 666.46, 668.44, 667.51.

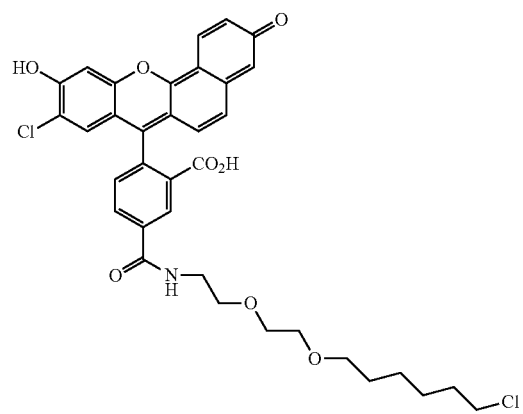

a compound of formula XVII

+

-continued

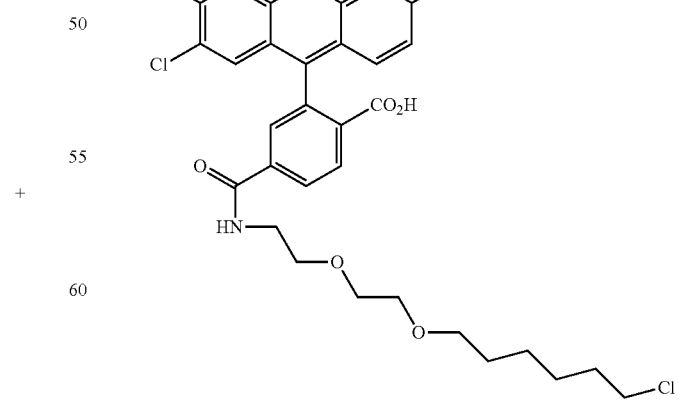

a compound of formula XVIII

N-{2-[2-(6-Chlorohexyloxy)-ethoxy]-ethyl}-seminaphthodimethylrhodamine-5-(and -6)-amide. The title compound was prepared using the above methodology. Purification was accomplished using preparative scale HPLC. Mass spectrum, m/e Calcd for $C_{37}H_{38}ClN_2O_7^-$: 657.24 (100%), 658.24 (42%), 659.23 (32%). Found: 657.46, 658.47, 659.45.

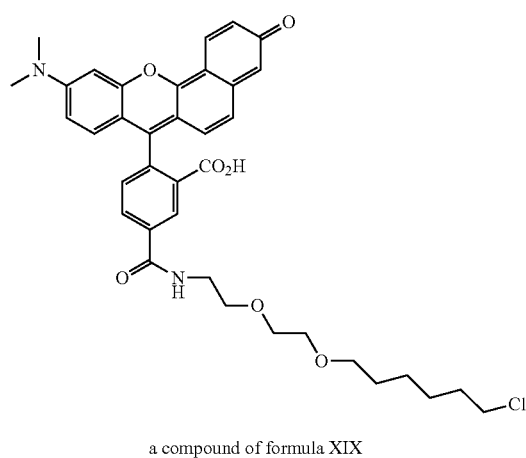

a compound of formula XIX

+

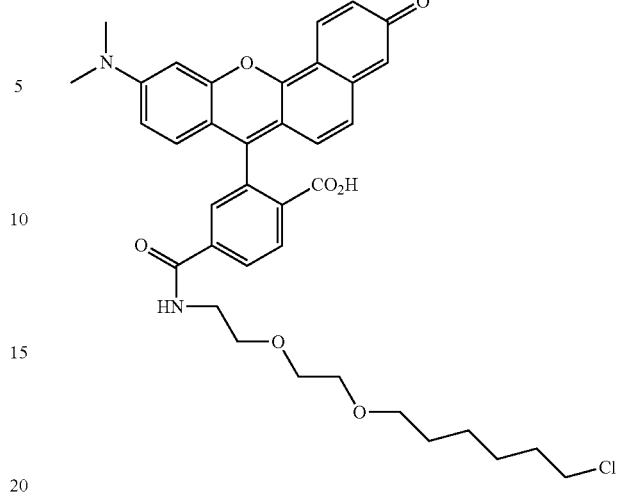

a compound of formula XX 6-(3',6'-dipivaloylfluorescein-5-(and -6)-carboxamido) hexanoic acid {2-[2-(6-chlorohexyloxy)-ethoxy]-ethyl}-amide. To a 100 ml round bottom flask containing 6-(3',6'-dipivaloylfluorescein-5-(and -6)-carboxamido) hexanoic acid succinimidyl ester (0.195 g, 0.26 mmol) was added 2-[2-(6-chlorohexyloxy)-ethoxy]-ethylamine (~0.44 mmol) in 25 ml $Et_2O$, followed by 2 ml of pyridine. The reaction mixture was allowed to stir overnight. After evaporation under reduced pressure, the residue was subjected to silica gel 60 column chromatography, progressively using 2% to 5% methanol in dichloromethane as eluent. The appropriate fractions were collected and dried under vacuum (0.186 g, 0.216 mmol, and 84% yield). Mass spectrum, m/e Calcd for $C_{47}H_{60}ClN_2O_{11}^+$: 863.39 (100%), 864.39 (54.4%), 865.39 (34.6%). Found: 862.94, 864.07, 864.94.

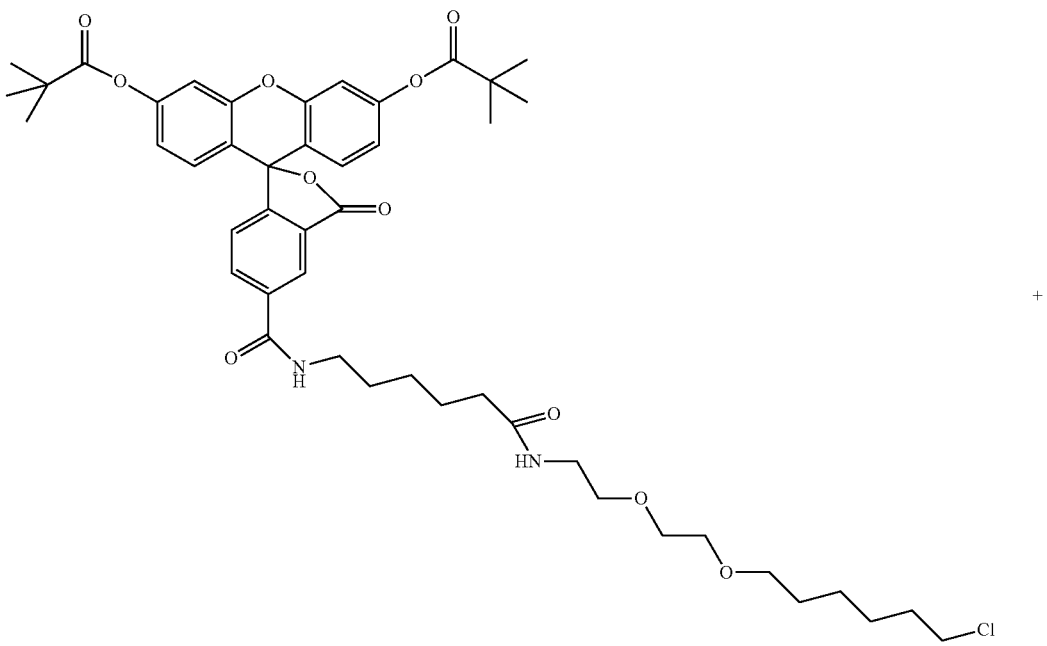

a compound of formula XXI

+

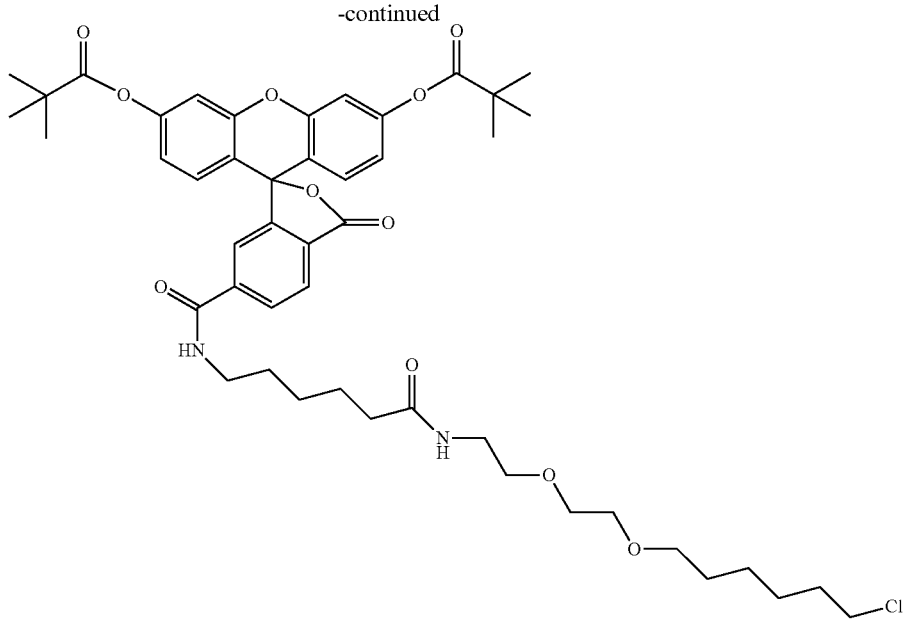

a compound of formula XXII 6-(fluorescein-5-(and -6)-carboxamido) hexanoic acid {2-[2-(6-chlorohexyloxy)-ethoxy]-ethyl}-amide. 6-(3',6'-dipivaloylfluorescein-5-(and -6)-carboxamido) hexanoic acid {2-[2-(6-chlorohexyloxy)-ethoxy]-ethyl}-amide (0.186 g, 0.216 mmol) was dissolved in 5 ml methanol and 0.5 ml 2M sodium carbonate(aq) added. The reaction mixture was stirred for 16 hours, then filtered. Purification was accomplished using preparative scale HPLC. Separation of structural isomers was realized. Mass spectrum, m/e Calcd for $C_{37}H_{44}ClN_2O_9^+$: 695.27 (100.0%), 696.28 (42.2%), 697.27 (32.3%). Found:

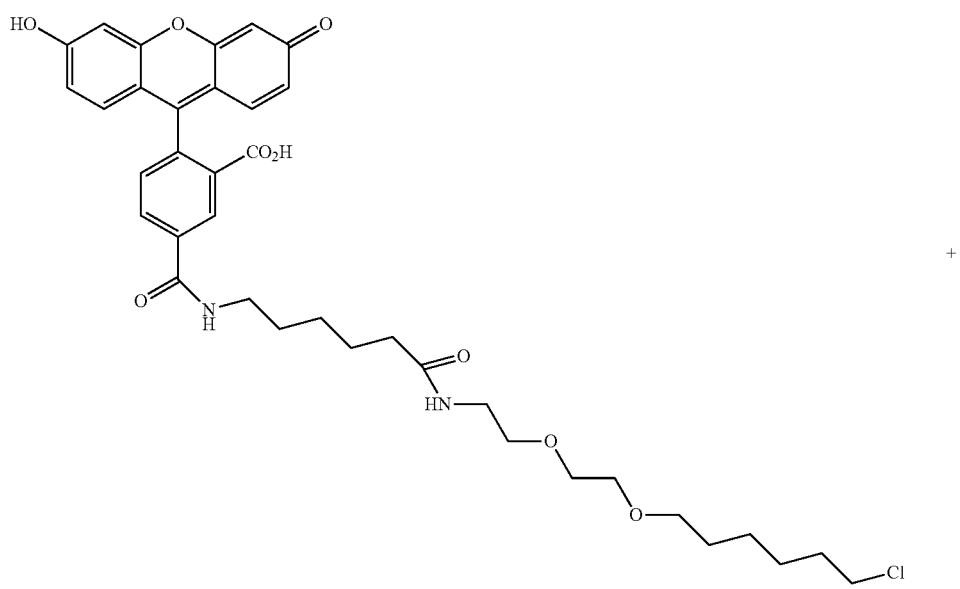

a compound of formula XXIII

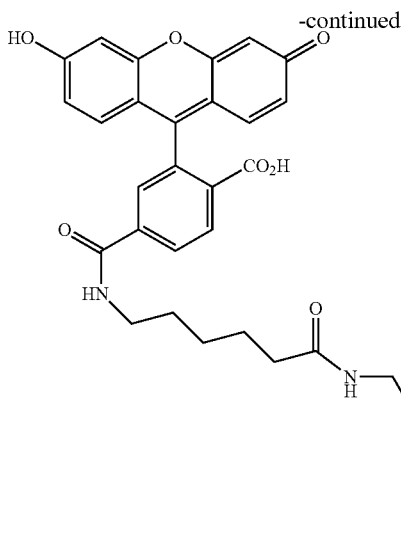

a compound of formula XXIV

{2-[2-(4-Chlorobutoxy)-ethoxy]ethyl}-carbamic acid anthracen-9-ylmethyl ester. A 50 ml round bottom flask was charged with [2-(2-Hydroxyethoxy)-ethyl]-carbamic acid anthracen-9-ylmethyl ester (0.25 g, 0.74 mmol) and fresh sodium hydride, 60% dispersion in mineral oil (150 mg, 3.75 mmol) under inert atmosphere. 10 ml anhydrous THF was added and the reaction allowed to stir for 5 minutes. After this point, 1-chloro-4-Iodobutane (180 μl, 1.5 mmol) is added via syringe. The reaction is stirred at room temperature for 24 hours. Silica gel 60 is co-absorbed onto the reaction mixture with loss of solvent under reduced pressure. Silica gel column chromatography takes place initially with heptane as eluent, followed by 10%, 20%, and 30% ethyl acetate. A total of 0.1 g (32% yield) of product is isolated from appropriate fractions: $^1$H NMR (CDCl$_3$) δ 8.50 (s, H-10), 8.40 (d, H-1, 8), 8.03 (d, H-4, 5), 7.53 (dt, H-2, 3, 6, 7), 6.15 (s, CH$_2$-anth), 5.19 (m, exchangeable, NH), 3.93-3.32 (m, 12H) 1.69-1.25 (m, 4H). Mass spectrum, m/e Calcd for C$_{24}$H$_{28}$ClNO$_4$.H$_2$O: 447.18 (100.0%), 448.18 (27.1%). Found: 447.17, 448.41.

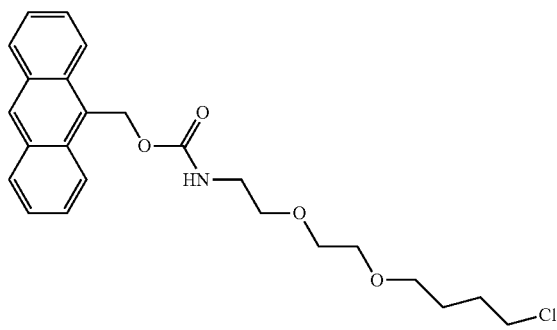

a compound of formula XXV 2-(2-{2-[2-(2-Chloroethoxy)-ethoxy]-ethoxy}-ethyl)-isoindole-1,3-dione. 2-(2-{2-[2-(2-Hydroxy-ethoxy)-ethoxy]-ethoxy}-ethyl)-isoindole-1,3-dione (0.5 g, 1.55 mmol) was prepared by the method of Nielsen, J. and Janda, K.D. (Methods: A Companion to Methods in Enzymology 6, 361-371 (1994)). To this reagent was added polystyrene-supported triphenylphosphine about 3 mmol P/g (0.67 g, 2 mmol) and 6 ml carbon tetrachloride, into a 25 ml round bottom fitted with a reflux condenser. The reaction set-up was sparged with argon then heated to reflux for 2 hours. Upon cooling, more polystyrene-supported triphenylphosphine (0.1 g, 0.3 mmol) was added and the reaction refluxed for an additional one hour. The cooled solution was filtered and the resin washed with additional carbon tetrachloride. Evaporation of solvent yielded 0.4 g (75.5% yield) of pure title compound: $^1$H NMR (CDCl$_3$) δ 7.82 (dd, 2H), 7.69 (dd, 2H), 3.88 (t, 2H), 3.71 (q, 4H), 3.63-3.56 (m, 12H). Mass spectrum, m/e Calcd for C$_{16}$H$_{21}$ClNO$_5$$^+$: 342.11 (100.0%), 344.11 (32.0%). Found: 341.65, 343.64.

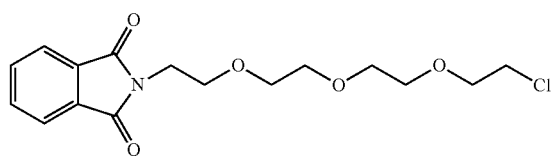

a compound of formula XXVI

2-[2-(2-{2-[2-(2-Chloroethoxy)-ethoxy]-ethoxy}-ethoxy)-ethyl]-isoindole-1,3-dione. The title compound was prepared according to the previous example in 89% yield: $^1$H NMR (CDCl$_3$) δ 7.77 (dd, 2H), δ 7.64 (dd, 2H), 3.83 (t, 2H), 3.67 (m, 4H), 3.60-3.52 (m, 14H). Mass spectrum, m/e Calcd for C$_{18}$H$_{25}$ClNO$_6$$^+$: 386.14 (100.0%), 388.13 (32.0%). Found: 385.88, 387.83.

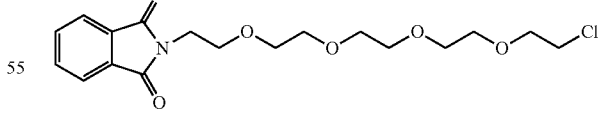

a compound of formula XXVII

2-{2-[2-(2-{2-[2-(2-Chloroethoxy)-ethoxy]-ethoxy}-ethoxy)-ethoxy]-ethyl}-isoindole-1,3-dione. The title compound was prepared according to the synthesis of 2-(2-{2-[2-(2-Chloro-ethoxy)-ethoxy]-ethoxy}-ethyl)-isoindole-1,3-dione in 92% yield: $^1$H NMR (CDCl$_3$) δ 7.84 (dd, 2H), 7.71 (dd, 2H), 3.90 (t, 2H), 3.74 (q, 4H), 3.67-3.58 (m, 18H). Mass spectrum, m/e Calcd for C$_{20}$H$_{29}$ClNO$_7$$^+$: 430.16 (100.0%). Found: 429.85.

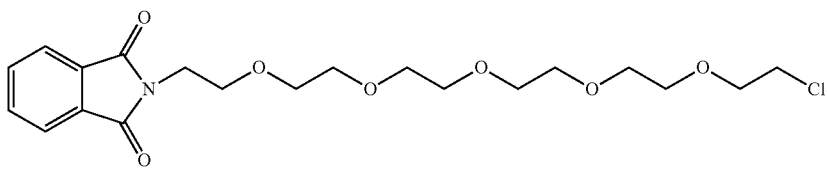

a compound of formula XXVIII

The intermediate compound 2-{2-[4-(2-chloroethyl)phenoxy]-ethoxy}ethanaminium chloride, which can be used to prepare substrates of the invention can be prepared as illustrated below and as described in the following steps a-c.

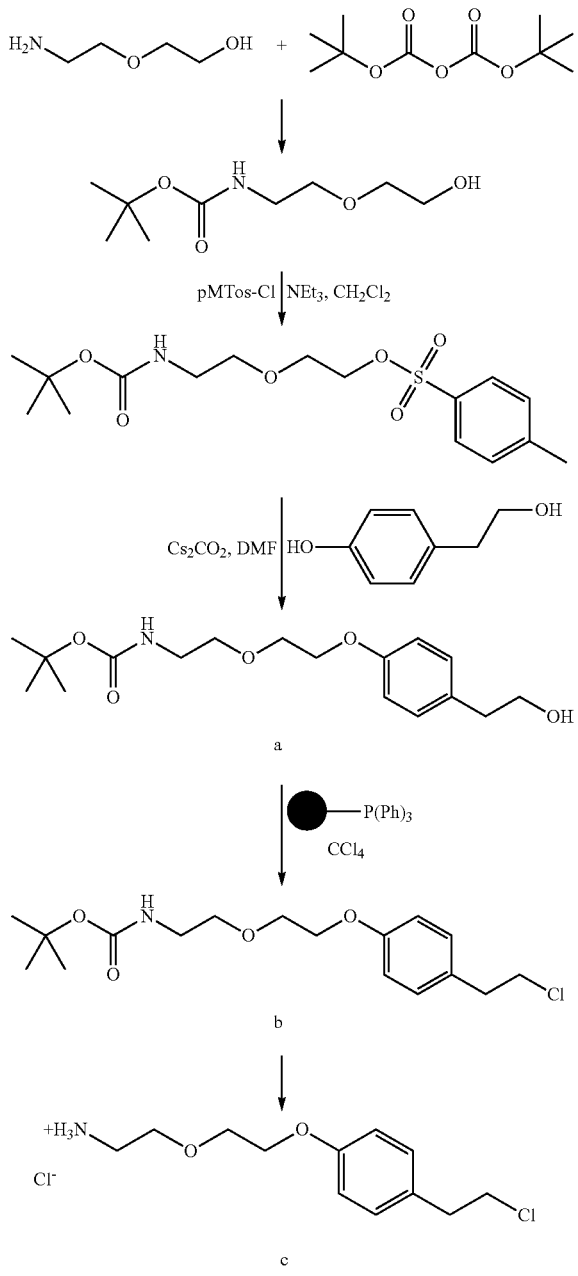

a. tert-butyl 2-{2-[4-(2-hydroxyethyl)phenoxy]ethoxy}-ethylcarbamate. A 100 ml round bottom flask was charged with 4-hydroxyphenethyl alcohol (1.14 g, 8.2 mmol), cesium carbonate (4.02 g, 12.4 mmol), and tert-butyl 2-(2-{[(4-methylphenoxy)sulfonyl]oxy}ethoxy)-ethylcarbamate (2.96 g, 8.2 mmol) (prepared using standard chemistry). This reaction mixture was slurried with 10 ml of DMF and heated to 60° C. by use of an oil bath. The reaction proceeded for 19 hours at which point was it was cooled and the DMF removed under reduced pressure. Upon adding dichloromethane the reaction mixture was filtered through a plug of celite and then the solvent removed. The resultant solid was dried under high vacuum. A near quantitative yield of product was isolated: $^1$H NMR (CDCl$_3$) δ 7.11 (d, 2H, Ar), 6.98 (d, 2H, Ar), 4.97 (bs, exchangeable, NH), 4.07 (dd, CH$_2$—O), 3.79 (t, CH$_2$—OH), 3.78 (dd, CH$_2$—O), 3.57 (t, CH$_2$—O), 3.30 (bm, CH$_2$—NH), 2.78 (t, CH$_2$—Ar), 1.82 (bs, exchangeable, OH) 1.41 (s, 9H, CH$_3$). Mass spectrum, m/e Calcd for $C_{17}H_{28}NO_5^+$: 326.20 (100%), 327.20 (19.5%). Found: 326.56, 327.57.

b. tert-butyl 2-{2-[4-(2-chloroethyl)phenoxy]ethoxy}ethylcarbamate. To tert-butyl 2-{2-[4-(2-hydroxyethyl)phenoxy]ethoxy}ethylcarbamate (0.56 g, 1.7 mmol) dissolved in 10 ml carbon tetrachloride was added triphenylphosphine bound on styrene (861 mg, 2.6 mmol of about 3 mmol/g resin). The reaction mixture was heated to reflux for 2 hours. After the required time the reaction was cooled and filtered. After drying a quantitative yield of product was isolated. $^1$H NMR (CDCl$_3$) δ 7.11 (d, 2H, Ar), 6.86 (d, 2H, Ar), 4.95 (bs, exchangeable, NH), 4.08 (dd, CH$_2$—O), 3.79 (dd, CH$_2$—O), 3.65 (t, CH$_2$—Cl), 3.59 (t, CH$_2$—O), 3.32 (bm, CH$_2$—NH), 2.99 (t, CH$_2$—Ar), 1.70 (bs, exchangeable, OH) 1.42 (s, 9H, CH$_3$). Mass spectrum, m/e Calcd for $C_{17}H_{27}ClNO_4^+$: 344.16 (100%), 346.16 (32%). Found: 344.57, 346.55.

c. 2-{2-[4-(2-chloroethyl)phenoxy]ethoxy}ethanaminium chloride. tert-butyl 2-{2-[4-(2-chloroethyl)phenoxy]ethoxy}ethylcarbamate (1.7 mmol) was dissolved in 5 ml dichloromethane and triethylsilane (0.5 ml, 5% v/v) was added. At this point trifluoroacetic acid (5 ml) was added dropwise to the solution at room temperature. The reaction mixture turned golden brown upon addition and was allowed to stir for one hour. All volatiles were removed under reduced atmosphere, the residue was re-dissolved in CH$_2$Cl$_2$, and washed twice with dilute HCl. The aqueous fractions were lyophilized overnight. The remaining oily residue was dissolved in anhydrous DMF to be used as a stock solution in further reactions.

The intermediate compound 2-(2-{[5-(3-chloropropyl)-2-furyl]methoxy}ethoxy)ethanamine, which can be used to prepare substrates of the invention can be prepared as illustrated below and as described in the following steps d-g.

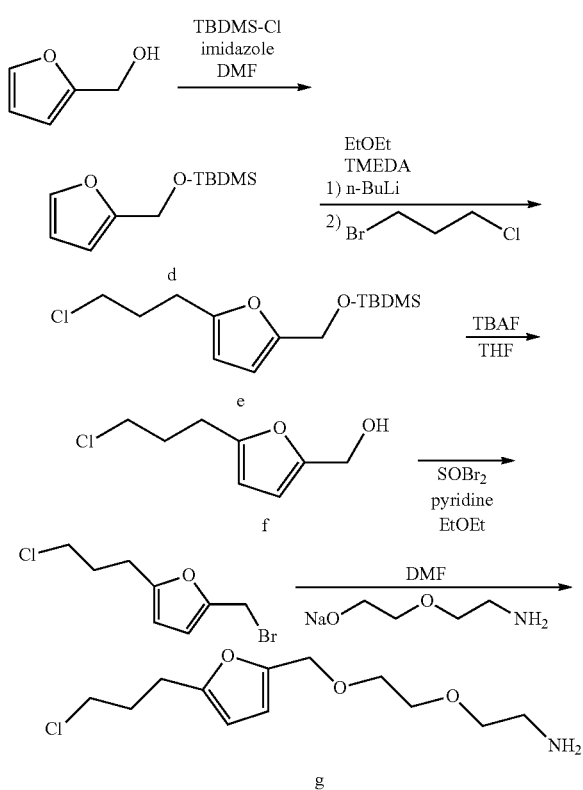

d. 2-(t-butyldimethylsilyloxymethyl)furan. To a 1 liter flask containing dimethyl formamide (150 mL) was added furfuryl alcohol (17.7 mL, 0.20 mol), t-butyldimethylsilyl chloride (33.7 g, 0.22 mole), and imidazole (15.3 g, 0.22 mol). After 22 hours stirring at RT, the reaction was filtered and the volatiles removed in vacuo. The resulting material was partitioned between diethyl ether (500 mL) and a saturated aqueous solution of citric acid (100 mL). Additionally, the ether layer was washed 2×100 mL sat. citric acid. The combined aqueous layers were back extracted 1×50 mL ether. The combined organic layers were washed 1×100 mL water followed by 1×100 mL brine. The ether layer was dried over anhydrous sodium sulfate, filtered, and evaporated to yield 28.1 g (65% yield). $^1$H NMR: (DMSO-$d_6$) δ 0.01 (s, 6H), 0.82 (s, 9H), 4.55 (s, 2H), 6.29 (d, 1H), 6.36 (dd, 1H), 7.58 (d, 1H)

e. 2-(3-chloropropyl)-5-(t-butyldimethylsilyloxymethyl) furan. A solution of 2-(t-butyldimethylsilyloxymethyl)furan (5 g, 0.023 mol) in THF (48 mL) was dried over 3 Å molecular sieves. After the sieves were removed, an additional 10 mL THF was added along with TMEDA (3.47 mL, 0.023 mol), and the solution was cooled to 0° C. in an ice bath. A solution of BuLi (10.1 mL of 2.5M in hexane, 0.025 mol) was added dropwise over 25 minutes. The mixture was allowed to stir for 1 hour. 1-chloro-3-iodopropane (5.64 g, 0.028 mol) was injected rapidly. After 2 hours TLC indicated completion. The solvent was evaporated, and the material was partitioned between ether (100 mL) and 5% citric acid (100 mL). The ether layer was washed with water (50 mL) and then brine (50 mL). The ether solution was dried with sodium sulfate, filtered, and evaporated. The resulting material was flashed on silica using 20/1 heptane/EtOAc. Appropriate fraction were combined and evaporated to yield 4.9 g (75% yield). TLC: $R_f$ 0.6 (Heptane/EtOAc 5/1) $^1$H NMR: (CDCl$_3$) δ 0.00 (s, 6H), 0.83 (s, 9H), 2.01 (p, 2H), 2.71 (t, 2H), 3.48 (t, 2H), 4.51 (s, 2H), 5.88 (d, 1H), 6.04 (d, 1H)

f. [5-(3-chloropropyl)-2-furyl]methanol. A solution of 2-(3-chloropropyl)-5-(t-butyldimethylsilyloxymethyl)furan (4.88 g, 0.017 mol) in THF (50 mL) was cooled to 0° C. To the above solution was added a chilled solution of tetrabutylammonium fluoride (1 M in THF, 18.2 mL, 0.018 mol). After 20 minutes, TLC indicated reaction completion. Acetic acid (2 mL) was added to the solution. The solution was evaporated. The resulting syrup was partitioned between ether (150 mL) and sat. citric acid (100 mL). Additionally, the ether layer was washed with saturated bicarbonate (60 mL and then water (60 mL). The combined aqueous layers were back extracted with ether (50 mL). The combined ether layers were dried with sodium sulfate, filtered, and evaporated to yield 3.4 g yellow syrup (99% crude yield). The material was further purified on silica, eluting with heptane/EtOAc (5/1) to yield 1.6 g (47% yield). TLC: $R_f$ 0.5 (Heptane/EtOAc 1/1) $^1$H NMR: (CDCl$_3$) δ 2.05 (p, 2H), 2.74 (t, 2H), 3.21 (bs, 1H), 3.51 (t, 2H), 4.45 (s, 2H), 5.94 (d, 1H), 6.11 (d, 1H)

g. 2-(2-{[5-(3-chloropropyl)-2-furyl]methoxy}ethoxy) ethanamine. A solution of [5-(3-chloropropyl)-2-furyl] methanol (500 mg, 2.5 mmol) in ether (6 mL) was dried over 3 Å molecular sieves. After the sieves were removed, pyridine (245 μL, 3.0 mmol) was added to the solution. Thionyl bromide (215 μL, 2.9 mmol) was added dropwise to the solution. After 7 hours of stirring, the solution was rapidly injected into a solution of sodium 2-[2-aminoethoxy]ethoxide (534 mg, 4.2 mmol) in DMF (3 mL). (Sodium 2-[2-aminoethoxy] ethoxide was previously prepared by adding 60% NaH dispersion (2.85 g, 0.07 mol) subsequently cleaned with heptane to a solution of 2-aminoethoxyethanol (5 g, 0.04 mol) in diglyme (10 mL), stirred for 5 hours, and evaporated.) After 2 hours the reaction was placed in the freezer. After 18 hours the reaction was partitioned between dichloromethane (DCM) (50 mL) and water (50 mL). Water layer was extracted with additional 30 mL DCM. The combined DCM layers were washed with water (30 mL). The DCM layer were extracted with diluted HCl (1N, 30 mL) followed by water (20 mL). The acidic aqueous solutions were adjusted to pH=10 with diluted sodium hydroxide and back extracted with 2×20 ml DCM. The DCM was washed with brine, dried with sodium sulfate, filtered, and evaporated to yield 380 mg (58% yield). Used without further purification. TLC: $R_f$ 0.5 (IPA/NH$_4$OH/water 8/1/1 exposed with ninhydrin solution) Mass spectrum, m/e Calcd for $C_{12}H_{21}ClNO_3^+$: 262.1 (100%), 264.1 (32%) Found: 262.6, 264.6

General Methodology for Reporter Group Conjugation to 2-{2-[4-(2-chloroethyl)phenoxy]ethoxy}ethanamine or 2-(2-{[5-(3-chloropropyl)-2-furyl]methoxy}ethoxy)ethanamine. To one equivalent of the succinimidyl ester of the reporter group in DMF is added 1.5 equivalents of substrate stock solution, followed by diisopropylethylamine. The reaction is stirred from 8 to 16 hours at room temperature. Purification is accomplished by preparative scale HPLC or silica gel chromatography.

Using the General Procedure Above, the Following Substrates (XXIX-XXXIV) of the Invention were Prepared.

2-{2-[4-(2-chloroethyl)phenoxy]ethoxy}ethyl-tetramethylrhodamine-6-carboxamide. The title compound was prepared using the general methodology starting with 6-carboxytetramethylrhodamine succinimidyl ester. Purification was accomplished using preparative scale HPLC. Separation of structural isomers was realized. UV/Vis (MeOH): 544 (max) Mass spectrum, m/e Calcd for $C_{37}H_{39}ClN_3O_6^+$: 656.25 (100%), 658.25 (32.4%). Found: 656.37, 658.37. This compound is referred to herein as carboxytetramethylrhodamine-p-phenethyl-Cl.

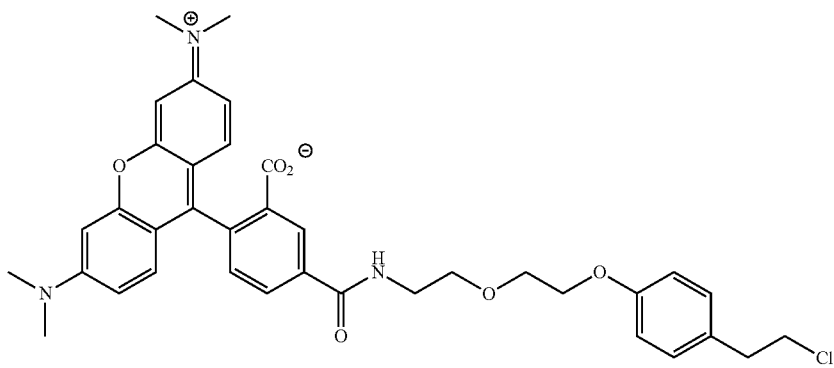

a compound of formula XXIX

2-{2-[4-(2-chloroethyl)phenoxy]ethoxy}ethyl-fluorescein-5-(and -6)-carboxamide. The title compounds were prepared using the general methodology starting with 5(6)-carboxyfluorescein succinimidyl ester. Purification and separation of isomers was accomplished using preparative scale HPLC. Mass spectrum, m/e Calcd for $C_{33}H_{27}ClNO_8^-$: 600.14 (100%), 601.15 (37.4%), 602.14 (32.1%). Found: 600.18, 601.24, 602.21. This compound is referred to herein as carboxyfluorescein-p-phenethyl-Cl.

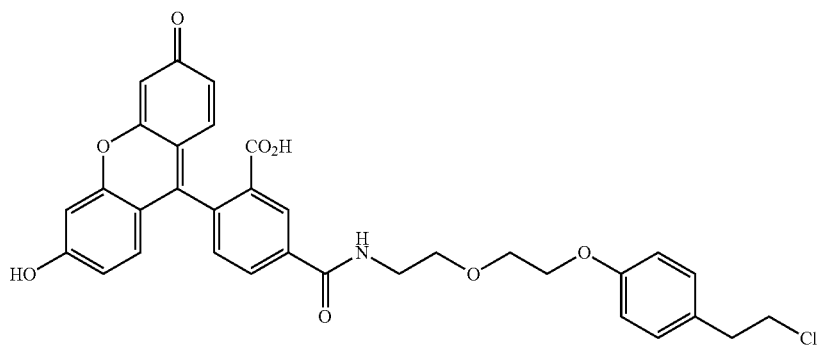

a compound of formula XXX

2-{2-[4-(2-chloroethyl)phenoxy]ethoxy}ethyl-biotin-carboxamide. The title compound was prepared using the general methodology starting with D-biotin succinimidyl ester. Purification was accomplished using preparative scale HPLC. Mass spectrum, m/e Calcd for $C_{22}H_{33}ClN_3O_4S^+$: 470.19 (100%). Found: 470.19. This compound is referred to herein as biotin-p-phenethyl-14-Cl.

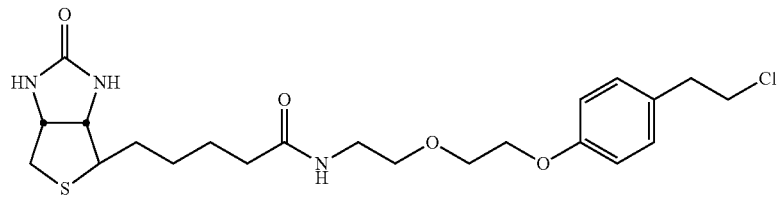

a compound of formula XXXI

2-{2-[4-(2-chloroethyl)phenoxy]ethoxy}ethyl-3',6'-diacetylfluorescein-6-carboxamide. To a 10 ml round bottom flask containing either N-{2-[4-(2-chloroethyl)-1-ethoxyphenyl]ethyl}-fluorescein-6-carboxamide (12.3 mg,) was added 2 ml of acetic anhydride followed by 0.25 ml of pyridine. The reaction mixture was allowed to 1 hour. After evaporation under reduced pressure, the residue was co-evaporated with toluene two times. The solid was then dried under vacuum (0.186 g, 0.216 mmol, and 84% yield). Mass spectrum, m/e Calcd for $C_{37}H_{33}ClNO_{10}^{+}$: 686.18 (100%), 687.18 (41.9%), 688.18 (34.1%). Found: 686.55, 687.61, 688.60.

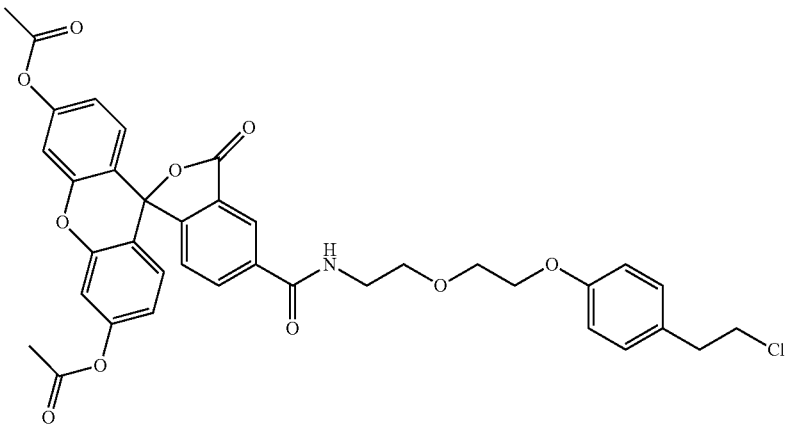

a compound of formula XXXII

N-[2-(2-{[5-(3-chloropropyl)-2-furyl]methoxy}ethoxy)ethyl]tetramethylrhodamine-6-carboxyamide. The title compound was prepared using the general methodology starting with 6-carboxytetramethylrhodamine succinimidyl ester. Purification was accomplished using preparative scale HPLC. $^{1}$H NMR: (CD$_3$OD) δ 2.04 (p, 2H), 2.75 (t, 2H), 3.26 (s, 12H), 3.60 (m, 10H), 4.38 (s, 2H), 5.97 (d, 1H), 6.20 (d, 1H) 6.99 (d, 2H), 7.08 (dd, 2H), 7.15 (d, 2H), 7.81 (s, 1H), 8.19 (d, 1H), 8.39 (d, 1H), 8.73 (bt, 1H) Mass spectrum, m/e Calcd for $C_{37}H_{41}ClN_3O_7^{+}$: 674.26 (100.0%), 675.27 (42.0%), 676.26 (32.4%) Found: 674.5, 675.5, 676.5. This compound is referred to herein as carboxytetramethylrhodamine-furanyl-propyl-Cl.

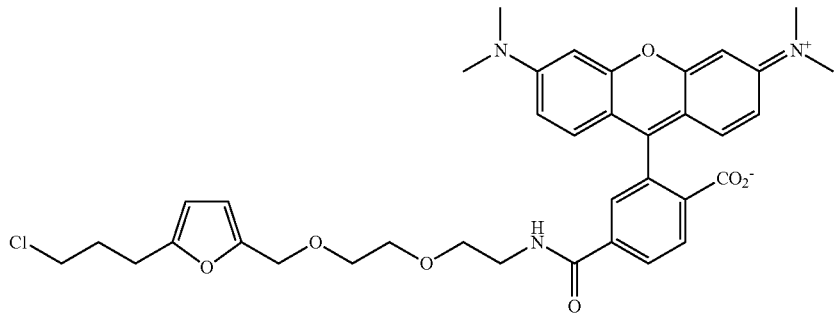

a compound of formula XXXIII

N-[2-(2-{[5-(3-chloropropyl)-2-furyl]methoxy}ethoxy)ethyl]-fluorescein-6-carboxamide. The title compounds were prepared using the general methodology starting with 5(6)-carboxyfluorescein succinimidyl ester. Purification and separation of isomers was accomplished using preparative scale HPLC. Mass spectrum, m/e Calcd for $C_{33}H_{31}ClNO_9^{+}$: 620.17 (100%), 602.17 (32.1%). Found: 620.47, 622.49. This compound is referred to herein as carboxyfluorescein-furanyl-propyl-Cl.

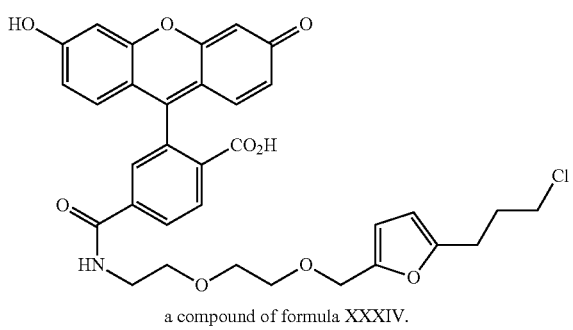 [SMILES: O=C(NCCOCCOCc1ccc(CCCCl)o1)c1ccc(C(=O)O)c(-c2c3ccc(=O)cc-3oc3cc(O)ccc23)c1]

a compound of formula XXXIV.

VI. Exemplary Methods of Use

The invention provides methods to monitor the expression, location and/or trafficking of molecules in a cell, as well as to monitor changes in microenvironments within a cell, and to isolate, image, identify, localize, display or detect one or more molecules which may be present in a sample, e.g., in a cell, which methods employ a hydrolase substrate and/or a mutant hydrolase of the invention. The substrates of the invention are preferably soluble in an aqueous or mostly aqueous solution, including water and aqueous solutions having a pH greater than or equal to about 6. Stock solutions of substrates of the invention, however, may be dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. The concentration of a substrate of the invention and a corresponding mutant hydrolase to be used is dependent upon the experimental conditions and the desired results, e.g., to obtain results within a reasonable time, with minimal background or undesirable labeling. The concentration of a substrate of the invention typically ranges from nanomolar to micromolar. The required concentration for the substrate of the invention with a corresponding mutant hydrolase is determined by systematic variation in substrate until satisfactory labeling is accomplished. The starting ranges are readily determined from methods known in the art.

In one embodiment, a substrate which includes a functional group with optical properties is employed with a mutant hydrolase to label a sample. Such a substrate is combined with the sample of interest comprising the mutant hydrolase for a period of time sufficient for the mutant hydrolase to bind the substrate, after which the sample is illuminated at a wavelength selected to elicit the optical response of the functional group. Optionally, the sample is washed to remove residual, excess or unbound substrate. In one embodiment, the labeling is used to determine a specified characteristic of the sample by further comparing the optical response with a standard or expected response. For example, the mutant hydrolase bound substrate is used to monitor specific components of the sample with respect to their spatial and temporal distribution in the sample. Alternatively, the mutant hydrolase bound substrate is employed to determine or detect the presence or quantity of a certain molecule. In another embodiment, the mutant hydrolase bound substrate is used to analyze the sample for the presence of a molecule that responds specifically to the functional group.

In contrast to intrinsically fluorescent proteins, e.g., GFP, a mutant hydrolase bound to a fluorescent substrate does not require a native protein structure to retain fluorescence. After the fluorescent substrate is bound, the mutant hydrolase may be detected, for example, in denaturing electrophoretic gels, e.g., SDS-PAGE, or in cells fixed with organic solvents, e.g., paraformaldehyde. Fragments of the mutant hydrolase that contain the reactive nucleophilic amino acid may also be detected by the bound fluorophore, for example, to monitor proteolytic processes.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or X-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample comprising a mutant hydrolase or a fusion thereof or in a localized portion of the sample comprising a mutant hydrolase or a fusion thereof. Comparison of the degree of optical response with a standard or expected response can be used to determine whether and to what degree the sample comprising a mutant hydrolase or a fusion thereof possesses a given characteristic.

In another embodiment, the functional group is a ligand for an acceptor molecule. Where the substrate comprises a functional group that is a member of a specific binding pair (a ligand), the complementary member (the acceptor) or the substrate, may be immobilized on a solid or semi-solid surface, such as a polymer, polymeric membrane or polymeric particle (such as a polymeric bead), or both may be in solution. In one embodiment, protein-protein interactions may be detected using an electrical conducting substrate coated surface. Representative specific binding pairs include biotin and avidin (or streptavidin or anti-biotin), IgG and protein A or protein G, drug and drug receptor, toxin and toxin receptor, carbohydrate and lectin or carbohydrate receptor, peptide or protein and peptide or protein receptor, two or more proteins which interact, for instance, protein kinase A (PKA) regulatory subunit and PKA catalytic subunit, an enzyme and its substrate, e.g., a protease, kinase, or luciferase and a substrate therefor, a cofactor for an enzyme and the enzyme, sense DNA or RNA and antisense (complementary) DNA or RNA, hormone and hormone receptor, and ion and chelator, and the like. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. Where the functional group is a chelator of calcium, sodium, magnesium, potassium, or another biologically important metal ion, the substrate comprising such a functional group functions as an indicator of the ion. Alternatively, such a substrate may act as a pH indicator. Preferably, the detectable optical response of the ion indicator is a change in fluorescence.

A sample comprising a mutant hydrolase or a fusion thereof is typically labeled by passive means, i.e., by incubation with the substrate. However, any method of introducing the substrate into the sample comprising a mutant hydrolase or a fusion thereof, such as microinjection of a substrate into a cell or organelle, can be used to introduce the substrate into the sample comprising a mutant hydrolase or a fusion thereof. The substrates of the present invention are generally nontoxic to living cells and other biological components, within the concentrations of use.

A sample comprising a mutant hydrolase or a fusion thereof can be observed immediately after contact with a substrate of the invention. The sample comprising a mutant hydrolase or a fusion thereof is optionally combined with other solutions in the course of labeling, including wash solutions, permeabilization and/or fixation solutions, and other solutions containing additional detection reagents. Washing following contact with the substrate generally improves the detection of the optical response due to the decrease in non-specific background after washing. Satisfactory visualization is possible without washing by using lower labeling concentrations. A number of fixatives and fixation conditions are known in the art, including formaldehyde, paraformaldehyde, formalin, glutaraldehyde, cold methanol and 3:1 methanol: acetic acid. Fixation is typically used to preserve cellular morphology and to reduce biohazards when working with pathogenic samples. Selected embodiments of the substrates are well retained in cells. Fixation is optionally followed or accompanied by permeabilization, such as with acetone, ethanol, DMSO or various detergents, to allow bulky substrates of the invention, to cross cell membranes, according to methods generally known in the art. Optionally, the use of a substrate may be combined with the use of an additional detection reagent that produces a detectable response due to the presence of a specific cell component, intracellular substance, or cellular condition, in a sample comprising a mutant hydrolase or a fusion thereof. Where the additional detection reagent has spectral properties that differ from those of the substrate, multi-color applications are possible.

At any time after or during contact with the substrate comprising a functional group with optical properties, the sample comprising a mutant hydrolase or a fusion thereof is illuminated with a wavelength of light that results in a detectable optical response, and observed with a means for detecting the optical response. While some substrates are detectable colorimetrically, using ambient light, other substrates are detected by the fluorescence properties of the parent fluorophore. Upon illumination, such as by an ultraviolet or visible wavelength emission lamp, an arc lamp, a laser, or even sunlight or ordinary room light, the substrates, including substrates bound to the complementary specific binding pair member, display intense visible absorption as well as fluorescence emission. Selected equipment that is useful for illuminating the substrates of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This colorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample comprising a mutant hydrolase or a fusion thereof is examined using a flow cytometer, a fluorescence microscope or a fluorometer, the instrument is optionally used to distinguish and discriminate between the substrate comprising a functional group which is a fluorophore and a second fluorophore with detectably different optical properties, typically by distinguishing the fluorescence response of the substrate from that of the second fluorophore. Where the sample comprising a mutant hydrolase or a fusion thereof is examined using a flow cytometer, examination of the sample comprising a mutant hydrolase or a fusion thereof optionally includes isolation of particles within the sample comprising a mutant hydrolase or a fusion thereof based on the fluorescence response of the substrate by using a sorting device.

In one embodiment, a mutant hydrolase and a corresponding substrate which includes a functional group are employed to label a cell, e.g., a cell in an organism such as a cell in transgenic animal, a cell in an animal administered cells comprising the mutant hydrolase and/or substrate of the invention, or cells in culture, or a cellular component. For instance, cells are contacted with a vector encoding the mutant hydrolase, such as one encoding a fusion between the mutant hydrolase and a nuclear localization signal. The expression of the vector in the cell which may be in a transgenic animal or administered to an animal, may be transient, regulatable or stable. Then the cell or an animal comprising the cell is contacted with a substrate of the invention recognized by the mutant hydrolase. Alternatively, cells are concurrently contacted with the vector and the substrate. Then the presence or location of the functional group in the animal, cell, a lysate thereof, or a subcellular fraction thereof, is detected or determined. In another embodiment, a mutant hydrolase and a corresponding substrate which includes a functional group comprising a triplet sensitizer are employed to selectively inactivate or destroy a molecule and/or cellular activity, e.g., in a cell. In this embodiment, after contacting a sample comprising mutant hydrolase or a fusion thereof with a substrate comprising a triplet sensitizer, the sample is exposed to UV light.

To label proteins in vitro or in vivo, a hydrolase substrate may be attached to an amino acid or a tRNA, e.g., an aminoacylated tRNA such as an aminoacylated initiator methionyl tRNA for N-terminal modification of in vitro synthesized proteins, to an amber suppressor tRNA for C-terminal labeling of proteins, including amino acids attached to a tRNA using a mutant tRNA synthetase. A hydrolase substrate may also be attached to a protein by an intein-mediated method. The protein of interest is expressed as a fusion protein with a carboxyl terminal intein domain, preferably a "mini-intein" lacking a homing endonuclease domain, and more preferably the *Mycobacterium xenopi* (Mxe) GyrA mini-intein. Treatment of the fusion protein with a reducing thiol reagent, such as reduced sodium 2-mercaptoethanesulfonate or 2-mercaptoethanol, in the presence of the cysteine-hydrolase substrate, e.g., cysteine-haloalkane, results in cleavage of the fusion protein at the amino-terminal cysteine residue of the intein portion of the fusion and covalent attachment of the cysteine-hydrolase substrate, e.g., cysteine-haloalkane, to the carboxyl terminus of the protein of interest.

Accordingly, proteins can be expressed from cDNA or mRNA without the need for making fusion proteins and those proteins can be purified using a mutant hydrolase. Moreover, protein microarrays can be made from the in vitro translated proteins, for instance, using immobilized mutant hydrolase, without the need for a fusion tag, and those proteins as well as proteins which interact with those proteins, isolated. Further, the use of a substrate which includes a fluorophore allows for the rapid detection, as well as the purification, of expressed proteins. For in vivo labeling of proteins in a cell, a substrate which includes a methionine or other naturally occurring or normaturally occurring amino acid may be employed, and newly synthesized proteins as well as proteins which interact with those proteins, can be purified optionally using an immobilized muant hydrolase, without the need for a fusion tag. This approach may also be used for isolating marker proteins for differential protein expression analysis, and also with mass spectrometry. Multiplexing is also possible using substrates with different fluorophores.

The substrates and mutant hydrolases of the invention are particularly useful to isolate, display or detect molecules in a sample. In one embodiment, a protein microarray may be prepared in which a mutant hydrolase is immobilized onto a surface of a solid support and a substrate of the invention modified to include one or more functional groups which bind a single protein, a functional or structural class of proteins, or proteins in general, for protein immobilization (FIG. 57). For example, fusion protein systems such as a thioredoxin patch, intein based approaches or other methods are employed to immobilize a mutant hydrolase onto a solid surface. Modified substrates for immobilizing proteins are then added. The substrate may be modified with succinimidyl ester/aldehyde (for general immobilization of proteins), glutathione (for immobilizing GST fusion proteins), NTA or metal (for immobilizing His-tagged proteins), or specific ligands for immobilizing specific classes of proteins. For example, an enzyme substrate or an inhibitor of an enzyme linked to a hydrolase substrate may be used for immobilizing a particular class of enzymes, e.g., caspases or reverse transcriptases, or a DNA which binds certain proteins linked to a hydrolase substrate may be used to prepare a protein microarray for DNA binding proteins, e.g., for developing chip based assays. Similarly, to study protein-protein interactions including isolating protein complexes, a mutant hydrolase can be immobilized on magnetic or non-magnetic particles, e.g., MagneSil particles. These methods can avoid preparing new fusion proteins, e.g., a new library, as only a substrate for a protein(s) of interest needs to be prepared, for instance, for GST fusion libraries.

Alternatively, the substrate may be immobilized onto a surface to allow stable attachment of mutant hydrolases, and fusions thereof, onto the surface. The mutant hydrolases may be obtained from living cells or by cell-free methods, e.g., coupled transcription and translation in a cellular lysate. The bound proteins may be useful for analyzing characteristics such as binding to other molecules or enzymatic activity. It may also be useful for stably immobilizing an enzymatic activity for bioconversions or detection capabilities. It may also be useful for stably immobilizing a specific binding activity for purification or selective adsorption capabilities. Multiple substrates may be immobilized onto the surface, either at different locations or as a mixture, to allow attachment of multiple mutant hydrolases. The substrate may also be immobilized with other binding molecules such as biotin or para-substituted benzylguanine In one embodiment, a fusion to a mutant hydrolase may be used to identify proteins that bind to the fusion. Proteins that bind to the fusion protein may be separated from other unbound proteins by binding the mutant hydrolase to a substrate immobilized onto a surface. By this means, the unbound proteins in solution may be washed from the stationary bound proteins. Other molecules that bind to the fusion protein, such as nucleic acids or small molecules, may also be identified by this method. To increase the binding stability of the molecules bound to the mutant hydrolase, various chemical cross-linking methods may be employed to covalently interconnect the bound molecules. Reversible cross-linkers are preferred, so that the bound molecules may be subsequently unbound for analysis, e.g., identification and/or isolation.

After combining a mutant hydrolase with a substrate, it may be necessary to inactivate remaining unreacted substrate in the mixture. This may be done by adding wild-type hydrolase to the mixture to convert the remaining unreacted substrate into product. For example, unreacted chloroalkane substrate may be converted to the corresponding alcohol by addition of a wild-type or other catalytically competent dehalogenase. The unreacted substrate may be free in solution or bound to a surface. If bound to a surface, addition of a catalytically competent hydrolase would convert the substrate its corresponding product, thereby preventing further binding of mutant hydrolase to the surface.

The substrates and mutant hydrolases of the invention may also be used in tandem affinity purification (TAP), a method for the purification of proteins or protein complexes, which uses two consecutive affinity purification steps. Each purification step employs a ligand for an affinity tag, for instance, His-tag, a GST-tag, a Strep-tag, a biotin-tag, an immunoglobulin binding domain, e.g., an IgG binding domain, a calmodulin binding peptide and the like, which is fused to a protein of interest. A mutant hydrolase of the invention may be employed as an affinity tag. For example, a fusion containing a mutant hydrolase and calmodulin binding peptide (CBP) or protein complexes therewith may be purified by calmodulin attached to a solid phase followed by a hydrolase substrate attached to a solid phase. The purified proteins or complexes may then be analyzed by Western blotting or mass spectrometry. Using TAP, proteins or protein complexes may be purified from various types of host cells, such as bacteria, *Drosophila*, plant, mammalian cells, as well as cell free protein expression systems, and can identify protein-protein interactions. The use of a mutant hydrolase and hydrolase substrate in TAP, e.g., for a final affinity purification step, allows for the analysis of proteins in real-time, followed by TAP at various time points or after various drug treatments. Since the mutant hydrolase fusion is attached covalently to the substrate, purified protein complexes will not contain the hydrolase.

In another embodiment, a biotinylated hydrolase substrate binds avidin labeled antibodies which bind to an antigen. This complex may be subjected to immunoprecipitation, e.g., by using eppendorff tubes containing immobilized mutant hydrolase (FIG. 58).

To detect some molecules, a solution (free) or immobilized system may be employed. In one embodiment, a hydrolase substrate modified with a small molecule or a compound could be used for detecting modifications of the attached small molecule or a compound. For example, to detect a kinase such as phosphatidylinositol 3 (PI3) kinase, a hydrolase substrate modified with a lipid such as phosphatidylinositol is contacted with a sample containing a PI3 kinase, which phosphorylates phosphatidylinositol. The resulting modified hydrolase substrate is then covalently attached to the hydrolase. The phosphorylated phosphatidylinositol is detected by electrophoretic or fluorescencemethods. Electrophoretic detection methods include performing a standard kinase asssay using radiolabeld nucleotides such as gamma $^{32}$PATP followed by autoradiography or by fluorescence detection using fluorescently labeled NTA complexed with $Ga^{3+}$ or $Fe^{3+}$. Specific binding of $Ga^{3+}$ or $Fe^{3+}$ complexed NTA to phosphate groups allows for the electrophoretic detection of phosphorylated phosphatidylinositol. PI3 kinase activity may also be detected in free solution using FRET or fluorescence polarization (FP). For this, a fluorescently labeled, phosphatidylinositol containing hydrolase substrate may be used. Phosphorylated phosphatidylinositol is detected using a different fluorophore labeled NTA complexed with $Ga^{3+}$ or $Fe^{3+}$. For fluorescence polarization (FP), a nonfluorescent phosphatidylinositol containing hydrolase substrate is added to a test sample, followed by the addition of $Ga^{3+}$ or $Fe^{3+}$. The resulting hydrolase substrate is added to immobilized or free mutant hydrolase. Fluorescence polarization is assayed using fluorescence labeled NTA, which binds to $Ga^{3+}$ or $Fe^{3+}$.

To detect phosphodiesterase, a hydrolase substrate which includes fluorescently labeled cAMP and a different fluorophore may be employed. Hydrolysis of cAMP indicates phosphodiesterase activity. Phosphodiesterase activity can be detected using FRET after capturing the substrate with free or immobilized dehalogenase, e.g., in protein microarray format.

Nucleic acid molecules attached to a hydrolase substrate may be employed to purify or display other nucleic acid molecules, proteins or protein based complexes. For ribosome display or purification, e.g., for use in directed evolution, a hydrolase substrate is bound at the 3' end of a mRNA without a stop codon. The substrate is added to an in vitro translation mixture and the resulting protein-DNA-mRNA complex is purified using immobilized mutant hydrolase. Similarly, to isolate, detect or display specific genes, a hydrolase substrate which includes fluorophore labeled DNA or RNA, e.g., a fluorophore labeled single stranded DNA, which binds a gene of interest, and a different fluorophore or quencher, is used to isolate, detect or display that gene from a complex mixture using fluorescence based methods such as FRET. Such a method could be useful in diagnostics as well as bioweapon detection.

The substrates and mutant hydrolases of the invention may be employed in various formats to detect cAMP (FIGS. 59A-B). In one embodiment, fluorescence quenching is used with two fusion proteins and two substrates. One substrate includes a fluorophore and the other includes quencher dye for the fluorophore. One fusion protein includes a mutant hydrolase and the regulatory subunit of PKA, and the other includes a mutant hydrolase and PKA catalytic subunit (FIG. 59A). Each fusion protein is contacted with one of the substrates and then the complexes are mixed together. In presence of cAMP, the quencher dye is no longer in close proximity to the fluorophore. Thus, cAMP is measured by measuring fluorescence. In another embodiment, two hydrolase substrates each with a different fluorophore are employed and cAMP is measured by measuring FRET.

In another embodiment, one fusion protein includes a first mutant hydrolase and the regulatory subunit of PKA, and the other fusion protein includes a protein that is different than the first mutant hydrolase (a second protein) and binds a second substrate and the PKA catalytic subunit. The mutant hydrolase binds a hydrolase substrate that includes at least one fluorophore. The second protein binds a second substrate, which is modified with a quencher for the at least one fluorophore that does not affect the substrate's binding to the second protein. The second protein may be GST, thioredoxin, AGT, a different mutant hydrolase which is specific for a different substrate than the first mutant hydrolase, a mutant hydrolase that is capable of binding the same substrate as the first mutant hydrolase, or other substrate binding protein. Each fusion protein is contacted with the respective substrate, the complexes are mixed together, and cAMP is measured by measuring fluorescence. In the presence of cAMP, the quencher is no longer in close proximity to the fluorophore. In another embodiment, the second protein binds a second substrate which is modified with a different fluorophore than the fluorophore linked to the hydrolase substrate, which different fluorophore does not affect the binding of the second substrate to the second protein. Each fusion protein is contacted with its respective substrate, the complexes are mixed together, and FRET employed to measure cAMP. In the presence of cAMP, the two fluorophores are no longer in close proximity. In yet another embodiment, one fusion protein includes a mutant hydrolase and the regulatory subunit of PKA, and the other fusion protein includes a fluorescent protein and the PKA catalytic subunit. Fluorescent proteins include but are not limited to GFP, YFP, EGFP, and DsRed. Each fusion protein is contacted with its respective substrate and then the complexes are mixed together. In the presence of cAMP, the fluorescence protein and the mutant hydrolase bound to the fluorophore containing substrate are no longer in close proximity. In another embodiment, BRET is employed to detect cAMP. One substrate which includes a fluorophore is contacted with a fusion protein which includes a mutant hydrolase and a regulatory subunit of PKA, and another fusion which includes a luciferase and a regulatory subunit of PKA. When the regulatory subunit from each fusion protein dimerizes, BRET is observed. BRET is disrupted in presence of cAMP (see FIG. 59B).

A mutant hydrolase and substrate may be employed in molecular imprinting, a technique devised to generate a polymeric material that is analyte specific. Molecular imprinting is a process for preparing polymers that are selective for a particular compound (the print molecule) (Arshady et al., 1981). The technique involves: (1) prearranging the print molecule and the monomers and allowing complementary interactions (non-covalent or reversible covalent) to develop; (2) polymerizing around the print molecule-monomer complex; and (3) removing the print molecule from the polymer by extraction. Polymerization thus preserves the complementarity to the print molecule and the polymer will selectively adsorb the print molecule. Molecularly imprinted polymers (MIPS) with a hydrolase substrate bind to the hydrolase and fusions thereof, and may be used to purify fusion proteins, prepare protein microarrays, study protein-protein interaction, and TAP.

The functional group of the substrate may bind to another protein, either reversibly or covalently. An example of a functional group that binds reversibly to a protein is a hapten that binds to an antibody, e.g., a single-chain antibody (scFv). An example of a functional group that binds covalently to another protein is a chloroalkane that binds to a mutant dehalogenase, or a para-substituted benzylguanine that binds to O-alkylguanine-DNA alkyltransferase (AGT). A first fusion protein comprising a mutant hydrolase may be bound to a second protein as a means for implementing or modulating a biochemical or biological process. For example, gene transcription may be modulated by a DNA binding protein fused to a mutant hydrolase bound to a transcriptional activator, e.g., VP16. In such an example, gene transcription would be increased by addition of a substrate causing the mutant hydrolase fused to the DNA binding protein to bind to the transcriptional activator. In another example, the activity of a protein in a cell may be modulated by its location(s) within the cell. For example, the activity of a protein may be changed by binding the protein to a mutant hydrolase fused to a second protein, which upon binding redirects or preferentially redistributes the protein to a different subcellular compartment. An example may be a transcription factor located predominately in the non-nuclear portion of a cell, where upon binding to a mutant hydrolase fused to a nuclear targeting sequence, results in the transcription factor moving to the nucleus. In such an example, the addition of a substrate to cause binding of the transcription factor to the mutant hydrolase may thereby modulate gene expression mediated by the transcription factor.

The substrate may have multiple reactive groups to allow interconnection of mutant hydrolases. When fused to proteins having a binding activity, interconnection of the mutant hydrolases may yield a multivalent binding complex. Such multivalent complexes may have useful properties, such as higher apparent binding efficiency (e.g., higher avidity). For example, interconnecting two or more single-chain antibodies may yield more efficient binding to the corresponding antigen. In another example, the DNA binding domain of a lambda phage repressor protein fused to a mutant hydrolase may bind more efficiently to DNA upon addition of a substrate to interconnect the mutant hydrolases. Multivalent complexes having different binding proteins fused to mutant hydrolases can allow different molecules, e.g., antigens, to be bound together via the complex.

Fusing mutant hydrolases together may allow multiple substrates to bind to a single protein. These substrates may be the same or different. By this means, the fused mutant hydrolases may serve as a bridging molecule between the substrates. This may be useful to covalently interconnect molecules, such as functional groups, surfaces, or other molecules. For example, a substrate bound to a surface may be covalently attached to a polynucleotide bound to a substrate by using a bi-valent fused mutant hydrolase. Heteromultivalent molecules may be made by fusing different mutant hydrolases, or fusing mutant hydrolases to other protein(s) capable of making stable covalent bonds, e.g., AGT.

In one embodiment, a substrate includes more than one functional group, e.g., an optically detectable molecule and a ligand for an acceptor molecule, two different proteins, e.g., AGT and a fluorescent protein or a luciferase, an optically detectable molecule and a protease recognition site, or an optically detectable molecule and a protease recognition site, and a quencher of the optically detectable molecule. For example, a substrate of the invention may include a fluorophore, a protease recognition site and a quencher molecule. The substrate is taken up by a cell which expresses the mutant hydrolase. In the presence of the protease, the quencher is removed from the substrate, resulting in a fluorescence signal. The use of such a substrate can yield a real-time assay for the protease. The mutant may also be used for the detection of infectious agents and thus may be employed in clinical diagnostic applications as well as to detect bioweapons.

Other formats may be used to detect proteases such as caspases or a proteosome, e.g., the 20S proteosome may be detected (or isolated) with a branched peptide substrate. In one embodiment, a gene for a mutant hydrolase or another reporter protein, e.g., a luciferase, is used in a mammalian cell based expression system. In one embodiment, a protease, e.g., a caspase, recognition site is introduced into a protein which is a transcription repressor protein, e.g., a tet repressor protein or a lac repressor protein. In one embodiment, a protease recognition site is introduced into a loop region of the repressor protein or another region that does not inhibit the repressor function for the protein. A vector which includes a promoter linked to DNA which binds the transcription repressor protein linked to the reporter gene is introduced to a cell which contains the modified transcription repressor protein. In absence of the protease, the modified transcription repressor protein inhibits the expression of the reporter gene. In the presence of the protease, the modified transcription repressor protein is inactivated due to proteolytic cleavage of the protease site. As a result, the modified transcription repressor protein is not able repress transcription, which results in the expression of the reporter gene (FIG. 60A). In one embodiment, the modified transcription repressor protein gene and/or the reporter gene are stably transfected into cells. Such an assay may be used in conjunction with other assays, including those using a different reporter gene and/or for detecting a different molecule, for instance, a different protease, for multiplexing. The assay may also be used to detect infectious agents, e.g., for clinical diagnostic applications, as well as to detect bioweapons.

In one embodiment, a fusion of a mutant hydrolase and another protein is employed for chromatin immunoprecipitation. A fusion comprising a mutant hydrolase and a DNA binding protein is expressed in a cell. After a period of incubation, cells are fixed, sonicated and chromatin-hybrid protein complexes are isolated with a solid support having a hydrolase substrate or cells are lysed by sonication, and chromatin complexes are isolated by using a hydrolase substrate attached to a solid support. Unbound complexes or proteins are removed by washing followed by crosslinking the fusion protein to the chromatin or hydrolase substrate comprising a functional group, such as biotin, is added to the cells and incubated for a certain period of time. Cells are then fixed, sonicated and the chromatin complexes isolated with a solid support, e.g., one linked to streptavidin. An amplification reaction is employed to characterize the isolated chromatin.

In yet another embodiment, a fusion of a mutant hydrolase and a nucleic acid binding protein is employed in an in vitro nucleic acid binding assay. The fusion is immobilized onto a solid phase which contains a hydrolase substrate. Cell lysates or purified nucleic acids are incubated the immobilized fusion protein and bound nucleic acids are detected by gel electrophoresis or a polymerase reaction. Alternatively, the fusion is immobilized onto an electrochemically sensitive surface containing a hydrolase substrate. Nucleic acid binding is determined by an electrochemical alteration. These methods could be used for high throughput as well as multiplexed assays for two or more nucleic acid binding proteins In another embodiment, three vectors are employed: one vector expresses a GAL4, a protease recognition site, and VP16 fusion; a second vector includes a promoter linked to a GAL4 binding site linked to a transcription repressor protein gene; and a third vector which includes a promoter linked to a transcription repressor protein binding site(s) linked to the reporter gene (FIG. 60B). Binding of the GAL4 fusion to the GAL4 binding site results in the constitutive transcriptional activation of RNA polymerase. When the transcription repressor protein is being constitutively expressed, the expression of the reporter gene is inhibited. However, in presence of the protease, GAL4 and VP16 are separated and the transcription repressor protein is not synthesized. This results in the expression of the reporter gene. In other embodiments, a split ubiquitin (see U.S. Pat. No. 5,503,977) or adenyl cyclase, guanyl cyclase and/or modulator thereof (see U.S. Pat. No. 6,333,154) system may be employed. Such a system may be used for multiplexed assays using a combination of two or more different reporters such as luciferase and GFP or luciferase and a mutant hydrolase, multiplexed assays for proteases, e.g., using combinations of two or more protease recognition sites, for protease, e.g., caspase, inhibitor screening assays. The assay may be used to detect infectious agents, for instance, in clinical diagnostic applications as well as to detect bioweapons.

In a further embodiment, a cell based assay that employs reporters such as a mutant hydrolase or luciferase with short or shortened half-lives due to the presence of degradation/instability domains (a "protein destabilization sequence") is employed to detect one or more proteases (FIG. 60C). A protease, e.g., a caspase, site is introduced between the reporter protein and the protein destabilization domain(s). In the absence of the protease, the reporter protein is rapidly degraded. In presence of the protease, the destabilization domain is removed resulting in a reporter protein with a longer half-life. Such a system may be used for multiplexed assays using a combination of two or more different reporters such as luciferase and GFP or luciferase and mutant hydrolase, multiplexed assays using a combination of two or more proteases, or for protease or caspase inhibitor screening assays.

In one embodiment, intracellular movements may be monitored using a fusion of the mutant hydrolase of the invention. For example, beta-arrestin is a regulator of G-protein coupled receptors, that moves from the cytoplasm to the cell membrane when it is activated. A cell containing a fusion of a mutant hydrolase and beta-arrestin and a substrate of the invention allows the detection of the movement of beta-arrestin from the cytoplasm to the cell membrane as it associates with activated G-protein coupled receptors. The assay may be used to detect infectious agents, and so may be employed in clinical diagnostic applications as well as to detect bioweapons.

Other formats may be used to detect proteases such as caspases. In one embodiment, a fusion of a mutant hydrolase and another reporter protein, e.g., a luciferase, is constructed by incorporating a protease site at the junction of the fusion. This fusion protein is immobilized onto a solid support and used for the detection of proteases in a sample. A solid phase with the fusion protein is incubated with test sample lysate(s) and/or isolated protease(s). After a certain period of incubation, the lysate is removed and assayed for the presence of the reporter protein. In the presence of the protease, the reporter protein, e.g., luciferase, is released from the solid support into solution. This assay may be used in a protein microarray or a multi-well format and in conjunction with other assays, including those using a different reporter gene and/or for detecting a different molecule, for instance, a different protease, for multiplexing. The method could also be used for the detection of infectious agents, and thus useful for clinical diagnostic applications, as well as for the detection of bioweapons.

In another embodiment, FRET may be employed with a fusion of the mutant hydrolase and a fluorescent protein, e.g., GFP, or a fusion with a protein that binds fluorescent molecules, e.g., O-alkylguanine-DNA alkyltransferase (AGT) (Keppler et al., 2003). Alternatively, a fusion of a mutant hydrolase and a protein of interest and a second fusion of a fluorescent protein and a molecule suspected of interacting with the protein of interest may be employed to study the interaction of the protein of interest with the molecule, e.g., using FRET. One cell may contain the fusion of a mutant hydrolase and a protein of interest while another cell may contain the second fusion of a fluorescent protein and a molecule suspected of interacting with the protein of interest. A population with those two cells may be contacted with a substrate and an agent, e.g., a drug, after which the cells are monitored to detect the effect of agent administration on the two populations. In one embodiment, a fusion of a mutant hydrolase and a protein of interest which protein of interest interacts with a second protein, and a second fusion comprising the second protein and a mutant hydrolase may be employed to study the interaction of the protein of interest and the second protein or to detect a molecule which interacts with one or both proteins and alters their interaction, e.g., PKA regulatory subunit, PKA catalytic subunit and cAMP. In this embodiment, two substrates with at least one different functional group may be employed.

In yet another embodiment, the mutant hydrolase is fused to a fluorescent protein. The fusion protein can thus be detected in cells by detecting the fluorescent protein or by contacting the cells with a substrate of the invention and detecting the functional group in the substrate. The detection of the fluorescent protein may be conducted before the detection of the functional group. Alternatively, the detection of the functional group may be conducted before the detection of the fluorescent protein. Moreover, those cells can be contacted with additional substrates, e.g., those having a different functional group, and the different functional group in the cell detected, which functional group is covalently linked to mutant hydrolase not previously bound by the first substrate.

In yet another embodiment, a fusion of a mutant hydrolase and a transcription factor may be employed to monitor activation of transcription activation pathways. For example, a fusion of a mutant hydrolase to a transcription factor present in the cytoplasm in an inactive form but which is translocated to the nucleus upon activation (e.g., NF kappa Beta) can monitor transcription activation pathways.

In another embodiment, biotin is employed as a functional group in a substrate and the fusion includes a mutant hydrolase fused to a protein of interest suspected of interacting with another molecule, e.g., a protein, in a cell. The use of such reagents permits the capture of the other molecule which interacts in the cell with the protein fused to the mutant hydrolase, thereby identifying and/or capturing (isolating) the interacting molecule(s).

In one embodiment, the mutant hydrolase is fused to a protein that is secreted. Using that fusion and a substrate of the invention, the secreted protein may be detected and/or monitored. Similarly, when the mutant hydrolase is fused to a membrane protein that is transported between different vesicular compartments, in the presence of the substrate, protein processing within these compartments can be detected. In yet another embodiment, when the mutant hydrolase is fused to an ion channel or transport protein, or a protein that is closely associated with the channel or transport protein, the movement of ions across cell or organelle membranes can be monitored in the presence of a substrate of the invention which contains an ion sensitive fluorophore. Likewise, when the mutant hydrolase is fused to proteins associated with vesicals or cytoskeleton, in the presense of the substrate, transport of proteins or vesicals along cytoskeletal structures can be readily detected.

In another embodiment, the functional group is a drug or toxin. By combining a substrate with such a functional group with a fusion of a mutant hydrolase and a targeting molecule such as an antibody, e.g., one which binds to an antigen associated with specific tumor cells, a drug or toxin can be targeted within a cell or within an animal. Alternatively, the functional group may be a fluorophore which, when present in a substrate and combined with a fusion of a mutant hydrolase and a targeting molecule such as a single chain antibody, the targeting molecule is labeled, e.g., a labeled antibody for in vitro applications such as an ELISA.

In yet another embodiment, when fused to a protein expressed on the cell surface, a mutant hydrolase on the cell surface, when combined with a substrate of the invention, e.g., one which contains a fluorophore, may be employed to monitor cell migration (e.g., cancer cell migration) in vivo or in vitro. In one embodiment, the substrate of the invention is one that has low or no permeability to the cell membrane. Alternatively, such a system can be used to monitor the effect of different agents, e.g., drugs, on different pools of cells. In yet another embodiment, the mutant hydrolase is fused to a HERG channel. Cells expressing such a fusion, in the presence of a substrate of the invention which includes a K+-sensitive fluorophore, may be employed to monitor the activity of the HERG channel, e.g., to monitor drug-toxicity. In a further embodiment, such a fusion may be expressed on the surface of blood cells, such as exogenous cells introduced to an animal or endogenous cells in a transgenic animal the genome of which is modified to express such a fusion protein.

In another embodiment, the substrate of the invention includes a functional group useful to monitor for hydrophobic regions, e.g., Nile Red, in a cell or organism.

Thus, the mutant hydrolases and substrates of the invention are useful in a wide variety of assays, e.g., phage display, panning, ELISA, mass spectrometry, Western blot, fluorometric microvolume assay technology (FMAT), whole animal imaging, X-ray imaging, and cell and subcellular staining, or as a biosensor. For example, cells expressing or containing a mutant hydrolase or a fusion protein which includes a mutant hydrolase, are introduced, e.g., implanted or injected into an animal such as a human or non-human animal including a non-human mammal or non-human primate. The cells may be transiently transfected or stably express the mutant hydrolase or fusion thereof, or be otherwise contacted with the mutant hydrolase or fusion thereof so that it is associated with the cell. Different cell types can be used, including but not limited to cell lines, primary cultures, or stem cells (e.g., embryonic or adult stem cells). In one embodiment, the mutant hydrolase expressing or containing cells are contacted with a hydrolase substrate of the invention before introduction to an animal. In another embodiment, a hydrolase substrate of the invention is introduced to the animal before or after the mutant hydrolase expressing or containing cells are introduced to the animal. The presence, location or amount of the functional group of the hydrolase substrate in the whole animal or in tissue preparations (including but not limited to tissue biopsy or slices, cells isolated from a physiological sample, or in homogenized tissue), or physiological fluid samples such as blood samples and the like, is detected or determined. The mutant hydrolase, a fusion comprising the mutant hydrolase, and/or one or more substrates of the invention can be used alone or in combination with other optical or nuclear reporting systems (e.g., fluorescent proteins, luciferases, radionuclides, etc.), for instance, to image biological processes, to image transcriptional regulation of endogenous genes, and to image trafficking of cells (bone marrow-derived cells, blood cells, and the like). Optical imaging systems include those for microscopic resolution, e.g., epi, confocal and two photon, mesoscopic resolution, e.g., optical projection tomography, optical coherence tomography or laser speckle imaging, and macroscopic resolation with intrinsic contrast or molecular contrast, e.g., hyperspectral imaging, endoscopy, polarization imaging, fluorescence reflectance imaging, diffuse optical tomography, fluorescence resonance imaging, fluorescence molecular imaging or luminescence imaging.

The mutant hydrolase, a fusion comprising the mutant hydrolase, and/or one or more substrates of the invention can be also used in combination with different optically dense/contrast reagents, which may be employed as a separate agent or chemically attached to a hydrolase substrate. In one embodiment, a hydrolase substrate containing a contrast agent is introduced to an animal which contains cells expressing the mutant hydrolase or a fusion thereof (e.g., a transgenic animal harboring the gene coding for mutant hydrolase or fusion thereof). In another embodiment, a hydrolase substrate containing a contrast agent is introduced to cells expressing the mutant hydrolase or a fusion thereof and those cells are introduced to an animal. The contrast agent can then be detected using X-ray, MRI, or other techniques.

In one embodiment, a fusion of a mutant hydrolase and another protein and a hydrolase substrate bound to an electrochemically sensitive surface are employed to detect a molecule such as a physiological molecule, i.e., they are employed as a biosensor. For instance, the surface contains immobilized hydrolase substrate, and the presence of a molecule of interest in a test solution is determined by an electrochemical alteration. For example, a fusion comprising a mutant hydrolase and glucose oxidase is immobilized onto a platinum electrode, gold surface, gold nanoparticles or carbon nanotubes, having a hydrolase substrate. A test sample is added and the presence or quantity of glucose in the test sample determined. Likewise, cholesterol in a test sample may be determined using a mutant hydrolase-cholesterol oxidase fusion immobilized onto an electrochemically sensitive surface.

In another embodiment, the mutant hydrolase may be used as a biosensor for the detection of protease, protease inhibitor, kinase or kinase inhibitor and the like. For example, a protease site is fused to a mutant hydrolase protein and the resulting fusion immobilized onto an electrochemically sensitive surface such as electrode, a gold surface, gold nanoparticle, or carbon nanotube, having a hydrolase substrate. In presence of molecules such as a protease or kinase, there is a shift in the molecular weight, which may be detected by an electrochemical alteration. Inhibitors of those changes include inhibitors of the protein fused to the mutant hydrolase, e.g., protease inhibitors, which may also be detected using this method.

In another embodiment, a mutant hydrolase conjugated to a substrate other than hydrolase substrate, e.g., at the C-terminal end of the mutant hydrolase and/or a fusion of a mutant hydrolase and a protein conjugated to a substrate other than the hydrolase substrate. The biosensor surface contains immobilized hydrolase substrate. The presence of a biomolecule in the test solution is determined by an electrochemical alteration. The method may be used to capture, bind or otherwise provide a means for assaying certain molecules and could be used for the detection of pesticides, industrial toxic compounds, clinical diagnostics, infectious agents and bioweapons. In one embodiment, this method could be used for the detection of molecules including, but not limited to, a protease, protease inhibitor, kinase, kinase inhibitor, as well as the detection of the post-translational modification of proteins.

The invention will be further described by the following non-limiting examples.

EXAMPLE I

General Methodologies

Unless defined otherwise, all technical and scientific terms used herein have the same meaning as commonly understood by one of ordinary skill in the field of molecular biology and cellular signaling and modeling. Generally, the nomenclature used herein and the laboratory procedures in spectroscopy, drug discovery, cell culture, molecular genetics, plastic manufacture, polymer chemistry, diagnostics, amino acid and nucleic acid chemistry, and alkane chemistry described below are those well known and commonly employed in the art. Standard techniques are typically used for preparation of plastics, signal detection, recombinant nucleic acid methods, polynucleotide synthesis, and microbial culture and transformation (e.g., electroporation, lipofection).

The techniques and procedures are generally performed according to conventional methods in the art and various general references (see generally, Sambrook et. al. Molecular Cloning: A laboratory manual, 2d ed. (1989) Cold Spring Harbor Laboratory Press, Cold Spring Harbor, N.Y., and Lakowicz, J.R. Principles of Fluorescence Spectroscopy, New York: Plenum Press (1983) for fluorescent techniques, which are incorporated herein by reference) and which are provided throughout this document. Standard techniques are used for chemical synthesis, chemical analysis, and biological assays.

Materials

All oligonucleotides were synthesized, purified and sequenced by Promega Corporation (Madison, Wis.) or the University of Iowa DNA Facility (Iowa City, Iowa). Restriction enzymes and DNA modifying enzymes were obtained from Promega Corporation (Madison, Wis.), New England Biolabs, Inc. (Beverly, Mass.) or Stratagene Cloning Systems (La Jolla, Calif.), and were used according to the manufacturer's protocols. Competent E. coli JM109 were provided by Promega Corporation or purchased from Stratagene Cloning Systems. Small-scale plasmid DNA isolations were done using the Qiagen Plasmid Mini Kit (Qiagen Inc., Chatsworth, Calif.). DNA ligations were performed with pre-tested reagent kits purchased from Stratagene Cloning Systems. DNA fragments were purified with QIAquick Gel Extraction Kits or QIAquick PCR purification Kits purchased from Qiagen Inc.

The vectors used for generating DhaA mutants and their fusions were as follows: pET21 (Invitrogen, Carlsbad, Calif.), pRL-null (Promega, Madison, Wis.), pGEX-5x-3 (Amersham Biosciences; Piscataway, N.J.), and EGFP and DsRED2 (both from CLONTECH, Palo Alto, Calif.).

SDS-polyacrylamide gels and associated buffers and stains, as well as electroblot transfer buffers, were obtained from BioWhittaker Molecular Applications (Rockland, Me.). Protein molecular weight standards were purchased from Invitrogen.

Sigma-Aldrich was the source of Anti Flag$^R$ monoclonal antibody antibodies (anti FLAG$^R$ M2 monoclonal antibody (mouse) (F3165)), Anti FLAG$^R$ M2 HRP Conjugate and Anti FLAG$^R$ M2 FITC conjugate (A8592 and F4049, respectively). Chemicon (Temecula, Calif.) was the source of monoclonal anti-Renilla luciferase antibody (MAB4410). Promega Corp. was the source of HRP-conjugated goat anti-mouse IgG and HRP-conjugated streptavidin (W4021 and G714, respectively).

1-Cl-butane, 1-Cl-hexane, 1-Cl-octane, 1-Cl-decane, 1-Cl-butanol, 1-Cl-hexanol, 1-Cl-octanol, and 1-Cl-decanol were obtained from Aldrich or from Fluka (USA). All salts, monobasic potassium phosphate, dibasic potassium phosphate, imidazole, HEPES, sodium EDTA, ammonium sulfate, and Tris free base were from Fisher (Biotech Grade).

Glutathione Sepharose 4 FF, glutathione, MonoQ and Sephadex G-25 prepackaged columns were from Amersham Biosciences.

Luria-Broth ("LB") was provided by Promega Corporation.

Methods

PCR Reactions. DNA amplification was performed using standard polymerase chain reaction buffers supplied by Promega Corp. Typically, 50 µl reactions included 1× concentration of the manufacturer's supplied buffer, 1.5 mM MgCl$_2$, 125 µM dATP, 125 µM dCTP, 125 µM dGTP, 125 µM dTTP, 0.10-1.0 µM forward and reverse primers, 5 U AmpliTaq® DNA Polymerase and <1 ng target DNA. Unless otherwise indicated, the thermal profile for amplification of DNA was 35 cycles of 0.5 minutes at 94° C.; 1 minute at 55° C.; and 1 minute at 72° C.

DNA Sequencing. All clones were confirmed by DNA sequencing using the dideoxy-terminal cycle-sequencing method (Sanger et al., 1977) and a Perkin-Elmer Model 310 DNA sequencer. (Foster City, Calif.).

SDS-PAGE. Proteins were solubilized in a sample buffer (1% SDS, 10% glycerol, and 1.0 mM β-mercaptoethanol, pH 6.8; Promega Corporation), boiled for 5 minutes and resolved on SDS-PAGE (4-20% gradient gels; BioWhittaker Molecular Applications). Gels were stained with Coomassie Blue (Promega Corp.) for Western blot analysis or were analyzed on a fluoroimager (Hitachi, Japan) at an $E_{ex}/E_{em}$ appropriate for each fluorophore evaluated.

Western Blot Analysis. Electrophoretic transfer of proteins to a nitrocellulose membrane (0.2 um, Scheicher & Schuell, Germany) was carried out in 25 mM Tris base/188 mM glycine (pH 8.3), 20% (v/v) methanol for 2.0 hours with a constant current of 80 mA (at 4° C.) in Xcell II Blot module (Invitrogen). The membranes were rinsed with TBST buffer (10 mM Tris-HCl, 150 mM NaCl, pH 7.6, containing 0.05% Tween 20) and incubated in blocking solution (3% dry milk or 1% BSA in TBST buffer) for 30 minutes at room temperature or overnight at 4° C. Then membranes were washed with 50 ml of TBST buffer and incubated with anti-FLAG$^R$ monoclonal antibody M2 (dilution 1:5,000), anti-Renilla luciferase monoclonal antibody (dilution 1:5,000), or HRP-conjugated streptavidin (dilution 1:10,000) for 45 minutes at room temperature. Then the membranes were washed with TBST buffer (50 ml, 5 minutes, 3 times). The membranes that had been probed with antibody were then incubated with HRP-conjugated donkey anti-mouse IgG (30 minutes, room temperature) and then the washing procedure was repeated. The proteins were visualized by the enhanced chemiluminescence (ECL) system (Pharmacia-Amersham) according to the manufacturer's instructions. Levels of proteins were quantified using computer-assisted densitometry.

Protein Concentration. Protein was measured by the microtiter protocol of the Pierce BCA Protein assay (Pierce, Rockford, Ill.) using bovine serum albumin (BSA) as a standard.

Statistic Analysis. Data were expressed as mean+/−S.E.M. values from experiments performed in quadruplicate, representative of at least 3 independent experiments with similar results. Statistical significance was assessed by the student's t test and considered significant when $p<0.05$.

Bacterial Cells. The initial stock of DhSa cells containing pET-3a with Rhodococcus rodochorus (DhaA) was kindly provided by Dr. Clifford J. Unkefer (Los Alamos National Laboratory, Los Alamos, N. Mex.) (Schindler et al., 1999; Newman et al., 1999). Bacteria were cultured in LB using a premixed reagent provided by Promega Corp. Freezer stocks of E. coli BL21 (λDE3) pET3a (stored in 10% glycerol, −80° C.) were used to inoculate Luria-Bertani agar plates supplemented with ampicillin (50 µg/ml) (Sambrook et al., 1989). Single colonies were selected and used to inoculate two 10 ml cultures of Luria-Bertani medium containing 50 µg/ml ampicillin. The cells were cultured for 8 hours at 37° C. with shaking (220 rpm), after which time 2 ml was used to inoculate each of two 50 ml of Luria-Bertani medium containing 50 µg/ml ampicillin, which were grown overnight at 37° C. with shaking. Ten milliliters of this culture was used to inoculate each of two 0.5 L Luria-Bertani medium with ampicillin. When the $A_{600}$ of the culture reached 0.6, isopropyl-1-thio-β-D-galactopyranoside (IPTG) was added to a final concentration of 0.5 mM, and cultures were maintained for an additional 4 hours at 30° C. with shaking. The cells were then harvested by centrifugation and washed with 10 mM Tris-SO$_4$, 1 mM EDTA, pH 7.5. The cell pellets were stored at −70° C. prior to cell lysis.

Mammalian Cells. CHO-K1 cells (ATCC-CCL61) were cultured in a 1:1 mixture of Ham's F12 nutrients and Dulbecco's modified minimal essential medium supplemented with 10% fetal bovine serum (FBS), 100 U/ml penicillin, and 100 mg/ml streptomycin, in an atmosphere of 95% air and 5% $CO_2$ at 37° C.

Rat hippocampal (E18) primary neurons were isolated as described below. Briefly, fragments of embryonic (E18) rat hippocampus in Hibernate™ E media (GIBCO, Invitrogen, Carlsbad, Calif.), obtained from Dr. Brewer (Southern Illinois University), were dissociated and plated on poly-D-lysin coated (0.28 mg/cm$^2$; Sigma) glass/plastic-ware and cultured in serum-free Neurobasal™ media with B27 supplement (NB27, GIBCO). All media were changed every 2-3 days.

Transfection. To study transient expression of different proteins, cells were plated in 35 mm culture dishes or 24 well plates. At about 80-90% confluency, the cells were exposed to a mixture of lipofectamine/DNA/antibiotic free media according to the manufacturer's (GIBCO) instructions. The following day, media was replaced with fresh media and cells were allowed to grow for various periods of time.

Fluorescence

Fluorescence in cells in 96 well plates was measured on fluorescent plate reader CytoFluorII (Beckman) at an $E_{ex}/E_{em}$ appropriate for particular fluorophores (e.g., $E_{ex}/E_{em}$ for carboxytetramethylrhodamine is 540/575 nm).

EXAMPLE II

A DhaA-Based Tethering System

A. Wild-Type and Mutant DhaA Proteins and Fusions Thereof

Figure 1A:
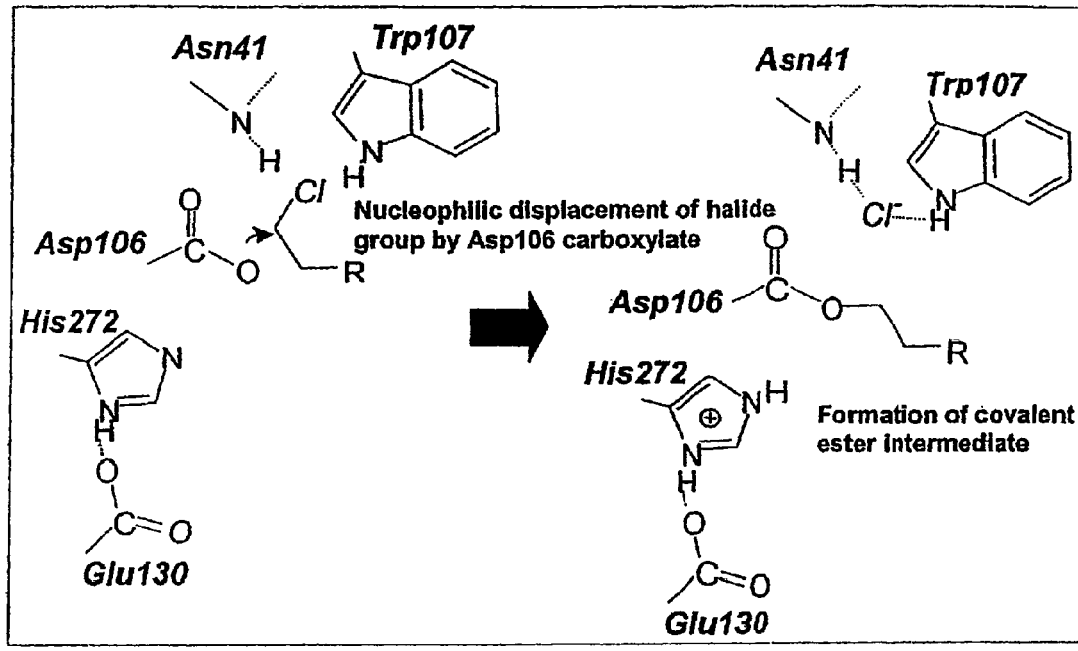
FIGS. 1A-B provide a schematic of the two-step catalytic mechanism of DhaA with an alkylhalide substrate. A). Nucleophilic displacement of a halide group by Asp106 carboxylate and the formation of a covalent ester intermediate. B). Hydrolysis of the covalent intermediate by an activated water molecule releasing alcohol and regenerating the catalytic Asp 106.
Figure 1B:
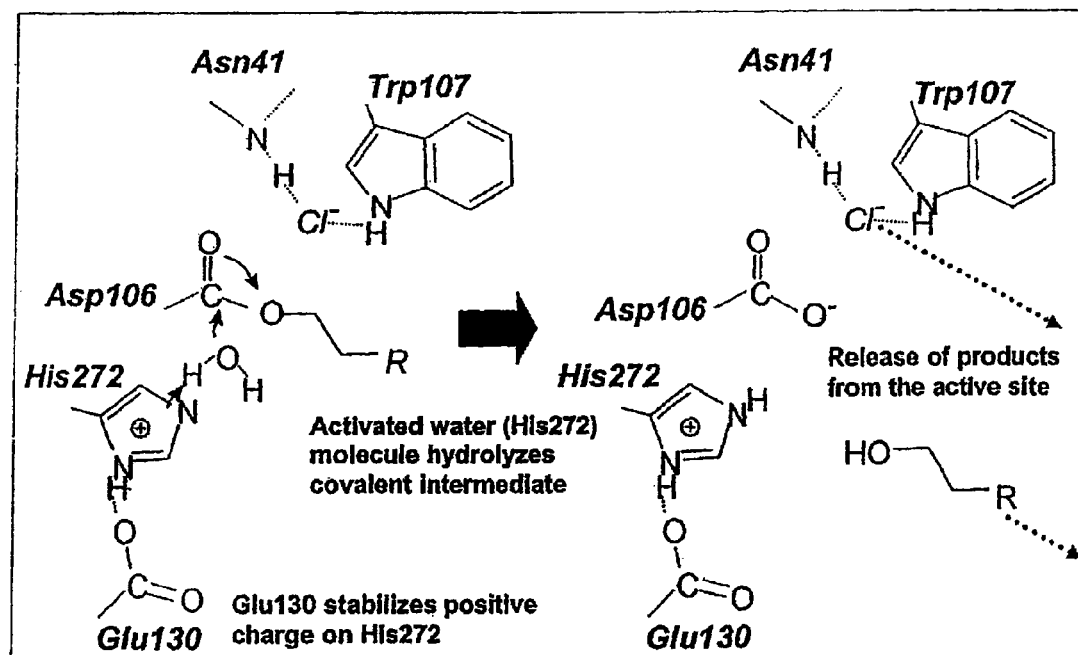
Figure 2A:
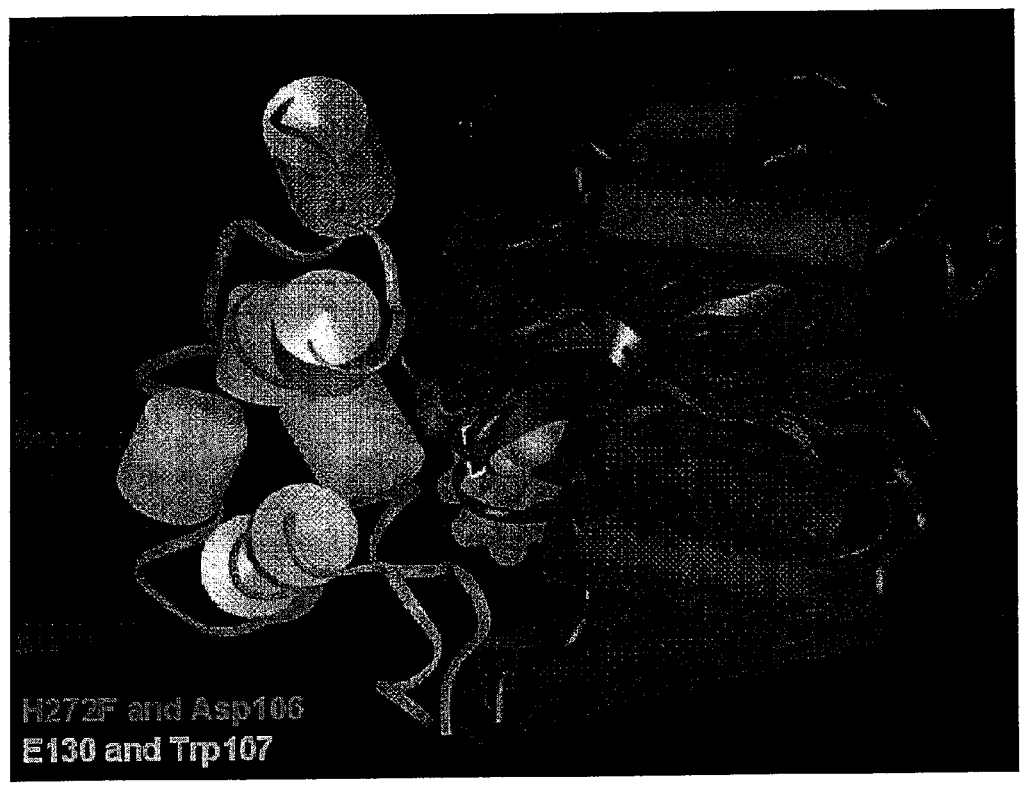
FIG. 2A shows a molecular model of the DhaA.H272F protein. The helical cap domain is shown in light blue. The α/β hydrolase core domain (dark blue) contains the catalytic triad residues. The red shaded residues near the cap and core domain interface represent H272F and the D106 nucleophile. The yellow shaded residues denote the positions of E130 and the halide-chelating residue W107.

The haloalkane dehalogenase gene from *Rhodococcus rhodochrous*, dhaA, encodes a monomeric 33 kDa enzyme that catalyzes the irreversible hydrolysis of a variety of haloalkanes (Kulakova et al. 1997), e.g., cleaves carbon-halogen bonds in aliphatic and aromatic halogenated compounds, e.g., $HaloC_3$-$HaloC_{10}$. A substantial amount of mechanistic and structural information is available on the haloalkane dehalogenases. The DhaA enzyme contains 293 amino acids and is a member of a superfamily of proteins containing an α/β hydrolase fold (FIG. 2A). The overall structures of the haloalkane dehalogenases from *Rhodococcus, Xanthobacter* and *Sphingomonas* are similar and each contains a triad of catalytic residues that is involved in the cleavage of halide-carbon bonds. In the case of DhaA, these residues are Asp106, E130, and His272 (Newman et al., 1999; FIG. 2B). FIGS. 1A-B show the overall catalytic mechanism for the DhaA enzyme. After substrate binding, nucleophilic attack by the carboxylate of an Asp residue on the substrate causes the cleavage of the halogen-carbon bond and the formation of an alkyl-ester intermediate (FIG. 1A). The next step in the dehalogenase reaction pathway is hydrolysis of the intermediate ester by a water molecule activated by the active site His residue (FIG. 1B). While the catalytic histidine residue is the base catalyst for the dealkylation of the covalent intermediate, it is not essential for the initial nucleophilic attack of the active site Asp. Protein variants that lack the crucial catalytic histidine residue have been shown to carry out the alkylation half reaction thereby producing a stable, covalent ester intermediate (Pries et al., 1995).

It is likely that substrate binds to DhaA to form an ES complex, after which nucleophilic attack by Asp 106 forms an ester intermediate, His272 then activates $H_2O$ that hydrolyzes the intermediate, releasing product from the catalytic center. To determine whether a point mutation of the catalytic His272 residue impairs enzymatic activity of the enzyme so as to enable covalent tethering of a functional group (FG) to this protein, mutant DhaAs were prepared.

Materials and Methods

To prepare mutant DhaA vectors, Promega's in vitro mutagenesis kit which is based on four primer overlap-extension method was employed (Ho et al., 1989) to produce DhaA.H272 to F, A, G, or H mutations. The external primers were oligonucleotides 5'-GCTTCACTTGTCGTCATCGTC-CTTGTAGTCA-3' (SEQ ID NO:1) and 5'-GCTTCACT-TGTCGTCATCGTCCTTGTAGTCA-3' (SEQ ID NO:2), and the internal mutagenic primers were as follows: H272F (5'-CCGGGATTGTTCTACCTCCAGGAAGAC-3'), SEQ ID NO:3), H272A (5'-CCGGGATTG GCCTACCTCCAGGAAGAC-3'; SEQ ID NO:4), H272G (5'-CCGGGATTGCAGTACCTCCAGGAAGAC-3'; SEQ ID NO:5), and H272Q (5'-CCGGGATTG GGCTACCTCCAGGAAGAC-3'; SEQ ID NO:6) (the mutated codons are underlined). The mutated dehalogenase genes were subcloned into the pET-3a vector. For overexpression of mutant dehalogenases, the pET-3a vector was transformed into competent *E. coli* BL21 (DE3). The DhaA sequence in clones was confirmed by DNA sequencing. Unless otherwise noted DhaA.WT and DhaA.H272F proteins generally contain GST at the N-terminus and a FLAG epitope at the C-terminus.

GST-DhaA (WT or H272F/A/G/H mutants) fusion cassettes were constructed by cloning the appropriate DhaA coding regions into SalI/NotI sites of pGEX5x3 vector. Two primers (5'-ACGCGTCGACGCCGCCATGTCA-GAAATCGGTACAGGC-3' and 5'-ATAAGAATGCGGC-CGCTCAAGCGCTTCAACCGGTGAGT-GCGGGGAGCCAGCGCGC-3'; SEQ ID NOs:7 and 8, respectively) were designed to add a SalI site and a Kozak consensus sequence to the 5' coding regions of DhaA, to add a NotI, EcoR47III, and AgeI restriction site and stop codons to the 3' coding region of DhaA, and to amplify a 897 bp fragment from a DhaA (WT or mutant) template. The resulting fragments were inserted into the SalI/NotI site of pGEX-5X-3, a vector containing a glutathione S-transferase (GST) gene, a sequence encoding a Factor Xa cleavage site, and multiple cloning sites (MCS) followed by a stop codon.

A Flag coding sequence was then inserted into the AgeI/EcoR47III restriction sites of the pGEX5X-3 vector. In frame with the six nucleotide AgeI site is a sequence for an 11 amino acid peptide, the final octapeptide of which corresponds to the Flag peptide (Kodak Imaging Systems, Rochester, N.Y.). Two complementary oligonucleotides (5'-CCGGTGACTA-CAAGGACGATGACGACAAGTGAAGC-3', sense, SEQ ID NO:9, and 5'-GCTTCACTTGTCGTCATCGTCCTTG-TAGTCA-3', antisense, SEQ ID NO:10) coding the Flag peptide (Kodak Imaging Systems, Rochester, N.Y.) were annealed. The annealed DNA had an AgeI site at the 5' end and an EcoR47III at the 3' end. The annealed DNA was digested with AgeI and EcoR47III and then subcloned into the GST-DhaA.WT or GST-DhaA.H272F mutant constructs at the AgeI and EcoR47III sites. All gene fusion constructs were confirmed by DNA sequencing. Unless otherwise noted DhaA.WT and DhaA.H272F proteins generally contain GST at the N-terminus and a FLAG epitope at the C-terminus.

To generate DhaA fusion proteins, enzyme expression was induced by the addition of isopropyl-b-D-thiogalactopyranoside (at a final concentration of 0.5 mM) when the culture reached an optical density of 0.6 at 600 nm. The cells were harvested in Buffer A (10 mM Tris-$SO_4$, 1 mM EDTA, 1 mM β-mercaptoethanol, and 10% glycerol, pH 7.5), and disrupted by sonication using a Vibra Cell™ sonicator (Sonics & Materials, Danbury, Conn., USA). Cell debris was removed by centrifugation at 19,800×g for 1 hour. The crude extract was further purified on a GSS-Sepharose 4 fast flow column (Amersham Biosciences; Piscataway, N.J.) according to the manufacturer's instructions. The elution fractions containing GST-DhaA fusion protein were pooled, dialyzed against a 10 mM Tris-SO$_4$ buffer (containing 20 mM Na$_2$SO$_4$ and 1 mM EDTA-Na$_2$) overnight at 4° C., and stored at −20° C. until use. To generate DhaA (WT or mutant), GST was cleaved from the fusion proteins with Factor Xa, and the products purified on GSS-Sepharose 4 (Amersham Biosciences; Piscataway, N.J.) according to the manufacturer's instructions. Homogeneity of the proteins was verified by SDS-PAGE. In some experiments, the cell free extract was fractionated using 45-70% saturated ammonium sulfate as described by Newman et al. (1999).

Results

Figure 3A:
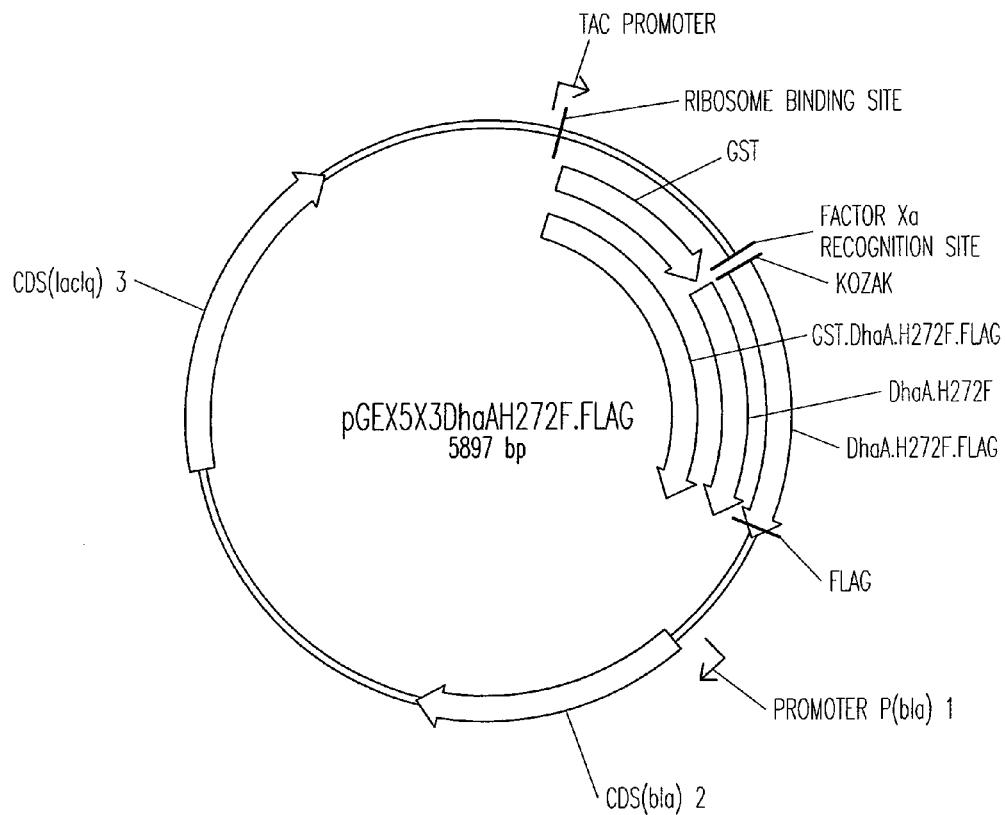
FIG. 3A illustrates the physical map of plasmid pGEX5X3DhaA.H272F.FLAG. This plasmid and pGEX5X3DhaA.D106C.FLAG (not shown) were used as the parental templates in mutagenesis and screening studies. The DhaA coding regions are fused at the N-terminus with glutathione S-transferase (GST) and at the C-terminus with the FLAG epitope. A Factor Xa cleavage site is situated between the GST and DhaA coding regions.
Figure 3B:
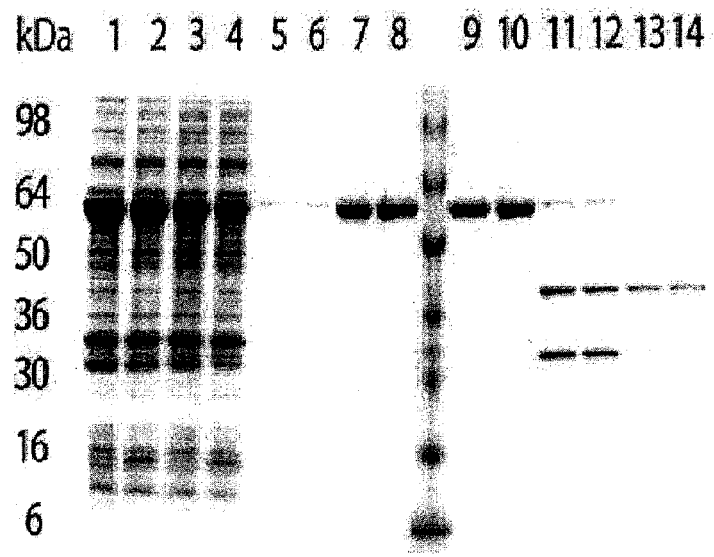
FIG. 3B shows the purification of GST-DhaA fusion proteins. DhaA.WT (odd numbered lanes) and DhaA.H272F (even numbered lanes) fusion proteins were found to be soluble and efficiently purified on GSS-Sepharose 4FF (lanes 3 and 4-crude E. coli supernatant; lanes 5 and 6-washes; lanes 7 through 10-purified proteins). Treatment of the fusion proteins with Factor Xa led to the formation of two proteins, GST and DhaA (WT or H272F mutant; lanes 11 and 12, respectively). Moreover, GST was efficiently removed on GSS-Sepharose 4FF (DhaA.WT or mutant; lanes 13 and 14, respectively). All proteins had the predicted molecular weight.

FIG. 3 shows robust, IPTG inducible production of DhaA.WT (lane 1) and DhaA.H272F (lane 2) fusion proteins. Moreover, the proteins were soluble and could be efficiently purified on Glutathione-Sepharose 4FF (lanes 5-10, odd numbered lanes correspond to DhaA.WT and even numbered lanes correspond to DhaA.H272F). Treatment of the fusion proteins with Factor Xa led to the formation of two proteins GST and DhaA (WT or H272F mutant, lanes 11 and 12, respectively), and GST was efficiently removed on Glutathione-Sepharose 4FF (WT or mutant, lanes 13 and 14, respectively). In addition, all proteins had the predicted molecular weight.

B. Mutation of H272 Impairs Ability of DhaA to Hydrolyze Cl-Alkanes.

Inability of an enzyme to release product of the enzymatic reaction into surrounding media is essential for the tethering system. This inability can be detected by significant reduction of the hydrolytic activity of the enzyme.

To study the effect of a point mutation on the activity of DhaA (WT or mutant) hydrolysis of Cl-alkanes, a pH-indicator dye system as described by Holloway et al. (1998) was employed.

Materials and Methods

The reaction buffer for a pH-indicator dye system consisted of 1 mM HEPES-SO$_4$ (pH 8.2), 20 mM Na$_2$SO$_4$, and 1 mM EDTA. Phenol red was added to a final concentration 25 µg/ml. The halogenated compounds were added to apparent concentrations that could insure that the dissolved fraction of the substrate was sufficient for the maximum velocity of the dehalogenation reaction. The substrate-buffer solution was vigorously mixed for 30 seconds by vortexing, capped to prevent significant evaporation of the substrate and used within 1-2 hours. Prior to each kinetic determination, the phenol red was titrated with a standardized solution of HCl to provide an apparent extinction coefficient. The steady-state kinetic constants for DhaA were determined at 558 nm at room temperature on a Beckman Du640 spectrophotometer (Beckman Coulter, Fullerton, Calif.). Kinetic constants were calculated from initial rates using the computer program SigmaPlot. One unit of enzyme activity is defined as the amount required to dehalogenate 1.0 mM of substrate/minute under the specific conditions.

Results

Figure 4:
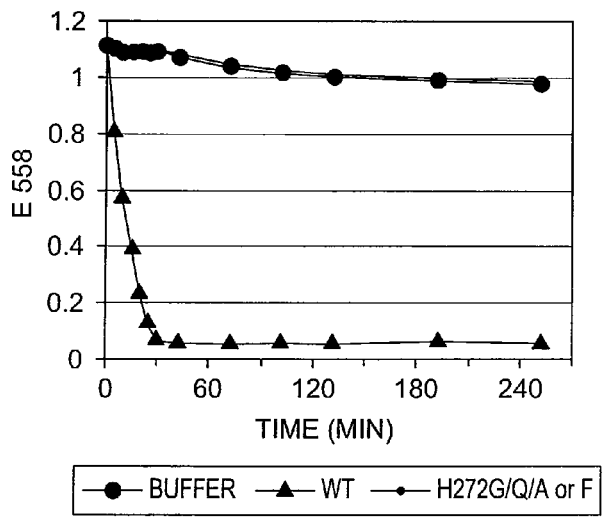
FIG. 4 illustrates the hydrolysis of 1-Cl-butane by DhaA.WT and mutant DhaAs.

As shown in FIG. 4, using 0.1 mg/ml of enzyme and 10 mM substrate at pH 7.0-8.2, no catalytic activity was found with any of four mutants. Under these conditions, the wild-type enzyme had an activity with 1-Cl-butane of 5 units/mg of protein. Thus, the activity of the mutants was reduced by at least 700-fold.

Aliquots of the supernatant obtained from *E. coli* expressing DhaA (WT or one of the mutants) were treated with increasing concentrations of (NH$_4$)$_2$SO$_4$. The proteins were exposed to each (NH$_4$)$_2$SO$_4$ concentration for 2 hours (4° C.), pelleted by centrifugation, dialyzed overnight against buffer A, and resolved on SDS-PAGE.

Figure 5A:
FIG. 5 shows precipitation of DhaA.WT and DhaA.H272F/A/G/Q mutants with various concentrations of $(NH_4)_2SO_4$. Lanes 1, 5, and 9, 0% $(NH_4)_2SO_4$; lanes 2, 6, and 10, 10% $(NH_4)_2SO_4$; lanes 3, 7, and 11, 10-45% $(NH_4)_2SO_4$; and lanes 4, 8, and 12, 45-70% $(NH_4)_2SO_4$. Panel A: lanes 1-4, DhaA.WT; lanes 5-8, DhaA.H272G; and lanes 9-12, DhaA.H272Q. Panel B: lanes 1-4, DhaA.WT; lanes 5-8, DhaA.H272F; and lanes 9-12, DhaA.H272A.
Figure 5B:

As shown in FIG. 5, a major fraction of DhaA.WT and the DhaA.H272F mutant was precipitated by 45-70% of (NH$_4$)$_2$SO$_4$. No precipitation of these proteins was observed at low (NH$_4$)$_2$SO$_4$ concentrations. In contrast, the DhaA.H272Q, DhaA.H272G and DhaA.H272A mutants could be precipitated by 10% (NH$_4$)$_2$SO$_4$. This is a strong indication of the significant change of the physico-chemical characteristics of the DhaA.H272Q, DhaA.H272G and DhaA.H272A mutants. At the same time, the DhaA.H272F mutation had no significant effect on these parameters. These data are in good agreement with results of computer modeling of the effect of mutations on the 3-D structure of DhaA, indicating that among all tested mutants, only the DhaA.H272F mutation had no significant effect on the predicted 3-dimensional model (see FIG. 2). Based on these results, DhaA.H272F was chosen for further experiments.

To form a covalent adduct, the chlorine atom of Cl-alkane is likely positioned in close proximity to the catalytic amino acids of DhaA (WT or mutant) (FIGS. 2A-B). The crystal structure of DhaA (Newman et al., 1999) indicates that these amino acids are located deep inside of the catalytic pocket of DhaA (approximately 10 Å long and about 20 Å$^2$ in cross section). To permit entry of the reactive group in a substrate for DhaA which includes a functional group into the catalytic pocket of DhaA, a linker was designed to connect the Cl-containing substrate with a functional group so that the functional group is located outside of the catalytic pocket, i.e., so as not to disturb/destroy the 3-D structure of DhaA.

Figure 6:
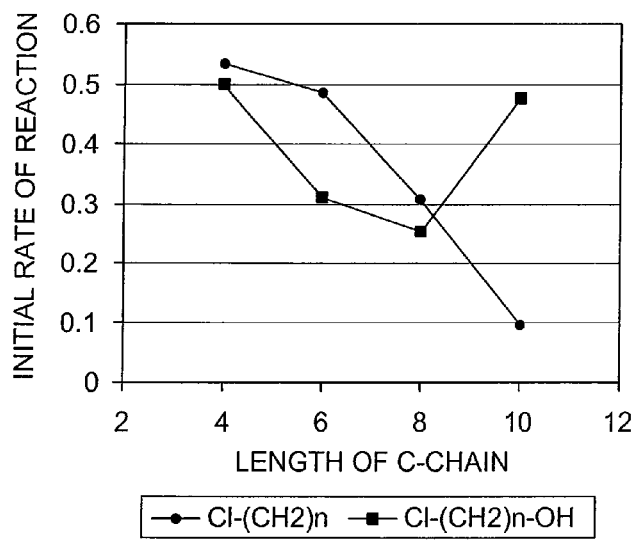
FIG. 6 depicts the substrate specificity of wild-type DhaA. Using a phenol red-based assay ($E_{558}$), the initial rate of the reaction was determined during the first 60 seconds after enzyme addition by four 15 second readings.

To determine if DhaA is capable of hydrolyzing Cl-alkanes with a long hydrophobic carbon chain, DhaA.WT was contacted with various Cl-alkane alcohols. As shown in FIG. 6, DhaA.WT can hydrolyze 1-Cl-alkane alcohols with 4-10 carbon atoms. Moreover, the initial rate of hydrolysis (IRH) of Cl-alkanes had an inverse relationship to the length of a carbon chain, although poor solubility of long-chain Cl-alkanes in aqueous buffers may affect the efficiency of the enzyme-substrate interaction. Indeed, as shown in FIG. 6, the IRH of 1-Cl-alkane-10-decanol is much higher than the IRH of 1-Cl-decane. More importantly, these data indicate that DhaA can hydrolyze Cl-alkanes containing relatively polar groups (e.g., HO-group).

Figure 7A:
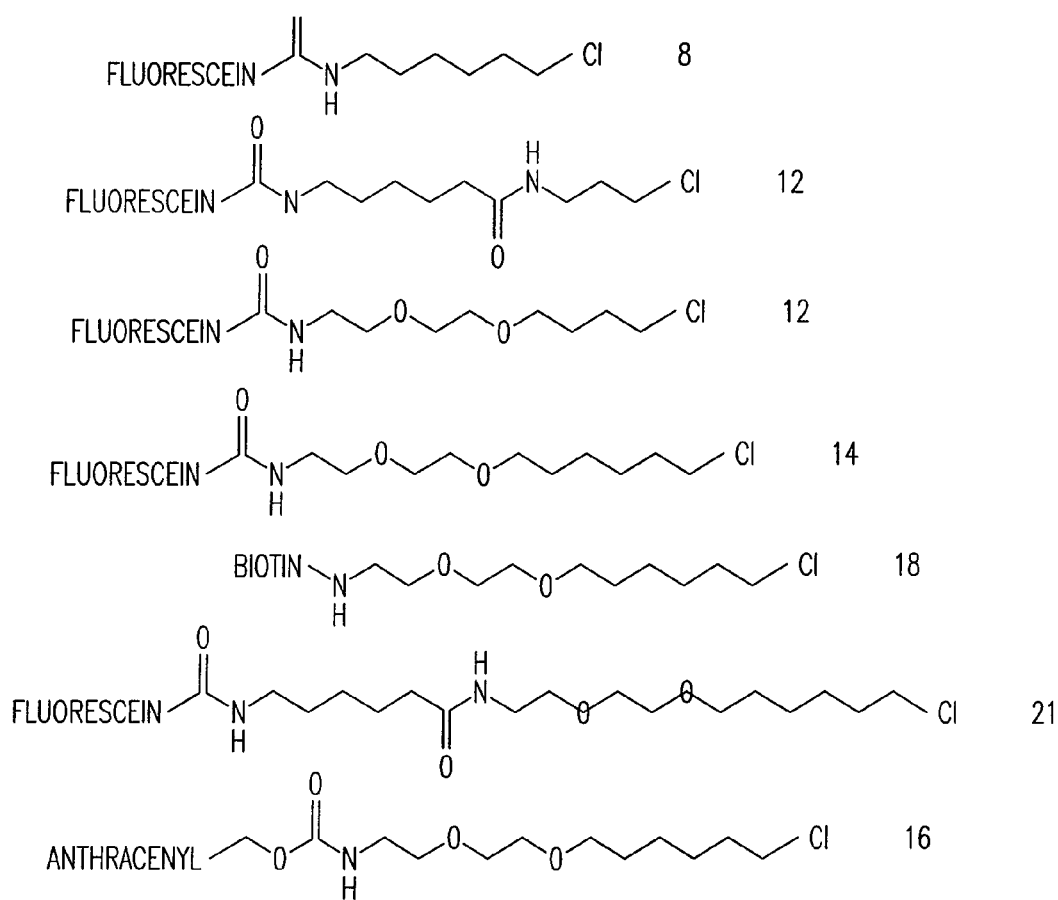

Carboxyfluorescein-modified Cl-alkanes with linkers of different length and/or hydrophobicity were prepared (FIG. 7). DhaA.WT efficiently hydrolyzed Cl-alkanes with a relatively bulky functional group (carboxyfluorescein) if the linker was 12 or more atoms long. No activity of DhaA.H272F/A/G/Q mutants was detected with any of the tested Cl-alkanes (data not shown). In addition, modification of the (CH$_2$)$_6$ region adjacent to the Cl-atom led to a significant reduction of the IRH of the 14-atom linker by DhaA.WT. Nevertheless, if the length and structure of the linker is compatible with the catalytic site of a hydrolase, the presence of a linker in a substrate of the invention has substantially no effect on the reaction.

Some of the samples were analyzed on an automated HPLC (Hewlett-Packard Model 1050) system. A DAD detector was set to record UV-visible spectra over the 200-600 nm range. Fluorescence was detected at an $E_{ex}/E_{em}$ equal 480/520 nm and 540/575 nm for carboxyfluorescein- and carboxytetramethylrhodamine-modified substrates, respectively. Ethanol extracts of Cl-alkanes or products of Cl-alkane hydrolysis were analyzed using analytical reverse phase C$_{18}$ column (Adsorbosphere HS, 5µ, 150×4.6 mm; Hewlett-Packard, Clifton, N.J.) with a linear gradient of 10 mM ammonium acetate (pH 7.0):ACN (acetonitrile) from 25:75 to 1:99 (v/v)

applied over 30 minutes at 1.0 ml/minute. Quantitation of the separated compounds was based on the integrated surface of the collected peaks.

Figure 8A:
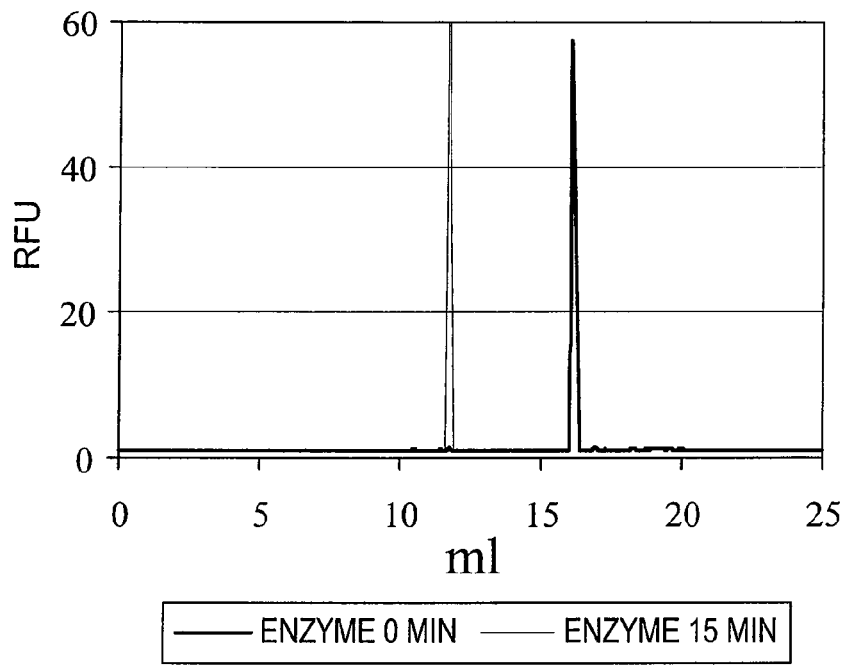
FIG. 8A shows a HPLC separation of products of carboxyfluorescein-$C_{10}H_{21}NO_2$—Cl hydrolysis by DhaA.WT and DhaA.H272F.
Figure 8B:
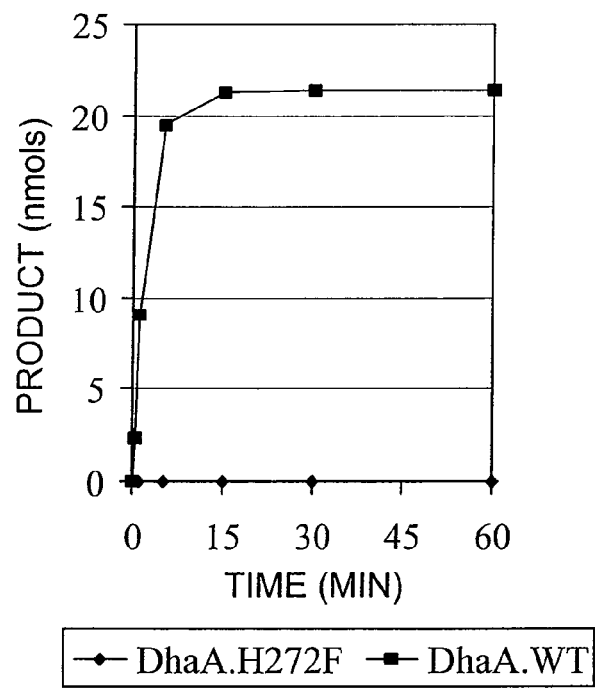
FIG. 8B shows a HPLC analysis of product (as a percent of substrate) generated by DhaA.WT and DhaA.H272F hydrolysis of carboxyfluorescein-$C_{10}H_{21}NO_2$—Cl over time.

FIG. 8A shows the complete separation of the substrate and the product of the reaction. FIG. 8B indicates that DhaA.WT very efficiently hydrolyzed carboxyfluorescein-$C_{10}H_{21}NO_2$—Cl. Similar results were obtained when carboxytetramethylrhodamine-$C_{10}H_{21}NO_2$—Cl or 5-carboxy-X-rhodamine-$C_{10}H_{21}NO_2$—Cl were used as substrates (data not shown). Taken together these data confirm the results of the pH-indicator dye-based assay showing complete inactivation of DhaA catalytic activity by the DhaA.H272F mutation.

C. Covalent Tethering of Functional Groups to DhaA Mutants In Vitro

Materials and Methods

MALDI analysis of proteins was performed at the University of Wisconsin Biotechnology Center using a matrix assisted laser desorption/ionization time-of-life (MALDI-TOF) mass spectrometer Bruker Biflex III (Bruker, USA.). To prepare samples, 100 μg of purified DhaA (WT or H272F mutant) or GST-DhaA (WT or H272F mutant) fusion protein (purified to about 90% homogeneity) in 200 μl of buffer (1 mM HEPES-$SO_4$ (pH 7.4), 20 mM $Na_2SO_4$, and 1 mM EDTA) were incubated with or without substrate (carboxyfluorescein-$C_{10}H_{21}NO_2$—Cl, at 1.0 mM, final concentration) for 15 minutes at room temperature. Then the reaction mixtures were dialyzed against 20 mM $CH_3COONH_4$ (pH 7.0) overnight at 4° C. and M/Z values of the proteins and protein-substrate complexes determined.

Oligonucleotides employed to prepare DhaA.D106 mutants include for DhaA.D106C:
5'-CTTGGGTTTGGAAGAGGTCGTCCTGGTCATCCAC TGCTGGGGC-3' (SEQ ID NO:13) and 5'-TGAGCCCCA GCAGTGGATGACCAGGACGACCTCTTCCAAACC-3' (SEQ ID NO:14);
for DhaA.D106Q:
5'-CTTGGGTTTGGAAGAGGTCGTCCTGGTCATCCAC CAGTGGGGC-3' (SEQ ID NO:34) and 5'-TGAGCCCCA CTGGTGGATGACCAGGACGACCTCTTCCAAACC-3' (SEQ ID NO:35);
for DhaA.D106E:
5'-CTTGGGTTTGGAAGAGGTCGTCCTGGTCATCCAC GAATGGGGC-3' (SEQ ID NO:52) and 5'-TGAGC CCCA TTCGTGGATGACCAGGACGACCTCTTCCAAACC-3' (SEQ ID NO:53); and
for DhaA.D106Y:
5'-CTTGGGTTTGGAAGAGGTCGTCCTGGTCATCCAC TACTGGGGC-3' (SEQ ID NO:54) and 5'-TGAGCCCCA GTAGTGGATGACCAGGACGACCTCTTCCAAACC-3' (SEQ ID NO:55). The annealed oligonucleotides contained a StyI site at the 5' end and the BlpI site at the 3' end. The annealed oligonucleotides were digested with StyI and BlpI and subcloned into DhaA.WT or DhaA.H272F at StyI and BlpI sites. All mutants were confirmed by DNA sequencing.

Results

To confirm that DhaA.H272 mutants were capable of binding Cl-alkanes with functional groups, these mutants or their GST-fusions, as well as the corresponding wild-type proteins or fusions, were contacted with carboxyfluorescein-$C_{10}H_{21}NO_2$—Cl, carboxytetramethylrhodamine-$C_{10}H_{21}NO_2$—Cl, 5-carboxy-X-rhodamine-$C_{10}H_{21}NO_2$—Cl, or biotin-$C_{10}H_{21}NO_2$—Cl for 15 minutes at room temperature. Then the proteins were resolved on SDS-PAGE. The gels containing proteins were incubated with carboxyfluorescein-$C_{10}H_{21}NO_2$—Cl, carboxytetramethylrhodamine-$C_{10}H_{21}NO_2$—Cl, or 5-carboxy-X-rhodamine-$C_{10}H_{21}NO_2$—Cl and were analyzed by fluoroimager (Hitachi, Japan) at an $E_{ex}/E_{em}$ appropriate for each fluorophore. Gels containing proteins incubated with biotin-$C_{10}H_{21}NO_2$—Cl were transferred to a nitrocellulose membrane and probed with HRP conjugated streptavidin.

Figure 9A:
FIG. 9 shows SDS-PAGE analysis of the binding of DhaA.WT (lanes 1, 3, and 5 in panel A and lanes 1-8 in panel B) and DhaA.H272F (lanes 2, 4, and 6 in panel A and lanes 9-14 in panel B), to carboxytetramethylrhodamine-$C_{10}H_{21}NO_2$—Cl (lanes 1 and 2 in panel A); carboxy-X-rhodamine-$C_{10}H_{21}NO_2$—Cl (lanes 3 and 4 in panel A); carboxyfluorescein-$C_{10}H_{21}NO_2$—Cl (lanes 5 and 6 in panel A); or biotin-$C_{10}H_{21}NO_2$—Cl (panel B). The concentration of biotin-$C_{10}H_{21}NO_2$—Cl in panel B as: 0 µM (lanes 1 and 8), 125 µM (lanes 2 and 9) 25 µM (lanes 3 and 10), 5 µM (lanes 4 and 11), 1 µM (lanes 5 and 12), 0.2 µM (lanes 6 and 13), and 0.04 µM (lanes 7 and 14).
Figure 9B:
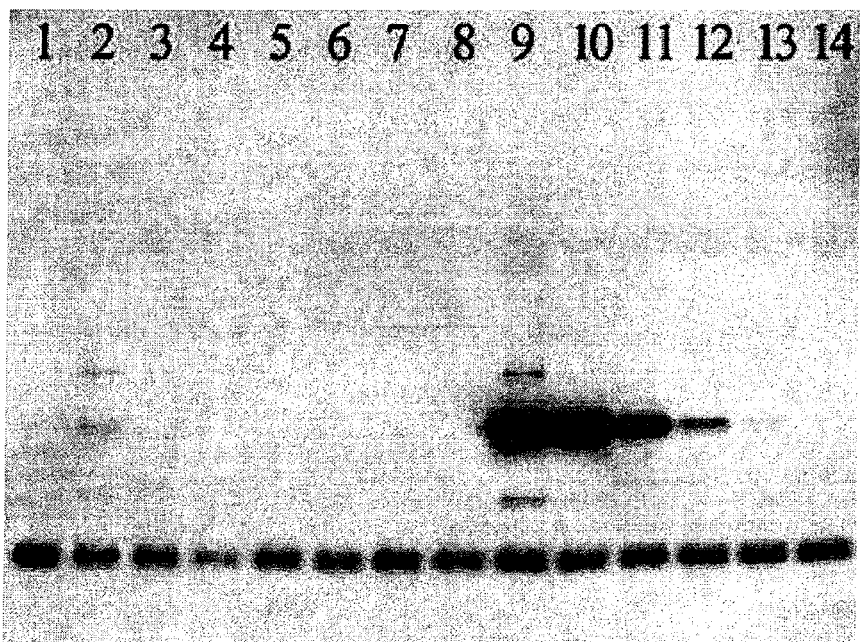

As shown in FIG. 9, carboxytetramethylrhodamine-$C_{10}H_{21}NO_2$—Cl (lanes 1 and 2 in panel A), carboxyfluorescein-$C_{10}H_{21}NO_2$—Cl (lanes 3 and 4 in panel A), and 5-carboxy-X-rhodamine-$C_{10}H_{21}NO_2$—Cl (lanes 5 and 6 in panel A) bound to DhaA.H272F (lanes 2, 4 and 6 in panel A) but not to DhaA.WT (lanes 1, 3 and 5 in panel A). Biotin-$C_{10}H_{21}NO_2$—Cl bound to DhaA.H272F (lanes 9-14 in panel B) but not to DhaA.WT (lanes 1-8 in panel B). Moreover, the binding of biotin-$C_{10}H_{21}NO_2$—Cl to DhaA.H272F (lanes 9-14 in panel B) was dose dependent and could be detected at 0.2 μM. Further, the bond between substrates and DhaA.H272F was very strong, since boiling with SDS did not break the bond.

Figure 10:
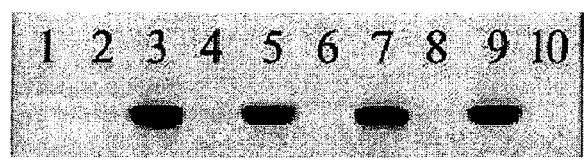
FIG. 10 illustrates that pretreatment of a mutant DhaA with a substrate, biotin-$C_{10}H_{21}NO_2$—Cl, blocks binding of another substrate. DhaA.WT-lanes 1 and 2; DhaA.H272 mutants: F, lanes 3 and 4; G, lanes 5 and 6; A, lanes 7 and 8; and Q, lanes 9 and 10. Samples 2, 4, 6, 8, and 10 were pretreated with biotin-$C_{10}H_{21}NO_2$—Cl.

All tested DhaA.H272 mutants, i.e. H272F/G/A/Q, bound to carboxytetramethylrhodamine-$C_{10}H_{21}NO_2$—Cl (FIG. 10). Further, the DhaA.H272 mutants bind the substrates in a highly specific manner, since pretreatment of the mutants with one of the substrates (biotin-$C_{10}H_{21}NO_2$—Cl) completely blocked the binding of another substrate (carboxytetramethylrhodamine-$C_{10}H_{21}NO_2$—Cl ) (FIG. 10).

Figure 11A:
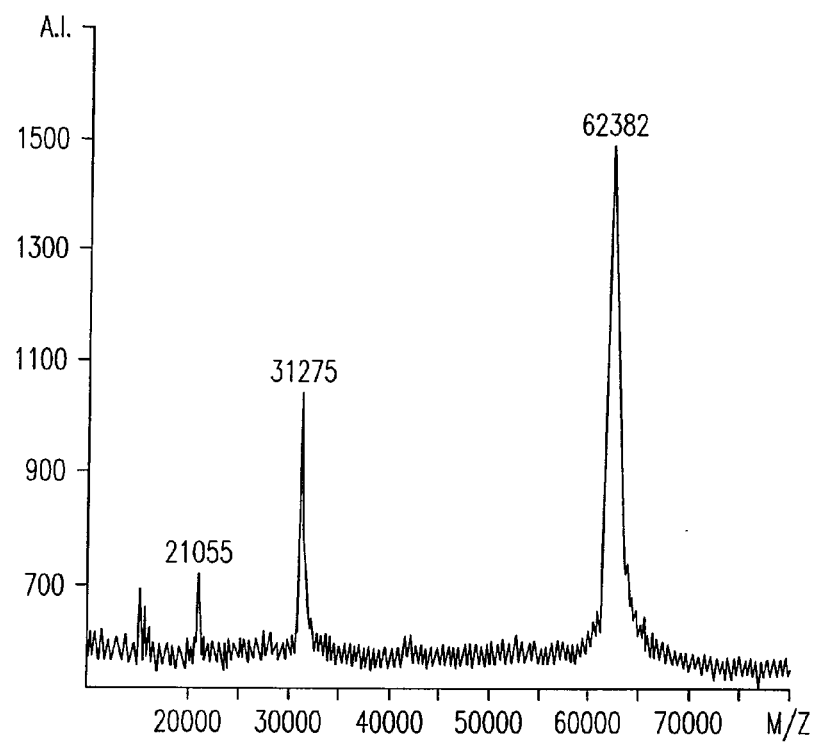
FIGS. 11A-B show MALDI-TOF analysis of enzyme substrate complexes. Mass spectra of DhaA.WT (panel A) or DhaA.H272F (panel B) GST fusions incubated with carboxyfluorescein-$C_{10}H_{21}NO_2$—Cl.
Figure 11B:
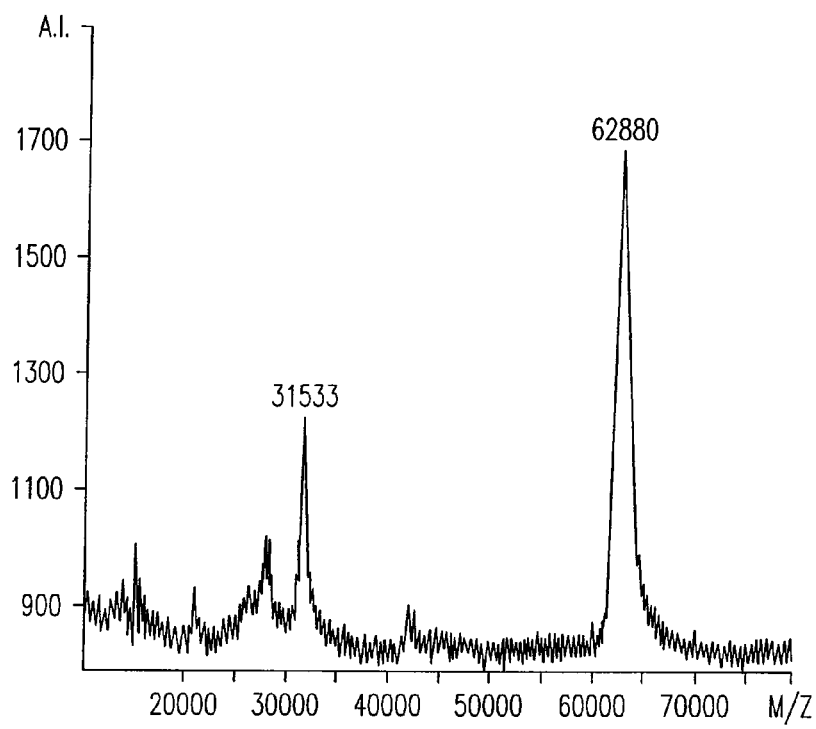

To determine the nature of the bond between Cl-alkanes and the DhaA.H272F mutant (or the GST-DhaA.H272F mutant fusion protein), these proteins were incubated with and without carboxyfluorescein-$C_{10}H_{21}NO_2$—Cl, and analyzed by MALDI. As shown in FIG. 11, the bond between mutant DhaA.H272F and carboxyfluorescein-$C_{10}H_{21}NO_2$—Cl is strong. Moreover, the analysis of the E*S complex indicated the covalent nature of the bond between the substrate (e.g., carboxyfluorescein-$C_{10}H_{21}NO_2$—Cl) and DhaA.H272F. The MALDI-TOF analysis also confirms that the substrate/protein adduct is formed in a 1:1 relationship.

DhaA mutants at another residue in the catalytic triad, residue 106, were prepared. The residue at position 106 in wild-type DhaA is D, one of the known nucleophilic amino acid residues. D at residue 106 in DhaA was substituted with nucleophilic amino acid residues other than D, e.g., C, Y and E, which may form a bond with a substrate which is more stable than the bond formed between wild-type DhaA and the substrate. In particular, cysteine is a known nucleophile in cysteine-based enzymes, and those enzymes are not known to activate water.

Figure 12:
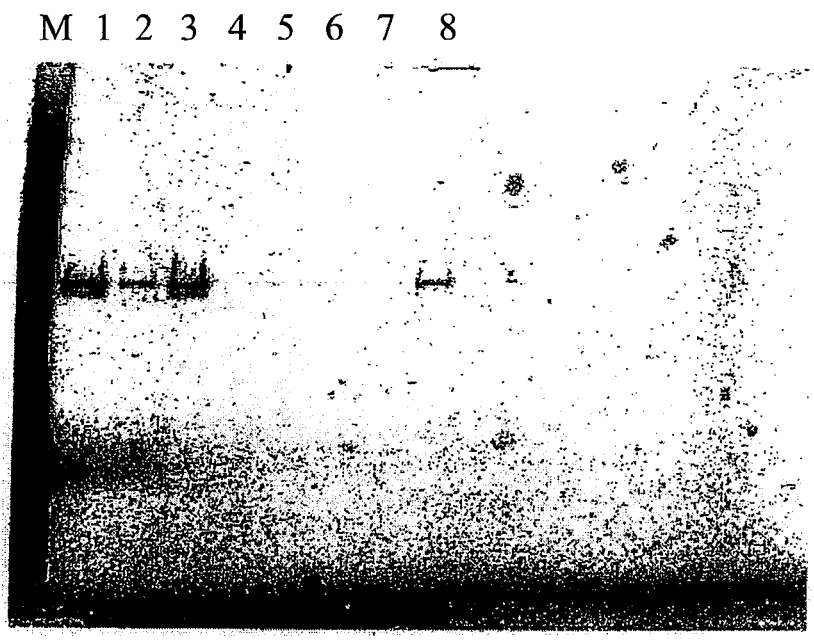
FIG. 12 illustrates SDS-PAGE analysis of the binding properties of DhaA mutants with substitutions at residue 106, and DhaA mutants with substitutions at residue 106 and residue 272, to carboxytetramethylrhodamine-$C_{10}H_{21}NO_2$—Cl. 2 µg of protein and 25 µM carboxytetramethylrhodamine-$C_{10}H_{21}NO_2$—Cl in 32 µl were incubated for one hour at room temperature. 10 µl of each reaction was loaded per lane. Lane 1-DhaA.D106C; lane 2-DhaA.D106C:H272F; lane 3-DhaA.D106E; lane 4-DhaA.D106E:H272F; lane 5-DhaA.D106Q; lane 6-DhaA.D106Q:H272F; lane 7-DhaA.WT; and lane 8-DhaA.H272F. The gel was imaged with a 570 nm filter.

A control mutant, DhaA.D106Q, single mutants DhaA.D106C, DhaA.D106Y, and DhaA.D106E, as well as double mutants DhaA.D106C:H272F, DhaA.D106E:H272F, DhaA.D106Q:H272F, and DhaA.D106Y:H272F were analyzed for binding to carboxytetramethylrhodamine-$C_{10}H_{21}NO_2$—Cl (FIG. 12). As shown in FIG. 12, carboxytetramethylrhodamine-$C_{10}H_{21}NO_2$—Cl bound to DhaA.D106C, DhaA.D106C:H272F, DhaA.D106E, and DhaA.H272F. Thus, the bond formed between carboxytetramethylrhodamine-$C_{10}H_{21}NO_2$—Cl and cysteine or glutamate at residue 106 in a mutant DhaA is stable relative to the bond formed between carboxytetramethylrhodamine-$C_{10}H_{21}NO_2$—Cl and DhaA.WT. Other substitutions at position 106 alone or in combination with substitutions at other residues in DhaA may yield similar results. Further, certain substitutions at position 106 alone or in combination with substitutions at other residues in DhaA may result in a mutant DhaA that forms a bond with only certain substrates.

EXAMPLE III

Tethering of Luciferase to a Solid Support Via a Mutant DhaA and a Substrate of the Invention Materials and Methods phRLuc-connector-DhaA.WT-Flag and phRLuc-connector-DhaA.H272F-Flag fusion cassettes were constructed by cloning the phRLuc coding region into the NheI/SalI sites of the pCIneo vector which contains a myristic acid attachment peptide coding sequence (MAS). Two primers (5'-GCT-TCACTTGTCGTCATCGTCCTTGTAGTCA-3'; SEQ ID NO:11) and (5'-GCTTCACTTGTCGTCATCGTCCTTG-TAGTCA-3'; SEQ ID NO:12) were designed to add NheI and SalI sites to the 5' and 3' coding regions, respectively, of phRLuc and to amplify a 900 bp fragment from a phRLuc template (pGL3 vector, Promega). Then, a myristic acid attachment peptide coding sequence was excised with NheI and SalI restriction enzymes and the amplified fragment containing phRLuc was inserted into the NheI/SalI restriction sites of pCIneo.DhaA.(WT or H272F)-Flag vector. The sequence of each construct was confirmed by DNA sequencing. Promega's TNT® T7Quick system was then used to generate fusion proteins in vitro.

Results

To demonstrate tethering of proteins to a solid support via DhaA.H272F-Cl-alkane bridge, vectors encoding a fusion protein of *Renilla* luciferase (hRLuc, N-terminus of the fusion), a protein connector (17 amino acids, see Table I), and DhaA (WT or H272F mutant) were prepared. The Flag epitope was then fused to the C-terminus of DhaA.

sciences). Collected fractions of R.Luc-connector-DhaA fusions were placed in SA-coated 96-well plate for 1 hour at room temperature, unbound proteins were washed out and luciferase activity was measured.

Figure 13:
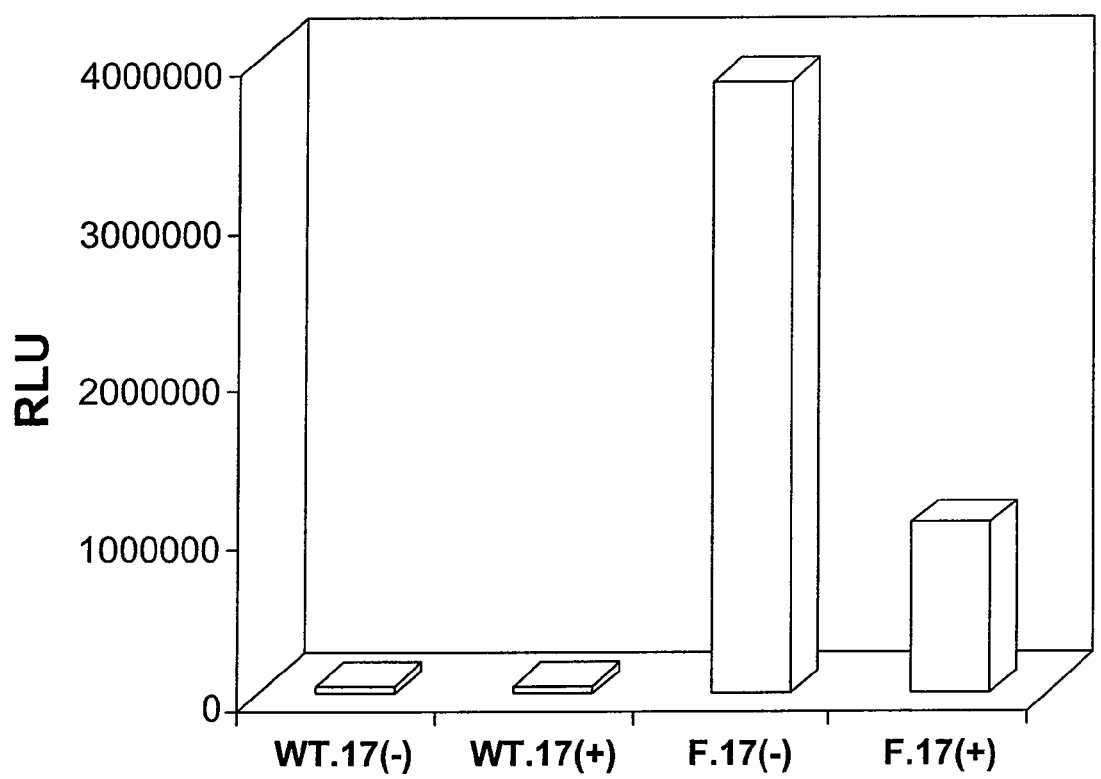
FIG. 13 depicts analysis of Renilla luciferase activity in samples having a fusion of luciferase and DhaA.H272 tethered to a solid support (a streptavidin coated plate). Capture of the fusion was accomplished using a substrate of DhaA (i.e., biotin-$C_{10}H_{21}NO_2$—Cl). No activity was found in fractions with a fusion of Renilla luciferase and DhaA.WT.

FIG. 13A shows *Renilla* luciferase activity captured on the plate. Analysis of these data indicated that only the fusion containing the mutant DhaA was captured. The efficiency of capturing was very high (more than 50% of *Renilla* luciferase activity added to the plate was captured). In contrast, the efficiency of capturing of fusions containing DhaA.WT as well as *Renilla* luciferase was negligibly small (<0.1%). Pretreatment of R.Luc-connector-DhaA.H272F with a non-biotinylated substrate (carboxytetramethylrhodamine-$C_{10}H_{21}NO_2$—Cl) decreased the efficiency of capturing by about 80%. Further, there was no effect of pretreatment with a nonbiotinylated substrate on the capturing of the R.Luc-connector-DhaA.WT or *Renilla* luciferase.

Taken together, these data demonstrate that active enzymes (e.g., *Renilla* luciferase) can be tethered to a solid support that forms part of a substrate of the invention (Cl-alkane-DhaA.H272F-bridge), and retain enzymatic activity.

EXAMPLE IV

Mutant DhaA and Substrate System In Vivo

A. Covalent Tethering of Functional Groups to DhaA Mutants In Vivo: in Prokaryotes and Eukaryotes Materials and Methods To study the binding of a substrate of the invention to a mutant hydrolase expressed in prokaryotes, *E. coli* cells BL21 (XDE3) pLys65 were transformed with pGEX-5X-3.DhaA.WT-Flag or pGEX-5X-3.DhaA.H272F-Flag, grown in liquid culture, and induced with IPTG. Either carboxytet-

TABLE I

| Fusion | Sequence | Peptide Connector |
|---|---|---|
| GST-DhaA | atcgaaggtcgtgggatccccaggaattcccgggtcgacgccgcc (SEQ ID NO: 26) | iegrgiprnsrvdaa (SEQ ID NO: 27) |
| GFP-DhaA | tccggatcaagcttgggcgacgaggtggacggcgggccctctagagccacc (SEQ ID NO: 28) | sgsslgdevdggpsrat (SEQ ID NO: 29) |
| DhaA-Rluc | accggttccggatcaagcttgcggtaccgcgggccctctagagcc (SEQ ID NO: 30) | tgsgsslryrgpsra (SEQ ID NO: 31) |
| Rluc-DhaA | tccggatcaagcttgcggtaccgcgggccctctagagccgtcgacgccgcc (SEQ ID NO: 32) | sgsslryrgpsravdaa (SEQ ID NO: 33) |
| DhaA-Flag | Accggt | Tg |

SDS-PAGE followed by Western blot analysis showed that the proteins had their predicted molecular weights and were recognized by anti-R.Luc and anti-Flag$^R$ M2 antibodies. In addition, all fusion proteins had *Renilla* luciferase activity (as determined by Promega's *Renilla* Luciferase Assay System in PBS pH 7.4 buffer).

Tethering of proteins to a solid support via a DhaA.H272F-Cl-alkane bridge was shown by using biotin-$C_{10}H_{21}N_1O_2$—Cl as a substrate and streptavidin (SA)-coated 96 well plates (Pierce, USA) as solid support. Translated proteins were contacted with biotin-$C_{10}H_{21}N_1O_2$—Cl substrate at 25 μM (final concentration), for 60 minutes at room temperature. Unbound biotin-$C_{10}H_{21}N_1O_2$—Cl was removed by gel-filtration on Sephadex G-25 prepackaged columns (Amersham Bioramethylrhodamine-$C_{10}H_{21}NO_2$—Cl or biotin-$C_{10}H_{21}N_1O_2$—Cl was added to the induced cells (final concentration, 25 μM). After 1 hour, cells were harvested, washed with cold PBS (pH 7.3), disrupted by sonication, and fractionated by centrifugation at 19,800×g for 1 hour. Soluble fractions were subjected to SDS-PAGE. Gels with proteins isolated from cells treated with carboxytetramethyl-rhodamine-$C_{10}H_{21}NO_2$—Cl were analyzed on a fluoroimager, while proteins from cells treated with biotin-$C_{10}H_{21}N_1O_2$—Cl were transferred to a nitrocellulose membrane and probed with HRP-conjugated streptavidin.

To study the binding of carboxytetramethylrhodamine-$C_{10}H_{21}NO_2$—Cl in mammalian cells, DhaA.WT-Flag and DhaA.H272F-Flag coding regions were excised from pGEX- 5X-3.DhaA.WT-Flag or pGEX-5X-3.DhaA.H272F-Flag, respectively, gel purified, and inserted into SalI/NotI restriction sites of pCIneo.CMV vector (Promega). The constructs were confirmed by DNA sequencing.

CHO-K1 cells were plated in 24 well plates (Labsystems) and transfected with a pCIneo-CMV.DhaA.WT-Flag or pCIneo-CMV.DhaA.H272F-Flag vector. Twenty-four hours later, media was replaced with fresh media containing 25 µM carboxytetramethylrhodamine-$C_{10}H_{21}NO_2$—Cl and the cells were placed into a $CO_2$ incubator for 60 minutes. Following this incubation, media was removed, cells were quickly washed with PBS (pH 7.4; four consecutive washes: 1.0 ml/cm$^2$; 5 seconds each) and the cells were solubilized in a sample buffer (1% SDS, 10% glycerol, and the like; 250 µl/well). Proteins (10 µl/lane) were resolved on SDS-PAGE (4-20% gradient gels) and the binding of the carboxytetramethylrhodamine-$C_{10}H_{21}NO_2$—Cl was detected by a fluoroimager (Hitachi, Japan) at $E_{ex}/E_{em}$ equal 540/575 nm.

Results

Figure 14A:
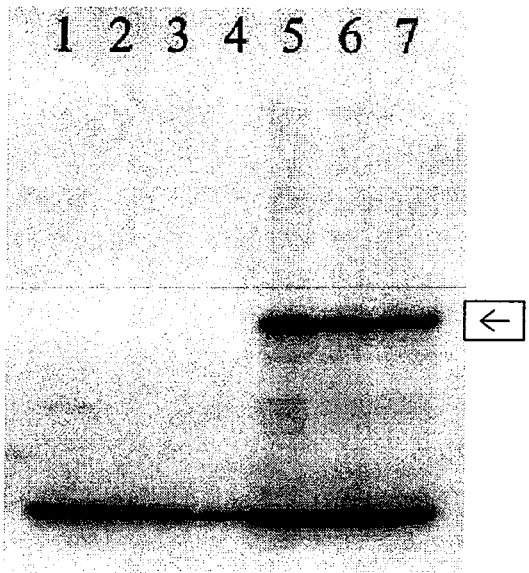
FIG. 14 shows SDS-PAGE analysis of two-fold serial dilutions of E. coli expressing either DhaA.WT (lanes 1-4 of each panel) or DhaA.H272F (lanes 5-7 of each panel) treated with biotin-$C_{10}H_{21}NO_2$—Cl (panel A) or carboxytetramethylrhodamine-$C_{10}H_{21}NO_2$—Cl (panel B) in vivo. Arrows mark proteins with $M_r$ corresponding to $M_r$ of DhaA.
Figure 15:
FIG. 15 shows the binding of carboxytetramethylrhodamine-$C_{10}H_{21}NO_2$—Cl to eukaryotic cell proteins in vivo. Two-fold serial dilutions of proteins from CHO-K1 cells expressing either DhaA.WT-Flag (lanes 1-4) or DhaA.H272F-Flag (lanes 5-8) were treated with carboxytetramethylrhodamine-$C_{10}H_{21}NO_2$—Cl. Arrows mark proteins with Mr corresponding to Mr of DhaA-Flag.

FIGS. 14A and B show the binding of biotin-$C_{10}H_{21}NO_2$—Cl (A) and carboxytetramethylrhodamine-$C_{10}H_{21}NO_2$—Cl (B) to *E. coli* proteins in vivo. The low molecular band on FIG. 14A is an *E. coli* protein recognizable by HRP-SA, while the fluorescence detected in the bottom part of Panel B was fluorescence of free carboxytetramethylrhodamine-$C_{10}H_{21}NO_2$—Cl. FIG. 15 shows the binding of carboxytetramethylrhodamine-$C_{10}H_{21}NO_2$—Cl to eukaryotic cell proteins in vivo.

Figure 14B:

Analysis of FIG. 14 and FIG. 15 showed that the DhaA.H272F-Flag mutant but not DhaA.WT-Flag binds carboxytetramethylrhodamine-$C_{10}H_{21}NO_2$—Cl or biotin-$C_{10}H_{21}N_1O_2$—Cl in vivo. Moreover, the bond between DhaA.H272F-Flag and the substrate was very strong (probably covalent), since boiling with SDS followed by SDS-PAGE did not disrupt the bond between the mutant enzyme and the substrate.

B. Permeability of Cell Membrane to Substrates of the Invention

Materials and Methods

CHO-K1 Cells (ATCC-CCL61) were cultured in a 1:1 mixture of Ham's F12 nutrients and Dulbecco's modified minimal essential medium supplemented with 10% fetal bovine serum (FBS), 100 U/ml penicillin, and 100 mg/ml streptomycin, in an atmosphere of 95% air and 5% $CO_2$ at 37° C.

To study uptake of different substrates, cells were plated in LT-II chambers (Nunc) or 96 well plates (Labsystems) at a density of 30,000 cells/cm$^2$. The following day, media was replaced with media containing different concentrations of the substrates and cells were placed back in a $CO_2$ incubator for 2, 5 or 15 minutes. At the end of the incubation, media containing substrate was removed and cells were quickly washed with PBS (pH 7.4; four consecutive washes: 1.0 ml/cm$^2$; 5 seconds each). Fresh media was then added to cells, and the cells were returned to the $CO_2$ incubator at 37° C. The level of fluorescence in cells in 96 well plates was measured on fluorescent plate reader CytoFluor II (Beckman) at $E_{ex}/E_{em}$ equal 480/520 nm and 540/575 nm for carboxyfluorescein- and carboxytetramethylrhodamine-modified substrates, respectively. Fluorescent images of the cells were taken on inverted epifluorescent microscope Axiovert-100 (Carl Zeiss) with filter sets appropriate for detection of FITC and carboxytetramethylrhodamine.

Results

As shown in FIG. 16, CHO-K1 cells treated with carboxytetramethylrhodamine-$C_{10}H_{21}NO_2$—Cl (25 nM, 5 minutes at 37° C.) could be quickly and efficiently loaded with carboxytetramethylrhodamine-$C_{10}H_{21}NO_2$—Cl. Image analysis indicated that the fluorescent dye crossed the cell membrane. FIG. 16 also shows that carboxytetramethylrhodamine-$C_{10}H_{21}NO_2$—Cl could be efficiently washed out of the cells. Taken together these data indicate that the plasma membrane of CHO-K1 cells is permeable to carboxytetramethylrhodamine-$C_{10}H_{21}NO_2$—Cl.

In contrast, carboxyfluorescein-$C_{10}H_{21}NO_2$—Cl did not cross the plasma membrane of CHO-K1 cells, even when cells were pretreated with carboxyfluorescein-$C_{10}H_{21}NO_2$—Cl at high concentrations (i.e., 100 µM) and for much longer periods of time (60 minutes) (data not shown). Thus, the different permeabilities of the cell plasma membrane for various substrates of the invention, e.g., carboxytetramethylrhodamine-$C_{10}H_{21}NO_2$—Cl and carboxyfluorescein-$C_{10}H_{21}NO_2$—Cl, provides a unique opportunity to label proteins expressed on the cell surface and proteins expressed inside the cell with different fluorophores, thereby allowing biplexing.

EXAMPLE V

DhaA-based Tethering for Cell Imaging In Vivo

A. Colocalization of GFP and Carboxytetramethylrhodamine-$C_{10}H_{21}NO_2$—Cl in Living Mammalian Cells Materials and Methods A GFP-connector-DhaA fusion cassette was constructed by replacing the *Renilla* luciferase coding region in Packard's vector coding GFP-DEVD-Rluc(h) (Packard #6310066) with DhaA.WT-Flag or DhaA.H272F-Flag coding regions. Two primers (5'-GGAAT GGGCCCTCTAGAGCGACGATGTCA-3'; SEQ ID NO:15, and 5'-CAGTCAGTCACGATGGATCCGCTC AA-3'; SEQ ID NO:16) were designed to add ApaI and BamHI sites (underlined) to the 5' and 3' coding regions of DhaA, respectively, and to amplify a 980 bp fragment from a pGEX-5X-3.DhaA.WT-Flag or pGEX-5X-3.DhaA.H272F-Flag template. The R.Luc coding region was excised with ApaI and BamHI restriction enzymes. Then the 980 bp fragment containing DhaA was inserted into the ApaI/BamHI site of the GFP-DEVD-Rluc(h) coding vector. The sequence of the gene fusion constructs was confirmed by DNA sequencing.

Cells transiently expressing GFP-connector-DhaA.WT-Flag or GFP-connector-DhaA.H272F-Flag fusion proteins were plated in LT-II chambers (Nunc) at a density of 30,000 cells/cm$^2$. The next day, media was replaced with fresh media containing 25 µM of carboxytetramethylrhodamine-$C_{10}H_{21}NO_2$—Cl and the cells were placed back into in a $CO_2$ incubator for 60 minutes. At the end of the incubation, media containing substrates was removed, cells were quickly washed with PBS (pH 7.4; four consecutive washes: 1.0 ml/cm$^2$; 5 seconds each) and new media was added to the cells. The cells were placed back into in a $CO_2$ incubator and after 60 minutes the cells were quickly washed with PBS (pH 7.4; four consecutive washes: 1.0 ml/cm$^2$; 5 seconds each). Fluorescent images of the cells were taken on inverted epifluorescent microscope Axiovert-100 (Carl Zeiss) with filter sets appropriate for detection of GFP and carboxytetramethylrhodamine.

Results

As shown by the images in FIG. 17, cells transfected with either GFP-connector-DhaA.WT-Flag or GFP-connector-DhaA.H272F-Flag showed robust expression of the protein(s) with light emitting characteristics of GFP. Analysis of the images of the same cells taken with a carboxytetramethylrhodamine-filter set showed that cells expressing GFPconnector-DhaA.WT-Flag were dark and could not be distinguished from cells that do not express this fusion protein. In contrast, cells expressing GFP-connector-DhaA.H272F-Flag were very bright and unmistakably recognizable.

Figure 18:
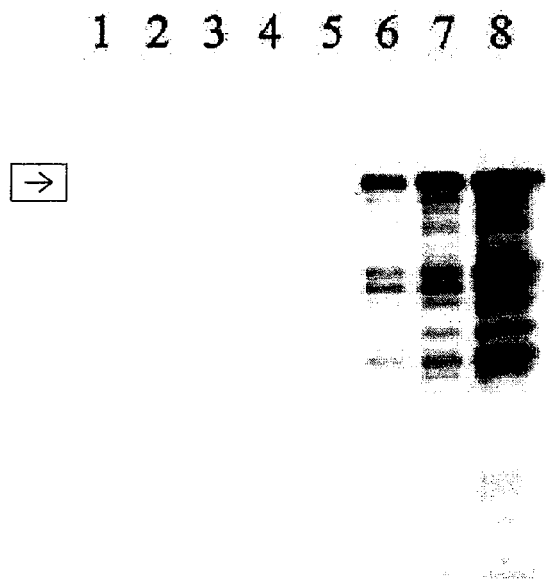
FIG. 18 shows Western blot analysis of proteins from cells transfected with GFP-connector-DhaA.WT-Flag (lanes 1-4) or GFP-connector-DhaA.H272F-Flag (lanes 5-8). CHO-K1 cells were transfected with either GFP-connector-DhaA.WT-Flag or GFP-connector-DhaA.H272F-Flag and then treated with carboxytetramethylrhodamine-$C_{10}H_{21}NO_2$—Cl (25

Western blot analysis of proteins isolated from CHO-K1 cells transfected with GFP-connector-DhaA.WT-Flag or GFP-connector-DhaA.H272F-Flag vectors showed that these cells expressed proteins that were recognized by an anti-Flag antibody and had the predicted molecular weight for the fusion proteins (data not shown). A fluoroscan of the SDS-PAGE gel with these proteins showed strong/covalent binding of carboxytetramethylrhodamine to GFP-connector-DhaA.H272F-Flag and no binding to GFP-connector-DhaA.WT-Flag (FIG. 18).

B. Fusion Partners of DhaA in DhaA.WT-Flag and DhaA.H272F-Flag are Functional

To determine whether fusion of two proteins leads to the loss of the activity of one or both proteins, several DhaA-based fusion proteins (see Table II) with DhaA at the C- or N-terminus of the fusion and a connector sequence, e.g., one having 13 to 17 amino acids, between the two proteins, were prepared. The data showed that the functional activity of both proteins in the fusion was preserved.

TABLE II

| N-Terminal protein | Connector | C-terminal protein | Function of protein #1 | Function of protein #2 |
|---|---|---|---|---|
| GST | + | DhaA.H272F | Binding to GSS column | binding |
| GFP | + | DhaA.H272F | Green fluorescence | binding |
| R.Luc | + | DhaA.H272F | hydrolysis of coelenterazine | binding |
| DhaA.H272F | + | R.Luc | Binding | hydrolysis of coelenterazine |
| DhaA.H272F | + | Flag | binding | Recognized by antibody |

C. Toxicity of Cl-Alkanes

Materials and Methods

To study the toxicity of Cl-alkanes, CHO-K1 cells were plated in 96 well plates to a density of 5,000 cells per well. The next day, media was replaced with fresh media containing 0-100 µM concentrations of Cl-alkanes and the cells were placed back into a $CO_2$ incubator for different periods of time. Viability of the cells was measured with CellTiter-Glo™ Luminescence Cell Viability Assay (Promega) according to the manufacturer's protocol. Generally, 100 µl of CellTiter-Glo™ reagent was added directly to the cells and the luminescence was recorded at 10 minutes using a DYNEX MLX microtiter plate luminometer. In some experiments, in order to prevent fluorescence/luminescence interference, the media containing fluorescent Cl-alkanes was removed and the cells were quickly washed with PBS (pH 7.4; four consecutive washes: 1.0 ml/cm$^2$; 5 seconds each) before addition of CellTiter-Glo™ reagent. Control experiments indicated that this procedure had no effect on the sensitivity or accuracy of the CellTiter-Glo™ assay.

Results

As shown in FIG. 19, carboxytetramethylrhodamine-$C_{10}H_{21}NO_2$—Cl showed no toxicity on CHO-K1 cells even after a 4 hour treatment at a 100 µM concentration the (the highest concentration tested). After a 24 hour treatment, no toxicity was detected at concentrations of 6.25 µM (the "maximum non-toxic concentration"). At concentrations>6.25 µM, the relative luminescence in CHO-K1 cells was reduced in a dose-dependent manner with an $IC_{50}$ of about 100 µM. No toxicity of biotin-$C_{10}H_{21}N_1O_2$—Cl was observed even after 24 hours of treatment at 100 µM. In contrast, carboxy-X-rhodamine-$C_{10}H_{21}NO_2$—Cl had a pronounced toxic effect as a reduction of the RLU in CHO-K1 cells could be detected after a 1 hour treatment. The $IC_{50}$ value of this effect was about 75 µM with no apparent ATP reduction at a 25 µM concentration. The $IC_{50}$ value of 5-carboxy-X-rhodamine-$C_{10}H_{21}NO_2$—Cl toxicity and the "maximum non-toxic concentration" of 5-carboxy-X-rhodamine-$C_{10}H_{21}NO_2$—Cl decreased in a time-dependent manner reaching 12.5 µM and 6.25 µM, respectively.

D. Detection of DhaA.D106C in CHO cells contacted with Carboxytetramethylrhodamine- or DiAc-Carboxyfluorescein-Containing Substrates and a Fixative CHO cells (ATCC, passage 4) were seeded into 8-well chamber slides (German coverglass system) at low density in DMEM:F12 media (Gibco) containing 10% FBS and 1 mM glutamine (growth media) without antibiotics. Two days later, cells were inspected using an inverted phase microscope. Two visual criteria were confirmed before applying the transfection reagents: 1) the level of cellular confluence per chamber was approximately 60-80%, and 2)>90% of the cells were adherent and showed a flattened morphology. The media was replaced with 150 µl of fresh pre-warmed growth media and cells were incubated for approximately 1 hour.

Cells were transfected using the TransIt TKO system (Miris). The TKO lipid was diluted by adding 7 µl of lipid per 100 µl of serum-free DMEM:F12 media, and then 1.2 µg of transfection-grade DhaA.D106C DNA was added per 100 µl of lipid containing media. The mixture was incubated at room temperature for 15 minutes, and then 25 µl aliquots were transferred into individual culture chambers (0.3 µg DNA). Cells were returned to the incubator for 5-6 hours, washed two times with growth media, 300 µl of fresh growth media was added, and then cells were incubated for an additional 24 hours.

Transfected or non-transfected control cells were incubated with 12.5 µM carboxytetramethylrhodamine-$C_{10}H_{21}NO_2$—Cl or 12.5 µM DiAc-carboxyfluorescein-$C_{10}H_{21}NO_2$—Cl in 10% FBS/DMEM for 30 minutes at 37° C. and 5% $CO_2$. Cells were washed with warm growth media three times, 300 µl fresh growth media was added, and then cells were incubated for 1 hour.

Growth media was replaced with warm PBS and live cells were visualized using a Zeiss Axiovert 100 inverted microscope equipped with a rhodamine filter set (Exciter filter=540, Emission filter=560LP) and a fluorescein filter set (Exciter filter=490, Emission filter=520), and a Spot CCD camera. Images were captured with exposure times of 0.15-0.60 seconds at gain settings of 4 or 16.

Discreet and specifically labeled transfected cells were evident in both carboxytetramethylrhodamine-$C_{10}H_{21}NO_2$—Cl and DiAc-carboxyfluorescein-$C_{10}H_{21}NO_2$—Cl labeled cells. The majority of cells were non-transfected cells and they did not retain the label.

The PBS was removed and cells were fixed with 3.7% paraformaldehyde/0.1% Triton in PBS for 15 minutes. The fixative was removed, PBS was added, and a second set of images was captured for both carboxytetramethylrhodamine-$C_{10}H_{21}NO_2$—Cl and DiAc-carboxyfluorescein-$C_{10}H_{21}NO_2$—Cl labeled cells.

The PBS was replaced with 50% methanol in PBS and cells were incubated for 15 minutes, followed by a 15 minute incubation in 95% methanol. A third set of images was captured and then an equal volume mixture of methanol and acetone was applied to the cells and incubated for 15 minutes. The media was replaced with PBS and a fourth set of images was collected.

Results suggested that the binding of the substrates to the DhaA.D106C mutant was stable following fixation with paraformaldehyde and subsequent processing of fixed cell samples in methanol and acetone. Furthermore, the brightness of the carboxytetramethylrhodamine or carboxyfluorescein fluorescence was unchanged under these conditions.

EXAMPLE VI

Mutant Beta-Lactamase (BlaZ)-based Tethering

The serine-β-lactamases, enzymes that confer bacterial resistance to β-lactam antibiotic, likely use the hydroxyl group of a serine residue (Ser70 in the class A consensus numbering scheme of Ambler et al. (1991)) to degrade a wide range of β-lactam compounds. The reaction begins with the formation of a precovalent encounter complex (FIG. 20A), and moves through a high-energy acylation tetrahedral intermediate (FIG. 20B) to form a transiently stable acyl-enzyme intermediate, forming an ester through the catalytic residue Ser70 (FIG. 20C). Subsequently, the acyl-enzyme is attacked by hydrolytic water (FIG. 20D) to form a high-energy deacylation intermediate (FIG. 20E) (Minasov et al., 2002), which collapses to form the hydrolyzed product (FIG. 20F). The product is then expelled, regenerating free enzyme. As in serine proteases, this mechanism requires a catalytic base to activate the serine nucleophile to attack the amide bond of the substrate and, following formation of the acyl-enzyme intermediate, to activate the hydrolytic water for attack on the ester center of the adduct.

A. Mutant β-Lactamase and Fusions Thereof
Materials and Methods

The plasmid pTS32 harboring *Staphylococcus aureus* PC1 blaZ gene (Zawadzke et al., 1995) was kindly provided by Dr. O. Herzberg (University of Maryland Biotechnology Institute). The blaZ gene has the following sequence: AGCTTAC-TAT GCCATTATTA ATAACTTAGC CATTTCAACA CCT-TCTTTCA AATATTTATAATAAACTATT GACACCGATA TTACAATTGT AATATTATTG ATTTATAAAA ATTA-CAACTGTAATATCGGA GGGTTTATTT TGAAAAAGTT AATATTTTA ATTGTAATTG CTTTAGTTTTAAGTG-CATGT AATTCAAACA GTTCACATGC CAAAGAGTTA AATGATTTAG AAAAAAAATATAATGCTCAT ATTGGT-GTTT ATGCTTTAGA TACTAAAAGT GGTAAGGAAG TAAAATTTAATTCAGATAAG AGATTTGCCT ATGCT-TCAAC TTCAAAAGCG ATAAATAGTG CTATTTTGT-TAGAACAAGTA CCTTATAATA AGTTAAATAA AAAAGTACAT ATTAACAAAG ATGATATAGTTGCT-TATTCT CCTATTTTAG AAAAATATGT AGGAAAAGAT ATCACTTTAA AAGCACTTATTGAGGCTTCA ATGA-CATATA GTGATAATAC AGCAAACAAT AAAATTATAA AAGAAATCGGTGGAATCAAA AAAGTTAAAC AACGTCTAAA AGAACTAGGA GATAAAGTAA CAAATCCAGTTAGATATGAG ATAGAATTAA ATTAC-TATTC ACCAAAGAGC AAAAAAGATA CTTCAACAC-CTGCTGCCTTC GGTAAGACCC TTAATAAACT TATCGCCAAT GGAAAATTAA GCAAAGAAAA-CAAAAAATTC TTACTTGATT TAATGTTAAA TAATAAAAGC GGAGATACTT TAATTAAAGACGGT-GTTCCA AAAGCTATA AGGTTGCTGA TAAAAGTGGT CAAGCAATAA CATATGCTTCTA-GAAATGAT GTTGCTTTTG TTTATCCTAA GGGC-CAATCT GAACCTATTG TTTTAGTCATTTTTACGAAT AAAGACAATA AAAGTGATAA GCCAAATGAT AAGT-TGATAA GTGAAACCGCCAAGAGTGTA ATGAAG-GAAT TTTAATATTC TAAATGCATA ATAAATACTG ATAACATCTTATATTTTGTA TTATATTTTG TAT-TATCGTT GAC (SEQ ID NO:36).

GST-blaZ (WT and E166D, N170Q, or E166D:N170Q mutants) fusion cassettes were constructed by introducing point mutations into the blaZ gene and cloning the blaZ coding regions into SalI/AgeI sites of pGEX5x3 vector. The internal mutagenic primers were as follows: E166D (5'-CCAGTTAGATATGACATAGAATTAAAT-TACTATTCACC-3', SEQ ID NO:56; 5'-GGTGAATAG-TAATTTAATTCTATGTCATATCTAACTGG-3', SEQ ID NO:57); N170Q (5'-CCAGTTAGATATGAGATAGAATTA-CAGTACTATTCACC-3', SEQ ID NO:58; and 5'-GGT-GAATAGTACTGTAATTCTATCTCATATCTAACTGG-3', SEQ ID NO:59); and E166D:N170Q (5'CCAGTTAGATAT-GACATAGAATTACAGTACTATTCACC-3'; SEQ ID NO:60 and 5'-GGTGAATAGTACTGTAATTCTATGT-CATATCTAACTGG-3; SEQ ID NO:61). Two external primers (5'-CAACAGGTCGACGCCGCCATGAAAGAGT-TAAATGATTTAG-3', SEQ ID NO:62; and 5'-GTAGTCACCGGTAAATTCCTTCATTA-CACTCTTGGC-3', SEQ ID NO:63) were designed to add N-terminal SalI site and a Kozak sequence to the 5' coding region, add an AgeI site to the 3' coding regions of blaZ, and to amplify a 806 bp fragment from a blaZ.WT template. The resulting fragment was inserted into the SalI/AgeI site of the vector pGEX-5X-3 containing a glutathione S-transferase (GST) gene, a sequence coding a Factor Xa cleavage site, and multiple cloning sites (MCS) followed by a sequence coding for Flag and stop codons. These gene fusion constructs were confirmed by DNA sequencing.

The GST-BlaZ (WT or mutants) fusion proteins were overexpressed in competent *E. coli* BL21 (λDE3) cells and purified essentially as described for DhaA and GST-DhaA fusion proteins (except the potassium phosphate buffer (0.1 M, pH 6.8) was used instead of Buffer A). Homogeneity of the proteins was verified by SDS-PAGE.

The chromogenic substrate 6-β-[(Furylacryloyl)amido]penicillanic acid triethylamine salt (FAP) was purchased from Calbiochem (La Jolla, Calif.). Hydrolysis of FAP was monitored by loss of absorbance at 344 nm (deltaE=1330 $M^{-1}$ $cm^{-1}$) on a Beckman Du640 spectrophotometer (Beckman Coulter, Fullerton, Calif.). All assays were performed at 25° C. in 0.1 M potassium phosphate buffer at pH 6.8.

In CCF2, the cephalosporin core links a 7-hydroxycoumarin to a fluorescein. In the intact molecule, excitation of the coumarin ($E_{ex}$–409 nm) results in FRET to the fluorescein, which emits green light ($E_{em}$–520 nm). Cleavage of CCF2 bp β-lactamase results in spatial separation of the two dyes, disrupting FRET such that excitation of coumarin now gives rise to blue fluorescence ($E_{ex}$–447 nm). CCF2 was purchased from Aurora Biosciences Corporation (San Diego, Calif.). Reduction of the FRET signal and an increase in blue fluorescence were measured on Fluorescence Multi-well Plate Reader CytoFluorII (PerSeptive Biosystems, Framingham, Mass., USA).

Results

All β-lactamases, including β-lactamase from *Staphylococcus aureus* PC1, hydrolyze β-lactams of different chemical structure. The efficiency of hydrolysis depends on the type of the enzyme and chemical structure of the substrate. Penicillin is considered to be a preferred substrate for β-lactamase from *Staphylococcus aureus* PC1.

The effect of point mutation(s) on the ability of β-lactamase to hydrolyze penicillins was studied as described in Zawadzke et al. (1995). As shown in FIG. 20, a GST-β- lactamase PC1 fusion protein efficiently hydrolyzed FAP. Hydrolysis of FAP by BlaZ.E166D, BlaZ.N170Q or BlaZ.E166D:N170Q BlaZ mutants could not be detected even after 60 minutes of co-incubation. Therefore, these mutations lead to significant inactivation of BlaZ.

To show that BlaZ.E166D, BlaZ.N170Q, or BlaZ.E166D: N170Q mutants bind β-lactams, and therefore different functional groups could be tethered to these proteins via β-lactams, GST fusions of these mutants were incubated with BOCELLIN™ FL, a fluorescent penicillin (Molecular Probes Inc., Eugene, Oreg.). Proteins were resolved on SDS-PAGE and analyzed on fluoroimager (Hitachi, Japan) at an $E_{ex}/E_{em}$ appropriate for the particular fluorophore. The data in FIG. 22 show that all BlaZ mutants bind bocellin. Moreover, the bond between BlaZ mutants and fluorescent substrates was very strong, and probably covalent, since boiling with SDS followed by SDS-PAGE did not disrupt the bond. Also, the binding efficiency of double mutant BlaZ.E166D:N170Q (judged by the strength of the fluorescent signal of protein-bound fluorophore) was much higher than binding efficiency of either of the single mutants, and the binding efficiency of BlaZ.N170Q was higher than binding efficiency of BlaZ.E166D. These data, in combination with current understanding of the role of the individual amino acids in hydrolysis of beta-lactams, show that additional mutations (e.g., a mutation of an auxiliary amino acid) can improve efficiency of tethering of functional groups to a mutated protein.

The effect of point mutation(s) on the ability of β-lactamase to hydrolyze cephalosporins was also studied using CCF2, a FRET-based substrate described by Zlokarnik et al. (1998). As shown in FIG. 23, the GST-β-lactamase PC1 fusion protein efficiently hydrolyzed CCF2 (lane 2). Single point mutations (i.e., E166D or N170Q) reduced the ability of the fusion proteins to hydrolyze CCF2 (lanes 3 and 4). The replacement of two amino acids (BlaZ.E166D:N170Q mutants, lane 5) had an even more pronounced effect on the CCF2 hydrolysis. However, all BlaZ mutants were capable of hydrolyzing CCF2.

Thus, an amino acid substitution at position 166 or 170, e.g., Glu166Asp or Asn170Gly enables the mutant beta-lactamase to trap a substrate and therefore tether the functional group of the substrate to the mutant beta-lactamase via a stable, e.g., covalent, bond. Moreover, mutation of an amino acid that has an auxiliary effect on $H_2O$ activation increased the efficiency of tethering.

EXAMPLE VII

Targeting of DhaA.H272F to the Nucleus and Cytosol of Living Cells

Materials and Methods

A GFP-connector-DhaA.H272F-NLS3 fusion cassette was constructed by inserting a sequence encoding NLS3 (three tandem repeats of the Nuclear Localization Sequence (NLS) from simian virus large T-antigen) into the AgeI/BamHI sites of a pCIneo.GFP-connector-DhaA.H272F-Flag vector. Two complementary oligonucleotides (5'-CCGGT-GATCCAAAAAAGAAGAGAAAGGTAGATC-CAAAAAAGAAGAGAAAGGTAGA TCCAAAAAA-GAAGAGAAAGGTATGAG-3', sense, SEQ ID NO:37, and 5'-GATCCTCATACCTTTCTCTTCTTTTTTG-GATCTACCTTTCTCTTCTTTTTTGGATCTACC TTTCTCTTCTTTTTTGGATCA-3', antisense, SEQ ID NO:38) coding for the NLS3 peptide, were annealed. The annealed DNA had an AgeI site at 5' end and a BamHI site at the 3' end. The annealed DNA was subcloned into the GFP-connector-DhaA.H272F-Flag construct at the AgeI/BamHI sites. The sequence of the gene fusion construct was confirmed by DNA sequencing.

A DhaA.H272F-β-arrestin2 fusion cassette was constructed by replacing the pGFP$^2$ coding region in Packard's vector encoding GFP$^2$-β-arrestin2 (Packard #6310176-1F1) with the DhaA.H272F-Flag coding region. Two primers (5'-ATTATGCTGAGTGATATCCC-3'; SEQ ID NO:39, and 5'-CTCGGTACCAAGCTCCTTGTAGTCA-3; SEQ ID NO:40) were designed to add a KpnI site to the 3' coding region of DhaA, and to amplify a 930 bp fragment from a pGEX5X-3.DhaA.H272F-Flag template. The pGFP$^2$ coding region was excised with NheI and KpnI restriction enzymes, then the 930 bp fragment containing encoding DhaA.H272F was inserted into the NheI and KpnI sites of the GFP$^2$-β-arrestin2 coding vector. The sequence of the fusion construct was confirmed by DNA sequencing.

CHO-K1 or 3T3 cells transiently expressing GFP-connector-DhaA.H272F-NLS3, GFP$^2$-β-arrestin2 or DhaA.H272F-β-arrestin2 fusion proteins were plated in LT-II chambers (Nunc) at a density of 30,000 cells/cm$^2$. The next day, media was replaced with fresh media containing 25 µM of carboxytetramethylrhodamine-$C_{10}H_{21}NO_2$—Cl and the cells were placed back into a $CO_2$ incubator for 60 minutes. At the end of the incubation, substrate media was removed, cells were quickly washed with PBS (pH 7.4; four consecutive washes: 1.0 ml/cm$^2$; 5 seconds each), and new media was added to the cells. The cells were placed back into a $CO_2$ incubator and after 60 minutes the cells were quickly washed with PBS (pH 7.4; 1.0 ml/cm$^2$). Fluorescent images of the cells were taken on confocal microscope Pascal-5 (Carl Zeiss) with filter sets appropriate for the detection of GFP and carboxytetramethylrhodamine.

Results

As shown by the images in FIG. 24, GFP and carboxytetramethylrhodamine were co-localized in the cell nucleus of cells expression GFP-connector-DhaA.H272F-NLS3 and contacted with carboxytetramethylrhodamine-$C_{10}H_{21}NO_2$—Cl.

As shown by the images in FIG. 25, GFP-β-arrestin2 expressing cells have a typical β-arrestin2 cytosolic localization. A fluoroscan of the SDS-PAGE gel of DhaA.H272F-β-arrestin2 showed strong binding of a carboxytetramethylrhodamine containing DhaA substrate to cells expressing DhaA.H272F-β-arrestin2.

EXAMPLE VIII

Site-Directed Mutagenesis of DhaA Catalytic Residue 130

Haloalkane dehalogenases use a three-step mechanism for cleavage of the carbon-halogen bond (FIGS. 1A-B). This reaction is catalyzed by a triad of amino acid residues composed of a nucleophile, base and acid which, for the haloalkane dehalogenase from *Xanthobacter autotrophicus* (DhlA), are residues Asp124, His289 and Asp260, respectively (Franken et al., 1991), and in the *Sphingomonas* and *Rhodococcus* dehalogenase enzymes, LinB and DhaA, respectively, the analogous triad of residues have been identified as Asp108, His272 and Glu132 (Hynkova et al., 1999) and Asp106, His272 and Glu130 (Newman et al., 1999). After substrate binding, nucleophilic attack by the carboxylate of an Asp residue on the substrate causes the cleavage of the halogen-carbon bond and the formation of an alkyl-ester intermediate. Site-directed mutagenesis studies on the DhlA Asp 124 residue shows that this first reaction proceeds by covalent catalysis with the formation of an alkyl-enzyme intermediate (Pries et al., 1994). The next step in the dehalogenase reaction pathway is hydrolysis of the intermediate ester by a water molecule activated by the active site His residue. While the catalytic histidine residue is the base catalyst for the dealkylation of the covalent intermediate, it is not essential for the initial nucleophilic attack of the active site Asp. Protein mutants that lack the crucial catalytic histidine residue have been shown to carry out the alkylation half reaction thereby producing a stable, covalent ester intermediate. For example, a His289Gln mutant of DhlA has previously been shown to accumulate the covalent alkyl-enzyme intermediate (Pries et al., 1995).

Unlike the haloalkane dehalogenase nucleophile and base residues, the role of the third member of the catalytic triad is not yet fully understood. The catalytic acid is hydrogen bonded to the catalytic His residue and may assist the His residue in its function by increasing the basicity of nitrogen in the imidazole ring. Krooshof et al. (1997), using site-directed mutagenesis to study the role of the DhlA catalytic acid Asp260, demonstrated that a D260N mutant was catalytically inactive. Furthermore, this residue apparently had an important structural role since the mutant protein accumulated mainly in inclusion bodies. The haloalkane dehalogenase from *Sphinogomonas paucimobilis* (LinB) is the enzyme involved in γ-hexachlorocyclohexane degradation (Nagata et al., 1997). Hynkova et al., (1999) replaced the putative catalytic residue (Glu-132) of the LinB with glutamine (Q) residue. However, no activity was observed for the E132Q mutant even at very high substrate concentrations.

To examine the role of the DhaA catalytic triad acid Glu130 in protein production and on the ability of the mutant protein to form covalent alkyl-enzyme intermediates with a fluorescent-labeled haloalkane substrate, site-directed mutagenesis was employed to replace the DhaA glutamate (E) residue at position 130 with glutamine, leucine and alanine Materials and Methods Strains and Plasmids Ultracompetent *E. coli* XL10 Gold (Stratagene; Tet$^r$ Δ(mcrA)183 Δ(mcrCB-hsdSMR-mrr)173 endA1 supE44 thi-1 recA1 gyrA96 relA1 lac Hte [F' proAB lacI $^q$ZΔM15 Tn10 (Tet$^r$) Amy Cam$^r$]) was used to as a host in transformation of site-directed mutagenesis reactions. *E. coli* strain JM109 (e14-(McrA) recA1 endA1 gyrA96 thi-1 hsdR17(rK– mK+) supE44 relA1 Δ(lac-proAB) [F' traD36 proAB lacI$^q$ZΔM15]) was used as the host for gene expression and whole cell enzyme labeling studies. A GST-DhaA-FLAG gene fusion cloned into plasmid pGEX5x3, designated pGEX5X3DhaAWT.FLAG, was used as the starting template for E130 mutagenesis. A mutant plasmid containing a H272F mutation in DhaA, designated pGEX5X3DhaAH272F- FLAG, was used as a positive control in labeling studies and the cloning vector pGEX5X3 was used as a negative control.

Site-Directed Mutagenesis of the DhaA E130 Residue

The sequence of the oligonucleotides used for mutagenesis is shown below. The underlined nucleotides indicate the position of the altered codons. The oligonucleotides were synthesized by Integrated DNA Technologies (Coralville, Iowa) at the 100 nmole scale and modified by phosphorylation at the 5' end.

DhaA E130Q
(SEQ ID NO: 41)
5' CAAAGGTATTGCATGTATGCAGTTCATCCGGCCTATCCCG 3'

DhaA E130L
(SEQ ID NO: 42)
5' GTCAAAGGTATTGCATGTATGCTGTTCATCCGGCCTATCCCGAC 3'

DhaA E130A
(SEQ ID NO: 43)
5' AGGTATTGCATGTATGGCGTTCATCCGGCCTATCCC 3'

Site-directed mutagenesis was performed using the QuikChange Multi kit according to the manufacturer's instructions (Stratagene, La Jolla, Calif.). The mutagenesis reactions were introduced into competent *E. coli* XL10 Gold cells and transformants were selected on LB agar plates containing ampicillin (100 μg/mL). Plasmid DNA isolated from individual transformants was initially screened for the loss of an EcoRI site due to replacement of the glutamate codon (GAAttc). Clones suspected of containing the desired codon change from each reaction were selected and subjected to DNA sequence analysis (SeqWright, Houston, Tex.). The primer used to confirm the sequence of the mutants in the pGEX5X3 vector was as follows: 5' GGGCTGGCAAGC- CACGTTTGGTG 3' (SEQ ID NO:64).

DhaA Mutant Analysis.

The three.DhaA.E130 substitution mutants were compared to the following constructs: Wild-type DhaA, DhaA.H272F, and a DhaA negative control (pGEX5X3 vector only). Overnight cultures of each clone were grown in 2 mL of LB containing ampicillin (100 μg/mL) by shaking at 30° C. The overnight cultures were diluted 1:50 into a sterile flask containing 50 mL fresh LB medium and ampicillin (100 μg/mL). The cultures were incubated with shaking at 25° C. to minimize the production of insoluble protein species. When the cultures reached mid-log phase ($OD_{600}$=0.6), IPTG (0.1 mM) was added and the cultures were incubated with shaking at 25° C. for an additional 22 hours. For labeling of whole cells with a carboxytetramethylrhodamine haloalkane conjugated substrate, the cell density of each culture was adjusted to $OD_{600}$=1 prior to adding substrate to a concentration of 15 μM. The cells were incubated with gentle agitation at 4° C. for approximately 18 hours. Following incubation, 20 μl of cells from each labeling reaction was added to 6 μl of 4×SDS loading dye and the samples were boiled for about 3 minutes prior to being loaded onto a 4-20% acrylamide gel (Tris glycine). For in vitro labeling studies, crude lysates of IPTG induced cultures were prepared by collecting 3 mL of cells ($OD_{600}$=1) and resuspending the resulting pellet in 75 μL PBS. Following a freeze/thaw step, 225 μL of 1× Cell Culture Lysis Reagent (Promega Corp., Madison, Wis.) containing 1.25 mg/mL lysozyme was added to facilitate lysis of the cells. A 20 μL sample of each lysate was combined with 25 μL of 1×PBS. The carboxytetramethylrhodamine labeled haloalkane substrate was added to a final concentration of 25 μM. The labeling reactions were incubated at room temperature for 2 hours. A 25 μl sample of each labeling reaction was added to 6 μl of 4×SDS loading dye and the samples were boiled for about 3 minutes prior to being loaded onto a 4-20% acrylamide gel (Tris glycine). The gels were imaged using a FluorImager SI instrument (Amersham Biosciences, Piscataway, N.J.) set to detect emission at 570 nm.

Cell-free lysates were generated by centrifugation of crude lysates for 15 minutes at 14,000 RPM. Protein production was monitored by SDS-PAGE and Western blot analysis. Proteins transferred to a PVDF membrane were incubated with an anti-FLAG$^R$ antibody conjugated with alkaline phosphatase (AP) (Sigma, St. Louis, Mo.). The blot was developed with the Western Blue stabilized substrate for alkaline phosphatase (Promega Corp., Madison, Wis.).

Results

The role of the DhaA catalytic acid in the hydrolysis of the alkyl-enzyme intermediate was probed by site-directed mutagenesis. The DhaA.WT codon E130 was replaced with a codon for glutamine (Q), leucine (L) or alanine (A), as these substitutions would likely be least disruptive to the structure of the enzyme. Following mutagenesis, restriction endonuclease screening and DNA sequence analysis was used to verify the desired codon changes. Sequence verified DhaA.E130Q, DhaA.E130L and DhaA.E130A clones, designated C1, A5 and A12, respectively, were chosen for further analysis. The E130 mutants were analyzed for protein expression and for their ability to form a covalent alkyl-enzyme intermediate with a carboxytetramethylrhodamine labeled haloalkane substrate. The three E130 gene variants were over-expressed in *E. coli* JM109 cells following induction with IPTG. SDS-PAGE analysis of crude cell lysates showed that cultures expressing the wild-type and mutant dhaA genes accumulated protein to approximately the same level (FIG. 26; lanes 2, 4, 6, 8, 10, and 12). Furthermore, the protein that was produced by constructs encoding DhaA.WT and DhaA.H272F was for the most part soluble since the amount of protein did not change appreciably after centrifugation (FIG. 26; lanes 3 and 5). The abundant 22 kDa protein bands present in the vector only lanes (FIG. 26; lanes 6 and 7) represented the GST protein. These results, however, are in stark contrast to the DhaA.E130Q, DhaA.E130L and DhaA.E130A mutants that appeared to accumulate predominantly insoluble DhaA protein. This conclusion is based on the observation that after centrifugation, there was a significant loss in the amount of DhaA protein present in cell-free lysates (FIG. 26; lanes 9, 11, and 13). Nevertheless, a protein band that comigrates with DhaA was clearly observed in each DhaA.E130 mutant lanes after centrifugation (+s) suggesting the presence of soluble enzyme. Western analysis was, therefore, used to determine if the protein bands observed in the DhaA.E130 mutants following centrifugation represented soluble DhaA material. The immunoblot shown in FIG. 27 confirmed the presence of soluble DhaA protein in each of the DhaA.E130 mutant cell-free lysates (lanes 9, 11, and 13).

The DhaA.E130 mutants were also examined for their ability to generate an alkyl-enzyme covalent intermediate. Crude lysates prepared from IPTG induced cultures of the various constructs were incubated in the presence of the carboxytetramethylrhodamine labeled substrate. FIG. 28 showed that the DhaA.H272F mutant (lane 3) was very efficient at producing this intermediate. No such product could be detected with either the DhaA.WT or negative control lysates. Upon initial examination, the DhaA.E130 mutants did not appear to produce detectable levels of the covalent product. However, upon closer inspection of the fluoroimage extremely faint bands were observed that could potentially represent minute amounts of the covalent intermediate (FIG. 28; lanes 5-7). Based on these results, the ability of whole cells to generate a covalent, fluorescent alkyl-enzyme intermediate was investigated.

FIG. 29 shows the results of an in vivo labeling experiment comparing each of the DhaA.E130 mutants with positive (DhaA.H272F mutant) and negative (DhaA-) controls. As expected, the DhaA.H272F mutant was capable of generating a covalent alkyl-enzyme intermediate as evidenced by the single fluorescent band near the molecular weight predicted for the DhaA fusion (FIG. 29, lane 3). As previously observed with the in vitro labeling results, no such product could be detected with either the wild-type or negative control cultures (FIG. 29, lanes 2 and 3) but very faint fluorescent bands migrating at the correct position were again detected with all three DhaA.E130 substituted mutants (FIG. 29, lanes 5-7). These results point to the possibility that the DhaA.E130Q, L and A mutants have the ability to trap covalent alkyl-enzyme intermediates. The efficiency of this reaction, however, appears to proceed at a dramatically reduced rate compared to the DhaA.H272F mutant enzyme.

The results of this mutagenesis study suggest that the DhaA catalytic acid residue DhaA.E130 plays an important structural role in the correct folding of the enzyme. The DhaA protein was clearly sensitive to substitutions at this amino acid position as evidenced by the presence of largely insoluble protein complexes in the DhaA.E130Q, DhaA.E130L and DhaA.E130A crude lysates. Nevertheless, based on SDS-PAGE and immunoblot analyses, a significant quantity of soluble DhaA protein was detected in the cell-free lysates of all three DhaA.E130 mutants.

EXAMPLE IX

Capturing of DhaA.H272F-Flag and DhaA.H272F-Flag *Renilla* Luciferase Fusion Proteins Expressed in Living Mammalian Cells Materials and Methods CHO-K1 cells were plated in 24 well plates (Labsystems) at a density of 30,000 cells/cm$^2$ and transfected with a pCIneo.DhaA.WT-Flag or pCIneo.hRLuc-connector-DhaA.H272F-Flag vector. Twenty-four hours later, media was replaced with fresh media containing 25 µM biotin-$C_{10}H_{21}N_1O_2$—Cl and 0.1% DMSO, or 0.1% DMSO alone, and the cells were placed in a $CO_2$ incubator for 60 minutes. At the end of the incubation, the media was removed, cells were quickly washed with PBS (pH 7.4; four consecutive washes; 1.0 ml/cm$^2$; 5 seconds each) and new media was added to the cells. In some experiments, the media was not changed. The cells were placed back in a $CO_2$ incubator.

After 60 minutes, media was removed, and the cells were collected in PBS (pH=7.4, 200 µl/well, RT) containing protease inhibitors (Sigma #P8340). The cells were lysed by trituriation through a needle (IM1 23GTW). Then, cell lysates were incubated with MagnaBind Streptavidin coated beads (Pierce #21344) according to the manufacturer's protocol. Briefly, cell lysates were incubated with beads for 60 minutes at room temperature (RT) using a rotating disk. Unbound material was collected; beads were washed with PBS (3×500 µl, pH=7.4, RT) and resuspended in SDS-sample buffer (for SDS-PAGE analysis) or PBS (pH=7.4, for determination of R.Luc activity). Proteins were resolved on SDS-PAGE, transferred to a nitrocellulose membrane, analyzed with anti-Flag-Ab or anti-R.Luc-Ab, and bound antibody detected by an enhanced chemiluminescence (ECL) system (Pharmacia-Amersham). Activity of hR.Luc bound to beads was determined using Promega's "*Renilla* Luciferase Assay System" according to the manufacturer's protocol.

Results

Capturing of proteins expressed in living cells allows for analysis of those proteins with a variety of analytic methods/techniques. A number of capturing tools are available although most of those tools require generation of a highly specific antibody or genetically fusing a protein of interest with specific tag peptides/proteins (Jarvik and Telmer, 1998; Ragaut et al., 1999). However, those tags have only limited use for live cell imaging. To capture DhaA.H272F and functional proteins fused to DhaA.H272F, SA-coated beads were used (Savage et al., 1992).

Biotin-$C_{10}H_{21}NO_2$—Cl was efficiently hydrolyzed by DhaA.WT, and covalently bound to DhaA.H272F and DhaA.H272F fusion proteins in vitro and in vivo. Moreover, binding was observed both in E. coli and in mammalian cells. Control experiments indicated that about 80% of the DhaA.H272F-Flag protein expressed in CHO-K1 cells was labeled after a 60 minute treatment.

CHO-K1 cells transiently expressing DhaA.H272F-Flag were treated with biotin-$C_{10}H_{21}NO_2$—Cl. Biotin-$C_{10}H_{21}NO_2$—Cl treated cells were lysed and cell lysates were incubated with SA-coated beads. Binding of DhaA.H272F to beads was analyzed by Western blot using anti-Flag$^R$ antibody. As shown in FIG. 30D, DhaA.H272F-Flag capturing was not detected in the absence of biotin-$C_{10}H_{21}NO_2$—Cl treatment. At the same time, more than 50% of the DhaA.H272F-Flag expressed in cells was captured on SA-coated beads if the cells were treated with biotin-$C_{10}H_{21}NO_2$—Cl.

To show the capturing of functionally active proteins fused to DhaA.H272F-Flag, cells were transfected with a vector encoding hR.Luc-connector-DhaA.H272F-Flag, and the luciferase activity captured on the beads measured. As shown in FIG. 30C, significant luciferase activity was detected on beads incubated with a lysate of biotin-$C_{10}H_{21}NO_2$—Cl treated cells. At the same time, no luciferase activity was detected on beads incubated with a lysate from cells that were not treated with biotin-$C_{10}H_{21}NO_2$—Cl. Moreover, no hR.Luc activity was detected on beads incubated with lysate from the cells treated with biotin-$C_{10}H_{21}NO_2$—Cl when free biotin-$C_{10}H_{21}NO_2$—Cl was not washed out.

Taken together, these data show that functionally active protein (hR.Luc) fused to the DhaA.H272F can be efficiently captured using biotin-$C_{10}H_{21}NO_2$—Cl and SA-coated beads. The capture is biotin-dependent, and can be competed-off by excess of biotin-$C_{10}H_{21}NO_2$—Cl. As a significant inhibitory effect of the beads on the hR.Luc activity was observed (data not shown), SDS-PAGE and Western blot analysis with anti-R.Luc antibody were used to estimate the efficiency of capture of hR.Luc-connector-DhaA.H272F-Flag fusion protein. As shown in FIG. 30D, more than 50% of hR.Luc-connector-DhaA.H272F-Flag fusion protein can be captured in biotin-dependent manner. This is in good agreement with the capturing efficiency of DhaA.H272F-Flag (see FIG. 30A).

EXAMPLE X

DhaA Mutants with Increased Rates of Covalent Bond Formation

Figure 2C:
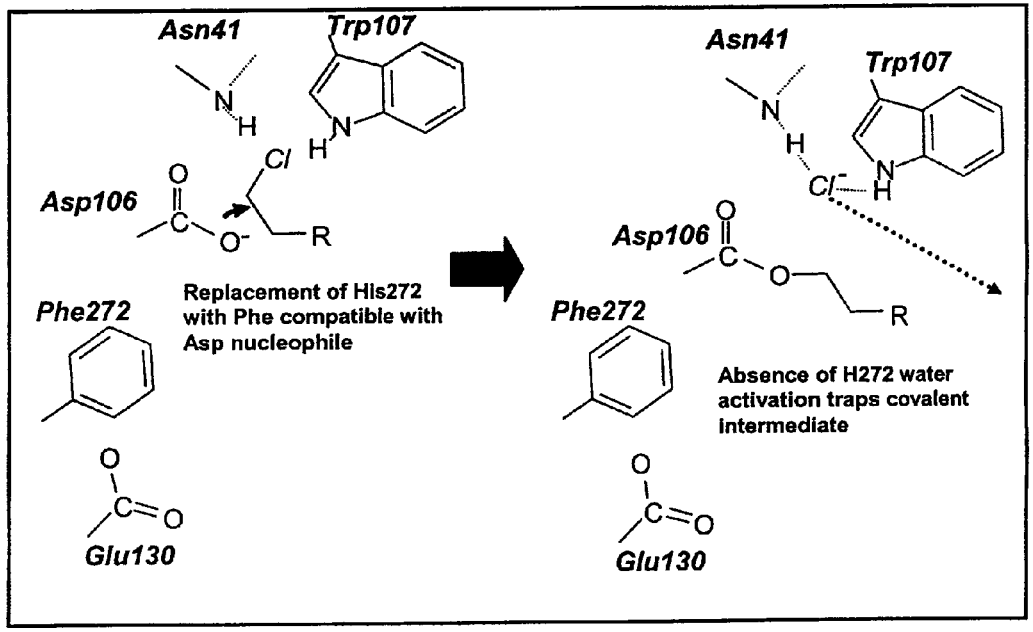
FIG. 2C illustrates the mechanism of covalent intermediate formation by DhaA.H272F with an alkylhalide substrate. Nucleophilic displacement of the halide group by Asp106 is followed by the formation of the covalent ester intermediate. Replacement of His272 with a Phe residue prevents water activation and traps the covalent intermediate.
Figure 2D:
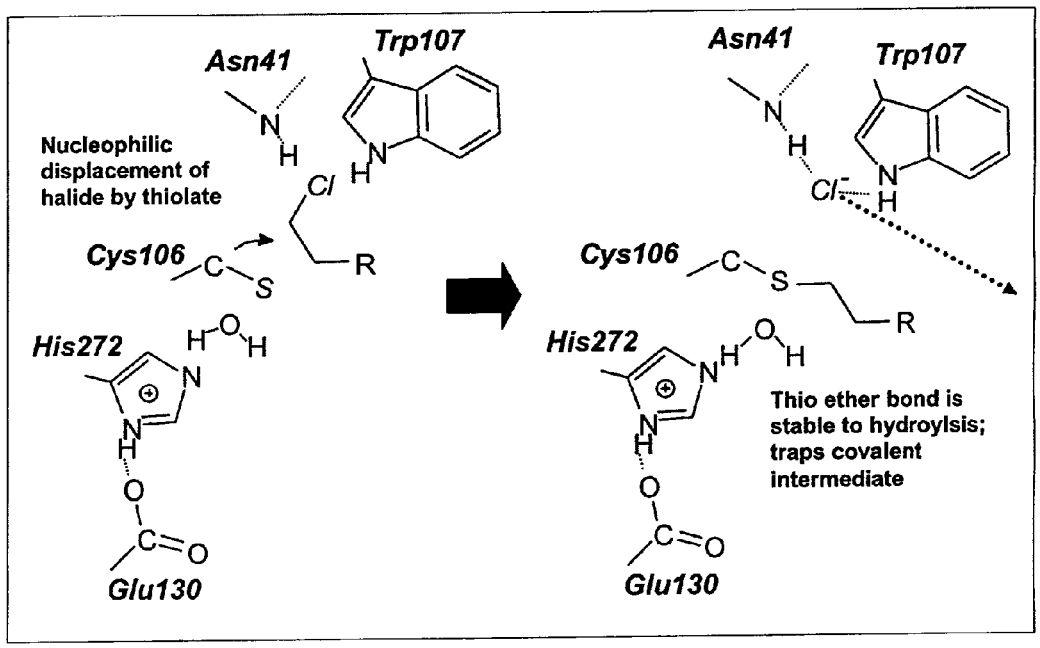
FIG. 2D depicts the mechanism of covalent intermediate formation by DhaA.D106C with an alkylhalide substrate. Nucleophilic displacement of the halide by the Cys106 thiolate generates a thioether intermediate that is stable to hydrolysis.
Figure 2E:
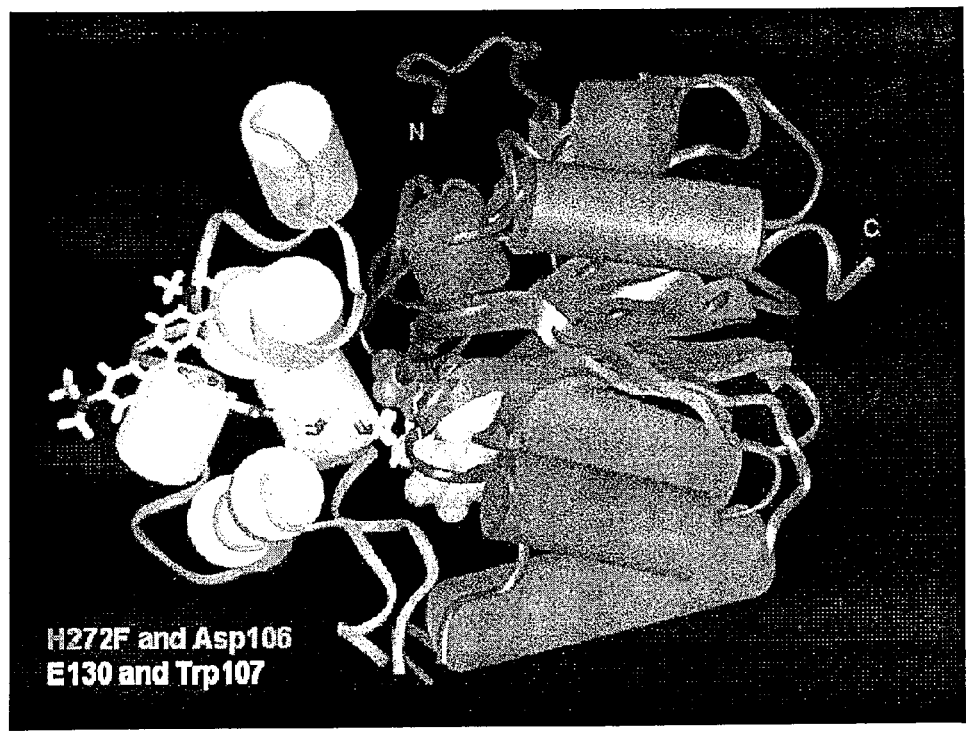
FIG. 2E depicts a structural model of the DhaA.H272F variant with a covalently attached carboxytetramethylrhodamine-$C_{10}H_{21}NO_2$—Cl ligand situated in the active site activity. The red shaded residues near the cap and core domain interface represent H272F and the D106 nucleophile. The yellow shaded residues denote the positions of E130 and the halide-chelating residue W107.
Figure 2F:
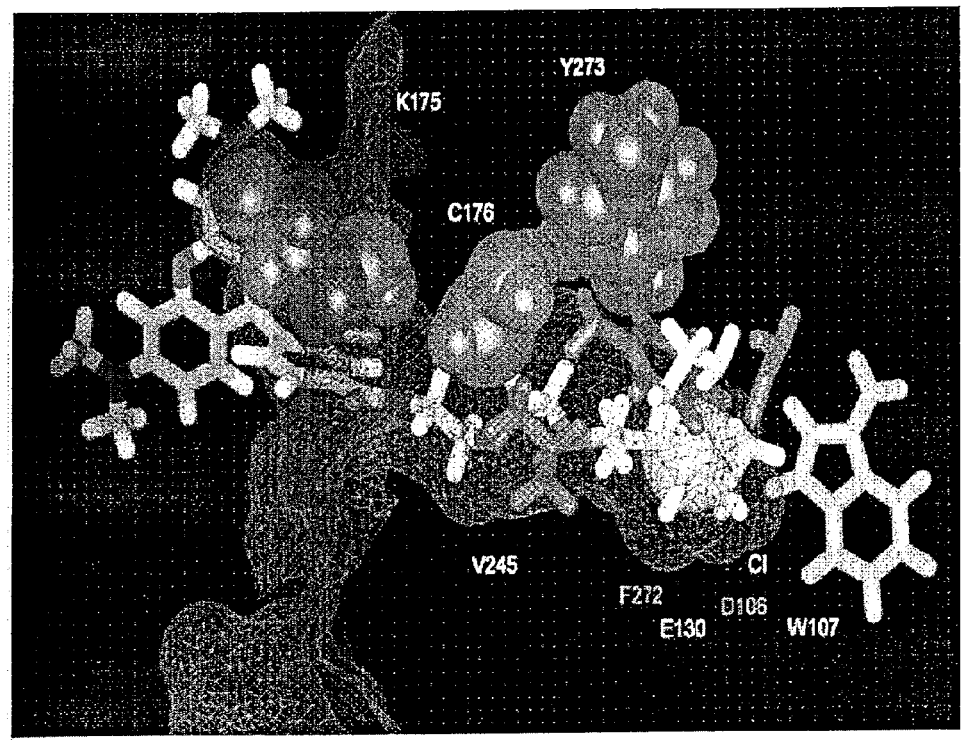
FIG. 2F shows a structural model of the DhaA.H272F substrate binding tunnel.

Replacement of the DhaA catalytic base His272 with a phenylalanine residue is compatible with the Asp nucleophile and resulted in a modified protein, designated DhaA.H272F, that accumulates substantial amounts of the covalent alkyl-enzyme intermediate (FIG. 2C). The absence of the water activating His272 residue allows trapping of the covalent ester intermediate (FIG. 2C). A structural model of such a mutant before binding and after binding a substrate is shown in FIGS. 2E and 2F respectively. Furthermore, a DhaA mutant containing a cysteine substitution for the nucleophile residue Asp106 was also capable of trapping covalent intermediates. This mutant, designated DhaA.D106C (FIG. 2D), displaces the halide moiety through the action of a thiolate nucleophile. The resulting thioether bond is stable to hydrolysis even in the presence of the water activating H272 residue (FIG. 2D).

The ability to generate a stable, covalent linkage between protein and haloalkane ligand provides for a universal reporter technology which can site-specifically label, localize, immobilize and/or fluorescently visualize proteins in mammalian cells (see Examples II-IX). In one example, active-site mutants of dehalogenase (DhaA) tether fusion proteins with those mutants via a stable, covalent bond to synthetic haloalkane conjugated substrates. To enhance the kinetics of DhaA.H272F and DhaA.D106C, modeling of protein-ligand (protein-substrate) complexes was employed in an effort to identify favorable interactions between DhaA and a substrate so as to optimize the rate of covalent bond formation.

Materials and Methods

Strains, growth conditions and plasmids. E. coli strains DH10B (F-mcrA Δ[mrr-hsdRMS-mcrBC]φ80lacZΔM15 ΔlacX74 deoR recA1 endA1 araD139 Δ(ara, leu)7697 galU galK rpsL nupG) and JM109 (e14-(McrA) recA1 endA1 gyrA96 thi-1 hsdR17($r_K$-$m_K$+) supE44 relA1 Δ(lac-proAB) [F' traD36 proAB lacI$^q$ZΔM15]) were used as the hosts for gene expression and for library screening. E. coli was routinely grown in Luria-Bertani (LB) or Terrific broth (TB) media (Sambrook et al., 2001). When required, Difco agar was added to the medium at 1.5% (w/v). Ampicillin (100 µg/mL; Amp) was added to the medium to select for recombinant plasmids. The E. coli expression plasmids pGEX5X3DhaA.H272F.FLAG and pGEX5X3DhaA.D106C.FLAG containing GST fusions to DhaA.H272F and DhaA.D106C, respectively, were used as the starting templates for site-directed mutagenesis. The expression vector pCI-Neo (Promega Corporation, Madison, Wis.) was used to examine expression and labeling of DhaA mutants in mammalian cells.

Reagents and Chemicals. All chemicals were purchased from Sigma-Aldrich (Milwaukee, Wis.). All enzymes were from Promega (Madison, Wis.) unless otherwise noted. The mutagenesis and PCR primers were synthesized by Promega Corp., SeqWright (Houston, Tex.) and Integrated DNA Technologies (Coralville, Iowa). Mutagenesis of DhaA was performed using the QuikChange Multi kit (Stratagene, La Jolla, Calif.). Carboxytetramethylrhodamine-$C_{10}H_{21}NO_2$—Cl, Carboxyfluorescein-$C_{10}H_{21}NO_2$—Cl, diacetyl carboxyfluorescein-$C_{10}H_{21}NO_2$—Cl, and biotin-containing chloroha-loalkane ligands (e.g., biotin-14-Cl, biotin-X-14-Cl, and biotin-PEG4-14-Cl, see FIG. 7) were synthesized by Promega Biosciences Inc. (San Luis Abispo, Calif.).

DNA Analysis and Protein Modeling. DNA analysis was performed using Vector NTI software package, version 8. Protein structures were obtained from the Protein Data Bank (PDB http://www.rcsb.org/pdb/). Structural analyses and modeling were performed with InsightII 2000.1 including modules Biopolymer, Discover, Homology, and Modeler (Accelrys http://www.accelrys.com/).

Mutagenesis and Library Construction. Recombinant DNA work was performed using standard protocols as described by Sambrook et al. (2001). Prior to mutagenesis, the sequence of DhaA templates was confirmed using the following oligonucleotides: forward primer "21972", 5'-GGGCTGGCAAGCCACGTTTGGTG-3' (SEQ ID NO:64) and reverse primer "21973", 5'-CCGGGAGCTG-CATGTGTCAGAGG-3' (SEQ ID NO:65).

The sequence of the oligonucleotides used for site-saturation mutagenesis of DhaA.H272F or DhaA.D106C residues 175 (Lys), 175 (Cys), and 273(Tyr) are shown below:

175 NNK:
(SEQ ID NO: 66)
5' ATCGAGGGTGCGCTCCCGNNKTGCGTCGTCCGTCCGCTTACGG 3'

176 NNK:
(SEQ ID NO: 67)
5' ATCGAGGGTGCGCTCCCGAAANNKGTCGTCCGTCCGCTTACGG 3'

175/176 NNK/NNK:
(SEQ ID NO: 68)
5' ATCGAGGGTGCGCTCCCGNNKNNKGTCGTCCGTCCGCTTACGG 3'

Y273 NNK = H272F:
(SEQ ID NO: 69)
5' ATCGGCCCGGGATTGTTCNNKCTCCAGGAAGACAACCCGG 3'

Y273 NNK = H272:
(SEQ ID NO: 70)
5' CGGCCCGGGATTGCACNNKCTCCAGGAAGACAACCCGGA 3'

V245T:
(SEQ ID NO: 83)
5' GGGCACACCCGGCACCCTGATCCCCCCGG 3'

The underlined nucleotides indicate the position of the altered codons. Site-directed mutagenesis was performed using the QuikChange Multi kit according to the manufacturer's instructions (Stratagene, La Jolla, Calif.). The mutagenesis reactions were introduced into competent *E. coli* and transformants were selected on LB agar plates containing Amp (100 μg/mL). Library quality was evaluated by DNA sequence analysis of 12-48 randomly selected clones from each library. Plasmids for sequence analysis were isolated from *E. coli* using Wizard SV Miniprep Kits (Promega Corp.). DNA sequence analysis was performed by SeqWright DNA Technology Services (Houston, Tex.).

Sequencing primers for analyzing the 175, 176 and 175/176 libraries included:

(SEQ ID NO: 71)
"175/176", 5'-GCCTATCCCGACGTGGGACG-3';

(SEQ ID NO: 72)
"255R", 5'-AGGTCTCGCGGCTTCGGCCGGGGG-3';

(SEQ ID NO: 73)
"F70", 5'-AAAATCGGACAAACCAGACCTCG-3';

(SEQ ID NO: 74)
"F189", 5'-ATCGCGAGCCCTTCCTCAAGCCTG-3';
and (SEQ ID NO: 75)
"R121", 5'-GTTCCGGATTGCGCTTGGCCCAGT-3'.

Screening Assay Development.

In Vivo Detection of Binding to DhaA Substrates.

*E. coli* colonies harboring DhaA.H272F or DhaA.D106C encoding plasmids were inoculated into 200 μL LB+100 μg/ml Amp and grown over night at 37° C. in flat bottom 96 wells plates. Overnight cultures were diluted 1:20 into 200 μL TB+100 μg/mL Amp+0.1 mM IPTG and grown overnight at 30° C. The volume of cells used for in vivo labeling was normalized to growth ($OD_{600}$). 50 to 100 μL of induced cells were transferred to a U-bottom 96 well plate, pelleted, re-suspended with 50 μl PBS+15 μM carboxytetramethyl-rhodamine-$C_{10}H_{21}NO_2$—Cl and labeled at room temperature for 60 minutes on a rotating shaker. To remove the unbound ligand, cells were harvested at 2500 rpm for 5 minutes, supernatants were discarded and the cells were re-suspended with 100 μl of 10 mM Tris-HCl pH 7.5, 0.9% NaCl and 0.05% Triton and washed for 15 minutes. This washing procedure was repeated 3 times. Fluorescence intensity was measured on a Tecan Safire plate reader using the following parameters: 545 nm excitation; 575 nm emission. The fluorescence intensity of DhaA mutants was compared to DhaA-, DhaA.H272F and DhaA.D106C control cells.

Substrate Capture Using Immobilized DhaA.

Purified DhaA.H272F or DhaA.D106C mutant proteins (purified, 50 ng from *E. coli* lysates generated using Fast-Break™ cell lysis reagent, Promega Corp.) was immobilized using 96-well microtiter plates (flat bottom; Nunc MaxiSorp) previously coated with anti-Flag M2 IgG (Sigma). Coating took place overnight at 4° C. using 100 μL, anti-Flag (5 μg/mL) in 0.1 M $NaHCO_3$ pH 9.6. The next day plates were emptied and blocked with 300 μL, PBS containing 3% BSA for 1 hour at 25° C. Plates were emptied and washed 4× with PBS containing 0.1% Tween 20 (PBST), and biotinylated substrate (varying concentrations of biotin-14-Cl, biotin-X-14-Cl, or biotin-PEG4-14-Cl) was added to the wells in 100 μL of PBS+0.05% Tween 20+0.5% BSA (PBSTB) and incubated for various times at 25° C. Reactions between immobilized DhaA and substrate were stopped by emptying plates and washing 4× with PBST. 100 μL Streptavidin (SA)-HRP (1:5,000 in PBSTB; Prozyme) was then added to the wells and incubated for 1 hour at 25° C. The plates were emptied and washed 8× with PBST, and TMB was added in a volume of 100 μL. After 15 minutes, color development was stopped by the addition of an equal volume of 0.2 M $H_2SO_4$ and signals were quantitated by measuring the absorbance at 450 nm.

Protein Capture Using MagneGST™ Paramagnetic Particles (PMPs). Bacterial colonies were picked into 96-well plates containing LB+Amp and incubated with shaking at 30° C. The cultures were diluted 1:20 into 96 well plates containing fresh TB medium, Amp and 0.1 mM IPTG. The plates were incubated at 30° C. with shaking overnight. The 96 well plates containing the IPTG induced cultures were centrifuged and supernatants removed. DhaA mutants were normalized for protein concentration by saturating protein capture on MagneGST™ PMPs. A cocktail containing MagneGST™ cell lysis reagent, MagneGST™ PMPs and carboxytetramethylrhodamine-$C_{10}H_{21}NO_2$—Cl (15 μM) was pipetted into the 96 well plates containing the cell pellets. The plates were shaken at about 900 rpm for 10 minutes at room temperature. The particles were washed three times with PBST using a MagnaBot® 96 magnetic separation device. The wash solution was removed and MagneGST™ elution solution was added and the plates were allowed to shake at room temperature (about 900 rpm for 5 minutes). Supernatants were transferred to a new, flat bottom, transparent 96 well plate and the fluorescence intensity was measured using an excitation wavelength at 550 nm and an emission wavelength at 580 nm.

Automated Library Screening. The DhaA mutant libraries were screened with the MagneGST™ based assay on a custom Tecan Freedom robotic workstation. The assay parameters were automated using the FACTS scheduling software and allowed the processing of multiple 96 well plates in parallel. The cell pellets were stored in a refrigerated Storex incubator (4° C.) until the plates were automatically retrieved for further processing. Reagents were transferred to plates using a TeMo liquid handling system (Tecan US). The plates were shaken at about 900 rpm for 10 minutes on Tecan Te-Shake™ at room temperature. The particles were washed with PBST using a MagnaBot® 96 magnetic separation devices that were adapted to be used on a TeMo liquid dispensing system and compatible with the FACTS scheduling software. Fluorescence intensity measurements were performed using a Tecan Safire spectrofluorometer. Raw fluorescence intensity data were imported into an Excel spreadsheet for analysis. The screening data was examined for wells with higher intensity than the parental controls indicating the potential presence of improved DhaA clones.

Secondary Library Screening. Following the initial screening, all clones showing at least 20% improvement over parental clones (i.e., DhaA.H272F or DhaA.D106C) were streaked onto LB plates supplemented with Amp. Four colonies at random of each identified hit were inoculated into 200 µL LB+Amp and grown overnight at 30° C. in flat bottom 96 well plates. Overnight cultures were diluted 1:50 into 200 µL TB ampicillin supplemented with 0.1 mM IPTG and grown overnight at 30° C. and 37° C. Induced cultures were re-assayed using the MagneGST™ based screen. All improved clones were sequenced and archived. Qiagen mini prep kit was used to prepare plasmid DNAs of sequencing. 2 ml cultures of all improved clones were archived at −70° C. in the presence of 1% DMSO.

DhaA Protein Purification. Proteins were purified on a small scale using the MagneGST™ protein purification system (Promega, Madison, Wis.). For protein purification, colonies were inoculated into 1 ml LB+100 µg/ml Amp and grown overnight at 30° C. Overnight cultures were diluted 1:50 into 10 mL of fresh LB+100 µg/mL Amp. These cultures were grown until $A_{600}$=0.6 at which point the cultures were induced with 0.1 mM IPTG and grown overnight at 25° C. The cell pellets of induced cultures were frozen at −70° C. for 15 minutes. To generate cell lysates, pellets were resuspended with 2 mL lysis buffer (containing 1 mM DTT+20 µL RQ DNase in the presence of 1× protease inhibitor cocktail (Becton-Dickinson Biosciences) and incubated on a rotating shaker for 30 minutes. Four mLs of a 25% slurry of MagneGST particles were equilibrated 3 times with the MagneGST binding/wash buffer prior to use. Following the final wash, the particles were resuspended in 1× volume of the binding/wash buffer. The particles were added directly to the lysate and the mixture was incubated for 30 minutes at room temperature on a rotating shaker to allow binding of the GST-DhaA fusion protein to the magnetic particles. Following washing of the particles 3 times with 2.5× volumes of washing binding buffer+1 mM DTT, the GST-DhaA protein was eluted by incubation for 15 minute with elution buffer (100 mM glutathione, 50 mM Tris HCl, pH 8.1, 1 mM DTT and 1× BD protease inhibition cocktail). The eluted protein was dialyzed twice against storage buffer (50 mM Tris HCl, pH 7.5, 200 mM NaCl, 1 mM DTT, 1 mM EDTA, 20% glycerol).

Large-scale purification of DhaA protein fusions was accomplished using Glutathione Sepharose 4 Fast Flow resin (Amersham Biosciences). Briefly, the pellet from a 500 mL culture of induced cells was resuspended in 20 mL of 1× phosphate buffered saline (PBS) containing 1 mM DTT (buffer A). Following the addition of lysozyme (10 mg/mL), the mixture was allowed to incubate at 4° C. for 30 minutes. The protease inhibitor PMSF was added to a final concentration of 2 mM just prior to sonication. Cleared lysates were added to the resin and incubated with mixing 2 hours to overnight at 4° C. Following two 40 mL batch washes with buffer A, the resin was added to a Wizard Maxi column (Promega Corp.). The column contents were washed 2× with 10 mL buffer A containing 0.3 M NaCl. The fusion protein was eluted in 2 mL fractions of buffer A containing 20 mM glutathione. The protein containing fractions were dialyzed twice with 1L buffer A containing 20% glycerol.

In Vitro Labeling of Purified DhaA Mutants. Covalent tethering of fluorescent substrates to DhaA mutants was detected by fluorimage gel analysis. GST-DhaA mutants (9 nM) were incubated with carboxytetramethylrhodamine-$C_{10}H_{21}NO_2$—Cl, carboxyfluorescein-$C_{10}H_{21}NO_2$—Cl, or rhodamine green-$C_{10}H_{21}NO_2$—Cl at various concentrations and temperatures in 50 mM Tris HCl (pH 7.5). Reactions were initiated by the addition of substrate, and for time course experiments 18 µL aliquots of the reactions were removed to tubes containing 6 µL SDS gel loading buffer, boiled for 5 minutes, and resolved on pre-poured, 4-20% gradient SDS-polyacrylamide gels in Tris-glycine (Invitrogen, Carlsbad, Calif.). Gels were fluorimaged using a Hitachi FM Bio II (535 nm excitation, 580 nm emission) and bands quantitated by either densitometry or ImageQuant (Amersham). Rate constants were calculated from the following second-order rate equation (Cornish-Bowden, 1995):

$$kt=(1/B_0-A_0)\ln[(B_0-x)A_0/(A_0-x)B_0]$$

where k=the rate constant; $B_0$=[reactant B] at time=0, mol/L (M); $A_0$=[reactant A] at time=0, mol/L (M); $B_0$−x=[reactant B] at time=t, mol/L (M); and $A_0$−x=[reactant A] at time=t, mol/L (M). A plot of ln [($B_0$−x)$A_o$/($A_o$−x) $B_0$] versus time should be linear, and k can be determined from the slope of the line, k ($B_0$−$A_0$).

Fluorescence Polarization (FP). Fluorescent polarization was used to analyze the reaction kinetics of DhaA mutants. Measurements were taken on the Beacon 2000 (Invitrogen, Carlsbad, Calif.) or in a 96 well format using the Ultra plate reader (Tecan, Research Triangle Park, N.C.). Carboxytetramethylrhodamine-$C_{10}H_{21}NO_2$—Cl or carboxyfluorescein-$C_{10}H_{21}NO_2$—Cl substrates (7.5-10 nM) were incubated with an excess of purified GST-DhaA proteins. For carboxytetramethylrhodamine-$C_{10}H_{21}NO_2$—Cl labeling studies the following concentrations of protein were used: parental protein, 15 µM; first generation DhaA mutants, 1.5-0.15 µM; and second generation DhaA mutants, 0.035 µM. For carboxyfluorescein-$C_{10}H_{21}NO_2$—Cl labeling studies the following concentrations of protein were used: parental protein, 15 µM, first generation clones, 1.5-0.15 µM, and second generation clones, 0.15 µM. Reactions were started by addition of protein to the substrates. Measurements of fluorescent polarization and fluorescent intensity were taken in 10-30 second intervals for 0.5-12 hours. Rate constants were calculated using the $2^{nd}$ order rate equation.

Thermostability Analysis. The thermostability profiles of the DhaA mutants were determined by measuring the residual activity of the purified proteins following 15, 30 or 60 minute incubations at 4, 22, 30, 37, 42, 50 or 60° C. The FP assay was performed at room temperature (about 25° C.). For these studies, 15 µM parental or 1.5-0.15 nM of $1^{st}$ generation clones were labeled with carboxytetramethylrhodamine-$C_{10}H_{21}NO_2$—Cl and 0.15 nM of $2^{nd}$ generation clones were labeled with carboxyfluorescein-$C_{10}H_{21}NO_2$—Cl. For each clone, the labeling rate (slope of the linear range) was calculated for each condition. The rate observed following a 15 minute incubation at 4° C. was arbitrarily assigned as 100% activity. The residual activity (%) was calculated for each condition. To determine stability, for each incubation time, the % of residual activity was plotted against the incubation temperatures. To calculate half-life, for each incubation temperature, the % of residual activity was plotted against the incubation time. The time where 50% activity was lost was extrapolated from the graph.

Use of Immobilized DhaA to Capture Chloroalkylated Molecules. Mutant DhaA (50 ng) was immobilized as above using microtiter plates coated with anti-Flag M2 IgG. Varying concentrations of chloroalkane were incubated at 25° C. with model molecules of interest in solution (PBSTB). In the case of biotinylated chloroalkanes, the molecule of interest was SA-HRP. In the case of carboxytetramethylrhodamine-$C_{10}H_{21}NO_2$—Cl, the molecule of interest was an anti-TMR IgG (Probes). The chloroalkylation reactions proceeded for 1 hour and were then added (in a volume of 100 µl) to washed plates containing immobilized DhaA. These incubations lasted for 1 to 2 hours at 25° C., and were stopped by emptying the plates and washing 4× with PBST. For the SA-HRP reactions, TMB was added to the plates in a volume of 100 µL. Color was developed for 15 minutes and then stopped by the addition of an equal volume of 0.2 M $H_2SO_4$. Signals were quantitated by measuring absorbance at 450 nm. For the carboxyetramethylrhodamine reactions, a secondary anti-rabbit IgG-HRP conjugate (100 L of a 1:5,000 dilution in PBSTB; 1 hour at 25° C.) was used to detect bound anti-carboxytetramethylrhodamine IgG. Plates were washed 8× with PBST, developed with TMB, and quantitated as above.

DhaA Capture Using Immobilized Chloroalkane Substrates. Biotinylated chloroalkane substrates, biotin-14-Cl, biotin-X-14-Cl, and biotin-PEG4-14-Cl, were immobilized using streptavidin high binding capacity coated 96 well microtiter plates (flat bottom, Pierce). Using an excess of substrate (about 2 µmol), the plates could bind approximately 75 µmol of biotin per well. Following immobilization of substrate for 1 hour at 25° C. in a buffer containing 100 µL PBS+0.05% Tween 20+0.5% BSA (PBSTB), plates were emptied and washed 4× with PBS containing 0.1% Tween 20 (PBST). Reactions between immobilized substrate and mutant DhaAs were performed using purified GST-DhaA-Flag fusions. Various concentrations of protein (100 µL; diluted in PBSTB) were incubated with immobilized substrate for various times at 25° C., and the reactions were stopped by emptying the plates and washing 4× with PBST. To detect bound DhaA, 100 µL anti-GST-HRP (Amersham) was added to each well at a 1:10,000 dilution (in PBSTB) and the plates incubated for 1 hour at 25° C. Plates were emptied and washed 8× with PBST and then TMB was added in a volume of 100 µL. After 15 minutes, color development was stopped by the addition of an equal volume of 0.2 M $H_2SO_4$, and signals were quantitated by measuring the absorbance at 450 nm.

Characterization of DhaA Mutants in Mammalian Cells. Select sequence verified DhaA mutants were cloned into the mammalian expression vector pCI-neo as follows: The DhaA-FLAG portion of the mutant genes were removed from pGEX5X3 with SalI and NotI restriction endonucleases. Fragments were separated by electrophoresis in 1% agarose (1×TAE), excised and purified using QIAquick Gel Extraction Kit (QIAGEN). The pCI-neo vector backbone was also digested with SalI and NotI, separated and purified in the same manner. Ligations were performed using Promega's LigaFast System, at an approximate insert:vector ratio of 5:1. DNA was transformed into chemically competent JM109 cells and plated onto LB agar plates containing Amp. Transformant colonies were picked into 96 well assay blocks (Fisher Scientific) containing 1 mL of LB+Amp and shaken overnight at 37° C. Cells were harvested and plasmids purified using the Wizard 96 plasmid purification kit (Promega Corp.). Plasmids were screened for the presence of the DhaA insert by a SalI-NotI restriction digest, and screened by electrophoresis in 1% agarose (1×TAE). Positive clones were verified by DNA sequence analysis.

Plasmid pHT2 was created to improve protein production in mammalian cells and to facilitate the generation of fusion proteins. DhaA.H272F YL was amplified from pCIneo containing DhaA.H272F YL-FLAG with oligonucloetides 10055643 (5' CTA TAG GCT AGC CAG CTG GCG CGG ATA TCG CCA CCA TGG GAT CCG AAA TCG GTA CAG GCT TCC CCT TCG 3; SEQ ID NO:84) and 10055644 (5' AGG GAA GCG GCC GCC TAC TTA ATT AAC TAT TAG CCG GCC AGC CCG GGG AGC CAG CGC GCG ATC TCA CTG C 3'; SEQ ID NO:85). The PCR product and destination vector were both cut with EcoRV/NotI, gel purified, ligated, and transformed into JM109. The DhaA protein encoded by pHT2, designated HT2, contained additional changes to the amino acid sequence of DhaA.H272F YL. In addition to the H272F, K175M, C176G, and Y273L substitutions, additional changes included: 1) a glycine insertion at position 2 to generate a better Koazak sequence; 2) a Ala292Gly substitution used to create a SmaI/XmaI/AvaI site; and an insertion of alanine and glycine (AlaGly) to the C-terminus to generate a NaeI site (FIG. 49).

Mammalian Cell Culture. CHO-K1 cells (ATCC-CCL61) or HeLa cells (ATCC-CCL2) were cultured in a Ham's F12 nutrients or Dulbecco's modified minimal essential medium (respectably) supplemented with 10% fetal bovine serum (FBS), 100 U/ml penicillin, and 100 mg/ml streptomycin, in an atmosphere of 95% air and 5% $CO_2$ at 37° C.

Mammalian Cell Transfection. To study transient expression of different proteins, cells were plated in 24 well plates (Labsystems) or 8 well LT cover glass chamber slides (Nunc) at a density of 30,000 cells/$cm^2$. At about 80-90% confluency, the cells were exposed to a mixture of lipofectamine/DNA/antibiotic free media according to the manufacturer's (Invitrogen) instructions. The following day, media was replaced with fresh media and cells were allowed to grow for various periods of time.

Cell-to-Gel Analysis. CHO-K1 cells were plated in 24 well plates (Labsystems) and transfected with a pCIneo-CM-V.DhaA mutant-Flag vector. Twenty-four hours (in some experiments 12, 24 or 48 hours) later, media was replaced with fresh media containing 0.2, −25.0 µM carboxytetramethylrhodamine-$C_{10}H_{21}NO_2$—Cl or DiAc carboxyfluorescein-$C_{10}H_{21}NO_2$—Cl and the cells were placed into a $CO_2$ incubator for 1, 5, 15 or 60 minutes. Following this incubation, media was removed, cells were quickly washed with PBS (pH 7.4; two consecutive washes: 1.0 ml/$cm^2$; 5 seconds each) and the cells were solubilized in a sample buffer (1% SDS, 10% glycerol, and the like; 200 µl/well). Proteins (2-10 µl/lane) were resolved on SDS-PAGE (4-20% gradient gels). Binding of the carboxytetramethylrhodamine-$C_{10}H_{21}NO_2$—Cl to proteins was quantified on a fluoroimager (Hitachi, Japan) at $E_{ex}/E_{em}$ equal 540/575 nm.

Cell Imaging. HeLa cells were plated in 8 well LT cover glass chamber slides (Nunc) and transfected with a pCIneo-CMV.DhaA mutant or β-arrestin2-connector-DhaA.H11YL vector. Twenty-four hours later, media was replaced with fresh media containing different concentrations (0.2-10.0 µM) of carboxytetramethylrhodamine-$C_{10}H_{21}NO_2$—Cl or DiAc carboxyfluorescein-$C_{10}H_{21}NO_2$—Cl and the cells were placed into a $CO_2$ incubator for 15 minutes. Following this incubation, media was removed and cells were quickly washed with PBS (pH 7.4; two consecutive washes: 1.0 ml/$cm^2$; 5 seconds each). For live cells imaging experiments, new media was added to the cells. The cells were placed back into a $CO_2$ incubator and after 60 minutes media was replaced with fresh media. Fluorescent images of the cells were taken on confocal microscope FluorView500 (Olympus) with filter sets appropriate for the detection of carboxyfluorescein and carboxytetramethylrhodamine. To fix cells, 200 ml of 3.7% paraformaldehyde in PBS (pH 7.4) containing 0.1% Triton-X100 was added to the cells. After 15 minutes room temperature (RT), cells were washed with PBS (pH 7.4) containing 1.0% Triton-X100 (10 minutes, RT). Detergent solution was replaced with PBS (pH 7.4), and images of the cells were taken on confocal microscope FluorView500 (Olympus). In some experiments cells were counterstained with 100 nM of MitoTracker$^R$ Green FM (Invitrogen, M-7514) or MitoTracker$^R$ Orange CMTMRos (Invitrogen, M-7510) for 15 minutes at 37° C.

Production of DhaA Fusions. A β-arrestin2-connector-HT2 fusion cassette was constructed by subcloning β-arrestin2 (See Example VII) into NheI/BamHI restriction sites of the pHT2 vector (Promega). Two primers (5'-CTATAG-GCTAGCCAGCTGGCGCGGATATCGCCAC-CATGGGGGAGAAACCCGGGACC AGGG-3'; SEQ ID NO:76, and 5'-GATTTCGGATCCCATTCTAGAGGGC-CCGCGGTACCGCAAGCTTGATCCGGAGCAGA GTTGATCATCATAGTCGTCATCC-3; SEQ ID NO:77) were designed to add a sequence encoding a connector and a BamHI site to the 3' end of β-arrestin2 coding region, and to amplify the fragment from a β-arrestin2-connector-DhaA.H272F template.

The phRLuc-connector-HT2-Flag fusion cassette was constructed by replacing the DhaA.H272F coding region in the vector encoding phRLuc-connector-DhaA.H272F-Flag (See Example IX) with the HT2 coding region. Two primers (5'-GCCC TCTAGAGCCGTCGACGCTGCCATGGGATCCGAAAT-CG-3'; SEQ ID NO:78, and 5'-GTAGTCACCGGTGCCG-GCCAGCCCGGGGAGCCAGCGCGCG-3'; SEQ ID NO:79) were designed to add a XbaI site to the 5'-end and a AgeI site to the 3'-end of the coding region for HT2, and to amplify a 925 bp fragment from a pHT2 template. The DhaA.H272F coding region was excised with XbaI and AgeI restriction enzymes, then the 925 bp fragment encoding HT2 was inserted into the XbaI and AgeI sites of the phRLuc-connector-DhaA.H272F-Flag coding vector. The sequence of all fusion constructs was confirmed by DNA sequencing.

*Renilla* Luciferase-HT2-Flag Fusion Proteins Expressed in Living Mammalian Cells.

CHO-K1 cells were plated in 24 well plates (Labsystems) and transfected with a pCIneo.hRLuc-connector-HT2-Flag vector. Twenty-four hours later, media was replaced with fresh media containing 25 µM biotin-X-14-Cl and 0.1% DMSO, or 0.1% DMSO alone, and the cells were placed in a $CO_2$ incubator for 60 minutes. At the end of the incubation, the media was removed, cells were quickly washed with PBS (pH 7.4; two consecutive washes; 1.0 ml/cm$^2$; 5 seconds each) and new media was added to the cells. In some experiments, the media was not changed. The cells were placed back in a $CO_2$ incubator.

After 60 minutes, media was removed, and the cells were collected in PBS (pH=7.4, 200 ml/well, RT) containing protease inhibitors (Sigma #P8340). The cells were lysed by trituriation through a needle (IM1 23GTW). Then, cell lysates were incubated with Streptavidin Magnasphere Paramagnetic Particles (Promega #Z5481) according to the manufacturer's protocol. Briefly, cell lysates were incubated with beads for 60 minutes at RT using a rotating disk. Unbound material was collected; beads were washed with PBS containing 0.5.% Triton-X100 (3×500 ml, pH=7.4, RT) and resuspended in SDS-sample buffer (for SDS-PAGE analysis) or PBS (pH=7.4, for determination of *Renilla* luciferase (R.Luc) activity). Proteins were resolved on SDS-PAGE, transferred to a nitrocellulose membrane, analyzed with anti-Flag-Ab, and bound antibody detected by an enhanced chemiluminescence (ECL) system (Pharmacia-Amersham).

Activity of hR.Luc bound to beads was determined using Promega's "*Renilla* Luciferase Assay System" according to the manufacturer's protocol.

Results

Generating a Structural Model for DhaA.H272F

A structural model was built for DhaA.H272F using InsightII Modeler. The reference structure for model calculation was 1BN6.pdb (*Rhodococcus* species DhaA). Five high-optimization models were calculated and one best model selected based on the overall lowest energy and lowest violations of structural parameters. The best model was then structurally aligned with the reference structure 1BN6.pdb to obtain a measure of their overall and pair-wise differences, expressed as the Root Mean Square Deviation (in Å) of aligned Cα atoms (FIG. 2A).

Identification of Substrate Tunnel

The structure of DhaA in the absence of substrate has been published and shows a buried active site cavity near the catalytic triad (FIG. 2A; Newman et al., 1999). However, it does not reveal the direction from which the substrate enters the active site cavity (the "substrate tunnel" or "ligand tunnel" herein). The likely location of the substrate tunnel was identified by analyzing structures of related haloalkane dehalogenases complexed with different substrates (Protein Database). In these complexes, none of the substrates fill the entire ligand tunnel, but structural superimposition showed that the substrates were located at slightly different positions, which, taken together, allowed inference of the likely overall position of the substrate tunnel. Superimposition of the substrate-free DhaA structure (1BN6.pdb) then allowed the identification of the corresponding substrate tunnel position in DhaA.H272F.

Generation of DhaA-Substrate Model

A structural model of DhaA.H272F with a covalently attached substrate was generated ("DhaA-substrate model"). First, carboxyfluorescein-$C_{10}H_{21}NO_2$—Cl was manually docked into the substrate tunnel of DhaA.H272F. Then a covalent bond was created between one of the carboxyl oxygens of the nucleophilic aspartate of DhaA and the terminal carbon of the substrate that becomes available after removal of the chloride (FIG. 2E). The length of this covalent bond was restrained to about 3 Å to approximate the transition state. The covalently attached substrate was energy minimized separately and then together with DhaA.H272F residues in the vicinity of the substrate. Energy minimizations were performed with Discover-3 using the CFF91 force field.

Identification of Residues for Mutagenesis

Residue numbering is based on the primary sequence of DhaA, which differs from numbering in the published crystal structure (1BN6.pdb). Using the DhaA substrate model, dehalogenase residues within 3 Å and 5 Å of the bound substrate were identified. These residues represented the first potential targets for mutagenesis. From this list residues were selected, which, when replaced, would likely remove steric hindrances or unfavorable interactions, or introduce favorable charge, polar, or other interactions. For instance, the Lys residue at position 175 is located on the surface of DhaA at the substrate tunnel entrance: removal of this large charged side chain might improve substrate entry into the tunnel (FIG. 2F). The Cys residue at position 176 lines the substrate tunnel and its bulky side chain causes a constriction in the tunnel: removal of this side chain might open up the tunnel and improve substrate entry (FIG. 2F). The Val residue at position 245 lines the substrate tunnel and is in close proximity to two oxygens of the bound substrate: replacement of this residue with threonine may add hydrogen bonding opportunities that might improve substrate binding (FIG. 2F). Lastly, Bosma et al. (2002) reported the isolation of a catalytically proficient mutant of DhaA with the amino acid substitution Tyr273Phe. This mutation, when recombined with a Cys176Tyr substitution, resulted in an enzyme that was nearly eight times more efficient in dehalogenating 1,2,3-trichloropropane (TCP) than the wild-type dehalogenase. Based on these structural analyses, the codons at positions 175, 176 and 273 were randomized, in addition to generating the site-directed V245T mutation. The resulting mutants were screened for improved rates of covalent bond formation with fluorescent (e.g., a compound of formula VI or VIII) and biotin (FIG. 7) coupled DhaA substrates.

Library Generation and Screening

The starting material for all library and mutant constructions were pGEX5X3 based plasmids (FIG. 3A) containing genes encoding DhaA.H272F and DhaA.D106C (FIG. 2B). These plasmids harbor genes that encode the parental DhaA mutants capable of forming stable covalent bonds with haloalkane ligands. Codons at positions 175, 176 and 273 in the DhaA.H272F and DhaA.D106C templates were randomized using a NNK site-saturation mutagenesis strategy. In addition to the single-site libraries at these positions, combination 175/176 NNK libraries were also constructed. Sequence analysis of random clones from these libraries, however, revealed the presence of a high (50%) frequency of clones with unaltered wild-type sequences. Troubleshooting the QuikChange Multi protocol by varying template concentrations and extending the number and duration of the DpnI treatments did not have a significant effect on this frequency. The rate of wild-type sequence contamination in the libraries was, therefore, taken into account when determining the number of clones to screen from each library. For example, a single site NNK library has a codon diversity of 32 that encodes all 20 amino acids. An approximately 5-fold oversampling of the library is required to cover 99% of the possible sequence variants (L=−V ln 0.01). This oversampling translates into the need to screen at least 160 individual clones. However, because the libraries were contaminated to a significant extent by wild-type sequences (about 50%), approximately 400 clones from each single-site library were typically examined. The combination 175/176 NNK NNK libraries had a theoretical codon diversity of 1024 encoding 400 different amino acid combinations. Approximately 3,000 to 4,000 clones from each double-site library were examined. In total, therefore, approximately 10,000 clones were selected for screening.

Three assays were evaluated as the primary screening tool for the DhaA mutant libraries. The first, an in vivo labeling assay, was based on the assumption that improved DhaA mutants in *E. coli* would have superior labeling properties. Following a brief labeling period with carboxytetramethylrhodamine-$C_{10}H_{21}NO_2$—Cl and cell wash, superior clones should have higher levels of fluorescent intensity at 575 nm. FIG. 31A shows that screening of just one 96 well plate of the DhaA.H272F 175/176 library was successful in identifying several potential improvements (i.e., hits). Four clones had intensity levels that were 2-fold higher than the parental clone. Despite the potential usefulness of this assay, however, it was not chosen as the primary screen because of the difficulties encountered with automation procedures and due to the fact that simple overexpression of active DhaA mutants could give rise to false positives.

The second assay that was considered as a primary screen was an in vitro assay that effectively normalized for protein concentration by capturing saturating amounts of DhaA mutants on immobilized anti-FLAG antibody in a 96 well format. FIG. 31B shows the screening results obtained from one plate of the DhaA.H272F 175/176 combination library using the protein capture assay. Like the in vivo assay, this assay was also able to clearly identify potential improved DhaA mutants from a large background of parental activities. Several clones produced signals up to 4-fold higher than the parent DhaA.H272F. This assay, however, was costly due to reagent expense and assay preparation time, and the automation of multiple incubation and washing steps. In addition, this assay was unable to capture some mutants that were previously isolated and characterized as being superior.

The assay that was ultimately adopted as the DhaA primary screen was based on MagneGST™ protein purification resin (Promega Corp.). An overview of this in vitro screening assay is shown in FIG. 32. Briefly, cell pellets from cultures grown in 96 well plates were resuspended in a reagent cocktail that contained lysis buffer, labeling reagent (substrate carboxytetramethylrhodamine-$C_{10}H_{21}NO_2$—Cl) and MagneGST resin. This significantly streamlined the assay by combining lysis, labeling and protein capture in a single step. Following a brief incubation period with shaking the resin during which proteins were magnetically captured, the wells were washed prior to elution of the labeled DhaA mutants. The eluates were examined for fluorescence intensity at 580 nm. This streamlined screening assay was easily adapted onto an automated Tecan robotic platform that could examine about twenty 96 well plates in a 6.5 hour period.

The automated MagneGST™-based assay was used to screen the DhaA mutant protein libraries. Screening of the DhaA.H272F and DhaA.D106C-based 175 single-site libraries failed to reveal hits that were significantly better than the parental clones (data not shown). FIGS. 33A-B show representative screening results of the 176 single-site and 175/176 combination libraries, respectively. The screen identified several clones with superior labeling properties compared to the parental controls. FIG. 34 shows two representative screening plates from the DhaA.H272F Y273 NNK library. Three clones with significantly higher labeling properties could be clearly distinguished from the background which included the DhaA.H272F parent. For clones with at least 50% higher activity than the DhaA.H272F parent, the overall hit rate of the libraries examined varied from between 1-3%. Similar screening results were obtained for the DhaA.D106C libraries (data not shown). The hits identified by the initial primary screen were located in the master plates, consolidated, regrown and reanalyzed using the MagneGST™ assay. Only those DhaA mutants with at least a 2-fold higher signal than the parental control upon reanalysis were chosen for sequence analysis.

Sequence Analysis of DhaA Hits

FIG. 35A shows the codons of the DhaA mutants identified following screening of the DhaA.H272F libraries. This analysis identified seven single 176 amino acid substitutions (C176G, C176N, C176S, C176D, C176T and C176A, and C176R). Interestingly, three different serine codons were isolated. Numerous double amino acid substitutions at positions 175 and 176 were also identified (K175E/C176S, K175C/C176G, K175M/C176G, K175L/C176G, K175S/C176G, K175V/C176N, K175A/C176S, and K175M/C176N). While seven different amino acids were found at the 175 position in these double mutants, only three different amino acids (Ser, Gly and Asn) were identified at position 176. A single K175M mutation identified during library quality assessment was included in the analysis. In addition, several superior single Y273 substitutions (Y273C, Y273M, Y273L) were also identified.

FIG. 35B shows the mutated codons of the DhaA mutants identified in the DhaA.D106C libraries. Except for the single C176G mutation, most of the clones identified contained double 175/176 mutations. A total of 11 different amino acids were identified at the 175 position. In contrast, only three amino acids (Gly, Ala and Gln) were identified at position 176 with Gly appearing in almost ¾ of the D106C double mutants.

Characterization of DhaA Mutants

Several DhaA.H272F and D106C-based mutants identified by the screening procedure produced significantly higher signals in the MagneGST assay than the parental clones. FIG. 36A shows that the DhaA.H272F based mutants A7 and H11, as well as the DhaA.D106C based mutant D9, generate a considerably higher signal with carboxytetramethyl-rhodamine-$C_{10}H_{21}NO_2$—Cl than the respective parents. In addition, all of the DhaA.H272F based mutants identified at the 273 position (Y273L "YL", Y273M "YM", and Y273C "YC") appeared to be significantly improved over the parental clones (FIG. 36B) using the biotin-PEG4-14-Cl substrate. The results of these analyses were consistent with protein labeling studies using SDS-PAGE fluorimage gel analysis (data not shown). In an effort to determine if combinations of the best mutations identified in the DhaA.H272F background were additive, the three mutations at residue 273 were recombined with the DhaA.H272F A7 and DhaA.H272F H11 mutations. In order to distinguish these recombined protein mutants from the mutants identified in round one of screening (first generation), they are referred to as "second generation" DhaA mutants.

To facilitate comparative kinetic studies several improved DhaA mutants were selected for purification using a Glutathione Sepharose 4B resin. In general, production of DhaA.H272F and DhaA.D106C based fusions in *E. coli* was robust, although single amino acid changes may have negative consequences on the production of DhaA (data not shown). As a result of this variability in protein production, the overall yield of the DhaA mutants also varied considerably (1-15 mg/mL). Preliminary kinetic labeling studies were performed using several DhaA.H272F derived mutants. FIG. 37A shows that many, if not all, of the mutants chosen for analysis had faster labeling kinetics than the H272F parent. In fact, upon closer inspection of the time course, the labeling of several DhaA mutants including the first generation mutant YL (lane 15) and the two second generation mutants, A7YM and H11YL (lanes 13 and 21, respectively) mutants appeared to be complete by 2 minutes. A more expanded time course analysis was performed on the DhaA.H272F A7 and the two second generation DhaA.H272F mutants A7YM and H11YL. As is evident from FIG. 37B, the labeling reactions of the two second generation clones are for the most part complete by the first time point (20 seconds). The A7 mutant, on the other hand, appears only to be reaching completion by the last time point (7 minutes). The fluorescent bands on gel were quantitated and the relative rates of product formation are shown in FIG. 37C. In order to determine a labeling rate, the concentration of the H11YL was reduced from 50 ng to 10 ng and a more refined time-course was performed. The results shown in FIG. 38A demonstrate that under these labeling conditions a linear initial rate can be measured. Quantitation of the fluorimaged gel data allowed second order rate constants to be calculated (FIG. 38B). Based on the slope observed, the second order rate constant for carboxytetramethylrhodamine-$C_{10}H_{21}NO_2$—Cl labeling of DhaA.H272F H11YL was $5.0 \times 10^5$ $M^{-1}sec^{-1}$.

Fluorescence polarization (FP) is ideal for the study of small fluorescent ligands binding to proteins. It is unique among methods used to analyze molecular binding because it gives direct nearly instantaneous measure of a substrate bound/free ratio. Therefore, an FP assay was developed as an alternative approach to fluorimage gel analysis of the purified DhaA mutants. FIG. 39A shows the relative labeling rate of the H272F parent, compared to the A7 and H11YL mutants. Under the labeling conditions used in this experiment, the second generation mutant DhaA.H272F H11YL was significantly faster than its A7 and H272F counterparts. To place this rate in perspective, approximately 42 and 420-fold more A7 and parental, i.e., DhaA.H272F, protein, respectively, was required in the reaction to obtain measurable rates. FIG. 39B shows the FP results using carboxyfluorescein-$C_{10}H_{21}NO_2$—Cl. Under the labeling conditions used in this experiment, it is evident that the H11YL mutant was also considerably faster than A7 and parental, DhaA.H272F proteins with the fluorescein-based substrate. However, it appears that labeling of H11YL with carboxyfluorescein-$C_{10}H_{21}NO_2$—Cl is markedly slower than labeling with the corresponding carboxytetramethylrhodamine-$C_{10}H_{21}NO_2$—Cl substrate. Four-fold more H11YL protein was used in the carboxyfluorescein-$C_{10}H_{21}NO_2$—Cl reaction (150 nM) versus the carboxytetramethylrhodamine-$C_{10}H_{21}NO_2$—Cl reaction (35 nM), yet the rate observed in FIG. 39B appears to be qualitatively slower than the observed carboxytetramethylrhodamine-$C_{10}H_{21}NO_2$—Cl rate shown in FIG. 39A.

Based on the sensitivity and truly homogenous nature of this assay, FP was used to characterize the labeling properties of the purified DhaA mutants with the fluorescently coupled substrates. The data from these studies was then used to calculate a second order rate constant for each DhaA mutant-substrate pair. The results of these analyses are shown in FIG. 40. The two parental proteins used in this study, DhaA.H272F and DhaA.D106C, were found to have comparable rates with the carboxytetramethylrhodamine and carboxyfluorescein-based substrates. However, in each case labeling was slower with the carboxyfluorescein-$C_{10}H_{21}NO_2$—Cl substrate. All of the first generation DhaA mutants characterized by FP had rates that ranged from 7 to 3555-fold faster than the corresponding parental protein. By far, the biggest impact on labeling rate by a single amino acid substitution occurred with the three replacements at the 273 position (Y273L, Y273M, and Y273C) in the DhaA.H272F background. Nevertheless, in each of the first generation DhaA.H272F mutants tested, labeling with the carboxyfluorescein-$C_{10}H_{21}NO_2$—Cl substrate always occurred at a slower rate (1.6 to 46-fold). Most of the second generation DhaA.H272F mutants were significantly faster than even the most improved first generation mutants. One mutant in particular, H11YL, had a calculated second order rate constant with carboxytetramethylrhodamine-$C_{10}H_{21}NO_2$—Cl that was over four orders of magnitude higher than the DhaA.H272F parent. The H11YL rate constant of $2.2 \times 10^6$ $M^{-1}$ $sec^{-1}$ was nearly identical to the rate constant calculated for a carboxytetramethylrhodamine-coupled biotin/streptavidin interaction (FIG. 41). This value is consistent with an on-rate of $5 \times 10^6$ $M^{-1}$ $sec^{-1}$ determined for a biotin-streptavidin interaction using surface plasmon resonance analysis (Qureshi et al., 2001). Several of the second generation mutants also had improved rates with the carboxyfluorescein-$C_{10}H_{21}NO_2$—Cl substrate, however, as noted previously, these rates were always slower than with the carboxytetramethylrhodamine-$C_{10}H_{21}NO_2$—Cl substrate. For example, the carboxyfluorescein-$C_{10}H_{21}NO_2$—Cl labeling rate of the DhaA.H272F H11YL mutant was 100-fold lower than the carboxytetramethylrhodamine-$C_{10}H_{21}NO_2$—Cl labeling rate.

Structure Analysis of the Improved DhaA.H272F H11YL Mutant.

Structural models were built for DhaA.H272F and DhaA.H272F H11YL using InsightII Modeler. The reference structure for model calculation was 1BN6.pdb (*Rhodococcus* species DhaA). Reference structures of two additional related haloalkane dehalogenases were included for calculation of the DhaA.H272F H11YL model: 1CV2.pdb (*Sphingomonas paucimobilis*) and 2DHD.pdb (*Xanthobacter autotrophicus*). For each sequence, five high-optimization models were calculated and one best model selected based on the overall lowest energy and lowest violations of structural parameters. These best models were then structurally aligned with the reference structure 1BN6.pdb to obtain a measure of their overall and pair-wise differences, expressed as the Root Mean Square Deviation (in Å) of aligned Cα atoms.

The substrate carboxytetramethylrhodamine-$C_{10}H_{21}NO_2$—Cl was covalently attached to the best structural models of DhaA.H272F and DhaA.H272F H11YL. First, the substrate was manually docked into the substrate tunnel, and then a covalent bond was created between one of the carboxyl oxygens of the nucleophilic aspartate of the protein and the terminal carbon of the substrate that becomes available after removal of the chloride. Substrate conformations were adjusted to be as similar as possible for both models. The initial models of DhaA.H272F and DhaA.H272F H11YL without and with covalently attached substrate were then prepared for energy minimization by adding hydrogens at pH 7.0 and assigning potentials using the CFF91 force field. Both models were energy minimized with Discover-3 using non-bond interactions with group-based or atom-based cutoffs, a distance-dependent dielectric of 1.0, and a final convergence of 0.01 for the last minimization step. The following minimization cascade was used for models without substrate: a) minimize hydrogens of whole system and fix other atoms, b) minimize side chains of residues within about 8 Å of substrate and fix other atoms, d) minimize residues within about 8 Å of substrate with harmonic Cα restraint and fix other atoms. This minimization cascade was used for models with substrate: a) minimize hydrogens of whole system and fix other atoms, b) minimize substrate and fix other atoms, c) minimize substrate plus side chains of residues within about 8 Å of substrate and fix other atoms, d) minimize substrate plus residues within about 8 Å of substrate with harmonic Cα restraint and fix other atoms. For all minimized models, bump checks were performed between the substrate and residues within about 8 Å of substrate to determine steric hindrances. The substrate tunnel shape and size was visualized by calculating a Connolly surface with default probe radius of 1.4 Å for residues within about 5 Å of the substrate. All models were superimposed structurally to evaluate changes in the position of specific residues.

Position of Relevant Residues. The nucleophile Asp 106 moves slightly more into the tunnel upon binding of carboxytetramethylrhodamine-$C_{10}H_{21}NO_2$—Cl in both mutants. W107, located next to nucleophile and responsible for holding substrate bound to active site in proper orientation for nucleophilic attack, does not change its position significantly. In DhaA.H272F, the F272 side chain is sticking into the tunnel in the absence of substrate, and rotates out of the tunnel about 45° in the presence of substrate. In DhaA.H272F H11YL, the F272 side chain does not stick into the tunnel and adjusts its position only slightly in the presence of substrate. This should facilitate substrate binding in DhaA.H272F H11YL. Glu130 shows a similar orientation in all structures except for DhaA.H272F with substrate, where the Glu130 side chain is pushed away from the tunnel by the F272 side chain rotation necessary to accommodate the substrate.

Overall Fit of Substrate into Substrate Tunnel. A bump check was performed of the minimized protein-substrate structures to show which atoms of the substrate "bump" into which atoms of the protein. A bump exists when two atoms overlap with at least 10% of their van der Waals radii. Carboxytetramethylrhodamine-$C_{10}H_{21}NO_2$—Cl shows bumps to Lys175 and Cys176 in DhaA.H272F, but no bumps to any residues in DhaA.H272 H11YL. This suggests that the mutations introduced in DhaA.H272F H11YL have widened the tunnel to some degree.

Figure 42A:
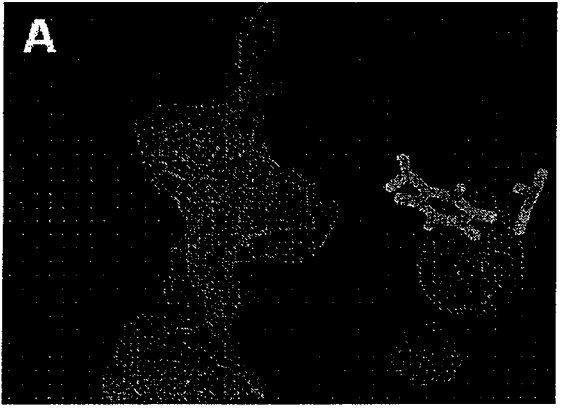
Figure 42B:
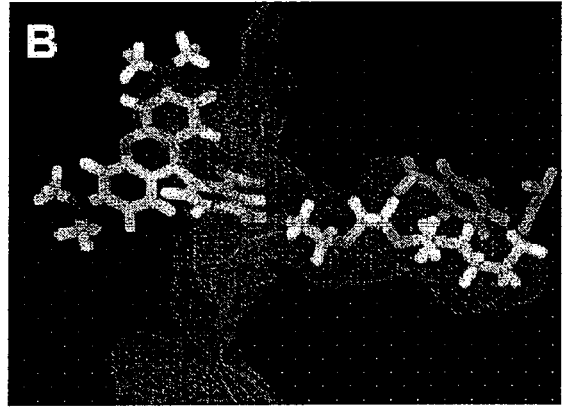
Figure 42C:
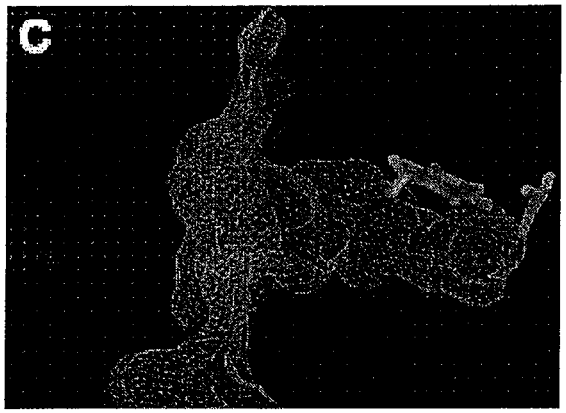
Figure 42D:
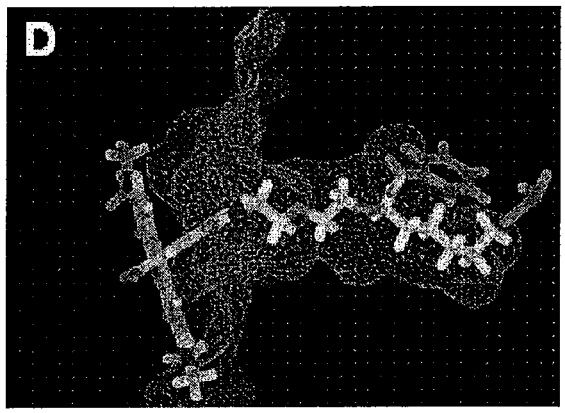

Substrate Tunnel Shape and Size. The substrate cavity was visualized as a Connolly surface with default probe radius of 1.4 Å. In the absence of substrate, DhaA.H272F shows a distinct tunnel entrance and a large cavity near the catalytic triad, separated by a strong constriction or discontinuity in the tunnel around Cys176 extending to Tyr273 (FIG. 42A). This constriction is pushed open when the substrate is bound (FIG. 42B). Mutant DhaA.H272F H11YL does not show any tunnel constriction at positions 176 and 273 but has a continuously wide and open tunnel both in the absence (FIG. 42C) and presence (FIG. 42D) of substrate, suggesting very easy substrate entry. The K175M mutation in DhaA.H272F H11YL does not seem to contribute significantly to the opening of the tunnel.

Figure 43A:
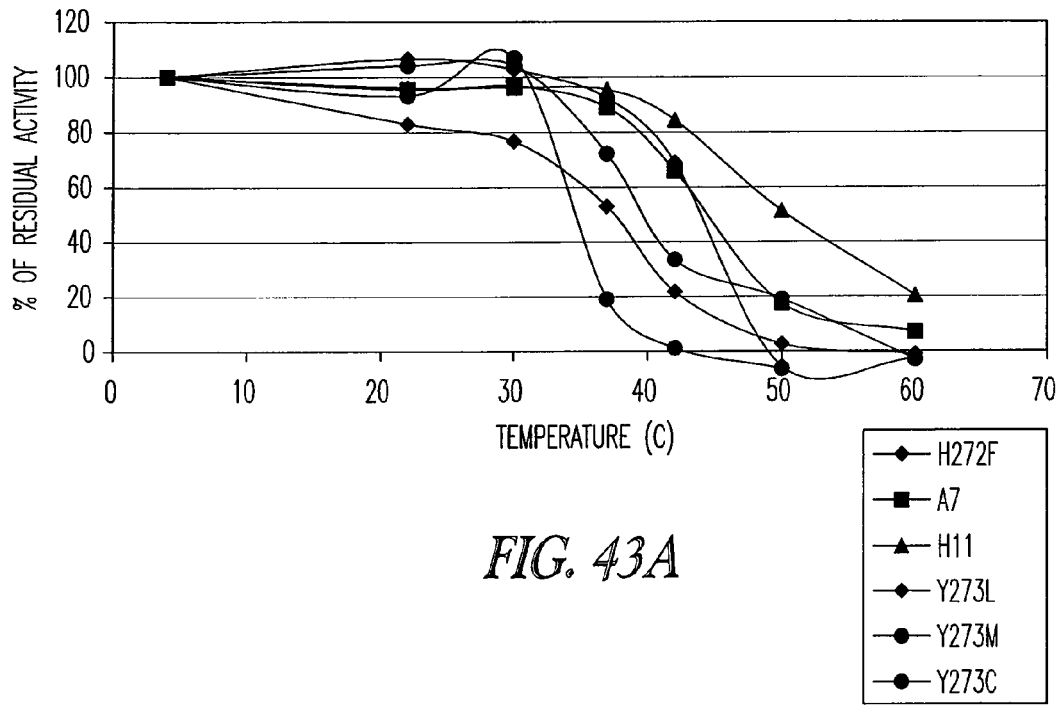
Figure 43B:
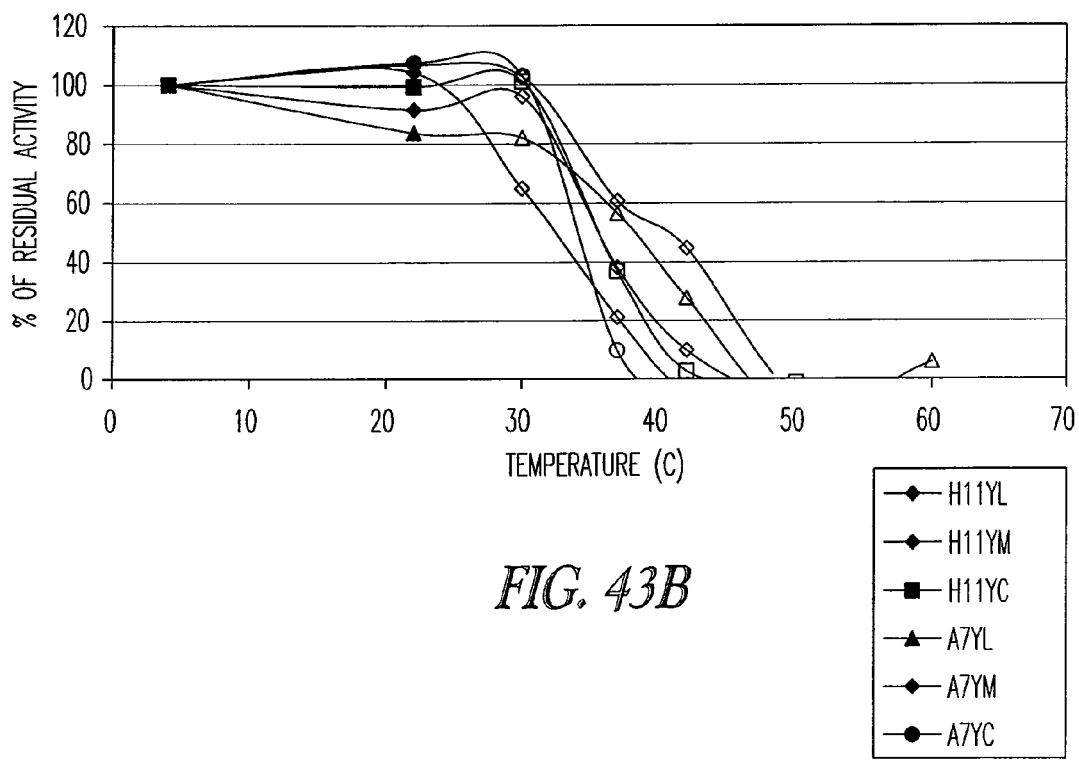

Thermostability Studies with DhaA Mutants. The thermostability profiles of selected first and second generation DhaA.H272F mutants were determined by measuring the residual activity of the purified proteins following 60 minute incubations at various temperature. FIG. 43A shows the thermostability profiles of the first generation DhaA.H272F mutants and corresponding parent. The most active first generation mutants (DhaA.H272F YL, DhaA.H272F YC and DhaA.H272F YM) were relatively unstable at temperatures above 30° C. This is in contrast to the DhaA.H272F parent and the DhaA.H272F A7 mutant protein that were stable up to temperatures of 40° C. One mutant, DhaA.H272F H11, retained significant labeling activity following incubation as high as 50° C. (half-life of 58 minutes at 50° C.). Of the second generation DhaA.H272F mutants, DhaA.H272F H11YL retained the most activity following incubation at 42° C. (FIG. 43B), however, certainly not to the degree of DhaA.H272F H11 (FIG. 43A). It is likely that the same mutations that confer thermostability on DhaA.H272F H11 (i.e., K175M and C176G) also contribute to the stabilization of the DhaA.H272FYL mutant.

Effect of Temperature on DhaA.H272F H11YL Reaction Kinetics. To examine the effect of temperature on reaction rates a labeling time course experiment was performed at room temperature and on ice (0° C.). Fluorimage gel analysis shows that the lower temperature does not impair the labeling rate with carboxytetramethylrhodamine-$C_{10}H_{21}NO_2$—Cl (FIG. 44). In fact, the rate at the lower reaction temperature appears to proceed at a faster rate. Calculation of the $2^{nd}$ order rate constant for the 0° C. reaction reveals a rate of $3.1 \times 10^6$ $M^{-1}$ $sec^{-1}$ compared to $5 \times 10^5$ $M^{-1}$ $sec^{-1}$ for the reaction incubated at 25° C.

Reaction Between DhaA Mutants and Immobilized Biotin Chloroalkane Substrates.

Figure 45A:
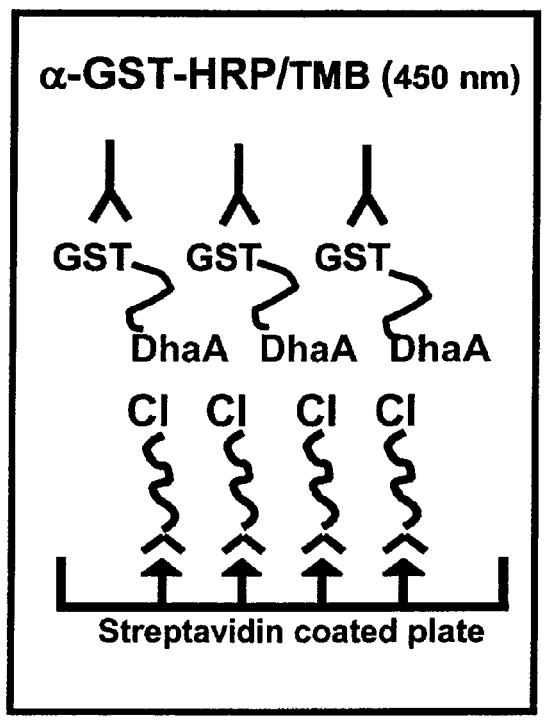
Figure 45B:
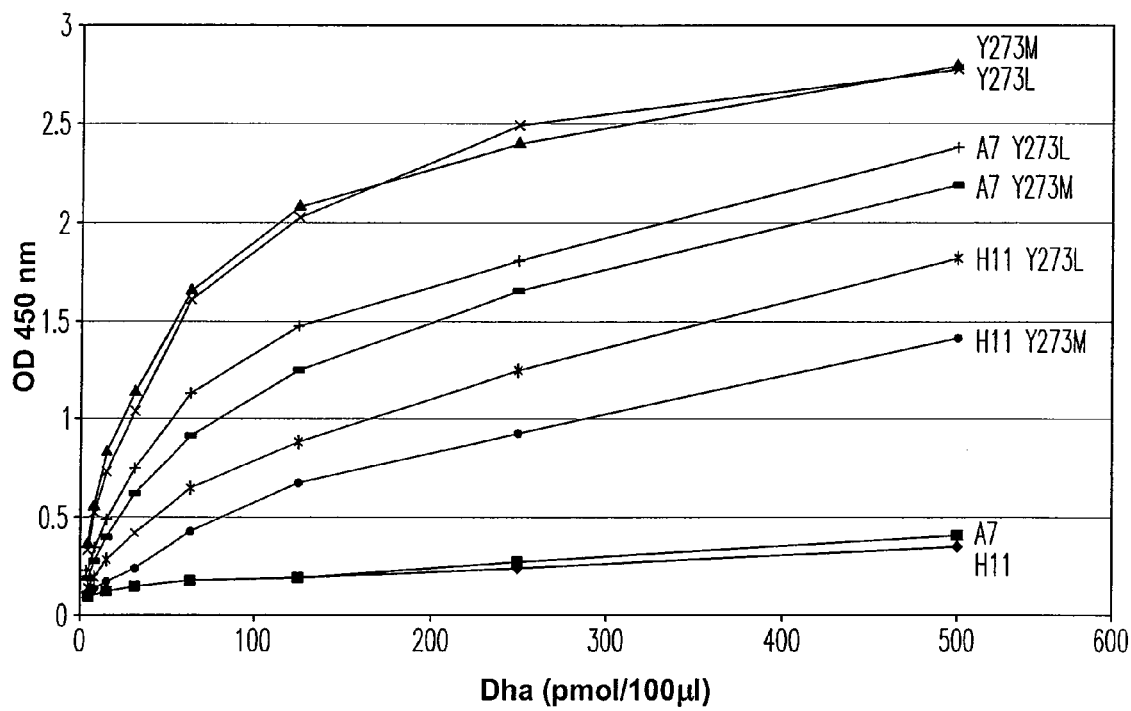

In order to investigate how well the improved DhaA mutants react with an immobilized substrate, an ELISA-type assay utilizing pre-coated streptavidin plates was employed (FIG. 45A). Eight DhaA.H272F mutants (A7, H11, YL, YM, H11YL, H11YM, A7YL and A7YM) were titrated against three different biotin containing substrates (FIG. 7). The biotin-PEG4-14-Cl results shown in FIG. 45B indicate that both DhaA.H272FYL and DhaA.H272FYM mutant proteins react most efficiently with that substrate. In addition, both DhaA.H272F A7YL and DhaA.H272F A7YM were more efficient than DhaA.H272F H11YL and DhaA.H272F H11YM. None of the best performing clones with the biotin-PEG4-14-Cl substrate bound as well to the other two biotin substrates, suggesting that biotin-PEG4-14-Cl is a preferred substrate (data not shown). The first generation DhaA mutants, DhaA.H272F A7 and H11, reacted poorly with all biotin substrates tested.

Characterization of DhaA Mutants in Mammalian Cells.

In Vivo and In Vitro Labeling of DhaA Mutants.

The production of some DhaA mutant proteins in *E. coli* was compromised at 37° C., while other improved DhaA mutants retained considerable activity when grown and induced at elevated temperatures. These clones may have a selective folding advantage at higher temperatures, and, as a result, may therefore be able to better tolerate mammalian cell culture conditions. Based on their superior kinetic and/or production performance, genes encoding the mutant proteins DhaA.H272F A7 and H11 (along with the two parents DhaA.H272F and DhaA.D106C) were cloned into the mammalian expression vector pCI-neo and transfected into CHO cells. A kinetic, in vivo labeling study showed that the two first generation mutants DhaA.H272F A7 and H11, demonstrated superior performance characteristics compared to parent DhaA.H272F at substrate concentrations of 5 µM (FIGS. 46A and B). Therefore, the ability of the DhaA.H272F mutants A7 and H11 to retain significant activity/production at 37° C. in *E. coli* correlated well with its superior performance in mammalian cells.

Three additional DhaA mutants were tested for carboxytetramethylrhodamine-$C_{10}H_{21}NO_2$—Cl labeling efficiency in transiently expressing CHO-K1 cells. FIGS. 46C-D show the labeling results comparing DhaA.H272F A7, DhaA.H272F H11YL and DhaA.D106C 30H4. At a carboxytetramethylrhodamine-$C_{10}H_{21}NO_2$—Cl substrate concentration of 5 µM, the second generation DhaA.H272F H11YL was labeled to completion in 15 minutes. This was half the time it required for complete labeling of DhaA.H272F A7. By contrast, DhaA.D106C 30H4 (the DhaA.H272F H11 equivalent in the DhaA.D106C background) required over 2 hours to achieve the same degree of labeling.

The dependence of labeling efficiency on substrate concentration with DhaA.H272F A7 and H11YL was also investigated. FIGS. 46A-C demonstrate the superior labeling properties of DhaA.H11YL in mammalian cell lysates, particularly at low carboxytetramethylrhodamine-$C_{10}H_{21}NO_2$—Cl substrate concentrations (i.e., 0.1 and 1.0 µM). This finding is consistent with the results of in vitro kinetic studies using purified DhaA proteins. Slightly slower binding kinetics of DhaA.H272F H11YL to carboxytetramethylrhodamine-$C_{10}H_{21}NO_2$—Cl were observed in vivo suggesting that the mammalian cell membrane may be limiting transport of the fluorescent ligand into cells (data not shown).

In Vivo Stability of DhaA Mutants. The stability of select DhaA mutants in transiently transfected mammalian cells was investigated. FIG. 48A shows the fluorescent signal obtained from the parental and two first generation mutants DhaA.H272F A7 and DhaA.H272F H11, after labeling cells with carboxytetramethylrhodamine-$C_{10}H_{21}NO_2$—Cl 12, 24, and 48 hours post-transfection. Quantitation of the fluorimage gel shows that the production of active protein from all four clones tested peaks at 24 hours post-transfection and then declined to the levels observed at 48 hours (FIG. 48B). However, CHO-K1 cells transfected with constructs encoding the H272F-derived mutants A7 and H11 retained the ability to produce more active protein after 48 hours than either of the two parental mutants. This is clearly evident from the robust fluorescent signal produced after carboxytetramethylrhodamine-$C_{10}H_{21}NO_2$—Cl labeling. This result suggests that the DhaA.H272F A7 and H11 mutants may be significantly more stable in vivo. FIGS. 47C-D show a similar stability analysis comparing DhaA.H272F A7 with the second generation mutant DhaA.H272F H11YL. CHO-K1 cells transfected with the construct encoding the DhaA.H272F H11YL mutant also retained a significant labeling potential at 48 hours. In fact, there was little to no detectable reduction in the signal produced by DhaA.H272F H11YL during the 24-48 hour period.

Imaging of DhaA.H272F H11YL in Live and Fixed Mammalian Cells.

As shown by the images in FIGS. 50A-B, DhaA.H272F H11YL expressed in mammalian cells could be efficiently labeled by carboxytetramethylrhodamine-$C_{10}H_{21}NO_2$—Cl or DiAc-carboxyfluorescein-$C_{10}H_{21}NO_2$—Cl. Images are bright and show excellent signal-to-noise ratio. As shown by the images in FIGS. 50C-D, DhaA.H272F H11YL HT2 (FIG. 49)*and* DhaA.H272F could be efficiently labeled with TAMRA-$C_{11}H_{21}N_1O_3$—Cl, and fixed with 3.7% paraformaldehyde. Images of the cells expressing DhaA.H11YL HT2 and stained with 0.2, 1.0 or 5.0 µM TAMRA-$C_{11}H_{21}N_1O_3$—Cl for 5 minutes are brighter than images of the cells expressing DhaA.H272F and stained with 5.0 µM carboxytetramethylrhodamine-$C_{10}H_{21}NO_2$—Cl for 30 minutes. This strongly indicates that in mammalian cells, carboxytetramethylrhodamine-$C_{10}H_{21}NO_2$—Cl labels DhaA.H272F H11YL HT2 with higher efficiency than DhaA.H272F.

Imaging of β-arrestin2-connector-DhaA.H272F H11YL HT2 Fusion Protein Expressed in Living Mammalian Cells.

As shown by the images in FIGS. 50E-F, β-arrestin2-connector-DhaA.H272F H11YL HT2 expressing cells have a typical cytosolic localization for β-arrestin2 using either DiAc-carboxyfluorescein-$C_{10}H_{21}NO_2$—Cl or carboxytetramethylrhodamine-$C_{10}H_{21}NO_2$—Cl to label the protein fusion.

Capturing of DhaA.H272F H11YL-Renilla Luciferase Fusion Protein Expressed in Living Mammalian Cells.

As shown in FIGS. 51A-B, significant luciferase activity was detected on beads incubated with a lysate of cells treated with biotin-X-14-Cl and excess of biotin-X-14-Cl was washed out. No luciferase activity was detected on beads incubated with a lysate from cells that were not treated with biotin-X-14-Cl. Moreover, no hR.Luc activity was detected on beads incubated with lysate from the cells treated with biotin-X-14-Cl when free biotin-X-14-Cl was not washed out. Taken together, these data show that functionally active protein (hR.Luc) fused to the DhaA.H272F H11YL HT2 can be efficiently captured using biotin-X-14-Cl and SA-coated beads. The capture is biotin-dependent, and can be competed-off by excess of biotin-X-14—Cl. As a significant inhibitory effect of the beads on the hR.Luc activity was observed (data not shown), SDS-PAGE and Western blot analysis with anti-R.Luc antibody were used to estimate the efficiency of capture of hR.Luc-connector-DhaA.H272F H11YL HT2 fusion protein. As shown in FIG. 51B, more than 50% of hR.Luc-connector-DhaA.H272F H11YL HT2 fusion protein can be captured in a biotin-dependent manner.

Reactivity of DhaA.H272F H11YL with Haloalkane Substrates Containing Modified Linkers. The substrate cavity of the *Rhodococcus* dehalogenase (DhaA) protein is significantly larger, in both length and breath, than the substrate tunnel of the *Xanthobacter* DhlA protein (Newman et al., 1999). As a result the labeling technology, DhaA mutants should be capable of accommodating a range of substrates containing different linker structures. Some examples of alternative substrates include the p-phenethyl and furanyl propyl derivatives, e.g., a compound such as those shown in FIG. 56. The reactivity of these modified haloalkane substrates was tested with the purified DhaA.H272F H11YL protein.

FIG. 52A shows the binding rates of various carboxytetramethylrhodamine-based substrates determined using FP analysis. The apparent binding rate constant determined for interaction of the carboxytetramethylrhodamine-p-phenethyl-Cl substrate to DhaA.H272F H11YL was only 3-fold lower than the rate determined for carboxytetramethylrhodamine-$C_{10}H_{21}NO_2$—Cl. However, no binding was detected for the carboxytetramethylrhodamine-furanyl propyl substrate under these reaction conditions. The relative labeling rates of the carboxytetramethylrhodamine-based substrates was confirmed using fluorimage gel analysis. Under the reaction conditions used, all three carboxytetramethylrhodamine substrates were found to react with the protein (FIG. 52B). The fluorescent bands on the gel were quantitated to determine the relative rates of product formation. A comparison of the slopes of product accumulation shows that the carboxytetramethylrhodamine-p-phenethyl-Cl substrate was significantly slower at labeling DhaA.H272F H11YL than the carboxytetramethylrhodamine-$C_{10}H_{21}NO_2$—Cl substrate (FIG. 52C). The carboxytetramethylrhodamine-furanyl-propyl-Cl substrate was over 100-fold slower than the carboxytetramethylrhodamine-$C_{10}H_{21}NO_2$—Cl substrate.

A similar in vitro labeling experiment was performed using carboxyfluorescein modified p-phenethyl and furanyl substrates. FIG. 53 shows the relative binding rates of the various carboxyfluorescein-based substrates using FP analysis. The apparent binding rate constant determined for the carboxyfluorescein-p-phenethyl-Cl substrate ($5.6 \times 10^3$ M$^{-1}$ sec$^{-1}$) was approximately 5-fold lower than that for carboxyfluorescein-14-Cl (FIG. 53A). As previously observed with the carboxytetramethylrhodamine chloroalkane binding experiments, no binding was detected for the carboxyfluorescein-furanyl substrate under these reaction conditions. The relative labeling rates of the carboxyfluorescein-based substrates was also determined using fluorimage gel analysis. FIG. 53B shows the amount of fluorescent product formed over the course of 20 minutes. Under the reaction conditions used all three carboxyfluorescein substrates were found to react with the protein (FIG. 53B). Quantitation of these product bands revealed that the DhaA.H272F H11YL labeled approximately 3-fold slower with the carboxyfluorescein-p-phenethyl-Cl substrate compared to the carboxyfluorescein-$C_{10}H_{21}NO_2$—Cl substrate (FIG. 53C). However, the labeling rate with the carboxyfluorescein-furanyl-propyl-Cl substrate was over 100-fold slower than the carboxyfluorescein-$C_{10}H_{21}NO_2$—Cl substrate.

The in vivo labeling rates of the various carboxytetramethylrhodamine-based substrates was determined in mammalian cells. CHO-K1 cells transiently transfected with pHT2 vector (DhaA.H272F H11YL) were labeled with different concentrations of carboxytetramethylrhodamine-Cl-alkanes for over a time course of 60 minutes. Cells were collected at various times, lysed, and proteins were resolved on SDS-PAGE. The presence of labeled protein was detected with a fluoroimager. FIG. 54A shows the accumulation of labeled product over time at various substrate concentrations of 1, 5 and 20 µM. Quantitation of fluorescent product accumulation demonstrates that labeling of DhaA.H272F H11YL with carboxytetramethylrhodamine-p-phenethyl-Cl substrate was comparable to the carboxytetramethylrhodamine-$C_{10}H_{21}NO_2$—Cl substrate at all concentrations tested (FIG. 54B). The labeling rate of the DhaA.H272F H11YL mutant with the carboxytetramethylrhodamine-furanyl-propyl-Cl substrate, however, was noticeably slower at the 1 and 5 µM substrate concentrations.

The biotin-p-phenethyl-Cl substrate was tested in its ability to react with immobilized DhaA protein. The general reaction scheme for the ELISA type assay performed is shown in FIG. 55A. Two pmol of DhaA.H272F H11YL was immobilized onto wells of a microtiter plate using anti-FLAG antibody. Following incubation with the haloalkane substrates (17 µM) and washing, the bound substrate was detected using a streptavidin-HRP conjugate. The amount of color after development was an indication of the reactivity of each biotin haloalkane substrate. FIG. 55B shows that the biotin-p-phenethyl substrate reacted with the immobilized DhaA protein but to a lesser extent than either the biotin-14-Cl and biotin-PEG4-14-Cl substrates.

EXAMPLE XI

Exemplary DhaA Fusions for Cell Surface Display

Many membranous enzymes, receptors, differentiation antigens and other biologically active proteins are bound to fatty acids, isoprenoids, diacylglycerols, and glycosylphosphatidylinositols (GPI) through post-translational processing, and anchored to the membrane by these lipids. GPI-linked proteins are expressed on a wide variety of cell types and have diverse functions ranging from control of cell adhesion (e.g., CD48, CD58, Thy-1/CD90) to protection against complement (CD55, CD59) and enzyme activity (alkaline phosphatase). These molecules are unique in that they are anchored to the outer leaflet of the plasma membrane only and thus do not extend into the cytoplasm. Without exception, GPI anchors are covalently linked to carboxyl-terminal ends of proteins. The core structure for GPI anchors in eukaryotes is composed of ethanolamine phosphate, trimannoside, glucosamine and inositol phospholipid in that order. All known GPI-anchored proteins are synthesized with a C-terminal cleavable peptide (reviewed in Stevens, 1995; Tiede et al., 1999; Sevelever et al., 2000). The C-terminal peptide (a) is comprised of 15-30 amino acids that are generally hydrophobic, (b) contains no downstream cytosolic domain (Medof and Tykocinski, (1990), and (c) establishes a pattern defined by certain sets of amino acids around the "cleavage-attachment" site. This site, which is the amino acid left after removal of the C-terminal signal and the attachment of the GPI anchor, has been termed the ω amino acid.

GPI is synthesized by sequential addition of sugars and ethanolamine phosphates to phosphatidylinositol in the endoplasmic reticulum (ER) (Udenfriend and Kodukula, 1995; Kinoshita and Inoue, 2000). The backbone structure of GPI is common among different species. Pre-formed GPI is attached to proteins in the ER. Precursor proteins to be modified with GPI have two signals. One at the N-terminus is a signal required for translocation across the ER membrane. The other, at the C-terminus, is a GPI attachment signal. The GPI attachment signal peptide is recognized by the GPI transamidase, which cleaves the signal peptide and replaces it with GPI.

To generate a GPI-anchored DhaA mutant, a strategy suggested by De Angelis et al. (1998) for generation of GPI-anchored GFP may be employed. This strategy requires an additional N-terminal leader peptide for directing the nascent polypeptide through to the ER membrane, and addition of a C-terminal sequence for GPI attachment, e.g., PNKGS-GTTSGTTRLLSGHTCFTLTGLLGTLVTMGLLT (SEQ ID NO:18). Using this strategy, Hiscox et al. (2002) successfully expressed GFP on the surface of CHO cells. The authors used three-stage PCR to ligate GFP downstream of the signal peptide of human CD59 (amino acids-25 to 1, e.g., MGIQGGSVLFGLLLVLAVFCHSGHSL; SEQ ID NO:25) and upstream of amino acids 67-102 of human CD59, e.g., FEHCNFNDVTTRLRENELTYYCCKKDLCNFNEQLEN (SEQ ID NO:44), which contains the GPI attachment site at residue 77.

GFP and DhaA have a drastically different structure. Therefore, to generate GPI-anchored DhaA mutant fusions for mammalian cells, a signal sequence and GPI attachment sequence of different GPI-anchored proteins, e.g. 5'-nucleotidase (CD73), CAMPATH (CD52), the decay accelerating factor (DAF or DC55), the membrane inhibitor of reactive lysis (CD59), leucocyte function associated protein-3 (LFA-3 or CD90), placental alkaline phosphatase (PLAP), acetylcholinesterase (AchE), Thy-1 (CD90), Prion, and the like, may be employed. To improve accessibility of substrates to the catalytic pocket, a peptide connector may be introduced between DhaA and the GPI attachment sequence.

Integrins are the major receptors connecting cells to the surrounding extracellular matrix (Danen & Yamada, 2001; Hohesnester & Engel, 2002). They not only support cell attachment but also act in concert with receptors for soluble factors to regulate survival, differentiation, and proliferation. In vitro, integrin $\alpha 5\beta 1'$-mediated cell adhesion to fibronectin is particularly efficient in supporting mitogen-dependent proliferation of fibroblastic, epithelial, and endothelial cells. Integrins are heterodimeric transmembrane receptors connected via scaffolding proteins to the cortical actin cytoskeleton. The extracellular regions of the $\alpha$ and $\beta$ subunits are non-covalently linked to form a globular head domain that binds specific extracellular matrix (ECM) with specificity determined by the particular combination of $\alpha$ and $\beta$ subunits. Sequencing of the human genome has identified as many as 24 $\alpha$ and 9 $\beta$ subunits, and 24 different functional integrins are currently known to exist in mammals.

To express DhaA mutants on the cell surface, a fusion of DhaA mutant and an integrin, e.g., an $\alpha$ or $\beta$ integrin, is employed. Such a fusion protein includes a transmembrane domain, cytosolic domain, and/or an extracellular stalk domain of integrin, and a DhaA mutant. The cytosolic domain of integrin may be a truncated domain, and an extracellular stalk domain of integrin may be replaced with an extracellular stalk domain of another protein (e.g., fractalkine), a portion of a stalk domain and/or a genetically engineered peptide, e.g., a synthetic peptide. Fusions of integrins with other proteins of interest, e.g., reporter proteins such as GFP, or enzymes such as luciferase, is also envisioned, e.g., for cell surface display of the protein of interest.

The cadherins comprise a family of calcium-dependent cell adhesion molecules that form and maintain adhesive contacts between cells of solid tissues (Takeichi et al., 1981; Hatta and Takeichi, 1986; Hatta et al., 1998). Cadherins are single-pass transmembrane proteins characterized by the presence of distinctive cadherin repeat sequences in their extracellular segment (Patel et al., 2003). Each of these repeats, consisting of 110 amino acids, forms a beta-sandwich domain. Cadherins typically have several of these "cadherin domains" tandemly repeated in their extracellular segments. The connections between these domains are rigidified by the specific binding of three $Ca^{2+}$ ions between each successive domain pair. Cadherins can be classified into several subfamilies (Nollet et al., 2000): type I (classical) and type II cadherins, which are ultimately linked to the actin cytoskeleton; the desmosomal cadherins (desmocollins and desmogleins), which are linked to intermediate filaments; and the protocadherins, which are expressed primarily in the nervous system. In addition, several "atypical" cadherins, proteins containing one or more cadherin repeat sequences but bearing no other hallmarks of cadherins, have also been described.

To express DhaA mutants on the cell surface, a fusion of DhaA mutant and a cadherin, e.g., cadherin type I, cadherin type II, or atypical cadherin, is employed. Such a fusion protein includes a transmembrane domain, cytosolic domain, one or more extracellular cadherin domains, and a DhaA mutant. The cytosolic domain of cadherin may be a truncated domain, and an extracellular cadherin domain(s) may be removed or replaced with an extracellular stalk domain of another protein or genetically engineered peptide. Truncated cadherin, T-cadherin, is a type of cadherin and is unusual because it lacks a transmembrane segment and the conserved W2, but has a GPI anchor.

To express DhaA or a DhaA fusion on a cell surface, an N-terminal leader peptide for directing the nascent polypeptide through the phospholipid bilayer of membrane (e.g., ER membrane) is needed. The N-terminal leader peptide may be a leader peptide of the fusion partner of a DhaA fusion polypeptide or a leader peptide of another polypeptide. In one embodiment, an additional peptide e.g., a connector) may be inserted between DhaA and the N-terminal leader peptide, DhaA and the transmembrane domain of a fusion partner, and/or DhaA and an extracellular domain(s) of a fusion partner.

Generally, to express DhaA mutants on the cell surface, a fusion of a DhaA mutant and any membrane protein that has a defined N-terminal extracellular domain(s) (e.g., ligand-gated ion channels such as n-methyl-D-aspartate (NMDA) receptors; 5-methyl-4-isoxazolopropionic acid (AMPA) receptors, glycine receptors, nicotinic acetylcholine receptors (nAChRs), P2X receptors, 5-hydroxytryptamine-3 (5-HT3) receptors) (for review see Galligan, 2002), may be employed. In one embodiment, a fusion of a DhaA mutant and any membrane protein that has an extracellular C-terminal domain (e.g., inhibitory glycine receptors, for a review see Breitinger and Becker, 2002) is employed. The DhaA is attached to or inserted into C-terminal domain of the protein. To improve performance of the fusion (e.g., accessibility of Cl-alkane ligands to the catalytic pocket of DhaA), a peptide connector might be introduced between DhaA and the C-terminal domain of protein. In another embodiment, a fusion of DhaA mutant and any membrane protein that has an extracellular loop domain (peptide chains connecting transmembrane domains of the protein, e.g., peptide chains connecting S1 and S2, S3 and S4, S5 and S6 transmembrane domains in alpha-subunit of a HERG channel (Blaustein and Miller, 2004) is employed. To improve performance of the fusion, a peptide connector may be introduced between DhaA and the N- and/or C-terminal fragments of the loop.

In yet another embodiment, when fused to a protein expressed on the cell surface, a mutant hydrolase on the cell surface, when combined with a ligand of the invention, e.g., one which contains a fluorophore, may be employed to monitor internalization of membrane protein. If ligand of invention is microenvironment sensitive, the system may be employed to monitor changes of environment surrounding membrane protein. In one embodiment, the ligand of the invention is one that has low or no permeability to the cell membrane. In one embodiment, labeling of DhaA expressed on cell surface with non-permeant ligand followed by treatment of the cells with cell permeant ligand, can be used to monitor simultaneously relocation of surface and internal pool of membrane protein. Alternatively, such a system can be used to monitor the effect of different agents, e.g., drugs, on different pools of membrane proteins.

In yet another embodiment, when fused to a protein expressed on the cell surface, a mutant hydrolase on the cell surface, when combined with a ligand of the invention, e.g., one which contains a detectable functional group, may be employed to monitor modification of the membrane proteins (e.g., proteolysis, glycosylation, etc.). Alternatively, such a system can be used to monitor the effect of different agents, e.g., drugs, on modification of the membrane proteins.

In yet another embodiment, when fused to an ion channel, a mutant hydrolase on the cell surface, when combined with a ligand of the invention, e.g., one which contains a microenvironmental sensitive functional group, may be employed to monitor functional activity of the channel. Alternatively, such a system can be used to monitor the effect of different agents (and/or conditions), e.g., drugs (and/or a change of temperature, stretching of cell membrane, interaction of the cells with solid surfaces, other cells, proteins) on ion channel activity.

REFERENCES

Ambler et al., *Biochem. J.*, 276:4710 (1991).
Arshady et al., *Macromol. Chem.*, 187:687 (1981).
Ausubel et al., *Current Protocols in Molecular Biology*, Vol. III, A.1(3-4), Supplement 38 (1997).
Blaustein and Miller, Nature, 427: 499-500 (2004).
Boshart et al., *Cell*, 41:521 (1985).
Bosma et al., *Appl. Environ. Microbial.*, 68:3582 (2002).
Breitinger and Becker, *ChemBioChem*, 3:1042 (2002).
Chalfie, M. and Kain, S. R., eds., *GFP: Green Fluorescent Protein Strategies and Applications* (Wiley, New York, 1998).
Cornish-Bowden, in Fundamentals of Enzyme Kinetics, pp 1-17, Portland Press Ltd., London (1995).
Cubitt et al., *Trends Biochem. Sci.*, 20:448 (1995).
Danen & Yamada, *J. Cell Physiology*, 189:1 (2001).
De Angelis et al., *Proc. Natl. Acad. Sci. USA*, 95:12312 (1998).
Ed Harlow, David Lane, In: *Antibodies: A Laboratory Manual*, Cold Spring Harbor Laboratory Press, p. 726 (1988)
Eu and Andrade, *Luminescence*, 16:57-63 (2001).
Farinas et al., *J. Biol. Chem.*, 274:7603 (1999).
Franken et al., *EMBO J.*, 10:1297 (1991).
Gardiner-Garden et al., *J. Mol. Biol.*, 196:261 (1987).
Gorman et al., *Proc Natl Acad Sci USA*, 79:6777 (1982).
Griffin et al., *Science*, 281:269 (1998).
Hatta and Takeichi, *Nature*, 320:447 (1986).
Hatta et al., *J. Cell Biol.*, 106:873 (1998).
Hermanson, *Bioconjugate Techniques*, Academic Press, San Diego, Calif. (1996).
Hiscox et al., *BBRC*, 293:714 (2002).
Ho et al., *Gene*, 77:51 (1989).
Hohesnester & Engel, *Matrix Biology*, 21:115 (2002).
Holloway et al., *J. Microbiol. Methods*, 32:31 (1998).
Hynkova et al., *FEBS Lett.*, 446:177 (1999).
Janssen et al., *Eur. J. Biochem.*, 171:67 (1988).
Janssen et al., *J. Bacteriol.*, 171:6791 (1989).
Jarvik and Telmer, *Ann. Rev. Genet.*, 32:601-618 (1998).
Keppler et al., *Nature Biotechnology*, 21:86 (2003).
Keuning et al., *J. Bacteriol.*, 163:635 (1985).
Kim et al., *Gene*, 91:217 (1990).
Kinoshita and Inoue, *Curr. Opin. Chem. Biol.*, 4: 632 (2000).
Kneen et al., *Biophys. J.*, 74:1591 (1998).
Krooshof et al., *Biochemistry*, 36:9571 (1997).
Kulakova et al., *Microbiology*, 143:109 (1997).
Kwon et al., *Anal. Chem.*, 76:5713 (2004).
Lakowicz, J.R. Principles of Fluorescence Spectroscopy, New York: Plenum Press (1983).
Llopis et al., *Proc. Natl. Acad. Sci. USA*, 95:6803 (1998).
Medof and Tykocinski, In: Welply J K, Jaworski E, editors. In: *Glycobiology*. New York: Wiley-Liss, p. 17-22 (1990)
Miesenböck et al., *Nature*, 394:192 (1998).
Minasov et al., *J. Am. Chem. Soc.*, 124:5333 (2002).
Miyawaki et al., *Nature*, 388:882 (1967).
Mizushima and Nagata, *Nucleic Acids Res.*, 18:5322 (1990).
Murray et al., *Nucleic Acids Res.*, 17:477 (1989).
Nagata et al., *Appl. Environ. Microbiol.*, 63:3707 (1997).
Nakamura et al., *Nucl. Acids. Res.*, 28:292 (2000).
Newman et al., *Biochemistry*, 38, 16105 (1999).
Nollet et al., *J Mol Biol*, 299:551 (2000).
Ormö et al., *Science*, 273:1392 (1996).
Pieters et al., *Bioorg. & Medicinal Chem. Lett.*, 9:161 (1999).
Pries et al., *Biochemistry*, 33:1242 (1994).
Pries et al., *J. Biol. Chem.*, 270:10405 (1995).
Qureshi et al., *J. Biol. Chem.*, 276:46422 (2001).
Ragaut et al., *Nat. Biotechnol.*, 17:1030-1032 (1999).
Rosomer et al., *J. Biol. Chem.*, 272:13270 (1997).
Sallis et al., *J. Gen. Microbiol.*, 136:115 (1990).
Sambrook et al., Cold Spring Harbor Laboratory Press, Cold Spring Harbor, N.Y. 2001.
Sanger et al., *Proc. Natl. Acad. Sci. U.S.A.*, 74:5463 (1977).
Savage et al., *Avidin-Biotin Chemistry: A Handbook* (Pierce Chemical Company, Rockford, Ill.) (1992).
Schindler, *Biochemistry*, 38:5772 (1999).
Scholtz et al., *J. Bacteriol.*, 169:5016 (1987).
Sevelever et al., In: Young N S, Moss J, editors. *Paroxysmal Nocturnal Hemoglobinuria and the Glycophosphoinositol-Linked Proteins*". San-Diego: CA: Academic Press, p 199 (2000).
Siegel and Isacoff, *Neuron*, 19:735 (1997).
Silverman, Mechanism-based enzyme in activation, in *Methods Enzymology*, 249:240 (1995).
Stevens, *Biochem. J.*, 310: 361 (1995).
Stroffekova et al., *Eur. J. Physiol.*, 442:859 (2001).
Takeichi et al., *Dev Biol.*, 87:340 (1981).
Tiede et al., *J. Biol. Chem.*, 380:503 (1999).
Tsien, *Ann. Rev. Biochem.*, 67:509 (1998).
Udenfriend and Kodukula, *Meth. Enzymol.*, 250:571 (1995).
Uetsuki et al., J Biol. Chem., 264:5791 (1989).
Wada et al., *Nucleic Acids Res.*, 18 Suppl:2367 (1990).
Yokota et al., *J. Bacteriol.*, 169:4049 (1987).
Zawadzke et al., *Protein Engineering*, 8:1275 (1995).
Zlokarnik et al., *Science*, 279:84 (1998).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated polynucleotide encoding a mutant dehalogenase having at least 85% amino acid sequence identity to SEQ ID NO:82, and having at least two amino acid substitutions, the mutant dehalogenase capable of forming a bond with a dehalogenase substrate that is more stable than the bond formed between the dehalogenase of SEQ ID NO:82 and the substrate, wherein one substitution is at an amino acid residue corresponding to residue 272 of SEQ ID NO:82, and wherein a second substitution is at an amino acid residue corresponding to residue 273 of SEQ ID NO: 82.

2. The polynucleotide of claim 1 wherein the mutant dehalogenase has at least 90% amino acid sequence identity to SEQ ID NO: 82.

3. The polynucleotide of claim 1 wherein the amino acid at the position corresponding to residue 272 is phenylalanine, glycine or alanine.

4. The polynucleotide of claim 1 wherein the amino acid at position 273 is leucine, methionine or cysteine.

5. The polynucleotide of claim 1 further comprising a substitution at the position corresponding to amino acid residue 175.

6. The polynucleotide of claim 5 wherein the amino acid at position 175 is methionine, valine, glutamate, aspartate, alanine, leucine, serine or cysteine.

7. The polynucleotide of claim 1 further comprising a substitution at the position corresponding to amino acid residue 176.

8. The polynucleotide of claim 7 wherein the amino acid at the position corresponding to residue 176 is serine, glycine, asparagine, aspartate, threonine, alanine or arginine.

9. The polynucleotide of claim 1 further comprising an open reading frame for one or more proteins of interest, such that expression of the polynucleotide yields a fusion protein comprising the mutant dehalogenase and the protein of interest.

10. A method of expressing the polynucleotide of claim 1 in a host cell, comprising the step of transforming or transfecting the host cell with an expression vector comprising the polynucleotide of claim 1 wherein the polynucleotide is expressed and wherein the encoded mutant dehalogenase polypeptide is produced.

11. The method of claim 10 wherein the host cell is a bacterial cell.

12. The method of claim 10 wherein the host cell is a mammalian cell.

* * * * *